US012371484B2

(12) United States Patent
Ubah et al.

(10) Patent No.: US 12,371,484 B2
(45) **Date of Patent: *Jul. 29, 2025**

(54) SPECIFIC BINDING MOLECULES

(71) Applicant: ELASMOGEN LTD, Aberdeen (GB)

(72) Inventors: Obinna Ubah, Aberdeen (GB); Caroline Barelle, Aberdeen (GB); Andrew Porter, Aberdeen (GB)

(73) Assignee: ELASMOGEN LTD, Aberdeen (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/440,437

(22) Filed: Feb. 13, 2024

(65) Prior Publication Data

US 2024/0247058 A1 Jul. 25, 2024

Related U.S. Application Data

(63) Continuation of application No. 16/650,889, filed as application No. PCT/EP2018/076333 on Sep. 27, 2018, now Pat. No. 11,919,949.

(60) Provisional application No. 62/667,126, filed on May 4, 2018, provisional application No. 62/563,948, filed on Sep. 27, 2017.

(51) Int. Cl.
*C07K 16/24* (2006.01)
*C07K 16/46* (2006.01)

(52) U.S. Cl.
CPC .......... *C07K 16/241* (2013.01); *C07K 16/468* (2013.01); *C07K 2317/24* (2013.01); *C07K 2317/52* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 6,180,370 B1 * | 1/2001 | Queen | A61P 19/02 | 435/69.6 |
| 8,496,933 B2 * | 7/2013 | Paniagua-Solis | A61P 29/00 | 424/130.1 |
| 9,399,677 B2 | 7/2016 | Paniagua-Solis et al. | | |
| 9,475,870 B2 | 10/2016 | Barelle et al. | | |
| 2014/0044716 A1 | 2/2014 | Paniagua-Solis et al. | | |
| 2014/0227259 A1 | 8/2014 | Ashman et al. | | |

FOREIGN PATENT DOCUMENTS

| | | |
|---|---|---|
| WO | 2003/014161 A2 | 2/2003 |
| WO | 2005/118629 A1 | 12/2005 |
| WO | 2011/056056 A2 | 5/2011 |
| WO | 2013/167883 A1 | 11/2013 |
| WO | 2014/173959 A2 | 10/2014 |
| WO | 2014/173975 A1 | 10/2014 |
| WO | 2015/200883 A2 | 12/2015 |

OTHER PUBLICATIONS

Kipriyanov, Sergey M., and Fabrice Le Gall. "Generation and production of engineered antibodies." Molecular biotechnology 26.1 (2004): 39-60.(Year: 2004).*
Stanfield, Robyn L et al. Journal of molecular biology vol. 367,2 (2007):358-72. doi:10.1016/j.jmb.2006.12.045 (Year: 2007).*
Emerson et al., Enhancement of Polymeric Immunoglobulin Receptor Transcytosis by Biparatopic VHH, VHH. PLoS ONE 6(10): e26299, 1-10 (Oct. 14, 2011).
Sela-Culang et al. The structural basis of antibody-antigen recognition. Frontiers in immunology, 2013, 302(4),1-13.
Janeway. The interaction of the antibody molecule with specific antigen. Immunobiology: The Immune System in Health and Disease. 2001, 1-5, https://www.ncbi.nlm.nih.gov/books/NBK27160/.
Stryer, Molecular Design of Life—Protein Structure and Function. Biochemistry 4th Edition. 1995, 18-23.
Colman. Effects of amino acid sequence changes on antibody-antigen interactions. Research in Immunology 145.1, 1994, 33-36.
Kipriyanov and Le Gall. Generation and production of engineered antibodies. Molecular biotechnology 26.1, 2004, 39-60.
Wesolowski, J., et al. Single domain antibodies: promising experimental and therapeutic tools in infection and immunity. Med Microbiol Immunol, 2009. 198(3), 157-174.
Wyatt et al., Intestinal permeability and the prediction of relapse in Crohn's disease. The Lancet 1993. 341(8858), 1437-1439.
Yoshinaga.S., K., et al., Characterization of a new human B7-related protein: B7RP-1 is the ligand to the co-stimulatory protein ICOS. Int. Immunol., 2000. 12(10), 1439-1447.
Zielonka S. et al. Structural insights and biomedical potential of IgNAR scaffolds from sharks. mAbs 2015. 7(1), 15-25.
Streltsov, V.A. et al. Structural evidence for evolution of shark Ig new antigen receptor variable domain antibodies from a cell-surface receptor (2004). Proc. Natl. Acad. Sci. U.S.A. 101(34), 12444-12449.
Streltsov, V.A., et al. Structure of a shark IgNAR antibody variabledomain and modeling of an early-developmentalisotype. Protein Sci., 2005. 14(11), 2901-2909.
Stanfield, R. L., et al. Crystal Structure of a Shark Single-Domain Antibody V Region in Complex with Lysozyme. Science, 2004. 305(5691), 1770-1773.
Stanfield, R. L., et al., Maturation of Shark Single-domain (IgNAR) Antibodies: Evidence for Induced-fit Binding. J MoL Biol., 2007. 367(2), 358-372.
Traunecker A, et al. Bispecific single chain molecules (Janusins) target cytotoxic lymphocytes on HIV infected cells. MBO J. 1991. 10, 3655-36.
Traunecker A, et al. Janusin: New molecular design for bispecific reagents. Int J Cancer Supp. 1992. 7, 51-52.
Neri D et al. High-affinity antigen binding by chelating recombinant antibodies (CRAbs). J Mol Biol. 1995. 246(3), 367-73.

(Continued)

*Primary Examiner* — Michael Szperka
*Assistant Examiner* — Lia E Taylor
(74) *Attorney, Agent, or Firm* — Arrigo, Lee, Guttman & Mouta-Bellum LLP

(57) ABSTRACT

The present invention relates to the formation of multi-domain specific binding molecules comprising VNARs. Specific binding domains that bind to Tumour Necrosis Factor alpha (TNFα) are also provided.

23 Claims, 39 Drawing Sheets

Specification includes a Sequence Listing.

(56) References Cited

OTHER PUBLICATIONS

Spiess C. et al. Alternative molecular formats and therapeutic applications for bispecific antibodies. Mol Immunol 2015. 67(2), 95-106.
Simmons D.P. et al. Dimerisation strategies for shark IgNAR single domain antibody fragments. Immunol Methods. 2006, 315(1-2), 171-184.
Strohl W.R. and Strohl L.M., Therapeutic Antibody Engineering, Woodhead Publishing. 2012, pp. 322/323.
Wang et al., Overexpression of protein kinase C-a in the epidermis of transgenic mice results in striking alterations in phorbol ester-induced inflammation and COX-2, MIP-2 and TNF-a expression but not tumor promotion. J. Cell Science 1999. 112(1), 137-146.
Shealy et al., Characterization of golimumab, a human monoclonal antibody speci!c for human tumor necrosis factor a. MAbs. 2010, 2(4), 428-439.
Suenaert P. et al., Anti-Tumor Necrosis Factor Treatment Restores the Gut Barrier in Crohn's Disease. Am J Gastroenterol 2002. 97(8): 2000-2004.
Shealy et al., Anti-TNF-60 antibody allows healing of joint damage in polyarthritic transgenic mice. Arthritis Research & Therapy. 2002, 4(5), p. R1-7.
Altschul et al. Basic Local Alignment Search Tool. J Mol Biol (1990). 215, 403-410.
Bird et al. Single Chain Antigen Binding Proteins. Science. (1988). 242, 423-426.
Bojalil R et al. Anti-tumor necrosis factorVNAR single domainsreduce lethality and regulate underlyinginflammatory response in a murine model ofendotoxic shock. BMC Immunology (2013). 14(17), 1-7.
Camacho Villegas T et al. Human TNF cytokine neutralization with a vNAR from Heterodontus francisci sharkA potential therapeutic use. (2013). mAbs 5(1), 80-85.
Clayburgh D.R et al. A porous defense: the leaky epithelial barrier in intestinal disease. Laboratory Investigation (2004). 84(3), 282-291.
Coppieters et al. Formatted Anti-Tumor Necrosis FactorVHH ProteinsDerived From Camelids Show Superior Potency andTargeting to Inflamed Joints in a Murine Model ofCollagen-Induced Arthritis. Arthritis & Rheumatism. (2006). 54(6), 1856-1866.
Muller M.R et al. Improving the pharmacokinetic properties of biologics by fusion to an anti-HSA shark VNAR domain. mAbs, Landes Bioscience (2012). 4(6), 673-685.
Kovalenko OV et al. Atypical Antigen Recognition Mode of a Shark Immunoglobulin New Antigen Receptor (IgNAR) Variable Domain Characterized by Humanization and Structural Analysis. J. Biol. Chem, (2013). 288 (24), 17408-17419.
Devereux, et al., A comprehensive set of sequene analysis programs for the VAX. Nucleic Acids Res (1984) 12, 387-395.
Dooley, H. and Flajnik, M. F., Shark immunity bites back: affinity maturation andmemory response in the nurse shark, Ginglymostomacirratum. Eur. J. Immunol., (2005), 35(3), 936-945.
Dooley, H., et al., Selection and characterization of naturally occurring single domain (IgNAR) antibody fragments from immunized sharks by phage display. Mol. Immunol, 2003. 40(1): p. 25-33.
Dooley, H., et al., First molecular and biochemical analysis of in vivo affinity maturation in an actothermic vertebrate. Proc Nat/ Acad Sci USA, 2006. 103(6), 1846-1851.
Els Conrath et al. Camel single-domain antibodies as molecular building units in biospecific and bivalent antibody constructs. J Biol Chem. 2001. 276(10), 7346-7350.
Assessment Report for Simponi. European Medicines Agency (2009). Doc Ref.: EMEA/446762/2009.
Assessment Report for Cimzia, European Medicines Agency (2009). Doc. Ref.: EMEA/664021/2009.
Flajnik M.F et al. A Case of Convergence: Why Did a Simple Alternative toCanonical Antibodies Arise in Sharks and Camels? PLoS Biol (2011), 9(8), 1-5, e1001120.
Greenberg A. S., et al. A new antigen receptor gene family that undergoes rearrangement and extensive somatic diversification in sharks. Nature, 1995, 374(6518), 168-173.
Haines et al. Immunohistochemistry: Forging the links between immunology and pathology. Veterinary Immunology and Immunopathology, 108 (2005) 151-156.
Hamers-Casterman, C. et al. Naturally occuring antibodies devoid of light chains. Nature, 1993. 363, 446-448.
Hidalgo, I.J., et al. Characterization of the Human Colon Carcinoma Cell Line (Caco-2) as a Model System for Intestinal Epithelial Permeability. Gastroenterology 1989. 96, 736-749.
Holliger P. et al., "Diabodies": Small bivalent and bispecific antibody fragments. Proc. tl. Acad. Sci. USA 1993. 90, 6444-6448.
Holliger P and Hudson P. Engineered antibody fragments and the rise of single domains. Nat. Biotechnology. (2005). 23(9), 1126-1136.
Huston et al. Protein engineering of antibody binding sites: Recovery of specific activity in an anti-digoxin single-chain Fv analogue produced in *Escherichia coli*. (1988) Proc Natl Acad Sci USA. 85, 5897-5883.
Irvine E.J. and Marshall J.K., Increased intestinal permeability precedes the onset of Crohn's disease in a subject with familial risk. Gastroenterology (2000). 119.6: 1740-1744.
Jahnichen S. et al. CXCR4 nanobodies (VHH-based single variabledomains) potently inhibit chemotaxis andHIV-1 replication and mobilize stem cells. Proc Nat/ Aced Sci USA. 2010. 107(47), 20565-20570.
Jost CR, et al. A single-chain bispecific Fv2 molecule produced in mammalian cells redirects lysis by activates CTL. Mol Immunol. 1996. 33(2), 211-219.
Jost C. and Pluckthun A. Engineered proteins with desired speci!city:DARPins, other alternative scaffolds and bispeci!c IgGs. Curr Opin Struct Biol. 2014. 27, 102-112.
Keffer et al. Transgenic mice expressing human turmour necrosis factor: a predictive genetic model of arthritis. EMBO J. (1991), 10(13), 4025-4031.
Kipriyanov S.M. et al., Bispecific Tandem Diabody for Tumor Therapy withImproved Antigen Binding and Pharmacokinetics. (1999). J. MoL Biol. 293, 41-56.
Kovaleva M. et al Shark variable new antigen receptor biologics—a novel tehcnology platform for therapeutic drug development. Expert Opin. Biol. Ther. 2014. 14(10), 1527-1539.
Ward E.S. et al. Binding activities of a repertoire of single immunoglobulin variable domains secreted from *Escherichia coli*. Nature 1989, 341, 544-546.
Kontermann R. Dual targeting strategies with bispecific antibodies. mAbs 2012. 4(2), 182-197.
Liu, J.L., et al. Selection of cholera toxin specific IgNAR single-domain antibodies from a näve shark library. MoL Immunol. 2007. 44(7), 1775-1783.
Liu, J.L., et al. Isolation of anti-toxin single domain antibodies from a semi-synthetic spiny dogfish shark display library. BMC Biotechnol, 2007. 7(78), 1-10. doi:10.1186/1472-6750-7-78.
Mack M, et al. A small bispecific antibody construct expressed as a functional single-chain molecule with high tumor cell cytotoxicity. Proc. Natl. Acad. Sci. USA 1995. 92, 7021-7025.
McCormack E. et al. Bi-speci!c TCR-anti CD3 redirected redirected T-cell targetingof NY-ESO-1- and LAGE-1-positive tumors. Cancer Immunol Immunother. 2013. 62(4), 773-785.
Mould et al. VegfbGene Knockout Mice Display Reduced Pathology and Synovial Angiogenesis in Both Antigen-Induced and Collagen-Induced Models of Arthritis. 2003, Arthritis & Rheumatology, 48(9), 2660-2669.
Nuttall, S.D., et al. Isolation of the new antigen receptor from wobbegong sharks and use as a scaffold for the display of protein loop libraries. Mol Immunol, 2001. 38(4), 313-26.
Nuttall, S.D., et al. Isolation and characterization of an IgNAR variable domain specific for the human mitrochondrial translocase receptor Tom70. Eur J Biochem, 2003. 270(17), 3543-54.
Nuttall, S.D., et al. Selection and affinity maturation of IgNAR variable domains targeting plasmodium falciparum AMA1. Proteins, 2004. 55(1): p. 187-97.

(56) References Cited

OTHER PUBLICATIONS

Pettit, A.R., et al. TRANCE/RANKL Knockout Mice Are Protected from Bone Erosion in a Serum Transfer Model of Arthritis. The American journal of pathology, 2001, 159(5), 1689-1699.
Riechmann et al. Single domain antibodies: comparison of camel VH and camelised human VH domains J. Immunol. Methods, 1999. 231, 25-38.
Roovers R.C. et al. A bi-paratopic anti-EGFR nanobody efficiently inhibits solid tumour growth. Int J Cancer. 2011, 129(8), 2013-2024.
Schmitz H. et al. Tumor necrosis factor-alpha (TNFa) regulates the epithelial barrier in the human intestinal cell line HT-29/B6. J. Cell Sci. 1999. 112(1), 137-146.
Schuerer-Maly C. et al. Colonic epithelial cell lines as a source of interleukin-8: stimulation by inflammatory cytokines and bacterial lipopolysaccharide. Immunology, 1994, 81(1), 85-91.
Schulzke J.D. et al., Epitehlial tight junctions in intestinal inflammation. Annals of the NY Academy of Sciences. 2009 1165, 294-300.
Scientific Discussion on Remicade, European Medicines Agency (2005) (http://www.ema.euroba.eu/docs/enGB/document library/EPAR - Scientific Discussion/human/000240/WC500050885.pdf).
Shao C.Y. et al. Rapid isolation of igNAR variable single-domain antibody fragments from a shark synthetic library. Mol Immunol. 2007. 44(4), 656-665.
Wang, F., et al. Interferon- and Tumor Necrosis Factor—Synergize to Induce Intestinal Epithelial Barrier Dysfunction by Up-Regulating Myosin Light Chain Kinase Expression. American Journal of Pathology. 2005, 166(2), 409-419.
Konning et al. Semi-synthetic vNAR libraries screened against therapeutic antibodies primarily deliver anti-idiotypic binders. Nature: Scientific Reports. 7, 9676, 1-13.
Rudikoff et al., Single amino acid substitution altering antigen-binding specificity. PNAS, 1982, 79(6), 1979-1983.
Tamura et al., Structural Correlates of an Anticarcinoma Antibody: Identification of Specificity-Determining Residues (SDRs) and Development of a Minimally Immunogenic Antibody Variant by Retention of SDRs Only. J Immunol, 2000, 164(3), 1432-1441.

* cited by examiner

Anti-hICOSL or mICOSL binding ELISA data of four VNAR-Fc combinations, using 1/8 dilution of supernatant from transiently transfected cells

SPECIFIC BINDING MOLECULES

CROSS-REFERENCE TO RELATED APPLICATIONS

This application is a continuation of U.S. application Ser. No. 16/650,889 filed on Mar. 26, 2020, which is a U.S. Natl. Stage of International Application PCT/EP2018/076333 filed Sep. 27, 2018, which claims the benefit of U.S. provisional application 62/563,948 filed Sep. 27, 2017, and claims the benefit of U.S. provisional application 62/667,126 filed May 4, 2018.

REFERENCE TO SEQUENCE LISTING SUBMITTED ELECTRONICALLY

The instant application contains a Sequence Listing which has been submitted electronically in XML file format and is hereby incorporated by reference in its entirety. Said XML copy, created on Jan. 24, 2024, is named P111682WOUSC01_st26.xml and is 159,744 bytes in size.

FIELD OF INVENTION

The present invention relates to the formation of multi-domain specific binding molecules comprising VNARs. Specific binding domains that bind to Tumour Necrosis Factor alpha (TNFα) are also provided.

BACKGROUND

The search for specific, increasingly efficacious, and diversified therapeutic weapons to combat diseases has utilised a myriad of distinct modalities. From the traditional small molecule to incrementally larger biologic pharmaceuticals, for example single binding domains (10-15 kDa) to full IgG (~150 kDa). Single domains currently under investigation as potential therapeutics include a wide variety of distinct protein scaffolds, all with their associated advantages and disadvantages.

Such single domain scaffolds can be derived from an array of proteins from distinct species. The Novel or New antigen receptor (IgNAR) is an approximately 160 kDa homodimeric protein found in the sera of cartilaginous fish (Greenberg A. S., et al., Nature, 1995. 374(6518): p. 168-173, Dooley, H., et al, Mol. Immunol, 2003. 40(1): p. 25-33; Müller, M. R., et al., mAbs, 2012. 4(6): p. 673-685)). Each molecule consists of a single N-terminal variable domain (VNAR) and five constant domains (CNAR). The IgNAR domains are members of the immunoglobulin-superfamily. The VNAR is a tightly folded domain with structural and some sequence similarities to the immunoglobulin and T-cell receptor Variable domains and to cell adhesion molecules and is termed the VNAR by analogy to the N Variable terminal domain of the classical immunoglobulins and T Cell receptors. The VNAR shares limited sequence homology to immunoglobulins, for example 25-30% similarity between VNAR and human light chain sequences (Dooley, H. and Flajnik, M. F., Eur. J. Immunol., 2005. 35(3): p. 936-945). Kovaleva M. et al Expert Opin. Biol. Ther. 2014. 14(10): p. 1527-1539 and Zielonka S. et al mAbs 2015. 7(1): p. 15-25 have recently provided summaries of the structural characterization and generation of the VNARs which are hereby incorporated by reference.

The VNAR does not appear to have evolved from a classical immunoglobulin antibody ancestor. The distinct structural features of VNARs are the truncation of the sequences equivalent to the CDR2 loop present in conventional immunoglobulin variable domains and the lack of the hydrophobic VH/VL interface residues which would normally allow association with a light chain domain, which is not present in the IgNAR structure and the presence in some of the VNAR subtypes of additional Cysteine residues in the CDR regions that are observed to form additional disulphide bridges in addition to the canonical Immunoglobulin superfamily bridge between the Cysteines in the Framework 1 and 3 regions N terminally adjacent to CDRs 1 and 3.

To date, there are three defined types of shark IgNAR known as I, II and Ill (FIG. 1). These have been categorized based on the position of non-canonical cysteine residues which are under strong selective pressure and are therefore rarely replaced.

All three types have the classical immunoglobulin canonical cysteines at positions 35 and 107 (numbering as in Kabat, E. A. et al. *Sequences of proteins of immunological interest. 5th ed.* 1991, Bethesda: US Dept. of Health and Human Services, PHS, NIH) that stabilize the standard immunoglobulin fold, together with an invariant tryptophan at position 36. There is no defined CDR2 as such, but regions of sequence variation that compare more closely to TCR HV2 and HV4 have been defined in framework 2 and 3 respectively. Type I has germline encoded cysteine residues in framework 2 and framework 4 and an even number of additional cysteines within CDR3. Crystal structure studies of a Type I IgNAR isolated against and in complex with lysozyme enabled the contribution of these cysteine residues to be determined. Both the framework 2 and 4 cysteines form disulphide bridges with those in CDR3 forming a tightly packed structure within which the CDR3 loop is held tightly down towards the HV2 region. To date Type I IgNARs have only been identified in nurse sharks—all other elasmobranchs, including members of the same order have only Type II or variations of this type.

Type II IgNAR are defined as having a cysteine residue in CDR1 and CDR3 which form intramolecular disulphide bonds that hold these two regions in close proximity, resulting in a protruding CDR3 (FIG. 2) that is conducive to binding pockets or grooves. Type I sequences typically have longer CDR3s than type II with an average of 21 and 15 residues respectively. This is believed to be due to a strong selective pressure for two or more cysteine residues in Type I CDR3 to associate with their framework 2 and 4 counterparts. Studies into the accumulation of somatic mutations show that there are a greater number of mutations in CDR1 of type II than type I, whereas HV2 regions of Type I show greater sequence variation than Type II. This evidence correlates well with the determined positioning of these regions within the antigen binding sites.

A third IgNAR type known as Type III has been identified in neonates. This member of the IgNAR family lacks diversity within CDR3 due to the germline fusion of the D1 and D2 regions (which form CDR3) with the V-gene. Almost all known clones have a CDR3 length of 15 residues with little or no sequence diversity.

Another structural type of VNAR, termed type (IIIb or IV), has only two canonical cysteine residues. So far, this type has been found primarily in dogfish sharks (Liu, J. L., et al. *Mol. Immunol.* 2007. 44(7): p. 1775-1783; Kovalenko O. V., et al. *J Biol Chem.* 2013. 288(24): p. 17408-19) and was also isolated from semisynthetic V-NAR libraries derived from wobbegong sharks (Streltsov, V. A. et al. (2004) *Proc. Natl. Acad. Sci. U.S.A.* 101(34): p. 12444-12449).

It has been shown however specific VNARs isolated from synthetic libraries formed from the VNAR sequences can bind with high affinity to other proteins (Shao C. Y. et al. *Mol Immunol.* 2007. 44(4): p. 656-65; WO2014/173959) and that the IgNAR is part of the adaptive immune system as cartilaginous fish can be immunized with antigen and responsive IgNARs obtained that bind to the antigen (Dooley, H., et al, *Mol. Immunol,* 2003. 40(1): p. 25-33; WO2003/014161). It has been shown that the IgNAR has a mechanism for combinatorial joining of V like sequences with D and J sequences similar to that of immunoglobulins and the T cell receptor (summarized by Zielonka S. et al *mAbs* 2015. 7(1): p. 15-25).

The VNAR binding surface, unlike the variable domains in other natural immunoglobulins, derives from four regions of diversity: CDR1, HV2, HV4 and CDR3 (see also Stanfield, R. L., et al, *Science,* 2004. 305(5691): p. 1770-1773; Streltsov, V. A., et al, *Protein Sci.,* 2005. 14(11): p. 2901-2909; Stanfield, R. L., et al., *J Mol. Biol.,* 2007. 367(2): p. 358-372), joined by intervening framework sequences in the order: FW1-CDR1-FW2-HV2-FW3a-HV4-FW3b-CDR3-FW4. The combination of a lack of a natural light chain partner and lack of CDR2 make VNARs the smallest naturally occurring binding domains in the vertebrate kingdom.

The IgNAR shares some incidental features with the heavy chain only immunoglobulin (HCAb) found in camelidae (camels, dromedaries and llamas, Hamers-Casterman, C. et al. *Nature,* 1993. 363, 446-448; Wesolowski, J., et al., *Med Microbiol Immunol,* 2009. 198(3): p. 157-74) Unlike the IgNAR the HCAb is clearly derived from the immunoglobulin family and shares significant sequence homology to standard immunogloblulins. Importantly one key distinction of VNARs is that the molecule has not had at any point in its evolution a partner light chain, unlike classical immunoglobulins or the HCAbs. Flajnik M. F. et al *PLOS Biol* 2011. 9(8): e1001120 and Zielonka S. et al *mAbs* 2015. 7(1): p. 15-25 have commented on the similarities and differences between, and the distinct evolutionary origins of, the VNAR and the immunoglobulin-derived $V_{HH}$ single binding domain from the camelids.

The binding domains derived from light and heavy chains (VL and VH respectively) of classical immunoglobulins, have been shown to be able to be linked together to form bivalent or multivalent and bispecific binding entities whether in the scFv format (Bird et al., 1988; Huston et al., 1988), in which the immunoglobulin VL and VH domains are joined by a short peptide linker Traunecker et al. (Traunecker A, et al. *EMBO J.* 1991. 10, p. 3655-36, Traunecker A, et al. *Int J Cancer* Suppl. 7, 51-52; Neri D. *J Mol Biol.* 1995. 246(3): p. 367-73 or as diabodies (Holliger P. et al., *Proc. Natl. Acad. Sci. USA* 1993. 90, 6444-6448; Holliger P. et al. *Nat. Biotechnol.* 15, 632-636. See Mack M, et al *Proc. Natl. Acad. Sci. USA* 1995. 92, p. 7021-7025, Jost C R, et al *Mol. Immunol.* 1996. 33, p. 211-219 for other early examples). Tandabs comprise two pairs of VL and VH domains connected in a single polypeptide chain (Kipriyanov S. M. et al., *J. Mol. Biol.* 293, 41-56 to form bispecific and bivalent for molecules).

Additionally $V_{HH}$S have been shown to be able to be linked together to form bivalent or multivalent and bispecific binding entities (Els Conrath et al. *J Biol Chem.* 2001. 276(10) p. 7346-7350). Similarly the variable domains from T cell receptors can be linked to immunoglobulin scFv to form bispecific formats (McCormack E. et al. *Cancer Immunol Immunother.* 2013. 62(4): p. 773-85). Single antibody variable domains from classical immunoglobulins (dABs: Ward E. S. et al. *Nature* 1989, 341, p. 544-546) can also be dimerized. The overall concept of bispecific binding molecules and current progress in their development has recently been reviewed by, for example, Kontermann R. *mAbs* 2012. 4(2): 185-197; Jost C. and Pluckthun A. *Curr Opin Struct Biol.* 2014. 27: p. 102-112; Spiess C. et al. *Mol Immunol* 2015. 67(2): 95-106.

In addition to bispecific molecules that recognize epitopes on separate molecules, the concept of linking two antibody binding domains that recognize adjacent epitopes on the same protein (biparatopic) has a long history (see Neri D. *J Mol Biol.* 1995. 246(3): p. 367-73). Biparatopic $V_{HH}$ molecules have been disclosed (for example, Jahnichen S. et al *Proc Natl Acad Sci USA.* 2010. 107(47): p. 20565-70; Roovers R. C. et al *Int J Cancer.* 2011 129(8): p. 2013-24).

However, it has been suggested that, unlike $V_{HH}$S, VNARs might not be able efficiently to form dimeric fusion molecules (Simmons D. P. et al. *Immunol Methods.* 2006 315(1-2): p. 171-84). (See also comments in *Bispecific Antibodies* Konterman R. E. Springer Publishing 2011; 6.6; also see comments in p322/323 of Strohl W. R. and Strohl L. M., *Therapeutic Antibody Engineering*, Woodhead Publishing 2012).

SUMMARY OF INVENTION

The present invention relates to the provision of multi-domain specific binding molecules comprising two or more VNAR domains. More particularly, the invention relates to the provision of bi- and multi-valent VNARs. The current inventors have recently shown that, contrary to the general understanding in the art, in fact dimeric, trimeric and bispecific fusions of VNARs can be formed.

Recently Muller M. R. et al *mAbs* 2012. 4(6): p. 673-685; WO2013/167883) disclosed a bispecific VNAR that comprises a VNAR in which one domain has specificity for human serum albumin (HSA), which allows the bivalent structure to bind in serum to HSA and so extend the biological half-life of the partner domain. Fusion of VNARs at both the N and C terminus of the HSA-binding VNAR was demonstrated with retention of function of the HSA binding domain. More recently, WO/2014/173975 discloses VNARS that can bind to ICOSL (CD275), a cell surface antigen expressed constitutively on antigen presenting cells (APCs) such as B cells, activated monocytes and dendritic cells and is the ligand for the B7 family member, ICOS (CD278) (Yoshinaga. S., K., et al., *Int. Immunol.,* 2000. 12(10): p. 1439-1447). Certain of these ICOSL VNARs can be linked to HSA-binding VNARS and it was shown that both domains retain functionality. Trimeric forms each recognizing different antigens (hICOSL, mICOSL and HSA) could be prepared and each domain shown to retain function.

However it has not been previously shown that bi- or multispecific VNARs could be formed that recognize the same or different epitopes on the same antigen. Additionally, and unexpectedly, bispecific molecules of this form show improved properties over bivalent molecules formed from the constituent monomers, or the monomer forms themselves, or the monomer joined to a VNAR recognizing HSA.

The present invention relates to specific VNAR domain sequences that have the capability of being combined into multivalent or multispecific entities and within which multidomain entity each domain retains binding function.

Therefore, in a first aspect of the present invention there is provided a multi-domain specific binding molecule comprising two or more VNAR domains which bind to the same or different epitopes of one or more specific antigens.

In certain preferred embodiments the VNARs in the multi-domain specific binding molecule of the first aspect of the invention bind the same antigen on a specific antigen.

In further preferred embodiments, the VNARs of multi-domain specific binding molecule bind different epitopes on a specific antigen. Multi-domain specific binding molecules in accordance with these embodiments may be termed bi-paratopic molecules, as further described herein.

In one embodiment specific VNAR binding domain sequences are combined into multivalent or multispecific entities and, within which multidomain entity each domain retains binding function, wherein the binding domains recognize distinct epitopes on a single antigen.

A preferred embodiment of the invention is a bi- or multi-specific binding molecule comprising two (or more) different VNAR domains wherein the binding specificity is for distinct epitopes on a single specific antigen and in which the resultant entity shows improved properties compared to the individual VNAR binding domains. An example of an improved property includes increased agonistic or antagonistic effect compared to the monomer VNARs.

Preferably the VNAR domains of the multi-domain specific binding molecule of the present invention are separated by a spacer sequence. More preferably, the spacer sequence has independent functionality which is exhibited in the binding molecule. In one embodiment, the spacer sequence is a VNAR domain or functional fragment thereof. In a specific example the spacer may be a VNAR or functional fragment thereof that binds serum albumin, including human serum albumin or ICOSL. In certain embodiments the spacer sequence comprises the amino acid sequence of any one of SEQ ID NO: 67, 77, 78, 79, 80, 81, 82, 83, 84, 85, 86, 87 or 88, or a functional fragment having at least 60% sequence identity thereto. In a further embodiment the spacer sequence may be the Fc portion of an immunoglobulin, including but not limited to a human immunoglobulin Fc region. The improved properties may partially or completely derive from the properties of the spacer, for example by passively separating the VNAR domains in space or by the inherent properties of the spacer such as serum albumin binding which may lead to a longer in vivo half-life for the resultant entity, or by the recognition of a second therapeutic auto-immune target such as ICOSL or by introduction of a capacity for engagement with cells of the immune system or complement, in the case of immunoglobulin Fc regions.

Embodiments of the multi-domain specific binding molecule of the invention comprising two or more VNAR domains separated by a spacer sequence may be referred to herein as a Quad-X format.

In other preferred embodiments, the multi-domain specific binding molecule may further comprise one or more non-VNAR domains. The one or more non-VNAR domains may be placed in any position relative to the VNAR domains. Typically, and in preferred embodiments, the non-VNAR domain will be C-terminal or N-terminal to the VNAR domains.

Embodiments of the multi-domain specific binding molecule of the invention comprising two or more VNAR domains and a non-VNAR domain that is C-terminal or N-terminal to the VNAR domains may be referred to herein as a Quad-Y format.

Exemplary non-VNAR domains include, but are not limited to, TNF R1 and immunoglobulin Fc.

The specific antigen can be from a group comprising a cytokine, a growth factor, an enzyme, a cell surface associated molecule, a cell-surface membrane component, an intracellular molecule, an extracellular matrix component, a stromal antigen, a serum protein, a skeletal antigen, a microbial antigen or an antigen from a normally immune-privileged location.

A further aspect of the invention is the specific combination of VNAR binding domains that recognize cytokines Also provided by the present invention are specific domains that recognize human TNF and bind to an epitope that is different from all other well characterized anti-TNF antibody and VHH binders that are currently used to treat disease.

Accordingly, in a second aspect the present invention provides a TNF-alpha specific VNAR binding domain comprising the following CDRs and hyper-variable regions (HV):

```
CDR1:
                        (SEQ ID NO. 68)
HCATSS
or
                        (SEQ ID NO. 69)
NCGLSS
or
                        (SEQ ID NO. 70)
NCALSS

HV2:
                        (SEQ ID NO. 71)
TNEESISKG

HV4:
                        (SEQ ID NO. 72)
SGSKS
or
                        (SEQ ID NO. 73)
EGSKS

CDR3:
                         (SEQ ID NO. 1)
ECQYGLAEYDV
or
                         (SEQ ID NO. 6)
SWWTQNWRCSNSDV
or
                        (SEQ ID NO. 11)
YIPCIDELVYMISGGTSGPIHDV
```

or a functional variant thereof with a sequence identity of at least 60%.

In particularly preferred embodiments, the TNF-alpha specific VNAR binding domain comprising the amino acid sequence of SEQ ID 2, 7 or 12, or a functional variant thereof with a sequence identity of at least 60%.

In preferred embodiments the TNF-alpha specific VNAR domain of the invention is modified at one or more amino acid sequence position to reduce the potential for immunogenicity in vivo, by for example humanization, deimmunization or similar technologies, while retaining functional binding activity for the specific epitopes on the specific antigen.

One embodiment of the invention is the specific combination of VNAR binding domains into a resultant multidomain binding molecule that recognize TNFα and which, in the forms outlined in this invention, provide improved functional properties over the individual binding domains. It is known that VNARs can be raised that are claimed to recognize TNFα (Camacho-Villegas T, et al MAbs. 2013. 5(1): P. 80-85; Bojalil R, et al BMC Immunol. 2013. 14:17; WO2011/056056; US20110129473; US20140044716).

These VNARs have not however been linked to form dimeric or bispecific forms. In addition these domains in a monomeric format are 70 to 200 times less potent than the monomeric anti-TNF VNAR domains described here.

Accordingly, the TNF-alpha specific VNAR binding domain of the second aspect of the invention may be used as one or both VNAR domains in the multi-domain specific binding molecule of the first aspect. Therefore, in a preferred embodiment there is provided a multi-domain specific binding molecule of the first aspect, wherein one or more of the VNAR domains have an amino acid sequence selected from the group comprising SEQ ID 2, 7 or 12, or a functional variant thereof with a sequence identity of at least 60%. In other preferred embodiments, there is provided a multi-domain specific binding molecule of the first aspect, wherein two or more of the VNAR domains have an amino acid sequence selected from the group comprising SEQ ID 2, 7 or 12, or a functional variant thereof with a sequence identity of at least 60%.

Other preferred embodiments of the first aspect of the invention include the multi-domain specific binding molecule of the first aspect comprising one or more of the VNAR domains having an amino acid sequence selected from the group comprising SEQ ID 65 or 66, or a functional variant thereof with a sequence identity of at least 60%. Yet further embodiments of the first aspect include the multi-domain specific binding molecule of the first aspect comprising two or more of the VNAR domains having an amino acid sequence selected from the group comprising SEQ ID 65 or 66, or a functional variant thereof with a sequence identity of at least 60%.

The VNAR domain or domains used in the first aspect of the invention may be modified at one or more amino acid sequence position to reduce the potential for immunogenicity in vivo, by for example humanization, deimmunization or similar technologies, while retaining functional binding activity for the specific epitopes on the specific antigen.

The present invention also provides an isolated nucleic acid comprising a polynucleotide sequence that encodes a binding molecule according to any aspect or embodiment described herein. Furthermore, there is provided herein a method for preparing a binding molecule according to the invention, comprising cultivating or maintaining a host cell comprising the polynucleotide under conditions such that said host cell produces the binding molecule, optionally further comprising isolating the binding molecule.

According to a further aspect of the invention, there is provided a pharmaceutical composition of a specific antigen binding molecule and/or the multi-domain specific binding molecule of the previous aspects of the invention.

Pharmaceutical compositions of the invention may comprise any suitable and pharmaceutically acceptable carrier, diluent, adjuvant or buffer solution. The composition may comprise a further pharmaceutically active agent. Such carriers may include, but are not limited to, saline, buffered saline, dextrose, liposomes, water, glycerol, ethanol and combinations thereof.

Such compositions may comprise a further pharmaceutically active agent as indicated. The additional agents may be therapeutic compounds, e.g. anti-inflammatory drugs, cytotoxic agents, cytostatic agents or antibiotics. Such additional agents may be present in a form suitable for administration to patient in need thereof and such administration may be simultaneous, separate or sequential. The components may be prepared in the form of a kit which may comprise instructions as appropriate.

The pharmaceutical compositions may be administered in any effective, convenient manner effective for treating a patient's disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg, 2 mg/kg, 10 mg/kg or up to 100 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention. The present invention also provides a kit comprising a pharmaceutical composition as defined herein with instructions for use.

According to a further aspect of the invention, there is provided a pharmaceutical composition of the previous aspect for use in medicine. Such uses include methods for the treatment of a disease associated with the interaction between the target antigen of the binding domain of the invention and its ligand partner(s) through administration of a therapeutically effective dose of a pharmaceutical composition of the invention as defined above. The composition may comprise at least one specific antigen binding molecule (VNAR domain) or multi-domain specific binding molecule of the invention, or a combination of such molecules and/or a humanized variant thereof.

In accordance with this aspect of the invention, there is provided a composition for use in the manufacture of a medicament for the treatment of a disease associated with the interaction between target antigen of the binding domain of the invention and its ligand partner(s).

Such compositions may comprise a further pharmaceutically active agent as indicated. The additional agents may be therapeutic compounds, e.g. anti-inflammatory drugs, cytotoxic agents, cytostatic agents or antibiotics. Such additional agents may be present in a form suitable for administration to patient in need thereof and such administration may be simultaneous, separate or sequential. The components may be prepared in the form of a kit which may comprise instructions as appropriate.

According to the invention, there is provided an antigen specific antigen binding molecule or multi-domain specific binding molecule of the invention for use in medicine. This aspect of the invention therefore extends to the use of such of an antigen specific antigen binding molecule or multi-domain binding molecule of the invention in the manufacture of a medicament for the treatment of a disease in a patient in need thereof. An antigen specific antigen binding molecule of the invention can also be used to prepare a fusion protein comprising such a specific binding molecule or multi-domain binding molecule as defined above in relation to pharmaceutical compositions of the invention. Such uses also embrace methods of treatment of diseases in patients in need of treatment comprising administration to the patient of a therapeutically effective dosage of a pharmaceutical composition as defined herein comprising an antigen specific antigen binding molecule or multi-domain binding molecule of the invention.

As used herein, the term "treatment" includes any regime that can benefit a human or a non-human animal. The treatment of "non-human animals" in veterinary medicine extends to the treatment of domestic animals, including horses and companion animals (e.g. cats and dogs) and farm/agricultural animals including members of the ovine, caprine, porcine, bovine and equine families. The treatment may be a therapeutic treatment in respect of any existing condition or disorder, or may be prophylactic (preventive treatment). The treatment may be of an inherited or an acquired disease. The treatment may be of an acute or chronic condition. The treatment may be of a condition/disorder associated with inflammation and/or cancer. The antigen specific antigen binding molecules or multi-domain specific binding molecules of the invention may be used in the treatment of a disorder, including, but not limited to osteoarthritis, scleroderma, renal disease, rheumatoid arthritis, inflammatory bowel disease, multiple sclerosis, atherosclerosis, or any inflammatory disease.

In a further aspect the present invention provides a method for treating a condition mediated by TNFα, the method comprising the administration of a therapeutically effective amount of a composition of the invention that specifically binds to TNFα.

In yet a further aspect the present invention provides a method for treating at least one condition mediated by ICOSL, comprising the administration of an effective amount of a composition of the invention that specifically binds to ICOSL.

A further aspect of the invention is the specific combination of VNAR binding domains that recognize cell-surface molecules. In certain embodiments, the VNARs of the multi-domain binding molecule bind different classes of ligand or target. One non-limiting example contemplated herein is a multi-domain specific binding molecule of the first aspect of the invention in which at least one VNAR domain binds a target associated with auto-immune disease and at least one VNAR domain binds to a target associated with the inflammatory response.

A particularly preferred multi-domain specific antigen binding molecule of the invention includes a TNF-specific VNAR and an ICOSL specific VNAR. Preferably, the TNF-specific VNAR is the VNAR of the second aspect of the invention.

One embodiment of the invention is the specific combination of VNAR binding domains into a resultant multidomain binding molecule that recognize ICOSL and which, in the forms outlined in this invention, provide improved functional properties over the individual binding domains.

In the present application reference is made to a number of drawings in which:

FIG. 1 Anti-hTNF-alpha IgNAR titration of immunized nurse shark plasma using anti-Nurse shark IgNAR hybridoma antibody ELISA titration of serum from immunized animals, pre-immunization and after bleed 5 Binding ELISA measurement of anti-rhTNF-α IgNAR titer in immunized nurse shark. Detection was carried out with GA8 monoclonal anti-nurse IgNAR antibody, and anti-mouse IgG-HRP conjugated antibody was used as secondary antibody.

FIG. 2 Neutralisation of hTNF-alpha induced cytotoxicity in L929 cells

In this assay, the ability of the anti-TNF domains (D1 and C4) and control anti-human serum albumin domain (BA11) to neutralize the activity of hTNF-α in a cell bio-assay was determined. Both the D1 and C4 domains demonstrated a similar level of concentration dependent neutralization (for calculated values see Table 2). The BA11 control does not recognize hTNF and so no neutralization was observed even at the highest concentrations. The hTNF-α+Actinomycin-D acted as control demonstrating classical cytotoxicity in the absence of a neutralizing domain.

FIG. 3 In vitro rhTNFα neutralization assay in L929 fibrosarcoma cell line.

Neutralisation of 10×LD80 [3 ng/ml rhTNFα], n=2 with duplicates per experiment, ±SD.

TNF30-Fc is a fusion of an anti-rhTNFα $V_{HH}$ nanobody isolated from immunized camelid fused to IgG Fc (Coppieters et al., Arthritis and Rheumatism, 2006, 54 (6): 1856-1866; Riechmann et al., J. Immunol. Methods, 1999. 231: 25-38)

Alb8-Fc is a $V_{HH}$ domain which recognizes HSA, fused to IgG Fc.

2V is a negative control VNAR which recognizes no known target. 2V-Fc is a fusion of 2V to IgG Fc.

Only those binders that were specific for hTNF (D1, C4 and TNF-30) were able to demonstrate neutralization of the activity of the free hTNF and in a concentration dependent manner. The neutralization potency was enhanced by conversion from a monomer to a bivalent Fc format. The combination of D1-Fc and C4-Fc together delivered a neutralization potency that was better than D1-Fc alone or C4-Fc alone. (see Table 2 for all calculated neutralization values). Both the controls, Alb-8 and 2V, were unable to neutralize even in this bivalent Fc format.

FIG. 4 Diagram of format of bivalent and bispecific constructs

FIG. 5 ELISA binding of dimeric VNARs together with a TNF-30 VHH control (TNF30-TNF30). All the tested VNAR domains D1, C4, B4 were either paired with themselves (eg D1-D1, C4-C4 etc) or paired with each other (eg D1-C4, D1-B4) in both possible orientations (eg C4-D1, B4-D1). The ELISA ranking placed the D1-D1 dimer pair as the best (lowest concentration of VNAR required to reach a saturating signal) and B4-C4 and B4-B4 as the worst performing in this ELSA format. A number of the VNAR pairings were better than the VHH dimer control.

FIG. 6 L929 assay to measure TNF neutralization by VNAR dimer pairs

The neutralizing ability of the anti-TNF a VNAR dimer pairs D1-D1, D1-C4, D1-B4 and the positive control anti-TNF VHH dimer (TNF30-TNF30) were assessed using an appropriate bioassay. The domain pairing showing the most potent neutralizing activity in this assay format was the VNAR pair D1-C4 (for calculated values of neutralisation see Table 2). hTNFα+actinomycin-D treated cells without any neutralizing domain provided an appropriate classical uninhibited cytotoxicity control.

FIG. 7 Neutralisation of hTNFα induced cytotoxicity in L929 cells using trimeric anti-hTNF-α VNARs The lead anti-hTNFα VNAR dimers (D1-D1 and D1-$C_4$) were reformatting into multivalent trimeric constructs by incorporating an anti-HSA humanised VNAR (soloMER™ BA11) in the middle of both dimeric constructs to achieve D1-BA11-D1 and D1-BA11-C4 respectively. The ability of these multivalent trimeric constructs and humira (Adalimumab) and TNF30-BA11-TNF30 to neutralize hTNFα was assessed in a classical L929 assay. The D1-BA11-C4 construct demonstrated comparable neutralizing potency as Adalimumab, and significantly improved potency than the VHH trimeric construct, and also the anti-hTNFα dimeric (D1-C4 and D1-D1) VNARs (see Table 2 for calculated ND50 values).

FIG. 8 Caco2 Epithelial Permeability in Polarized Caco2 cells

Caco-2 cells were treated and incubated for 18 h with 10 ng/ml TNFα, LPS and IFNγ+/−anti-TNFα protein. 5 μl of 10 mg/ml FITC-Dextran [3000-5000 kDa] was added to the apical chamber and transport across the membrane to the basolateral chamber was measured 24 h later. Treatment with VNAR/VHH monomers and VNAR control proteins was at 50 nM concentration, while Treatment with VNAR dimers (2C and 2D) and Adalimumab was at 25 nM.

BA11 and 2V are non-TNFα binding VNAR control, while B4 is a non-neutralising TNF-binding VNAR The ability of the anti-hTNFα VNAR constructs (monomers D1, C4, B4; dimers D1-D1, D1-$C_4$; trimers, D1-BA11-D1, D1-BA11-C4), VHH constructs TNF30, TNF30-TNF30, TNF30-BA11-TNF30, and Adalimumab to prevent intestinal barrier dysfunction in cytokine treated Caco-2 cells was assessed using this classical assay. The VNAR domains D1-C4 and D1-BA11-C4 demonstrated comparable efficacy to Adalimumab. Negative controls BA11 and 2V were unable to prevent intestinal barrier dysfunction.

FIG. 9 Epithelial Resistance in Polarized Caco-2 cells

Differentiated Caco-2 cells were treated and incubated for 24 h with 10 ng/ml TNFα and IFNγ+/−anti-TNFα. Effect of cytokine treatment on Trans-epithelial resistance was determined using a volt-ohm meter. Resistance was normalised to the surface area under treatment (ohm·cm$^2$).

Treatment with VNAR/VHH monomers and VNAR control proteins was at 50 nM concentration, while Treatment with VNAR dimers (2C and 2D) and Adalimumab was at 25 nM.

BA11 and 2V are non-TNFα binding VNAR control, while B4 is a non-neutralising TNF-binding VNAR

[n=1±SD with ≥8 replicates per treatment, one-way ANOVA and Dunnett's post-hoc test using GraphPad Prism 5)

The efficacy of the anti-hTNFα VNAR domains to restore epithelial resistance in cytokine treated Caco-2 cells were investigated in comparison with the efficacy of the VHH TNF30 and the clinically available Adalimumab at equimolar dosing range. The anti-hTNFα dimeric and trimeric VNAR domains demonstrated significant capacity in restoring epithelial resistance in a comparable fashion to the effect observed with Adalimumab. The negative controls BA11 and 2V did not restore epithelial resistance.

FIG. 10 Format of ICOSL VNAR-Fc fusions

FIG. 11 ICOSL ELISA binding data

Binding ELISA of the different anti-ICOSL Quad-X™ constructs to both human and mouse ICOS ligands.

FIG. 12 Formats for multivalent and multispecific VNARs of the invention incorporating the TNF R1 domain, ICOSL VNARs and human IgG Fc FIG. 13 Efficacy data for multivalent and multispecific VNARs incorporating the TNF R1 domain, ICOSL. VNARs and human IgG Fc, which provides additional improved functional characteristics.

VNAR-TNFR1 Fc bi-functional constructs demonstrate specific and potent efficacy in cell based neutralisation assays Format 1: anti-TNFα scFv Format 2: anti-mICOSL VNAR (CC3)

Format 3: anti-hICOSL scFv

Format 4: anti-hICOSL VNAR (2D4)

FIG. 14 hTNF-alpha Binding profile between VNAR T43 horn shark clone and VNAR Nurse shark D1 and C4.

Binding ELISA of the VNAR T43 from the Horn shark and VNAR D1 and C4 to 1 μg/ml hTNFα coated wells. The binding profile of T43 clone could not be determined at experimental concentration used.

FIG. 15 hTNF-alpha Neutralisation efficacy in L929 cells of VNAR T43 horn shark clone and VNAR Nurse shark D1 and C4

Comparison of the neutralising efficacy of anti-hTNFα VNAR monomers D1 and C4 compared to the Horn Shark T43 VNAR at equimolar dosing range. The T43 domain did not demonstrate any dose-dependent neutralising effect, and has similar profile as the unprotected cells treated with hTNFα and Actinomycin-D (See table 2)

FIG. 16 Binding profile of a successfully humanised anti-hTNF-alpha D1 (also known as D1 soloMER™)

Binding profile of a number of progressively improved framework humanised versions of VNAR D1 domain. D1-v1, D1-v2, D1-v3 and D1-v4 represents varying extents of humanisation, while VNAR D1 (wt) is the parental VNAR D1 domain. Substituting nurse shark framework amino acid residues with those of DPK-9, human germline kappa did not disrupt the ability of the humanised D1 versions to recognise hTNFα.

FIG. 17 Neutralisation efficacy in L929 cells of a D1 soloMER™

The capacity to neutralize hTNFα mediated cytotoxicity in L929 cells was assessed in a humanised VNAR D1 variant. The soloMER D1-v2 retained neutralizing potency for hTNFα induced cytotoxicity.

FIG. 18 Formats for multivalent and multispecific VNARs of the invention incorporating the human IgG Fc FIG. 19 hTNF-alpha Binding profile of multivalent/multispecific VNAR-Fc constructs Demonstrating the binding profile of biparatopic/bispecific D1-Fc-C4 (Quad-X™) vs biparatopic VNAR Fc constructs D1-Fc and C4-Fc. The anti-hTNF-α VNAR Quad-X™ D1-Fc-C4 retained binding to hTNFα, with binding profile comparable and slightly improved comparable to D1-Fc and C4-Fc.

FIG. 20 Assessing the hTNF-alpha Neutralising activity of the multivalent/multispecific VNAR-Fc constructs in L929

Assessing Neutralising potency of VNAR Quad-X™ D1-Fc-C4 vs Humira (Adalimumab) in an L929 cell based assay of hTNFα mediated cytotoxicity. VNAR Quad-X™ D1-Fc-C4 retained neutralising capacity and demonstrated a superior neutralising activity compared to Humira (see Table 2 for ND50 values).

FIG. 21 Formats for multivalent, bi-paratopic VNARs of the invention incorporating anti-mouse TNF-alpha VNAR; and anti-HSA soloMER™ BA11 or ICOSL VNAR domain, A5 or mouse IgG2a Fc FIG. 22A Mouse TNF-alpha binding profile of the bi-paratopic anti-mouse TNF-alpha VNAR constructs.

Reformatting a VNAR anti-mouse TNFα S17 domain as multivalent/multispecific trimer incorporating either an anti-ICOS ligand VNAR A5 or anti-HSA humanised VNAR, soloMER™ BA11. Both constructs retained recognition to mouse TNF-alpha.

FIG. 22B HSA binding profile of the bi-paratopic anti-mouseTNF-alpha VNAR constructs. Reformatting a VNAR anti-mouse TNFα S17 domain as multivalent/multispecific trimer incorporating either an anti-ICOS ligand VNAR A5 or anti-HSA humanised VNAR, soloMER™ BA11. S17-BA11-S17 retained binding to HSA, and the negative control, S17-A5-S17 did not recognise HSA.

FIG. 22C Mouse ICOS Ligand binding profile of the bi-paratopic dimeric/trimeric anti-ICOSL VNAR construct.

Binding profile of the reformatted S17-A5-S17 and A5-A5 homodimer to mouse ICOS ligand demonstrated that the reformatted trimeric construct incorporating an anti-mouse ICOS ligand VNAR A5 in the middle as S17-A5-S17 retained binding to mouse ICOS Ligand.

FIGS. 23A & B Mouse TNF-alpha Neutralisation in L929 profile of the bi-paratopic and IgG2a Fc fusion anti-mouse TNF-alpha VNAR S17 constructs respectively.

The Neutralising efficacy of the anti-mouse TNFα constructs (S17-A5-S17, S17-BA11-S17, S17-Fc) were assessed in a mouse TNFα mediated cytotoxicity L929 assay. Both trimeric S17 and the bi-paratopic S17-Fc constructs demonstrated neutralising activities against mouse TNFα mediated cytotoxicity in L929 cells. The S17-A5-S17 demonstrated the highest potency amongst the three constructs. BA11 was a negative control in the assay, also hTNFα+Actinomycin D represented a classical cytotoxicity effect observed in the absence of an anti-mouse TNFα inhibitor/neutraliser. Cells alone indicate healthy untreated cells.

FIG. 24 CHO-based huICOS/recombinant mouse ICOS Ligand-Fc (ICOSL-Fc) Neutralisation (blocking) Assay-ELISA based.

In this blocking assay, the multivalent VNAR constructs demonstrated significant capacity to block the mouse ICOSL-Fc from interacting with its cognate binding partner, ICOS on CHO cells. This leads to reduced/compromised detection of the Fc portion of the mouse ICOSL-Fc using an anti-human Fc-HRP antibody in a cell based ELISA format. A5-A5 dimer is the most potent blocker, followed by the S17-A5-S17, while S17 monomer is a negative control in this assay.

FIG. 25 Binding Cross-reactivity differences between the anti-hTNF-alpha VNAR vs VHH TNF30 and Humira®.

This figure illustrates the binding crossreactivity profile of the VNAR D1-C4 compared to the VHH TNF30 and Humira. The VNAR D1-C4 binds to only human, Dog and Cynomolgus TNFα; the VHH TNF30 including binding to human, dog and cynomolgus TNFα, binds weakly to pig TNFα and also human TNFB. Humira binds to human, dog, cynomolgus and mouse TNFα. Also see tables table 3A and 3B for detailed binding and neutralisation profiles of these anti-TNFα domains.

FIG. 26 BIAcore™ T200 epitope binning analysis of anti-hTNF-alpha VNAR heterodimer vs VHH TNF30 dimer.

This epitope binning data demonstrates that VNAR D1-C4 recognizes and interacts with distinct epitope on the hTNFα molecule from those recognised by VHH TNF30 domain. This assay involves reaching available epitope saturation with the first binding domain (in this instance, VNAR D1-C4 using saturating concentration determined as 100 times its KD value), and then followed with the second binding domain (TNF30).

FIG. 27 Functional binding to hTNF-alpha by Quad-X™ and Quad-Y™ constructs in an ELISA format.

FIG. 28 Assessing the hTNF-alpha Neutralising activity of the multivalent/multispecific VNAR-Fc constructs in L929

Assessing Neutralising potency of VNAR Quad-X™ D1-Fc-C4, Quad-Y™ D1-C4-Fc and C4-D1-Fc vs Humira (Adalimumab) in an L929 cell based assay of hTNFα mediated cytotoxicity. VNAR Quad-Y™ constructs retained neutralising capacity, with D1-C4-Fc construct demonstrating comparable neutralising activity as Quad-X™ in the presence of either 0.3 ng/ml or 3 ng/ml hTNF-alpha (see Table 2 for ND50 values).

FIG. 29 The effect of D1-Fc-C4 (Quad-X™) and Humira® on the body weight gain of experimental Tg197 mice. By the end of the study (10 weeks of age), the mean body weights of all groups treated twice weekly from week 3 were as follows: G1-Vehicle=19.3±1.4 g, G4-Humira® 10 mg/kg=24.4±1.5 g, G2-D1-Fc-C4 3 mg/kg=24.1±1.5 g, G5-D1-Fc-C4 10 mg/kg=24.1±1.7 g and G3-D1-Fc-D4 30 mg/kg=23.4±1.4 g. Control mice at week 3 had a mean body weight of 9.8±0.2 g. Error bars indicate standard error of the mean FIG. 30 The effect of D1-Fc-C4 (Quad-X™) and Humira® on in vivo arthritis scores of experimental Tg197 mice. By the end of the study (10 weeks of age), the mean in vivo disease severity scores of all groups treated twice weekly from week 3, were as follows: G1-Vehicle=1.36±0.07, G4-Humira® 10 mg/kg=0.25±0.05, G2-D1-Fc-C4 3 mg/kg=0.17±0.04, G5-D1-Fc-C4 10 mg/kg=0.17±0.04 and G3-D1-Fc-D4 30 mg/kg=0.17±0.04. Control mice at week 3 had an in vivo arthritic score=0.13±0.05. Error bars indicate standard error of the mean.

FIG. 31 The effect of D1-Fc-C4 (Quad-X™) and Humira® on arthritis histopathology scores of experimental Tg197 mice. By the end of the study (10 weeks of age), the mean arthritis histopathology scores of all groups treated twice weekly from week 3, were as follows: G1-Vehicle=2.94±0.12, G4-Humira® 10 mg/kg=0.42±0.07, G2-D1-Fc-C4 3 mg/kg=0.41±0.03, G5-D1-Fc-C4 10 mg/kg=0.50±0.05 and G3-D1-Fc-D4 30 mg/kg=0.42±0.07. Control mice at week 3 had a histopathology score=1.22±0.10. Error bars indicate standard error of the mean.

FIG. 32 Comparison of the effect of D1-Fc-C4 (Quad-X™) and Humira® on the in vivo arthritis scores versus the ankle histopathological scores of experimental Tg197 mice. By the end of study (10 weeks of age), the mean disease severity scores of all groups treated twice weekly from week 3, were as follows: G1-Vehicle=2.94±0.12 (HS) and 1.36±0.07 (AS), G4-Humira® 10 mg/kg=0.42±0.07 (HS) and 0.25±0.05 (AS), G2-D1-Fc-C4 3 mg/kg=0.41±0.03 (HS) and 0.17±0.04 (AS), G5-D1-Fc-C4 10 mg/kg=0.50±0.05 (HS) and 0.17±0.04 (AS) and G3-D1-Fc-D4 30 mg/kg=0.42±0.07 (HS) and 0.17±0.04 (AS). Error bars indicate standard error of the mean.

FIG. 33 Efficacy evaluation of D1-Fc-C4 (Quad-X™) at 0.5, 1 and 3 mg/kg and D1-BA11-C4 at 30 mg/kg vs Humira® at 1 mg/kg and 3 mg/kg in ameliorating arthritis pathology in the Tg197 model of arthritis.

FIG. 34 The effect of D1-Fc-C4 (Quad-X™) at 0.5, 1 and 3 mg/kg and D1-BA11-C4 at 30 mg/kg vs Humira® at 1 mg/kg and 3 mg/kg on the mean group weight of Tg197 model of arthritis.

FIG. 35 The effect of different Humira® dosing regimen on in vivo arthritic and histology scores. This was performed as a separate experiment but using identical methods to those described for FIGS. 29-32.

FIG. 36 Twelve rats were immunized with Interphotoreceptor Retinal Binding Protein (IRBP) to induce Experimental Auto-Immune Uveitis (EAU). Four animals each were treated via intraperitoneal injections with a (rodent protein specific) anti TNFα VNAR-Fc at 20 mg/kg on day 8, day 10 and day 12; four animals were treated with dexamethasone intraperitoneal on same days and four animals were treated with vehicle identically. The Optical Coherence Tomography (OCT) of both the anterior and posterior segment of the rats' eyes was performed on days 0, 7, 10, 12, 13, and 14. To minimize any scientific bias of the outcomes, OCT images were scored by an "experimentally blinded observer" for total inflammation using a validated scoring system. The experiment also included a vehicle control and a positive control using a standard dose of Dexamethazone steroid.

FIGS. 37A & B Assessing the hTNF-alpha Neutralizing activity of soloMER VNAR dimer constructs in L929 cells FIG. 38: Assessing the hTNF-alpha Neutralizing activity of S17-Fc vs S17-Fc-S17 (Quad-X™) constructs in L929 cells. The Fc used in the S17 constructs is derived from mouse IgG2a.

FIGS. 39A, B & C: Cross-reactivity binding profile of S17-Quad-X™ and D1-C4 Quad-X™ against human and mouse TNF-alpha Various nucleotide and amino acid sequences are provided herein as follows:

TNF VNAR D1 CDR3 AMINO ACID SEQUENCE

SEQ ID NO 1

ECQYGLAEYDV

TNF VNAR D1 AMINO ACID SEQUENCE (CDR1 and CDR3 single underlined)

SEQ ID NO 2

ARVDQTPQTITKETGESLTINCVLRDSHCATSSTYWYRKKSGSTNEESISKGGRYVETVNSGSK

SFSLRINDLTVEDSGTYRCASECQYGLAEYDVYGGGTVVTVN

TNF VNAR D1 AMINO ACID SEQUENCE WITH HIS AND MYC TAGS (double underlining) (CDR1 and CDR3 single underlined)

SEQ ID NO 3

ARVDQTPQTITKETGESLTINCVLRDSHCATSSTYWYRKKSGSTNEESISKGGRYVETVNSGSK

SFSLRINDLTVEDSGTYRCASECQYGLAEYDVYGGGTVVTVNAAAHHHHHHGAAESKLISEEDL

NUCLEOTIDE SEQUENCE CODING FOR TNF VNAR D1

SEQ ID NO 4

*GCTCGAGTGGACCAAACACCGCAAACAATAACAAAGGAGACGGGCGAATCACTGACCATCAACT*

*GTGTCCTACGAGATAGCCACTGTGCAACCTCCAGCACGTACTGGTATCGCAAAAAATCGGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCGCTTCCG*

*AGTGCCAATATGGACTGGCAGAATATGATGTATACGGAGGTGGCACTGTCGTGACTGTGAAT*

NUCLEOTIDE SEQUENCE CODING FOR TNF VNAR D1 WITH HIS AND MYC TAGS

SEQ ID NO 5

*GCTCGAGTGGACCAAACACCGCAAACAATAACAAAGGAGACGGGCGAATCACTGACCATCAACT*

*GTGTCCTACGAGATAGCCACTGTGCAACCTCCAGCACGTACTGGTATCGCAAAAAATCGGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCGCTTCCG*

*AGTGCCAATATGGACTGGCAGAATATGATGTATACGGAGGTGGCACTGTCGTGACTGTGAATGC*

*GGCCGCACATCATCATCACCATCACGGCGCCGCAGAATCAAAACTCATCTCAGAAGAGGATCTG*

TNF VNAR C4 CDR3 AMINO ACID SEQUENCE

SEQ ID NO 6

SWWTQNWRCSNSDV

TNF VNAR C4 AMINO ACID SEQUENCE (CDR1 and CDR3 underlined)

SEQ ID NO 7

RVDQTPQTITKETGESLTINCVLRDSNCGLSSTYWYRKKSGSTNEESISKGGRYVETINEGSKS

FSLRINDLTVEDSGTYRCKLSWWTQNWRCSNSDVYGGGTVVTVN

TNF VNAR C4 AMINO ACID SEQUENCE WITH HIS AND MYC TAGS (double underlining) (CDR1 and CDR3 single underlined)

SEQ ID NO 8

ARVDQTPQTITKETGESLTINCVLRDSNCGLSSTYWYRKKSGSTNEESISKGGRYVETINEGSK

SFSLRINDLTVEDSGTYRCKLSWWTQNWRCSNSDVYGGGTVVTVNAAAHHHHHH

GAAESKLISEEDL

-continued

NUCLEOTIDE SEQUENCE CODING FOR TNF VNAR C4

SEQ ID NO 9

*GCTCGAGTGGACCAAACACCGCAAACAATAACAAAGGAGACGGGCGAATCACTGACCATCAACT*

*GTGTCCTACGAGATAGCAACTGTGGGTTGTCCAGCACGTACTGGTATCGCAAAAAATCGGGCTC*

*AACAAACGAGGAGAGCATATCGAAAGGTGGACGATATGTTGAAACAATTAACGAAGGATCAAAG*

*TCCTTTTCTTTGAGAATTAATGATCTAACAGTTGAAGACAGTGGCACGTATCGATGCAAGTTAA*

*GCTGGTGGACCCAGAACTGGAGATGCTCAAATTCCGATGTATACGGAGGTGGCACTGTCGTGAC*

*TGTGAAT*

NUCLEOTIDE SEQUENCE CODING FOR TNF VNAR D1 WITH HIS AND MYC TAGS

SEQ ID NO 10

*GCTCGAGTGGACCAAACACCGCAAACAATAACAAAGGAGACGGGCGAATCACTGACCATCAACT*

*GTGTCCTACGAGATAGCAACTGTGGGTTGTCCAGCACGTACTGGTATCGCAAAAAATCGGGCTC*

*AACAAACGAGGAGAGCATATCGAAAGGTGGACGATATGTTGAAACAATTAACGAAGGATCAAAG*

*TCCTTTTCTTTGAGAATTAATGATCTAACAGTTGAAGACAGTGGCACGTATCGATGCAAGTTAA*

*GCTGGTGGACCCAGAACTGGAGATGCTCAAATTCCGATGTATACGGAGGTGGCACTGTCGTGAC*

*TGTGAATGCGGCCGCACATCATCATCACCATCACGGCGCCGCAGAATCAAAACTCATCTCAGAA*

*GAGGATCTG*

TNF VNAR B4 CDR3 AMINO ACID SEQUENCE

SEQ ID NO 11

YIPCIDELVYMISGGTSGPIHDV

TNF VNAR B4 AMINO ACID SEQUENCE (CDR1 and CDR3 single underlined)

SEQ ID NO 12

ARVDQTPQTITKETGESLTINCVLRDSNCALSSMYWYRKKSGSTNEESISKGGRYVETVNSGSK

SFSLRINDLTVEDSGTYRCKVYIPCIDELVYMISGGTSGPIHDVYGGGTVVTVN

TNF VNAR B4 AMINO ACID SEQUENCE WITH HIS AND MYC TAGS (double underlining) (CDR1 and CDR3 single underlined)

SEQ ID NO 13

ARVDQTPQTITKETGESLTINCVLRDSNCALSSMYWYRKKSGSTNEESISKGGRYVETVNSGSK

SFSLRINDLTVEDSGTYRCKVYIPCIDELVYMISGGTSGPIHDVYGGGTVVTVNAAAHHHHHH

GAAESKLISEEDL

NUCLEOTIDE SEQUENCE CODING FOR TNF VNAR B4

SEQ ID NO 14

*GCTCGAGTGGACCAAACACCGCAAACAATAACAAAGGAGACGGGCGAATCACTGACCATCAACT*

*GTGTCCTACGAGATAGTAACTGTGCATTGTCCAGCATGTACTGGTATCGCAAAAAATCTGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCAAGGTAT*

*ATATACCTTGCATCGATGAACTGGTATATATGATCAGTGGGGGTACCTCTGGCCCGATTCATGA*

*TGTATACGGAGGTGGCACTGTCGTGACTGTGAAT*

SEQ ID NO 15

GCTAGGCTCTAGAAATAATTTTGTTTAACTTTAAGAAGGAGATATACCATGGCTCGAGTGGACC

AAACACC

SEQ ID NO 16

CGCGCCGGATCCGCCACCTCCGCTACCGCCACCTCCGCTACCGCCACCTCCGCTACCGCCACCT

CCATTCACAGTCACGACAGTGCC

SEQ ID NO 17

GGTGGCGGATCCGGCGCGCACTCCGCTCGAGTGGACCAAACACCGC

SEQ ID NO 18

GTCCGGAATTCTCACAGATCCTCTTCTGAGATGAGTTTTTGTTCTGCGGCCCC

-continued

SEQ ID NO 19

AATTCCCCTCTAGAAGGCGCGCACTCCGCTCGAGTGGACCAAACACCG

NUCLEOTIDE SEQUENCE CODING FOR TNF VNAR B4 WITH HIS AND MYC TAGS

SEQ ID NO 20

*GCTCGAGTGGACCAAACACCGCAAACAATAACAAAGGAGACGGGCGAATCACTGACCATCAACT*

*GTGTCCTACGAGATAGTAACTGTGCATTGTCCAGCATGTACTGGTATCGCAAAAAATCTGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCAAGGTAT*

*ATATACCTTGCATCGATGAACTGGTATATATGATCAGTGGGGGTACCTCTGGCCCGATTCATGA*

*TGTATACGGAGGTGGCACTGTCGTGACTGTGAATGCGGCCGCACATCATCATCACCATCACGGC*

*GCCGCAGAATCAAAACTCATCTCAGAAGAGGATCTG*

TNF VNAR DIMER D1-D1 AMINO ACID SEQUENCE WITH HIS AND MYC TAGS (double underlining) (CDR1 and CDR3 single underlined, linker shown in italics)ESKLISEEDL

SEQ ID NO 21

ARVDQTPQTITKETGESLTINCVLRDSHCATSSTYWYRKKSGSTNEESISKGGRYVETVNSGSK

SFSLRINDLTVEDSGTYRCASECQYGLAEYDVYGGGTVVTVN*GGGGSGGGGGSGAHS*ARVDQTP

QTITKETGESLTINCVLRDSHCATSSTYWYRKKSGSTNEESISKGGRYVETVNSGSKSFSLRIN

DLTVEDSGTYRCASECQYGLAEYDVYGGGTVVTVNAAAHHHHHHGAAESKLISEEDL

NUCLEOTIDE SEQUENCE CODING FOR TNF VNAR DIMER D1-D1 WITH HIS AND MYC TAGS

SEQ ID NO 22

*GCTCGAGTGGACCAAACACCGCAAACAATAACAAAGGAGACGGGCGAATCACTGACCATCAACT*

*GTGTCCTACGAGATAGCCACTGTGCAACCTCCAGCACGTACTGGTATCGCAAAAAATCGGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCGCTTCCG*

*AGTGCCAATATGGACTGGCAGAATATGATGTATACGGAGGTGGCACTGTCGTGACTGTGAATGG*

*AGGTGGCGGTAGCGGAGGTGGTGGCGGATCCGGCGCGCACTCCGCTCGAGTGGACCAAACACCG*

*CAAACAATAACAAAGGAGACGGGCGAATCACTGACCATCAACTGTGTCCTACGAGATAGCCACT*

*GTGCAACCTCCAGCACGTACTGGTATCGCAAAAAATCGGGCTCAACAAACGAGGAGAGCATATC*

*GAAAGGTGGACGATATGTTGAAACAGTTAACAGCGGATCAAAGTCCTTTTCTTTGAGAATTAAT*

*GATCTAACAGTTGAAGACAGTGGCACGTATCGATGCGCTTCCGAGTGCCAATATGGACTGGCAG*

*AATATGATGTATACGGAGGTGGCACTGTCGTGACTGTGAATGCGGCCGCACATCATCATCACCA*

*TCACGGGGCCGCAGAACAAAAACTCATCTCAGAAGAGGATCTG*

TNF VNAR DIMER C4-C4 AMINO ACID SEQUENCE WITH HIS AND MYC TAGS (double underlining) (CDR1 and CDR3 single underlined, linker shown in italics)

SEQ ID NO 23

ARVDQTPQTITKETGESLTINCVLRDSNCGLSSTYWYRKKSGSTNEESISKGGRYVETINEGSK

SFSLRINDLTVEDSGTYRCKLSWWTQNWRCSNSDVYGGGTVVTVN*GGGGSGGGGGSGAHS*ARVD

QTPQTITKETGESLTINCVLRDSNCGLSSTYWYRKKSGSTNEESISKGGRYVETINEGSKSFSL

RINDLTVEDSGTYRCKLSWWTQNWRCSNSDVYGGGTVVTVNAAAHHHHHH

GAAEQKLISEEDL

NUCLEOTIDE SEQUENCE CODING FOR TNF VNAR DIMER C4-C4 WITH HIS AND MYC TAGS

SEQ ID NO 24

*GCTCGAGTGGACCAAACACCGCAAACAATAACAAAGGAGACGGGCGAATCACTGACCATCAACT*

*GTGTCCTACGAGATAGCAACTGTGGGTTGTCCAGCACGTACTGGTATCGCAAAAAATCGGGCTC*

*AACAAACGAGGAGAGCATATCGAAAGGTGGACGATATGTTGAAACAATTAACGAAGGATCAAAG*

-continued

*TCCTTTTCTTTGAGAATTAATGATCTAACAGTTGAAGACAGTGGCACGTATCGATGCAAGTTAA*

*GCTGGTGGACCCAGAACTGGAGATGCTCAAATTCCGATGTATACGGAGGTGGCACTGTCGTGAC*

*TGTGAACGGAGGTGGCGGTAGCGGAGGTGGTGGCGGATCCGGCGCGCACTCCGCTCGAGTGGAC*

*CAAACACCGCAAACAATAACAAAGGAGACGGGCGAATCACTGACCATCAACTGTGTCCTACGAG*

*ATAGCAACTGTGGGTTGTCCAGCACGTACTGGTATCGCAAAAAATCGGGCTCAACAAACGAGGA*

*GAGCATATCGAAAGGTGGACGATATGTTGAAACAATTAACGAAGGATCAAAGTCCTTTTCTTTG*

*AGAATTAATGATCTAACAGTTGAAGACAGTGGCACGTATCGATGCAAGTTAAGCTGGTGGACCC*

*AGAACTGGAGATGCTCAAATTCCGATGTATACGGAGGTGGCACTGTCGTGACTGTGAACGCGGC*

*CGCACATCATCATCACCATCACGGGGCCGCAGAACAAAAACTCATCTCAGAAGAGGATCTG*

TNF VNAR DIMER B4-B4 AMINO ACID SEQUENCE WITH HIS AND MYC TAGS (double underlining) (CDR1 and CDR3 single underlined, linker shown in italics)

SEQ ID NO 25

ARVDQTPQTITKETGESLTINCVLRDSNCALSSMYWYRKKSGSTNEESISKGGRYVETVNSGSK

SFSLRINDLTVEDSGTYRCKVYIPCIDELVYMISGGTSGPIHDVYGGGTVVTVN*GGGGSGGGGG*

*SGAHS*ARVDQTPQTITKETGESLTINCVLRDSNCALSSMYWYRKKSGSTNEESISKGGRYVETV

NSGSKSFSLRINDLTVEDSGTYRCKVYIPCIDELVYMISGGTSGPIHDVYGGGTVVTVNAAA

HHHHHHGAAEQKLISEEDL

NUCLEOTIDE SEQUENCE CODING FOR TNF VNAR DIMER B4-B4 WITH HIS AND MYC TAGS

SEQ ID NO 26

*GCTCGAGTGGACCAAACACCGCAAACAATAACAAAGGAGACGGGCGAATCACTGACCATCAACT*

*GTGTCCTACGAGATAGTAACTGTGCATTGTCCAGCATGTACTGGTATCGCAAAAAATCTGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCAAGGTAT*

*ATATACCTTGCATCGATGAACTGGTATATATGATCAGTGGGGGTACCTCTGGCCCGATTCATGA*

*TGTATACGGAGGTGGCACTGTCGTGACTGTGAATGGAGGTGGCGGTAGCGGAGGTGGTGGCGGA*

*TCCGGCGCGCACTCCGCTCGAGTGGACCAAACACCGCAAACAATAACAAAGGAGACGGGCGAAT*

*CACTGACCATCAACTGTGTCCTACGAGATAGTAACTGTGCATTGTCCAGCATGTACTGGTATCG*

*CAAAAAATCTGGCTCAACAAACGAGGAGAGCATATCGAAAGGTGGACGATATGTTGAAACAGTT*

*AACAGCGGATCAAAGTCCTTTTCTTTGAGAATTAATGATCTAACAGTTGAAGACAGTGGCACGT*

*ATCGATGCAAGGTATATATACCTTGCATCGATGAACTGGTATATATGATCAGTGGGGGTACCTC*

*TGGCCCGATTCATGATGTATACGGAGGTGGCACTGTCGTGACTGTGAATGCGGCCGCACATCAT*

*CATCACCATCACGGGGCCGCAGAACAAAAACTCATCTCAGAAGAGGATCTG*

TNF VNAR DIMER D1-C4 AMINO ACID SEQUENCE WITH HIS AND MYC TAGS (double underlining) (CDR1 and CDR3 single underlined, linker shown in italics)

SEQ ID NO 27

ARVDQTPQTITKETGESLTINCVLRDSHCATSSTYWYRKKSGSTNEESISKGGRYVETVNSGSK

SFSLRINDLTVEDSGTYRCASECQYGLAEYDVYGGGTVVTVN*GGGGSGGGGGSGAHS*ARVDQTP

QTITKETGESLTINCVLRDSNCGLSSTYWYRKKSGSTNEESISKGGRYVETINEGSKSFSLRIN

DLTVEDSGTYRCKLSWWVTQNWRCSNSDVYGGGTVVTVNAAA

HHHHHHGAAEQKLISEEDL

-continued

SEQ ID NO 28

NUCLEOTIDE SEQUENCE CODING FOR THE TNF VNAR DIMER D1-C4 WITH HIS AND MYC TAGS

*GCTCGAGTGGACCAAACACCGCAAACAATAACAAAGGAGACGGGCGAATCACTGACCATCAACT*

*GTGTCCTACGAGATAGCCACTGTGCAACCTCCAGCACGTACTGGTATCGCAAAAAATCGGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCGCTTCCG*

*AGTGCCAATATGGACTGGCAGAATATGATGTATACGGAGGTGGCACTGTCGTGACTGTGAATGG*

*AGGTGGCGGTAGCGGAGGTGGTGGCGGATCCGGCGCGCACTCCGCTCGAGTGGACCAAACACCG*

*CAAACAATAACAAAGGAGACGGGCGAATCACTGACCATCAACTGTGTCCTACGAGATAGCAACT*

*GTGGGTTGTCCAGCACGTACTGGTATCGCAAAAAATCGGGCTCAACAAACGAGGAGAGCATATC*

*GAAAGGTGGACGATATGTTGAAACAATTAACGAAGGATCAAAGTCCTTTTCTTTGAGAATTAAT*

*GATCTAACAGTTGAAGACAGTGGCACGTATCGATGCAAGTTAAGCTGGTGGACCCAGAACTGGA*

*GATGCTCAAATTCCGATGTATACGGAGGTGGCACTGTCGTGACTGTGAACGCGGCCGCACATCA*

*TCATCACCATCACGGGGCCGCAGAACAAAAACTCATCTCAGAAGAGGATCTG*

TNF VNAR DIMER D1-B4 AMINO ACID SEQUENCE WITH HIS AND MYC TAGS (double underlining) (CDR1 and CDR3 single underlined, linker shown in italics)

SEQ ID NO 29

ARVDQTPQTITKETGESLPINCVLRDSHCATSSTYWYRKKSGSTNEESISKGGRYVETVNSGSK

SFSLRINDLTVEDSGTYRCASECQYGLAEYDVYGGGTVVTVN*GGGGSGGGGGSGAHS*ARVDQTP

QTITKETGESLTINCVLRDSNCALSSMYWYRKKSGSTNEESISKGGRYVETVNSGSKSFSLRIN

DLTVEDSGTYRCKVYIPCIDELVYMISGGTSGPIHDVYGGGTVVTVNAAA

HHHHHHGAAEQKLISEEDL.

NUCLEOTIDE SEQUENCE CODIGN FOR THE TNF VNAR DIMER D1-B4 NUCLEOTIDE SEQUENCE WITH HIS AND MYC TAGS

SEQ ID NO 30

*GCTCGAGTGGACCAAACACCGCAAACAATAACAAAGGAGACGGGCGAATCACTGACCATCAACT*

*GTGTCCTACGAGATAGCCACTGTGCAACCTCCAGCACGTACTGGTATCGCAAAAAATCGGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCGCTTCCG*

*AGTGCCAATATGGACTGGCAGAATATGATGTATACGGAGGTGGCACTGTCGTGACTGTGAATGG*

*AGGTGGCGGTAGCGGAGGTGGTGGCGGATCCGGCGCGCACTCCGCTCGAGTGGACCAAACACCG*

*CAAACAATAACAAAGGAGACGGGCGAATCACTGACCATCAACTGTGTCCTACGAGATAGTAACT*

*GTGCATTGTCCAGCATGTACTGGTATCGCAAAAAATCTGGCTCAACAAACGAGGAGAGCATATC*

*GAAAGGTGGACGATATGTTGAAACAGTTAACAGCGGATCAAAGTCCTTTTCTTTGAGAATTAAT*

*GATCTAACAGTTGAAGACAGTGGCACGTATCGATGCAAGGTATATATACCTTGCATCGATGAAC*

*TGGTATATATGATCAGTGGGGGTACCTCTGGCCCGATTCATGATGTATACGGAGGTGGCACTGT*

*CGTGACTGTGAATGCGGCCGCACATCATCATCACCATCACGGGGCCGCAGAACAAAAACTCATC*

*TCAGAAGAGGATCTG*

TNF VNAR DIMER B4-D1 AMINO ACID SEQUENCE (His and Myc Tags - double underlining, CDR1 and CDR3 single underlined, linker shown in italics)

SEQ ID NO 31

ARVDQTPQTITKETGESLTINCVLRDSNCALSSMYWYRKKSGSTNEESISKGGRYVETVNSGSK

SFSLRINDLTVEDSGTYRCKVYIPCIDELVYMISGGTSGPIHDVYGGGTVVTVN*GGGGSGGGGG*

*SGAHS*ARVDQTPQTITKETGESLPINCVLRDSHCATSSTYWYRKKSGSTNEESISKGGRYVETV

-continued

NSGSKSFSLRINDLTVEDSGTYRCASECQYGLAEYDVYGGGTVVTVNAAA

HHHHHHGAAEQKLISEEDL

TNF VNAR DIMER B4-D1 NUCLEOTIDE SEQUENCE

SEQ ID NO 32

*GCTCGAGTGGACCAAACACCGCAAACAATAACAAAGGAGACGGGCGAATCACTGACCATCAACT*

*GTGTCCTACGAGATAGTAACTGTGCATTGTCCAGCATGTACTGGTATCGCAAAAAATCTGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCAAGGTAT*

*ATATACCTTGCATCGATGAACTGGTATATATGATCAGTGGGGGTACCTCTGGCCCGATTCATGA*

*TGTATACGGAGGTGGCACTGTCGTGACTGTGAATGGAGGTGGCGGTAGCGGAGGTGGTGGCGGA*

*TCCGGCGCGCACTCCGCTCGAGTGGACCAAACACCGCAAACAATAACAAAGGAGACGGGCGAAT*

*CACTGACCATCAACTGTGTCCTACGAGATAGCCACTGTGCAACCTCCAGCACGTACTGGTATCG*

*CAAAAAATCGGGCTCAACAAACGAGGAGAGCATATCGAAAGGTGGACGATATGTTGAAACAGTT*

*AACAGCGGATCAAAGTCCTTTTCTTTGAGAATTAATGATCTAACAGTTGAAGACAGTGGCACGT*

*ATCGATGCGCTTCCGAGTGCCAATATGGACTGGCAGAATATGATGTATACGGAGGTGGCACTGT*

*CGTGACTGTGAATGCGGCCGCACATCATCATCACCATCACGGGGCCGCAGAACAAAAACTCATC*

*TCAGAAGAGGATCTG*

TNF VNAR DIMER C4-B4 AMINO ACID SEQUENCE (His and Myc Tags - double underlining, CDR1 and CDR3 single underlined, linker shown in italics)

SEQ ID NO 33

ARVDQTPQTITKETGESLTINCVLRDSNCGLSSTYWYRKKSGSTNEESISKGGRYVETINEGSK

SFSLRINDLTVEDSGTYRCKLSWWTQNWRCSNSDVYGGGTVVTVN*GGGGSGGGGGSGAHS*ARVD

QTPQTITKETGESLTINCVLRDSNCALSSMYWYRKKSGSTNEESISKGGRYVETVNSGSKSFSL

RINDLTVEDSGTYRCKVYIPCIDELVYMISGGTSGPIHDVYGGGTVVTVNAAA

HHHHHHGAAEQKLISEED

TNF VNAR DIMER C4-B4 NUCLEOTIDE SEQUENCE

SEQ ID NO 34

*GCTCGAGTGGACCAAACACCGCAAACAATAACAAAGGAGACGGGCGAATCACTGACCATCAACT*

*GTGTCCTACGAGATAGCAACTGTGGGTTGTCCAGCACGTACTGGTATCGCAAAAAATCGGGCTC*

*AACAAACGAGGAGAGCATATCGAAAGGTGGACGATATGTTGAAACAATTAACGAAGGATCAAAG*

*TCCTTTTCTTTGAGAATTAATGATCTAACAGTTGAAGACAGTGGCACGTATCGATGCAAGTTAA*

*GCTGGTGGACCCAGAACTGGAGATGCTCAAATTCCGATGTATACGGAGGTGGCACTGTCGTGAC*

*TGTGAACGGAGGTGGCGGTAGCGGAGGTGGTGGCGGATCCGGCGCGCACTCCGCTCGAGTGGAC*

*CAAACACCGCAAACAATAACAAAGGAGACGGGCGAATCACTGACCATCAACTGTGTCCTACGAG*

*ATAGTAACTGTGCATTGTCCAGCATGTACTGGTATCGCAAAAAATCTGGCTCAACAAACGAGGA*

*GAGCATATCGAAAGGTGGACGATATGTTGAAACAGTTAACAGCGGATCAAAGTCCTTTTCTTTG*

*AGAATTAATGATCTAACAGTTGAAGACAGTGGCACGTATCGATGCAAGGTATATATACCTTGCA*

*TCGATGAACTGGTATATATGATCAGTGGGGGTACCTCTGGCCCGATTCATGATGTATACGGAGG*

*TGGCACTGTCGTGACTGTGAATGCGGCCGCACATCATCATCACCATCACGGGGCCGCAGAACAA*

*AAACTCATCTCAGAAGAGGATCTG*

TNF VNAR DIMER B4-C4 AMINO ACID SEQUENCE (His and Myc Tags - double underlining, CDR1 and CDR3 single underlined, linker shown in italics)

SEQ ID NO 35

ARVDQTPQTITKETGESLTINCVLRDSNCALSSMYWYRKKSGSTNEESISKGGRYVETVNSGSK

SFSLRINDLTVEDSGTYRCKVYIPCIDELVYMISGGTSGPIHDVYGGGTVVTVNG*GGGSGGGGG*

-continued

*SGAHS*ARVDQTPQTITKETGESLTINCVLRDSNCGLSSTYWYRKKSGSTNEESISKGGRYVETI

NEGSKSFSLRINDLTVEDSGTYRCKLSWWTQNWRCSNSDVYGGGTVVTVNAAA

HHHHHHGAAEQKLISEED

TNF VNAR DIMER B4-C4 NUCLEOTIDE SEQUENCE

SEQ ID NO 36

*GCTCGAGTGGACCAAACACCGCAAACAATAACAAAGGAGACGGGCGAATCACTGACCATCAACT*

*GTGTCCTACGAGATAGTAACTGTGCATTGTCCAGCATGTACTGGTATCGCAAAAAATCTGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCAAGGTAT*

*ATATACCTTGCATCGATGAACTGGTATATATGATCAGTGGGGGTACCTCTGGCCCGATTCATGA*

*TGTATACGGAGGTGGCACTGTCGTGACTGTGAATGGAGGTGGCGGTAGCGGAGGTGGTGGCGGA*

*TCCGGCGCGCACTCCGCTCGAGTGGACCAAACACCGCAAACAATAACAAAGGAGACGGGCGAAT*

*CACTGACCATCAACTGTGTCCTACGAGATAGCAACTGTGGGTTGTCCAGCACGTACTGGTATCG*

*CAAAAAATCGGGCTCAACAAACGAGGAGAGCATATCGAAAGGTGGACGATATGTTGAAACAATT*

*AACGAAGGATCAAAGTCCTTTTCTTTGAGAATTAATGATCTAACAGTTGAAGACAGTGGCACGT*

*ATCGATGCAAGTTAAGCTGGTGGACCCAGAACTGGAGATGCTCAAATTCCGATGTATACGGAGG*

*TGGCACTGTCGTGACTGTGAACGCGGCCGCACATCATCATCACCATCACGGGGCCGCAGAACAA*

*AAACTCATCTCAGAAGAGGATCTG*

TNF VNAR D1-BA11-C4 AMINO ACID SEQUENCE WITH HIS AND MYC TAGS
(His and Myc Tags - double underlining, CDR1 and CDR3 single underlined, linker shown in italics)

SEQ ID NO 37

ARVDQTPQTITKETGESLTINCVLRDSHCATSSTYWYRKKSGSTNEESISKGGRYVETVNSGSK

SFSLRINDLTVEDSGTYRCASECQYGLAEYDVYGGGTVVTVN*GGGGSGGGGSGGGGSGGGGSGA*

*HS*TRVDQSPSSLSASVGDRVTITCVLTDTSYPLYSTYWYRKNPGSSNKEQISISGRYSESVNKG

TKSFTLTISSLQPEDSATYYCRAMSTNIWTGDGAGTKVEIK*GGGGSGGGGSGGGGSGGGGSGAH*

*S*ARVDQTPQTITKETGESLTINCVLRDSNCGLSSTYWYRKKSGSTNEESISKGGRYVETINEGS

KSFSLRINDLTVEDSGTYRCKLSWWTQNWRCSNSDVYGG

GTVVTVNHHHHHHHEQKLISEEDL

NUCLEOTIDE SEQUENCE CODING FOR THE TNF VNAR D1-BA11-C4 WITH HIS AND MYC TAGS

SEQ ID NO 38

*GCTCGAGTGGACCAAACACCGCAAACAATAACAAAGGAGACGGGCGAATCACTGACCATCAACT*

*GTGTCCTACGAGATAGCCACTGTGCAACCTCCAGCACGTACTGGTATCGCAAAAAATCGGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCGCTTCCG*

*AGTGCCAATATGGACTGGCAGAATATGATGTATACGGAGGTGGCACTGTCGTGACTGTGAATGG*

*AGGTGGCGGATCCGGGGGTGGCGGTAGCGGAGGTGGCGGTAGCGGAGGTGGCGGTAGTGGAGCT*

*CATTCAACAAGAGTGGACCAAAGTCCAAGCTCTCTGTCCGCCAGTGTGGGCGACCGCGTGACCA*

*TCACCTGCGTCCTGACTGATACCAGCTATCCTCTGTACAGCACATACTGGTATCGGAAGAATCC*

*CGGTTCCAGCAACAAGGAGCAGATTTCCATCTCCGGCCGCTATAGTGAATCAGTCAACAAGGGC*

*ACTAAGTCCTTTACCCTGACAATCAGTTCCCTGCAGCCCGAGGACTCCGCCACCTATTACTGCA*

*GAGCTATGAGTACAAATATCTGGACCGGGGACGGAGCTGGTACCAAGGTGGAGATCAAGGGAGG*

*TGGCGGTTCCGGAGGTGGCGGTAGCGGAGGTGGCGGTAGCGGAGGTGGCGGTAGCGGGGCCCAT*

*TCTGCTCGAGTGGACCAAACACCGCAAACAATAACAAAGGAGACGGGCGAATCACTGACCATCA*

-continued

*ACTGTGTCCTACGAGATAGCAACTGTGGGTTGTCCAGCACGTACTGGTATCGCAAAAAATCGGG*

*CTCAACAAACGAGGAGAGCATATCGAAAGGTGGACGATATGTTGAAACAATTAACGAAGGATCA*

*AAGTCCTTTTCTTTGAGAATTAATGATCTAACAGTTGAAGACAGTGGCACGTATCGATGCAAGT*

*TAAGCTGGTGGACCCAGAACTGGAGATGCTCAAATTCCGATGTATACGGAGGTGGCACTGTCGT*

*GACTGTGAATCATCACCATCACCATCACCATGAACAAAAACTCATCTCAGAAGAGGATCTG*

TNF VNAR D1-BA11-D1 AMINO ACID SEQUENCE WITH HIS AND MYC TAGS (His and Myc Tags - double underlining, CDR1 and CDR3 single underlined, linker shown in italics)

SEQ ID NO 39

ARVDQTPQTITKETGESLTINCVLRDSHCATSSTYWYRKKSGSTNEESISKGGRYVETVNSGSK

SFSLRINDLTVEDSGTYRCASECQYGLAEYDVYGGGTVVTVN*GGGGSGGGGSGGGGSGGGGSGA*

*HS*TRVDQSPSSLSASVGDRVTITCVLTDTSYPLYSTYWYRKNPGSSNKEQISISGRYSESVNKG

TKSFTLTISSLQPEDSATYYCRAMSTNIWTGDGAGTKVEIK*GGGGSGGGGSGGGGSGGGGSGAH*

*S*ARVDQTPQTITKETGESLTINCVLRDSHCATSSTYWYRKKSGSTNEESISKGGRYVETVNSGS

KSFSLRINDLTVEDSGTYRCASECQYGLAEYDVYGG

GTVVTVNHHHHHHHEQKLISEEDL

NUCLEOTIDE SEQUENCE CODING FOR THE TNF VNAR D1-BA11-D1 WITH HIS AND MYC TAGS

SEQ ID NO 40

*GCTCGAGTGGACCAAACACCGCAAACAATAACAAAGGAGACGGGCGAATCACTGACCATCAACT*

*GTGTCCTACGAGATAGCCACTGTGCAACCTCCAGCACGTACTGGTATCGCAAAAAATCGGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCGCTTCCG*

*AGTGCCAATATGGACTGGCAGAATATGATGTATACGGAGGTGGCACTGTCGTGACTGTGAATGG*

*AGGTGGCGGATCCGGGGGTGGCGGTAGCGGAGGTGGCGGTAGCGGAGGTGGCGGTAGTGGAGCT*

*CATTCAACAAGAGTGGACCAAAGTCCAAGCTCTCTGTCCGCCAGTGTGGGCGACCGCGTGACCA*

*TCACCTGCGTCCTGACTGATACCAGCTATCCTCTGTACAGCACATACTGGTATCGGAAGAATCC*

*CGGTTCCAGCAACAAGGAGCAGATTTCCATCTCCGGCCGCTATAGTGAATCAGTCAACAAGGGC*

*ACTAAGTCCTTTACCCTGACAATCAGTTCCCTGCAGCCCGAGGACTCCGCCACCTATTACTGCA*

*GAGCTATGAGTACAAATATCTGGACCGGGGACGGAGCTGGTACCAAGGTGGAGATCAAGGGAGG*

*TGGCGGTTCCGGAGGTGGCGGTAGCGGAGGTGGCGGTAGCGGAGGTGGCGGTAGCGGGGCCCAT*

*TCTGCTCGAGTGGACCAAACACCGCAAACAATAACAAAGGAGACGGGCGAATCACTGACCATCA*

*ACTGTGTCCTACGAGATAGCCACTGTGCAACCTCCAGCACGTACTGGTATCGCAAAAAATCGGG*

*CTCAACAAACGAGGAGAGCATATCGAAAGGTGGACGATATGTTGAAACAGTTAACAGCGGATCA*

*AAGTCCTTTTCTTTGAGAATTAATGATCTAACAGTTGAAGACAGTGGCACGTATCGATGCGCTT*

*CCGAGTGCCAATATGGACTGGCAGAATATGATGTATACGGAGGTGGCACTGTCGTGACTGTGAA*

*TCATCACCATCACCATCACCATGAACAAAAACTCATCTCAGAAGAGGATCTG*

TNF VNAR D1-BA11-B4 AMINO ACID SEQUENCE WITH HIS AND MYC TAGS (His and Myc Tags - double underlining, CDR1 and CDR3 single underlined, linker shown in italics)

SEQ ID NO 41

ARVDQTPQTITKETGESLTINCVLRDSHCATSSTYWYRKKSGSTNEESISKGGRYVETVNSGSK

SFSLRINDLTVEDSGTYRCASECQYGLAEYDVYGGGTVVTVN*GGGGSGGGGSGGGGSGGGGSGA*

*HS*TRVDQSPSSLSASVGDRVTITCVLTDTSYPLYSTYWYRKNPGSSNKEQISISGRYSESVNKG

TKSFTLTISSLQPEDSATYYCRAMSTNIWTGDGAGTKVEIK*GGGGSGGGGSGGGGSGGGGSGAH*

*S*ARVDQTPQTITKETGESLTINCVLRDSNCALSSMYWYRKKSGSTNEESISKGGRYVETVNSGS

-continued

KSFSLRINDLTVEDSGTYRCKVYIPCIDELVYMISGGTSGPIHDVYGG

GTVVTVNHHHHHHHEQKLISEEDL

NUCLEOTIDE SEQUENCE CODING FOR THE TNF VNAR D1-BA11-B4 WITH HIS AND MYC TAGS

SEQ ID NO 42

*GCTCGAGTGGACCAAACACCGCAAACAATAACAAAGGAGACGGGCGAATCACTGACCATCAACT*

*GTGTCCTACGAGATAGCCACTGTGCAACCTCCAGCACGTACTGGTATCGCAAAAAATCGGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCGCTTCCG*

*AGTGCCAATATGGACTGGCAGAATATGATGTATACGGAGGTGGCACTGTCGTGACTGTGAATGG*

*AGGTGGCGGATCCGGGGGTGGCGGTAGCGGAGGTGGCGGTAGCGGAGGTGGCGGTAGTGGAGCT*

*CATTCAACAAGAGTGGACCAAAGTCCAAGCTCTCTGTCCGCCAGTGTGGGCGACCGCGTGACCA*

*TCACCTGCGTCCTGACTGATACCAGCTATCCTCTGTACAGCACATACTGGTATCGGAAGAATCC*

*CGGTTCCAGCAACAAGGAGCAGATTTCCATCTCCGGCCGCTATAGTGAATCAGTCAACAAGGGC*

*ACTAAGTCCTTTACCCTGACAATCAGTTCCCTGCAGCCCGAGGACTCCGCCACCTATTACTGCA*

*GAGCTATGAGTACAAATATCTGGACCGGGGACGGAGCTGGTACCAAGGTGGAGATCAAGGGAGG*

*TGGCGGTTCCGGAGGTGGCGGTAGCGGAGGTGGCGGTAGCGGAGGTGGCGGTAGCGGGGCCCAT*

*TCTGCTCGAGTGGACCAAACACCGCAAACAATAACAAAGGAGACGGGCGAATCACTGACCATCA*

*ACTGTGTCCTACGAGATAGTAACTGTGCATTGTCCAGCATGTACTGGTATCGCAAAAAATCTGG*

*CTCAACAAACGAGGAGAGCATATCGAAAGGTGGACGATATGTTGAAACAGTTAACAGCGGATCA*

*AAGTCCTTTTCTTTGAGAATTAATGATCTAACAGTTGAAGACAGTGGCACGTATCGATGCAAGG*

*TATATATACCTTGCATCGATGAACTGGTATATATGATCAGTGGGGGTACCTCTGGCCCGATTCA*

*TGATGTATACGGAGGTGGCACTGTCGTGACTGTGAATCATCACCATCACCATCACCATGAACAA*

*AAACTCATCTCAGAAGAGGATCTG*

ICOS VNAR 2D4-Fc-2D4 AMINO ACID SEQUENCE (linkers shown in italics, Fc portion underlined)

SEQ ID NO 43

TRVDQTPRTATKETGESLTINCVLTDTDYGLFSTSWFRKNPGTTDWERMSIGGRYVESVNKGAK

SFSLRIKDLTVADSATYYCKAFTWPWEWPDRWFRPWYDGAGTVLTVN*GGGGSGGGADQ*EPKSSD

KTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLDSDGSFFLYSKLTVD

KSRWQQGNVFSCSVMHEALHNHYTQKSLSLSPGK*TAAAATAAAATAAAATAAAA*TRVDQTPRTA

TKETGESLTINCVLTDTDYGLFSTSWFRKNPGTTDWERMSIGGRYVESVNKGAKSFSLRIKDLT

VADSATYYCKAFTWPWEWPDRWFRPWYDGAGTVLTVN

ICOS VNAR 2D4-Fc-2D4 NUCELOTIDE SEQUENCE

SEQ ID NO 44

*ACACGTGTTGACCAGACACCGCGTACCGCAACCAAAGAAACCGGTGAAAGCCTGACCATT*

*AATTGTGTTC TGACCGATAC CGATTATGGT TTGTTCTCCA CCAGCTGGTT TCGTAAAAAT*

*CCGGGTACAA CCGATTGGGA ACGTATGAGC ATTGGTGGTC GTTATGTTGA AAGCGTGAAT*

*AAAGGTGCCA AAAGCTTTAG CCTGCGCATT AAAGATCTGA CCGTTGCAGA TAGCGCAACC*

*TATTACTGTA AAGCATTCAC TTGGCCGTGG GAATGGCCGG ACCGTTGGTT CCGTCCGTGG*

*TATGATGGTG CAGGCACCGT TCTGACCGTT AATGGCGGTG GTGGTTCTGG TGGTGGTGCT*

*GATCAGGAGC CCAAATCTTC TGACAAAACT CACACATGTC CACCGTGCCC AGCACCTGAA*

-continued

CTCCTGGGTG GACCGTCAGT CTTCCTCTTC CCCCCAAAAC CCAAGGACAC CCTCATGATC

TCCCGGACCC CTGAGGTCAC ATGCGTGGTG GTGGACGTGA GCCACGAAGA CCCTGAGGTC

AAGTTCAACT GGTACGTGGA CGGCGTGGAG GTGCATAATG CCAAGACAAA GCCGCGGGAG

GAGCAGTACA ACAGCACGTA CCGTGTGGTC AGCGTCCTCA CCGTCCTGCA CCAGGACTGG

CTGAATGGCA AGGAGTACAA GTGCAAGGTC TCCAACAAAG CCCTCCCAGC CCCCATCGAG

AAAACCATCT CCAAAGCCAA AGGGCAGCCC CGAGAACCAC AGGTGTACAC CCTGCCCCCA

TCCCGGGAGG AGATGACCAA GAACCAGGTC AGCCTGACCT GCCTGGTCAA AGGCTTCTAT

CCCAGCGACA TCGCCGTGGA GTGGGAGAGC AATGGGCAGC CGGAGAACAA CTACAAGACC

ACGCCTCCCG TGCTGGACTC CGACGGCTCC TTCTTCCTCT ATAGCAAGCT CACCGTGGAC

AAGAGCAGGT GGCAGCAGGG GAACGTCTTC TCATGCTCCG TGATGCATGA GGCTCTGCAC

AACCACTACA CGCAGAAGAG CCTCTCCCTG TCCCCGGGTA AAACCGCCGC CGCCGCCACC

GCCGCCGCCG CCACCGCCGC CGCCGCCACC GCCGCGGCCG CCACACGTGT TGATCAGACA

CCGCGTACCG CAACCAAAGA AACCGGTGAA AGCCTGACCA TTAATTGTGT TCTGACCGAT

ACCGATTATG GTTTGTTCTC CACCAGCTGG TTTCGTAAAA ATCCGGGTAC AACCGATTGG

GAACGTATGA GCATTGGTGG TCGTTATGTT GAAAGCGTGA ATAAAGGTGC CAAAAGCTTT

AGCCTGCGCA TTAAAGATCT GACCGTTGCA GATAGCGCAA CCTATTACTG TAAAGCATTC

ACTTGGCCGT GGGAATGGCC GGACCGTTGG TTCCGTCCGT GGTATGATGG TGCAGGCACC

GTTCTGACCG TTAAT

ICOS VNAR 2D4-Fc-CC3 AMINO ACID SEQUENCE (linkers shown in italics, Fc portion underlined)

SEQ ID NO 45

TRVDQTPRTATKETGESLTINCVLTDTDYGLFSTSWFRKNPGTTDWERMSIGGRYVESVNKGAK

SFSLRIKDLTVADSATYYCKAFTWPWEWPDRWFRPWYDGAGTVLTVN*GGGGSGGGADQ*EPKSSD

KTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLDSDGSFFLYSKLTVD

KSRWQQGNVFSCSVMHEALHNHYTQKSLSLSPGK*TAAAATAAAATAAAATAAAA*TRVDQTPRTA

TKETGESLTINCVLTDTEYGLFSTSWFRKNPGTTDWERMSIGGRYVESVNKGAKSFSLRIKDLT

VADSATYYCKALGWWPPAFPHWYDGAGTVLTVN

ICOS VNAR 2D4-Fc-CC3 NUCELOTIDE SEQUENCE

SEQ ID NO 46

ACACGTGTTG ACCAGACACC GCGTACCGCA ACCAAAGAAA CCGGTGAAAG CCTGACCATT

AATTGTGTTC TGACCGATAC CGATTATGGT TTGTTCTCCA CCAGCTGGTT TCGTAAAAAT

CCGGGTACAA CCGATTGGGA ACGTATGAGC ATTGGTGGTC GTTATGTTGA AAGCGTGAAT

AAAGGTGCCA AAAGCTTTAG CCTGCGCATT AAAGATCTGA CCGTTGCAGA TAGCGCAACC

TATTACTGTA AAGCATTCAC TTGGCCGTGG GAATGGCCGG ACCGTTGGTT CCGTCCGTGG

TATGATGGTG CAGGCACCGT TCTGACCGTT AATGGCGGTG GTGGTTCTGG TGGTGGTGCT

GATCAGGAGC CCAAATCTTC TGACAAAACT CACACATGTC CACCGTGCCC AGCACCTGAA

CTCCTGGGTG GACCGTCAGT CTTCCTCTTC CCCCCAAAAC CCAAGGACAC CCTCATGATC

TCCCGGACCC CTGAGGTCAC ATGCGTGGTG GTGGACGTGA GCCACGAAGA CCCTGAGGTC

AAGTTCAACT GGTACGTGGA CGGCGTGGAG GTGCATAATG CCAAGACAAA GCCGCGGGAG

GAGCAGTACA ACAGCACGTA CCGTGTGGTC AGCGTCCTCA CCGTCCTGCA CCAGGACTGG

CTGAATGGCA AGGAGTACAA GTGCAAGGTC TCCAACAAAG CCCTCCCAGC CCCCATCGAG

-continued

*AAAACCATCT CCAAAGCCAA AGGGCAGCCC CGAGAACCAC AGGTGTACAC CCTGCCCCCA*

*TCCCGGGAGG AGATGACCAA GAACCAGGTC AGCCTGACCT GCCTGGTCAA AGGCTTCTAT*

*CCCAGCGACA TCGCCGTGGA GTGGGAGAGC AATGGGCAGC CGGAGAACAA CTACAAGACC*

*ACGCCTCCCG TGCTGGACTC CGACGGCTCC TTCTTCCTCT ATAGCAAGCT CACCGTGGAC*

*AAGAGCAGGT GGCAGCAGGG GAACGTCTTC TCATGCTCCG TGATGCATGA GGCTCTGCAC*

*AACCACTACA CGCAGAAGAG CCTCTCCCTG TCCCCGGGTA AAACCGCCGC CGCCGCCACC*

*GCCGCCGCCG CCACCGCCGC CGCCGCCACC GCCGCGGCCG CCACACGTGT TGATCAGACA*

*CCGCGTACCG CAACCAAAGA AACCGGTGAA AGCCTGACCA TTAATTGTGT TCTGACCGAT*

*ACCGAGTATG GTTTGTTCTC CACCAGCTGG TTTCGTAAAA ATCCGGGTAC AACCGATTGG*

*GAACGTATGA GCATTGGTGG TCGTTATGTT GAAAGCGTGA ATAAAGGTGC CAAAAGCTTT*

*AGCCTGCGCA TTAAAGATCT GACCGTTGCA GATAGCGCAA CCTATTACTG TAAAGCACTG*

*GGTTGGTGGC CGCCGGCTTT CCCGCATTGG TATGATGGTG CAGGCACCGT TCTGACCGTT*

*AAT*

ICOS VNAR CC3-Fc-2D4 AMINO ACID SEQUENCE (linkers shown in italics, Fc portion underlined)

SEQ ID NO 47

TRVDQTPRTATKETGESLTINCVLTDTEYGLFSTSWFRKNPGTTDWERMSIGGRYVESVNKGAK

SFSLRIKDLTVADSATYYCKALGWWPPAFPHWYDGAGTVLTVN*GGGGSGGGGRT*EPKSSDKTHT

CPPCPAPEAAGAPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGSFFLYSKLTVDKSRW

QQGNVFSCSVMHEALHNHYTQKSLSLSPGK*TAAAATAAAATAAAATAAAA*TRVDQTPRTATKET

GESLTINCVLTDTDYGLFSTSWFRKNPGTTDWERMSIGGRYVESVNKGAKSFSLRIKDLTVADS

ATYYCKAFTWPWEWPDRWFRPWYDGAGTVLTVN

ICOS VNAR CC3-Fc-2D4 NUCLEOTIDE SEQUENCE

SEQ ID NO 48

*ACACGTGTTG ATCAGACACC GCGTACCGCA ACCAAAGAAA CCGGTGAAAG CCTGACCATT*

*AATTGTGTTC TGACCGATAC CGAGTATGGT TTGTTCTCCA CCAGCTGGTT TCGTAAAAAT*

*CCGGGTACAA CCGATTGGGA ACGTATGAGC ATTGGTGGTC GTTATGTTGA AAGCGTGAAT*

*AAAGGTGCCA AAAGCTTTAG CCTGCGCATT AAAGATCTGA CCGTTGCAGA TAGCGCAACC*

*TATTACTGTA AAGCACTGGG TTGGTGGCCG CCGGCTTTCC CGCATTGGTA TGATGGTGCA*

*GGCACCGTTC TGACCGTTAA TGGCGGTGGT GGTTCTGGTG GTGGTGGTCG TACGGAGCCC*

*AAATCTTCTG ACAAAACTCA CACATGCCCA CCGTGCCCAG CACCTGAAGC CGCTGGGGCA*

*CCGTCAGTCT TCCTCTTCCC CCCAAAACCC AAGGACACCC TCATGATCTC CCGGACCCCT*

*GAGGTCACAT GCGTGGTGGT GGACGTGAGC CACGAAGACC CTGAGGTCAA GTTCAACTGG*

*TACGTGGACG GCGTGGAGGT GCATAATGCC AAGACAAAGC CGCGGGAGGA GCAGTACAAC*

*AGCACGTACC GTGTGGTCAG CGTCCTCACC GTCCTGCACC AGGACTGGCT GAATGGCAAG*

*GAGTACAAGT GCAAGGTCTC CAACAAAGCC CTCCCAGCCC CCATCGAGAA AACCATCTCC*

*AAAGCCAAAG GGCAGCCCCG AGAACCACAG GTGTACACCC TGCCCCCATC CCGGGAGGAG*

*ATGACCAAGA ACCAGGTCAG CCTGACCTGC CTGGTCAAAG GCTTCTATCC CAGCGACATC*

*GCCGTGGAGT GGGAGAGCAA TGGGCAGCCG GAGAACAACT ACAAGACCAC GCCTCCCGTG*

*CTGGACTCCG ACGGCTCCTT CTTCCTCTAT AGCAAGCTCA CCGTGGACAA GAGCAGGTGG*

*CAGCAGGGGA ACGTCTTCTC ATGCTCCGTG ATGCATGAGG CTCTGCACAA CCACTACACG*

-continued

*CAGAAGAGCC TCTCCCTGTC CCCGGGTAAA ACCGCCGCCG CCGCCACCGC CGCCGCCGCC*

*ACCGCCGCCG CCGCCACCGC CGCGGCCGCC ACACGTGTTG ATCAGACACC GCGTACCGCA*

*ACCAAAGAAA CCGGTGAAAG CCTGACCATT AATTGTGTTC TGACCGATAC CGATTATGGT*

*TTGTTCTCCA CCAGCTGGTT TCGTAAAAAT CCGGGTACAA CCGATTGGGA ACGTATGAGC*

*ATTGGTGGTC GTTATGTTGA AAGCGTGAAT AAAGGTGCCA AAAGCTTTAG CCTGCGCATT*

*AAAGATCTGA CCGTTGCAGA TAGCGCAACC TATTACTGTA AAGCATTCAC TTGGCCGTGG*

*GAATGGCCGG ACCGTTGGTT CCGTCCGTGG TATGATGGTG CAGGCACCGT TCTGACCGTT*

*AAT*

ICOS VNAR CC3-Fc-CC3 AMINO ACID SEQUENCE (linkers shown in italics, Fc portion underlined)

SEQ ID NO 49

TRVDQTPRTATKETGESLTINCVLTDTEYGLFSTSWFRKNPGTTDWERMSIGGRYVESVNKGAK

SFSLRIKDLTVADSATYYCKALGWWPPAFPHWYDGAGTVLTVN*GGGGSGGGGRT*EPKSSDKTHT

CPPCPAPEAAGAPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGSFFLYSKLTVDKSRW

QQGNVFSCSVMHEALHNHYTQKSLSLSPGK*TAAAATAAAATAAAATAAAA*TRVDQTPRTATKET

GESLTINCVLTDTEYGLFSTSWFRKNPGTTDWERMSIGGRYVESVNKGAKSFSLRIKDLTVADS

ATYYCKALGWWPPAFPHWYDGAGTVLTVN

ICOS VNAR CC3-Fc-CC3 NUCLEOTIDE SEQUENCE

SEQ ID NO 50

*ACACGTGTTG ATCAGACACC GCGTACCGCA ACCAAAGAAA CCGGTGAAAG CCTGACCATT*

*AATTGTGTTC TGACCGATAC CGAGTATGGT TTGTTCTCCA CCAGCTGGTT TCGTAAAAAT*

*CCGGGTACAA CCGATTGGGA ACGTATGAGC ATTGGTGGTC GTTATGTTGA AAGCGTGAAT*

*AAAGGTGCCA AAAGCTTTAG CCTGCGCATT AAAGATCTGA CCGTTGCAGA TAGCGCAACC*

*TATTACTGTA AAGCACTGGG TTGGTGGCCG CCGGCTTTCC CGCATTGGTA TGATGGTGCA*

*GGCACCGTTC TGACCGTTAA TGGCGGTGGT GGTTCTGGTG GTGGTGGTCG TACGGAGCCC*

*AAATCTTCTG ACAAAACTCA CACATGCCCA CCGTGCCCAG CACCTGAAGC CGCTGGGGCA*

*CCGTCAGTCT TCCTCTTCCC CCCAAAACCC AAGGACACCC TCATGATCTC CCGGACCCCT*

*GAGGTCACAT GCGTGGTGGT GGACGTGAGC CACGAAGACC CTGAGGTCAA GTTCAACTGG*

*TACGTGGACG GCGTGGAGGT GCATAATGCC AAGACAAAGC CGCGGGAGGA GCAGTACAAC*

*AGCACGTACC GTGTGGTCAG CGTCCTCACC GTCCTGCACC AGGACTGGCT GAATGGCAAG*

*GAGTACAAGT GCAAGGTCTC CAACAAAGCC CTCCCAGCCC CCATCGAGAA AACCATCTCC*

*AAAGCCAAAG GGCAGCCCCG AGAACCACAG GTGTACACCC TGCCCCCATC CCGGGAGGAG*

*ATGACCAAGA ACCAGGTCAG CCTGACCTGC CTGGTCAAAG GCTTCTATCC CAGCGACATC*

*GCCGTGGAGT GGGAGAGCAA TGGGCAGCCG GAGAACAACT ACAAGACCAC GCCTCCCGTG*

*CTGGACTCCG ACGGCTCCTT CTTCCTCTAT AGCAAGCTCA CCGTGGACAA GAGCAGGTGG*

*CAGCAGGGGA ACGTCTTCTC ATGCTCCGTG ATGCATGAGG CTCTGCACAA CCACTACACG*

*CAGAAGAGCC TCTCCCTGTC CCCGGGTAAA ACCGCCGCCG CCGCCACCGC CGCCGCCGCC*

*ACCGCCGCCG CCGCCACCGC CGCGGCCGCC ACACGTGTTG ATCAGACACC GCGTACCGCA*

*ACCAAAGAAA CCGGTGAAAG CCTGACCATT AATTGTGTTC TGACCGATAC CGAGTATGGT*

*TTGTTCTCCA CCAGCTGGTT TCGTAAAAAT CCGGGTACAA CCGATTGGGA ACGTATGAGC*

*ATTGGTGGTC GTTATGTTGA AAGCGTGAAT AAAGGTGCCA AAAGCTTTAG CCTGCGCATT*

-continued

*AAAGATCTGA CCGTTGCAGA TAGCGCAACC TATTACTGTA AAGCACTGGG TTGGTGGCCG*

*CCGGCTTTCC CGCATTGGTA TGATGGTGCA GGCACCGTTC TGACCGTTAA T*

SoloMER ™ VNAR D1-v1 AMINO ACID SEQUENCE WITH HIS TAG

SEQ ID NO 51

ARVDQSPSSLSASVGDRVTITCVLRDSHCATSSTYWYRKKSGSTNEESISKGGRYVETVNSGSK

SFSLRINDLTVEDSGTYRCASECQYGLAEYDVYGGGTKVEIKHHHHHH

NUCLEOTIDE SEQUENCE CODING FOR THE SoloMER ™ VNAR D1-v1 WITH HIS TAG

SEQ ID NO 52

*GCCCGCGTGGACCAGTCCCCCTCCTCCCTGTCCGCCTCCGTGGGCGACCGCGTGACCATCACC*

*TGCGTGCTGCGCGACTCCCACTGCGCCACCTCCTCCACCTACTGGTACCGCAAGAAG*

*TCCGGCTCCACCAACGAGGAGTCCATCTCCAAGGGGGGCCGCTACGTGGAGACCGTGAACTCC*

*GGCTCCAAGTCCTTCTCCCTGCGCATCAACGACCTGACCGTGGAGGACTCCGGCACC*

*TACCGCTGCGCCTCCGAGTGCCAGTACGGCCTGGCCGAGTACGACGTGTACGGCGGCGGCACC*

*AAGGTGGAGATCAAGCACCACCACCACCACCAC*

SoloMER ™ VNAR D1-v2 AMINO ACID SEQUENCE WITH HIS TAG

SEQ ID NO 53

ARVDQSPSSLSASVGDRVTITCVLRDSHCATSSTYWYRKKSGSTNEESISKGGRYVETVNSGSK

SFTLTISSLQPEDFATYYCASECQYGLAEYDVYGGGTKVEIKHHHHHH

NUCLEOTIDE SEQUENCE CODING FOR THE SoloMER ™ VNAR D1-v2 WITH HIS TAG

SEQ ID NO 54

*GCCCGCGTGGACCAGTCCCCCTCCTCCCTGTCCGCCTCCGTGGGCGACCGCGTGACCATCACC*

*TGCGTGCTGCGCGACTCCCACTGCGCCACCTCCTCCACCTACTGGTACCGCAAGAAG*

*TCCGGCTCCACCAACGAGGAGTCCATCTCCAAGGGGGGCCGCTACGTGGAGACCGTGAACTCC*

*GGCTCCAAGTCCTTCACCCTGACCATCTCCTCCCTGCAGCCCGAGGACTTCGCCACC*

*TACTACTGCGCCTCCGAGTGCCAGTACGGCCTGGCCGAGTACGACGTGTACGGCGGCGGCACC*

*AAGGTGGAGATCAAGCACCACCACCACCACCAC*

SoloMER ™ VNAR D1-v3 AMINO ACID SEQUENCE WITH HIS TAG

SEQ ID NO 55

ARVDQSPSSLSASVGDRVTITCVLRDSHCATSSTYWYQQKPGKTNEESISKGGRYVETVNSGSK

SFTLTISSLQPEDFATYYCASECQYGLAEYDVYGGGTKVEIKHHHHHH

NUCLEOTIDE SEQUENCE CODING FOR THE SoloMER ™ VNAR D1-v3 WITH HIS TAG

SEQ ID NO 56

*GCCCGCGTGGACCAGTCCCCCTCCTCCCTGTCCGCCTCCGTGGGCGACCGCGTGACCATCACC*

*TGCGTGCTGCGCGACTCCCACTGCGCCACCTCCTCCACCTACTGGTACCAGCAGAAG*

*CCCGGCAAGACCAACGAGGAGTCCATCTCCAAGGGGGGCCGCTACGTGGAGACCGTGAACTCC*

*CTCCAAGTCCTTCACCCTGACCATCTCCTCCCTGCAGCCCGAGGACTTCGCCACC*

*TACTACTGCGCCTCCGAGTGCCAGTACGGCCTGGCCGAGTACGACGTGTACGGCGGCGGCACC*

*AAGGTGGAGATCAAGCACCACCACCACCACCAC*

SoloMER ™ VNAR D1-v4 AMINO ACID SEQUENCE WITH HIS TAG

SEQ ID NO 57

ARVDQSPSSLSASVGDRVTITCVLRDSHCATSSTYWYRKKPGSTNEESISKGGRFSGSGSSGSK

SFTLTISSLQPEDFATYYCASECQYGLAEYDVFGQGTKVEIKHHHHHH

NUCLEOTIDE SEQUENCE CODING FOR THE SoloMER ™ VNAR D1-v4 WITH HIS TAG

SEQ ID NO 58

*GCCCGCGTGGACCAGTCCCCCTCCTCCCTGTCCGCCTCCGTGGGCGACCGCGTGACCATCACC*

*TGCGTGCTGCGCGACTCCCACTGCGCCACCTCCTCCACCTACTGGTACCGCAAGAAG*

*CCCGGCTCCACCAACGAGGAGTCCATCTCCAAGGGGGGCCGCTTCTCCGGCTCCGGCTCCTCC*

-continued

*GGCTCCAAGTCCTTCACCCTGACCATCTCCTCCCTGCAGCCCGAGGACTTCGCCACC*

*TACTACTGCGCCTCCGAGTGCCAGTACGGCCTGGCCGAGTACGACGTGTTCGGCCAGGGCACC*

*AAGGTGGAGATCAAGCACCACCACCACCACCAC*

Quad-X ™ D1-Fc-C4 AMINO ACID SEQUENCE (Fc portion underlined)

SEQ ID NO 59

ARVDQTPQTITKETGESLTINCVLRDSHCATSSTYWYRKKSGSTNEESISKGGRYVETVNSGSK

SFSLRINDLTVEDSGTYRCASECQYGLAEYDVYGGGTVVTVNGSGGGSGGGGSGEPKSSDKTHT

CPPCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVYTLPP

SRDELTKNQVSLTCLVKGFYPSDIAVEWESNGQPENNYKTTPPVLDSDGSFFLYSKLTVDKSRW

QQGNVFSCSVMHEALHNHYTQKSLSLSPGKGGGGSGGGGSGGGGSGGGGSGAHSARVDQTPQTI

TKETGESLTINCVLRDSNCGLSSTYWYRKKSGSTNEESISKGGRYVETINEGSKSFSLRINDLT

VEDSGTYRCKLSWWTQNWRCSNSDVYGGGTVVTVN

NUCLEOTIDE SEQUENCE CODING FOR THE Quad-X ™ D1-Fc-C4

SEQ ID NO 60

*GCTCGAGTGGACCAAACACCGCAAACAATAACAAAGGAGACGGGCGAATCACTGACCATCAACT*

*GTGTCCTACGAGATAGCCACTGTGCAACCTCCAGCACGTACTGGTATCGCAAAAAATCGGGCTC*

*AACAAACGAGGAGAGCATATCGAAAGGTGGACGATATGTTGAAACAGTTAACAGCGGATCAAAG*

*TCCTTTTCTTTGAGAATTAATGATCTAACAGTTGAAGACAGTGGCACGTATCGATGCGCTTCCG*

*AGTGCCAATATGGACTGGCAGAATATGATGTATACGGAGGTGGCACTGTCGTGACTGTGAATGG*

*ATCCGGTGGTGGGTCCGGAGGAGGTGGCTCAGGAGAGCCCAAATCTAGCGACAAAACTCACACA*

*TGCCCACCGTGCCCAGCACCTGAACTCCTGGGGGGACCGTCAGTCTTCCTCTTCCCCCCAAAAC*

*CCAAGGACACCCTCATGATCTCCCGGACCCCTGAGGTCACATGCGTGGTGGTGGACGTGAGCCA*

*CGAAGACCCTGAGGTCAAGTTCAACTGGTACGTGGACGGCGTGGAGGTGCATAATGCCAAGACA*

*AAGCCGCGGGAGGAGCAGTACAACAGCACGTACCGGGTGGTCAGCGTCCTCACCGTCCTGCACC*

*AGGACTGGCTGAATGGCAAGGAGTACAAGTGCAAGGTCTCCAACAAAGCCCTCCCAGCCCCCAT*

*CGAGAAAACCATCTCCAAAGCCAAAGGGCAGCCCCGAGAACCACAGGTGTACACCCTGCCCCCA*

*TCCCGGGATGAGCTGACCAAGAACCAGGTCAGCCTGACCTGCCTGGTCAAAGGCTTCTATCCCA*

*GCGACATCGCCGTGGAGTGGGAGAGCAATGGGCAGCCGGAGAACAACTACAAGACCACGCCTCC*

*CGTGCTGGACTCCGACGGCTCCTTCTTCCTCTACAGCAAGCTCACCGTGGACAAGAGCAGGTGG*

*CAGCAGGGGAACGTCTTCTCATGCTCCGTGATGCATGAGGCTCTGCACAACCACTACACGCAGA*

*AGAGCCTCTCCCTGTCTCCGGGGAAAGGAGGTGGCGGTTCCGGAGGTGGCGGTAGCGGAGGTGG*

*CGGTAGCGGAGGTGGCGGTAGCGGGGCCCATTCTGCTCGAGTGGACCAAACACCGCAAACAATA*

*ACAAAGGAGACGGGCGAATCACTGACCATCAACTGTGTCCTACGAGATAGCAACTGTGGGTTGT*

*CCAGCACGTACTGGTATCGCAAAAAATCGGGCTCAACAAACGAGGAGAGCATATCGAAAGGTGG*

*ACGATATGTTGAAACAATTAACGAAGGATCAAAGTCCTTTTCTTTGAGAATTAATGATCTAACA*

*GTTGAAGACAGTGGCACGTATCGATGCAAGTTAAGCTGGTGGACCCAGAACTGGAGATGCTCAA*

*ATTCCGATGTATACGGAGGTGGCACTGTCGTGACTGTGAAT*

Quad-Y-D1C4 ™ D1-C4-Fc AMINO ACID SEQUENCE (Fc portion underlined)

SEQ ID NO 61

ARVDQTPQTITKETGESLTINCVLRDSHCATSSTYWYRKKSGSTNEESISKGGRYVETVNSGSK

SFSLRINDLTVEDSGTYRCASECQYGLAEYDVYGGGTVVTVNGGGGSGGGGGSGAHSARVDQTP

QTITKETGESLTINCVLRDSNCGLSSTYWYRKKSGSTNEESISKGGRYVETINEGSKSFSLRIN

-continued

DLTVEDSGTYRCKLSWWTQNWRCSNSDVYGGGTVVTVNGGGSGGGGSGEPKSSDKTHTCPPCPA

PELLGGPSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQGNVF

SCSVMHEALHNHYTQKSLSLSPGK

NUCLEOTIDE SEQUENCE CODING FOR THE Quad-Y-D1C4 ™ AMINO ACID SEQUENCE

SEQ ID NO 62

GCTCGAGTGGACCAAACACCGCAAACAATAACAAAGGAGACGGGCGAATCACTGACCATCAACT

GTGTCCTACGAGATAGCCACTGTGCAACCTCCAGCACGTACTGGTATCGCAAAAAATCGGGCTC

AACAAACGAGGAGAGCATATCGAAAGGTGGACGATATGTTGAAACAGTTAACAGCGGATCAAAG

TCCTTTTCTTTGAGAATTAATGATCTAACAGTTGAAGACAGTGGCACGTATCGATGCGCTTCCG

AGTGCCAATATGGACTGGCAGAATATGATGTATACGGAGGTGGCACTGTCGTGACTGTGAATGG

AGGTGGCGGTAGCGGAGGTGGTGGCGGATCCGGGGCGCACTCCGCTCGAGTGGACCAAACACCG

CAAACAATAACAAAGGAGACGGGCGAATCACTGACCATCAACTGTGTCCTACGAGATAGCAACT

GTGGGTTGTCCAGCACGTACTGGTATCGCAAAAAATCGGGCTCAACAAACGAGGAGAGCATATC

GAAAGGTGGACGATATGTTGAAACAATTAACGAAGGATCAAAGTCCTTTTCTTTGAGAATTAAT

GATCTAACAGTTGAAGACAGTGGCACGTATCGATGCAAGTTAAGCTGGTGGACCCAGAACTGGA

GATGCTCAAATTCCGATGTATACGGAGGTGGCACTGTCGTGACTGTGAACGGTGGTGGGTCCGG

AGGAGGTGGCTCAGGAGAGCCCAAATCTAGCGACAAAACTCACACATGCCCACCGTGCCCAGCA

CCTGAACTCCTGGGGGGACCGTCAGTCTTCCTCTTCCCCCCAAAACCCAAGGACACCCTCATGA

TCTCCCGGACCCCTGAGGTCACATGCGTGGTGGTGGACGTGAGCCACGAAGACCCTGAGGTCAA

GTTCAACTGGTACGTGGACGGCGTGGAGGTGCATAATGCCAAGACAAAGCCGCGGGAGGAGCAG

TACAACAGCACGTACCGTGTGGTCAGCGTCCTCACCGTCCTGCACCAGGACTGGCTGAATGGCA

AGGAGTACAAGTGCAAGGTCTCCAACAAAGCCCTCCCAGCCCCCATCGAGAAAACCATCTCCAA

AGCCAAAGGGCAGCCCCGAGAACCACAGGTGTACACCCTGCCCCCATCCCGGGATGAGCTGACC

AAGAACCAGGTCAGCCTGACCTGCCTGGTCAAAGGCTTCTATCCCAGCGACATCGCCGTGGAGT

GGGAGAGCAATGGGCAGCCGGAGAACAACTACAAGACCACGCCTCCCGTGCTGGACTCCGACGG

CTCCTTCTTCCTCTACAGCAAGCTCACCGTGGACAAGAGCAGGTGGCAGCAGGGGAACGTCTTC

TCATGCTCCGTGATGCATGAGGCTCTGCACAACCACTACACGCAGAAGAGCCTCTCCCTGTCTC

CGGGGAAA

Quad-Y-C4D1 ™ C4-D1-Fc AMINO ACID SEQUENCE (Fc portion underlined)

SEQ ID NO 63

ARVDQTPQTITKETGESLTINCVLRDSNCGLSSTYWYRKKSGSTNEESISKGGRYVETINEGSK

SFSLRINDLTVEDSGTYRCKLSWWTQNWRCSNSDVYGGGTVVTVNGGGGSGGGGGSGAHSARVD

QTPQTITKETGESLTINCVLRDSHCATSSTYWYRKKSGSTNEESISKGGRYVETVNSGSKSFSL

RINDLTVEDSGTYRCASECQYGLAEYDVYGGGTVVTVNGGGSGGGGSGEPKSSDKTHTCPPCPA

PELLGGPSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQGNVF

SCSVMHEALHNHYTQKSLSLSPGK

-continued

NUCLEOTIDE SEQUENCE CODING FOR THE Quad-Y-C4D1 ™ AMINO ACID SEQUENCE

SEQ ID NO 64

*GCTCGAGTGGACCAAACACCGCAAACAATAACAAAGGAGACGGGCGAATCACTGACCATCAACT*

*GTGTCCTACGAGATAGCAACTGTGGGTTGTCCAGCACGTACTGGTATCGCAAAAAATCGGGCTC*

*AACAAACGAGGAGAGCATATCGAAAGGTGGACGATATGTTGAAACAATTAACGAAGGATCAAAG*

*TCCTTTTCTTTGAGAATTAATGATCTAACAGTTGAAGACAGTGGCACGTATCGATGCAAGTTAA*

*GCTGGTGGACCCAGAACTGGAGATGCTCAAATTCCGATGTATACGGAGGTGGCACTGTCGTGAC*

*TGTGAACGGAGGTGGCGGTAGCGGAGGTGGTGGCGGATCCGGGGCGCACTCCGCTCGAGTGGAC*

*CAAACACCGCAAACAATAACAAAGGAGACGGGCGAATCACTGACCATCAACTGTGTCCTACGAG*

*ATAGCCACTGTGCAACCTCCAGCACGTACTGGTATCGCAAAAAATCGGGCTCAACAAACGAGGA*

*GAGCATATCGAAAGGTGGACGATATGTTGAAACAGTTAACAGCGGATCAAAGTCCTTTTCTTTG*

*AGAATTAATGATCTAACAGTTGAAGACAGTGGCACGTATCGATGCGCTTCCGAGTGCCAATATG*

*GACTGGCAGAATATGATGTATACGGAGGTGGCACTGTCGTGACTGTGAATGGTGGTGGGTCCGG*

*AGGAGGTGGCTCAGGAGAGCCCAAATCTAGCGACAAAACTCACACATGCCCACCGTGCCCAGCA*

*CCTGAACTCCTGGGGGGACCGTCAGTCTTCCTCTTCCCCCCAAAACCCAAGGACACCCTCATGA*

*TCTCCCGGACCCCTGAGGTCACATGCGTGGTGGTGGACGTGAGCCACGAAGACCCTGAGGTCAA*

*GTTCAACTGGTACGTGGACGGCGTGGAGGTGCATAATGCCAAGACAAAGCCGCGGGAGGAGCAG*

*TACAACAGCACGTACCGTGTGGTCAGCGTCCTCACCGTCCTGCACCAGGACTGGCTGAATGGCA*

*AGGAGTACAAGTGCAAGGTCTCCAACAAAGCCCTCCCAGCCCCCATCGAGAAAACCATCTCCAA*

*AGCCAAAGGGCAGCCCCGAGAACCACAGGTGTACACCCTGCCCCCATCCCGGGATGAGCTGACC*

*AAGAACCAGGTCAGCCTGACCTGCCTGGTCAAAGGCTTCTATCCCAGCGACATCGCCGTGGAGT*

*GGGAGAGCAATGGGCAGCCGGAGAACAACTACAAGACCACGCCTCCCGTGCTGGACTCCGACGG*

*CTCCTTCTTCCTCTACAGCAAGCTCACCGTGGACAAGAGCAGGTGGCAGCAGGGGAACGTCTTC*

*TCATGCTCCGTGATGCATGAGGCTCTGCACAACCACTACACGCAGAAGAGCCTCTCCCTGTCTC*

*CGGGGAAA*

2D4

SEQ ID NO 65

TRVDQTPRTATKETGESLTINCVLTDTDYGLFSTSWFRKNPGTTDWERMSIGGRYVESVNKGAK

SFSLRIKDLTVADSATYYCKAFTWPWEWPDRWFRPWYDGAGTVLTVN

CC3

SEQ ID NO 66

TRVDQTPRTATKETGESLTINCVLTDTEYGLFSTSWFRKNPGTTDWERMSIGGRYVESVNKGAK

SFSLRIKDLTVADSATYYCKALGWWPPAFPHWYDGAGTVLTVN

BA11

SEQ ID NO 67

TRVDQSPSSLSASVGDRVTITCVLTDTSYPLYSTYWYRKNPGSSNKEQISISGRYSESVNKGTK

SFTLTISSLQPEDSATYYCRAMSTNIWTGDGAGTKVEIK

CDR1

SEQ ID NO 68

HCATSS

CDR1

SEQ ID NO 69

NCGLSS

CDR1

SEQ ID NO 70

NCALSS

-continued

HV2

SEQ ID NO 71

TNEESISKG

HV4

SEQ ID NO 72

SGSKS

HV4

SEQ ID NO 73

EGSKS

NARF4For1

SEQ ID NO 74

ATA ATC AAG CTT GCG GCC GCA TTC ACA GTC ACG ACA GTG CCA CCT C

NARF4For2

SEQ ID NO 75

ATA ATC AAG CTT GCG GCC GCA TTC ACA GTC ACG GCA GTG CCA TCT C

NARF1Rev

SEQ ID NO 76

ATA ATA AGG AAT TCC ATG GCT CGA GTG GAC CAA ACA CCG

E06

SEQ ID NO 77

TRVDQTPRTATRETGESLTINCVLTDTSYPLYSTYWYRKNPGSSNKEQISISGRYVESVNKGTK

SFSLRIKDLTVADSATYICRAMGTNIWTGDGAGTVLTVN hE06v1.10

SEQ ID NO 78

TRVDQSPSSLSASVGDRVTITCVLTDTSYPLYSTYWYRKNPGSSNKEQISISGRYSESVNKGTK

SFTLTISSLQPEDFATYYCRAMGTNIWTGDGAGTKVEIK

AC9

SEQ ID NO 79

TRVDQSPSSLSASVGDRVTITCVLTDTSYPLYSTYWYRKNPGSSNKEQISISGRYSESVNKGTK

SSTLTISSLQPEDFATYYCRAMGTNIWTGDGAGTKVEIK

AD4

SEQ ID NO 80

TRVDQSPSSLSASVGDRVTITCVLTDTSYPLYSTYWYRKNPGSSNKEQISMSGRYSESVNKSTK

SFTLTISSLQPEDFATYYCRAMGTNIWTGDGAGTKVEIK

AG11

SEQ ID NO 81

TRVDQSPSSLSASVGDRVTITCVLTDTSYPLYSTYWYRKNPGSSNKEQISISGRYSESVNKGTK

SFTLTISSLQPEDFATYYCRAMGTNIWTGDGAGTKVETK

AH7

SEQ ID NO 82

TRVDQTPSSLSASVGDRVTITCVLTDTSYPLYSTYWYRKNPGSSNKEQISISGRYSESVNKGTK

SSTLTISSLQPEDFATYYCRAMGTNIWTGDGAGTKVEIK

BB10

SEQ ID NO 83

TRVDQSPSSLSASVGDRVTITCVLTDTSYPLYSTYWYRKNPGSSNKEQISISGRYSESVNKGTK

SFTLTISSLQPEDFATYYCRAMGTNFWTGDGAGTKVEIK

BB11

SEQ ID NO 84

TRVDQSPSSLSASVGDRVTITCVLTDTSYPLYSTYWYRKNPGSSNKEQISISGRYSESVNKGTK

SFTLTISSLQPEDFATYYCRAMATNIWTGDGAGTKVEIK

BC3

SEQ ID NO 85

TRVDQSPSSLSASVGDRVTITCVLTDTSYPLYSTYWYRKNPGSNNKEQISISGRYSESVNKGTK

SFTLTISSLQPEDFATYYCRAMGTNIWTGDGAGTKVEIK

-continued

BD12

SEQ ID NO 86

TRVDQSPSSLSASVGDRVTITCVLTDTSYPLYSTYWYRKNPGSSNKEQISISGRYSESVNKGTN

SFTLTISSLQPEDFATYYCRAMGTNIWTGDGAGTKVEIK

BE4

SEQ ID NO 87

TRVDQSPSSLSASVGDRVTITCVLTDTSYSLYSTYWYRKNPGSSNKEQISISGRYSESVNKGTK

SFTLTISSLQPEDFATYYCRAMGTNIWTGDGAGTKVEIK

BH4

SEQ ID NO 88

TRVDQSPSSLSASVGDRVTITCVLTDTSYPLYSTYWYRKNPGSSNKEQISISGRYSESVNKGTK

SFTLTISSLQPEDFATYYCRAMGTNLWTGDGAGTKVEIK

TNF VNAR DIMER D1-C4 with $(Gly_4Ser)_3$ AMINO ACID SEQUENCE WITH HIS TAG (linker shown in italics and tag double underlined)

SEQ ID NO 89

ARVDQTPQTITKETGESLTINCVLRDSHCATSSTYWYRKKSGSTNEESISKGGRYVETVNSGSK

SFSLRINDLTVEDSGTYRCASECQYGLAEYDVYGGGTVVTVN*GGGGSGGGGGSGGGS*ARVDQTP

QTITKETGESLTINCVLRDSNCGLSSTYWYRKKSGSTNEESISKGGRYVETINEGSKSFSLRIN

DLTVEDSGTYRCKLSWWTQNWRCSNSDVYGGGTVVTVNAAAHHHHHH

TNF VNAR DIMER D1-C4 with $(Gly_4Ser)_3$ NEUCLEOTIDE SEQUENCE WITH HIS TAG

SEQ ID NO 90

GCTCGAGTGGACCAAACACCGCAAACAATAACAAAGGAGACGGGCGAATCACTGACCATCAACT

GTGTCCTACGAGATAGCCACTGTGCAACCTCCAGCACGTACTGGTATCGCAAAAAATCGGGCTC

AACAAACGAGGAGAGCATATCGAAAGGTGGACGATATGTTGAAACAGTTAACAGCGGATCAAAG

TCCTTTTCTTTGAGAATTAATGATCTAACAGTTGAAGACAGTGGCACGTATCGATGCGCTTCCG

AGTGCCAATATGGACTGGCAGAATATGATGTATACGGAGGTGGCACTGTCGTGACTGTGAATGG

AGGTGGCGGTAGCGGAGGTGGTGGCGGATCCGGCGGTGGTTCCGCTCGAGTGGACCAAACACCG

CAAACAATAACAAAGGAGACGGGCGAATCACTGACCATCAACTGTGTCCTACGAGATAGCAACT

GTGGGTTGTCCAGCACGTACTGGTATCGCAAAAAATCGGGCTCAACAAACGAGGAGAGCATATC

GAAAGGTGGACGATATGTTGAAACAATTAACGAAGGATCAAAGTCCTTTTCTTTGAGAATTAAT

GATCTAACAGTTGAAGACAGTGGCACGTATCGATGCAAGTTAAGCTGGTGGACCCAGAACTGGA

GATGCTCAAATTCCGATGTATACGGAGGTGGCACTGTCGTGACTGTGAACGCGGCCGCACATCA

TCATCACCATCAC

TNF soloMER ™ DIMER D1v2-C4v1 with $(Gly_4Ser)_3$ AMINO ACID SEQUENCEWITH HIS TAG (linker shown in italics and tag double underlined)

SEQ ID NO 91

ARVDQSPSSLSASVGDRVTITCVLRDSHCATSSTYWYRKKSGSTNEESISKGGRYVETVNSGSK

SFTLTISSLQPEDFATYYCASECQYGLAEYDVYGGGTKVEIK*GGGGSGGGGGSGGGS*ARVDQSP

SSLSASVGDRVTITCVLRDSNCGLSSTYWYRKKSGSTNEESISKGGRYVETINEGSKSFSLRIN

DLTVEDSGTYRCKLSWWTQNWRCSNSDVYGGGTKVEIKAAAHHHHHH

TNF soloMER ™ DIMER D1v2-C4v1 with $(Gly_4Ser)_3$ NUCLEOTIDE SEQUENCE WITH HIS TAG

SEQ ID NO 92

GCCCGCGTGGACCAGTCCCCCTCCTCCCTGTCCGCCTCCGTGGGCGACCGCGTGACCATCACCT

GCGTGCTGCGCGACTCCCACTGCGCCACCTCCTCCACCTACTGGTACCGCAAGAAGTCCGGCTC

CACCAACGAGGAGTCCATCTCCAAGGGGGGCCGCTACGTGGAGACCGTGAACTCCGGCTCCAAG

TCCTTCACCCTGACCATCTCCTCCCTGCAGCCCGAGGACTTCGCCACCTACTACTGCGCCTCCG

AGTGCCAGTACGGCCTGGCCGAGTACGACGTGTACGGCGGCGGCACCAAGGTGGAGATCAAGGG

-continued

AGGTGGCGGTAGCGGAGGTGGTGGCGGATCCGGCGGTGGTTCCGCCCGCGTGGACCAGTCCCCC

TCCTCCCTGTCCGCCTCCGTGGGCGACCGCGTGACCATCACCTGCGTGCTGCGCGACTCCAACT

GCGGCCTGTCCTCCACCTACTGGTACCGCAAGAAGTCCGGCTCCACCAACGAGGAGTCCATCTC

CAAGGGCGGCCGCTACGTGGAGACCATCAACGAGGGCTCCAAGTCCTTCTCCCTGCGCATCAAC

GACCTGACCGTGGAGGACTCCGGCACCTACCGCTGCAAGCTGTCCTGGTGGACCCAGAACTGGC

GCTGCTCCAACTCCGACGTGTACGGCGGCGGCACCAAGGTGGAGATCAAGGCGGCCGCACATCA

TCATCACCATCAC

TNF soloMER ™ DIMER D1v2-C4v1 with $(Gly_4Ser)_5$ AMINO ACID SEQUENCE WITH HIS TAG (linker shown in italics and tag double underlined)

SEQ ID NO 93

ARVDQSPSSLSASVGDRVTITCVLRDSHCATSSTYWYRKKSGSTNEESISKGGRYVETVNSGSK

SFTLTISSLQPEDFATYYCASECQYGLAEYDVYGGGTKVEIK*GGGGSGGGGSGGGGSGGGGSGG*

*GGS*ARVDQSPSSLSASVGDRVTITCVLRDSNCGLSSTYWYRKKSGSTNEESISKGGRYVETINE

GSKSFSLRINDLTVEDSGTYRCKLSWWTQNWRCSNSDVYGGGTKVEIKAAAHHHHHH

TNF soloMER ™ DIMER D1v2-C4v1 with $(Gly_4Ser)_5$ NUCLEOTIDE SEQUENCE WITH HIS TAG

SEQ ID NO 94

GCCCGCGTGGACCAGTCCCCCTCCTCCCTGTCCGCCTCCGTGGGCGACCGCGTGACCATCACCT

GCGTGCTGCGCGACTCCCACTGCGCCACCTCCTCCACCTACTGGTACCGCAAGAAGTCCGGCTC

CACCAACGAGGAGTCCATCTCCAAGGGGGGCCGCTACGTGGAGACCGTGAACTCCGGCTCCAAG

TCCTTCACCCTGACCATCTCCTCCCTGCAGCCCGAGGACTTCGCCACCTACTACTGCGCCTCCG

AGTGCCAGTACGGCCTGGCCGAGTACGACGTGTACGGCGGCGGCACCAAGGTGGAGATCAAGGG

TGGTGGTGGTAGCGGTGGTGGCGGTTCAGGTGGCGGTGGTTCTGGCGGTGGCGGTAGTGGCGGA

GGTGGTAGTGCCCGCGTGGACCAGTCCCCCTCCTCCCTGTCCGCCTCCGTGGGCGACCGCGTGA

CCATCACCTGCGTGCTGCGCGACTCCAACTGCGGCCTGTCCTCCACCTACTGGTACCGCAAGAA

GTCCGGCTCCACCAACGAGGAGTCCATCTCCAAGGGCGGCCGCTACGTGGAGACCATCAACGAG

GGCTCCAAGTCCTTCTCCCTGCGCATCAACGACCTGACCGTGGAGGACTCCGGCACCTACCGCT

GCAAGCTGTCCTGGTGGACCCAGAACTGGCGCTGCTCCAACTCCGACGTGTACGGCGGCGGCAC

CAAGGTGGAGATCAAGGCGGCCGCACATCATCATCACCATCAC

TNF S17-Quad-X ™ with $(Gly_4Ser)_5$ AMINO ACID SEQUENCE (Fc portion underlined)

SEQ ID NO 95

ASVNQTPRTATKETGESLTINCVLTDTHAKVFTTSWFRKNPGTTDWERMSIGGRYVESVNKGAK

SFSLRIKDLTVADSATYICRAGGYLSQPRVYWDVYGAGTVLTVNGGGGSGGGGRTEPRGPTIKP

CPPCKCPAPNLLGGPSVFIFPPKIKDVLMISLSPIVTCVVVDVSEDDPDVQISWFVNNVEVHTA

QTQTHREDYNSTLRVVSALPIQHQDWMSGKEFKCKVNNKDLPAPIERTISKPKGSVRAPQVYVL

PPPEEEMTKKQVTLTCMVTDFMPEDIYVEWTNNGKTELNYKNTEPVLDSDGSYFMYSKLRVEKK

NWVERNSYSCSVVHEGLHNHHTTKSFSRTPGKGGGGSGGGGSGGGGSGGGGSGAHSASVNQTPR

TATKETGESLTINCVLTDTHAKVFTTSWFRKNPGTTDWERMSIGGRYVESVNKGAKSFSLRIKD

LTVADSATYICRAGGYLSQPRVYWDVYGAGTVLTVN

TNF S17-Quad-X ™ with $(Gly_4Ser)_5$ NUCLEOTIDE SEQUENCE

SEQ ID NO 96

GCAAGCGTTAATCAGACACCGCGTACCGCAACCAAAGAAACCGGTGAAAGCCTGACCATTAATT

GTGTTCTGACCGATACCCATGCTAAAGTTTTCACTACCAGCTGGTTTCGTAAAAATCCGGGTAC

AACCGATTGGGAACGTATGAGCATTGGTGGTCGTTATGTTGAAAGCGTGAATAAAGGTGCCAAA

-continued

```
AGCTTTAGCCTGCGCATTAAAGATCTGACCGTTGCAGATAGCGCAACCTATATCTGTCGTGCCG

GTGGTTACCTGTCTCAGCCGCGTGTTTACTGGGATGTTTATGGTGCAGGCACCGTTCTGACCGT

TAATGGCGGTGGTGGTTCTGGTGGTGGTGGTCGTACGGAGCCTCGAGGCCCCACAATCAAGCCC

TGTCCTCCATGCAAATGCCCAGCACCTAACCTCTTGGGTGGACCATCCGTCTTCATCTTCCCTC

CAAAGATCAAGGATGTACTCATGATCTCCCTGAGCCCCATAGTCACATGTGTGGTGGTGGATGT

GAGCGAGGATGACCCAGATGTCCAGATCAGCTGGTTTGTGAACAACGTGGAAGTACACACAGCT

CAGACACAAACCCATAGAGAGGATTACAACAGTACTCTCCGGGTGGTCAGTGCCCTCCCCATCC

AGCACCAGGACTGGATGAGTGGCAAGGAGTTCAAATGCAAGGTCAACAACAAAGACCTCCCAGC

GCCCATCGAGAGAACCATCTCAAAACCCAAAGGGTCAGTAAGAGCTCCACAGGTATATGTCTTG

CCTCCACCAGAAGAAGAGATGACTAAGAAACAGGTCACTCTGACCTGCATGGTCACAGACTTCA

TGCCTGAAGACATTTACGTGGAGTGGACCAACAACGGGAAAACAGAGCTAAACTACAAGAACAC

TGAACCAGTCCTGGACTCTGATGGTTCTTACTTCATGTACAGCAAGCTGAGAGTGGAAAAGAAG

AACTGGGTGGAAAGAAATAGCTACTCCTGTTCAGTGGTCCACGAGGGTCTGCACAATCACCACA

CGACTAAGAGCTTCTCCCGGACTCCGGGTAAAGGAGGTGGCGGTTCCGGAGGTGGCGGTAGCGG

AGGTGGCGGTAGCGGAGGTGGCGGTAGCGGGGCCCATTCTGCAAGCGTTAATCAGACACCGCGT

ACCGCAACCAAAGAAACCGGTGAAAGCCTGACCATTAATTGTGTTCTGACCGATACCCATGCTA

AAGTTTTCACTACCAGCTGGTTTCGTAAAAATCCGGGTACAACCGATTGGGAACGTATGAGCAT

TGGTGGTCGTTATGTTGAAAGCGTGAATAAAGGTGCCAAAAGCTTTAGCCTGCGCATTAAAGAT

CTGACCGTTGCAGATAGCGCAACCTATATCTGTCGTGCCGGTGGTTACCTGTCTCAGCCGCGTG

TTTACTGGGATGTTTATGGTGCAGGCACCGTTCTGACCGTTAAT
```

DETAILED DESCRIPTION OF THE INVENTION

Definitions

Amino acids are represented herein as either a single letter code or as the three-letter code or both.

The term "affinity purification" means the purification of a molecule based on a specific attraction or binding of the molecule to a chemical or binding partner to form a combination or complex which allows the molecule to be separated from impurities while remaining bound or attracted to the partner moiety.

The term "Complementarity Determining Regions" or CDRs (i.e., CDR1 and CDR3) refers to the amino acid residues of a VNAR domain the presence of which are necessary for antigen binding. Each VNAR typically has CDR regions identified as CDR1 and CDR3. Each complementarity determining region may comprise amino acid residues from a "complementarity determining region" and/or those residues from a "hypervariable loop" (HV). In some instances, a complementarity determining region can include amino acids from both a CDR region and a hypervariable loop. According to the generally accepted nomenclature for VNAR molecules, a CDR2 region is not present.

"Framework regions" (FW) are those VNAR residues other than the CDR residues. Each VNAR typically has five framework regions identified as FW1, FW2, FW3a, FW3b and FW4. VNAR domains therefore typically have the structure FW1-CDR1-FW2-HV2-FW3a-HV4-FW3b-CDR3-FW4 in the N- to C-terminal direction.

"Cell", "cell line", and "cell culture" are used interchangeably (unless the context indicates otherwise) and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, etc. Eukaryotic cells use control sequences such as promoters, polyadenylation signals, and enhancers.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell.

The "detection limit" for a chemical entity in a particular assay is the minimum concentration of that entity which can be detected above the background level for that assay. For example, in the phage ELISA, the "detection limit" for a particular phage displaying a particular antigen binding fragment is the phage concentration at which the particular phage produces an ELISA signal above that produced by a control phage not displaying the antigen binding fragment.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each other. Preferably, the two portions of the polypeptide are obtained from heterologous or different polypeptides.

The term "fusion protein" in this text means, in general terms, one or more proteins joined together by chemical means, including hydrogen bonds or salt bridges, or by peptide bonds through protein synthesis or both.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from an allogenic or xenogenic source. The DNA may, optionally, include marker or selection genes, for example, antibiotic resistance genes, temperature resistance genes, etc.

A "highly diverse position" refers to a position of an amino acid located in the variable regions of the light and heavy chains that have a number of different amino acid represented at the position when the amino acid sequences of known and/or naturally occurring antibodies or antigen binding fragments are compared. The highly diverse positions are typically in the CDR regions.

"Identity" describes the relationship between two or more polypeptide sequences or two or more polynucleotide sequences, as determined by comparing the sequences. Identity also means the degree of sequence relatedness (homology) between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., *Nucleic Acids Res,* 1984, 12, 387 BLASTP, BLASTN, and FASTA (Atschul et al., *J. Molec. Biol.* (1990) 215, 403).

Preferably, the amino acid sequence of the protein has at least 60% identity, using the default parameters of the BLAST computer program (Atschul et al., *J. Mol. Biol.* 1990 215, 403-410) provided by HGMP (Human Genome Mapping Project), at the amino acid level, to the amino acid sequences disclosed herein.

More preferably, the protein sequence may have at least 65%, 66%, 67%, 68%, 69%, 70%, 75%, 80%, 85%, 90% and still more preferably 95% (still more preferably at least 96%, 97%, 98% or 99%) identity, at the nucleic acid or amino acid level, to the amino acid sequences as shown herein.

The protein may also comprise a sequence which has at least 60%, 65%, 66%, 67%, 68%, 69%, 70%, 75%, 80%, 85%, 90%, 95%, 96%, 97%, 98%, or 99% identity with a sequence disclosed herein, using the default parameters of the BLAST computer program provided by HGMP, thereto.

A "library" refers to a plurality of VNARs or VNAR fragment sequences or the nucleic acids that encode these sequences. The origin of the library can be from non-natural sources or synthetic in nature where diversity has been engineered into a natural or combination of natural frameworks or can be from a natural source as exemplified from VNAR domains isolated from RNA extracted from an immunized animal.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation or by silica purification. The DNA fragments that are to be ligated together are put in solution in about equimolar amounts. The solution will also contain ATP, ligase buffer, and a ligase such as T4 DNA ligase at about 10 units per 0.5 \ig of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

A "mutation" is a deletion, insertion, or substitution of a nucleotide(s) relative to a reference nucleotide sequence, such as a wild type sequence.

"Natural" or "naturally occurring" VNARs, refers to VNARs identified from a non-synthetic source, for example, from a tissue source obtained ex vivo, or from the serum of an animal of the Elasmobranchii subclass. These VNARs can include VNARs generated in any type of immune response, either natural or otherwise induced. Natural VNARs include the amino acid sequences, and the nucleotide sequences that constitute or encode these antibodies. As used herein, natural VNARs are different than "synthetic VNARs", synthetic VNARs referring to VNAR sequences that have been changed from a source or template sequence, for example, by the replacement, deletion, or addition, of an amino acid, or more than one amino acid, at a certain position with a different amino acid, the different amino acid providing an antibody sequence different from the source antibody sequence.

The term "nucleic acid construct" generally refers to any length of nucleic acid which may be DNA, cDNA or RNA such as MRNA obtained by cloning or produced by chemical synthesis. The DNA may be single or double stranded. Single stranded DNA may be the coding sense strand, or it may be the non-coding or anti-sense strand. For therapeutic use, the nucleic acid construct is preferably in a form capable of being expressed in the subject to be treated.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promotor or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contingent and in reading frame. However, enhancers do not have to be contiguous. Linking is accomplished by ligation at convenient restriction sites. If such sites do not exist, the synthetic oligonucleotide adapters or linkers are used in accord with conventional practice.

"Phage display" is a technique by which variant polypeptides are displayed as fusion proteins to at least a portion of coat protein on the surface of phage, e.g., filamentous phage, particles. Phage display technology allows for the preparation of large libraries of randomized protein variants which can be rapidly and efficiently sorted for those sequences that bind to a target antigen with high affinity. The display of peptide and protein libraries on phage can be used for screening millions of polypeptides for ones with specific binding properties. Polyvalent phage display methods have been used for displaying small random peptides and small proteins through fusions to the genes encoding coat proteins pill, pV III, pVI, pVII or pIX of filamentous phage.

A "phagemid" is a plasmid vector having a bacterial origin of replication, e.g., ColEI, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle. An example of a phagemid display vector is pWRIL-1.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, fl, fd, Pf3 phage or a derivative thereof, or a lambdoid phage, such as lambda, 21, phi80, phi81, or a derivative thereof.

The term "protein" means, in general terms, a plurality of amino acid residues joined together by peptide bonds. It is used interchangeably and means the same as peptide, oligopeptide, oligomer or polypeptide, and includes glycoproteins and derivatives thereof. The term "protein" is also intended to include fragments, analogues, variants and derivatives of a protein wherein the fragment, analogue, variant or derivative retains essentially the same biological activity or function as a reference protein. Examples of protein analogues and derivatives include peptide nucleic acids, and DARPins (Designed Ankyrin Repeat Proteins). A "polypeptide of the invention" is TNFα specific antigen binding molecule as defined herein.

A fragment, analogue, variant or derivative of the protein may be at least 25 preferably 30 or 40, or up to 50 or 100, or 60 to 120 amino acids long, depending on the length of the original protein sequence from which it is derived. A length of 90 to 120, 100 to 1 10 amino acids may be convenient in some instances.

The fragment, derivative, variant or analogue of the protein may be (i) one in which one or more of the amino acid residues are substituted with a conserved or non-conserved amino acid residue (preferably, a conserved amino acid residue) and such substituted amino acid residue may or may not be one encoded by the genetic code, or (ii) one in which one or more of the amino acid residues includes a substituent group, or (iii) one in which the additional amino acids are fused to the mature polypeptide, such as a leader or auxiliary sequence which is employed for purification of the polypeptide. Such fragments, derivatives, variants and analogues are deemed to be within the scope of those skilled in the art from the teachings herein.

"Oligonucleotides" are short-length, single- or double-stranded polydeoxynucleotides that are chemically synthesized by known methods (such as phosphotriester, phosphite, or phosphoramidite chemistry, using solid-phase techniques). Further methods include the polymerase chain reaction (PCR) used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides can be purified on polyacrylamide gels or molecular sizing columns or by precipitation. DNA is "purified" when the DNA is separated from non-nucleic acid impurities (which may be polar, non-polar, ionic, etc.).

A "source" or "template" VNAR", as used herein, refers to a VNAR or VNAR antigen binding fragment whose antigen binding sequence serves as the template sequence upon which diversification according to the criteria described herein is performed. An antigen binding sequence generally includes within a VNAR preferably at least one CDR, preferably including framework regions.

A "transcription regulatory element" will contain one or more of the following components: an enhancer element, a promoter, an operator sequence, a repressor gene, and a transcription termination sequence.

"Transformation" means a process whereby a cell takes up DNA and becomes a "transformant". The DNA uptake may be permanent or transient. A "transformant" is a cell which has taken up and maintained DNA as evidenced by the expression of a phenotype associated with the DNA (e.g., antibiotic resistance conferred by a protein encoded by the DNA).

A "variant" or "mutant" of a starting or reference polypeptide (for example, a source VNAR or a CDR thereof), such as a fusion protein (polypeptide) or a heterologous polypeptide (heterologous to a phage), is a polypeptide that (1) has an amino acid sequence different from that of the starting or reference polypeptide and (2) was derived from the starting or reference polypeptide through either natural or artificial mutagenesis. Such variants include, for example, deletions from, and/or insertions into and/or substitutions of, residues within the amino acid sequence of the polypeptide of interest. For example, a fusion polypeptide of the invention generated using an oligonucleotide comprising a non-random codon set that encodes a sequence with a variant amino acid (with respect to the amino acid found at the corresponding position in a source VNAR or antigen binding fragment) would be a variant polypeptide with respect to a source VNAR or antigen binding fragment. Thus, a variant CDR refers to a CDR comprising a variant sequence with respect to a starting or reference polypeptide sequence (such as that of a source VNAR or antigen binding fragment). A variant amino acid, in this context, refers to an amino acid different from the amino acid at the corresponding position in a starting or reference polypeptide sequence (such as that of a source VNAR or antigen binding fragment). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A "wild-type" or "reference" sequence or the sequence of a "wild-type" or "reference" protein/polypeptide, such as a coat protein, or a CDR of a source VNAR, may be the reference sequence from which variant polypeptides are derived through the introduction of mutations. In general, the "wild-type" sequence for a given protein is the sequence that is most common in nature.

Similarly, a "wild-type" gene sequence is the sequence for that gene which is most commonly found in nature. Mutations may be introduced into a "wild-type" gene (and thus the protein it encodes) either through natural processes or through man induced means. The products of such processes are "variant" or "mutant" forms of the original "wild-type" protein or gene.

General methods for DNA manipulation, transfection methods and culture methods are well known to those skilled in the art. In this respect, reference is made to Molecular Cloning: A Laboratory Manual (Fourth Edition) Cold Spring Harbor Publishing.

Isolation of VNARs

VNAR domains may be obtained from phage-displayed libraries constructed using tissues from target-immunized sharks (Dooley, H., et al. *Mol Immunol,* 2003. 40(1): p. 25-33; Nuttall, S. D., et al, Proteins, 2004. 55(1): p. 187-97; and Dooley, H., et al., *Proc Natl Acad Sci USA,* 2006. 103(6): p. 1846-51), WO2003/014161, incorporated by reference describes a useful method for immunizing a shark and obtaining binding domains.

VNAR binding domains may also be obtained from synthetic libraries comprising VNAR sequences. WO2014/173959, incorporated by reference, describes a useful method for developing VNAR libraries and obtaining binding domains.

Additionally it has been shown that libraries with synthetic diversity targeted to CDR3 can be used to obtain binding domains based on VNAR structures (Nuttall, S. D., et al. *Mol Immunol,* 2001. 38(4): p. 313-26; Nuttall, S. D., et al. *Eur J Biochem,* 2003. 270(17): p. 3543-54; Shao, C. Y., et al. *Mol Immunol,* 2007. 44(4): p. 656-65 and Liu, J. L., et al. *BMC Biotechnol,* 2007. 7: p. 78; WO2005/118629.

VNARS of the invention may be further adapted to reduce potential immunogenicity when administered to man (humanization).

Humanization of antibody variable domains is a technique well-known in the art to modify an antibody which has been raised, in a species other than humans, against a therapeutically useful target so that the humanized form may avoid unwanted immunological reaction when administered to a human subject. The methods involved in humanization are summarized in Almagro J. C and William Strohl W. Antibody Engineering: *Humanization, Affinity Maturation, and Selection Techniques in Therapeutic Monoclonal Antibodies: From Bench to Clinic*. Edited by An J. 2009 John Wiley & Sons, Inc and in Strohl W. R. and Strohl L. M., *Therapeutic Antibody Engineering*, Woodhead Publishing 2012.

Although IgNARs have distinct origins compared to immunoglobulins and have very little sequence homology compared to immunoglobulin variable domains there are some structural similarities between immunoglobulin and IgNAR variable domains, so that similar processes can be applied to the VNAR domain. For example, WO2013/167883, incorporated by reference, provides a description of the humanization of VNARs, see also Kovalenko O. V., et al. *J Biol Chem.* 2013. 288(24): p. 17408-19.

Protein Expression

Nucleic acid sequences encoding antigen specific antigen binding molecules or multi-domain specific binding molecules of the invention may be present in a nucleic acid construct. Such nucleic acid constructs may be in the form of a vector, for example, an expression vector, and may include, among others, chromosomal, episomal and virus-derived vectors, for example, vectors derived from bacterial plasmids, from bacteriophage, from transposons, from yeast episomes, from insertion elements, from yeast chromosomal elements, from viruses such as baculo-viruses, papova-viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host, may be used for expression in this regard.

The nucleic acid construct may suitably include a promoter or other regulatory sequence which controls expression of the nucleic acid. Promoters and other regulatory sequences which control expression of a nucleic acid have been identified and are known in the art. The person skilled in the art will note that it may not be necessary to utilise the whole promoter or other regulatory sequence. Only the minimum essential regulatory element may be required and, in fact, such elements can be used to construct chimeric sequences or other promoters. The essential requirement is, of course, to retain the tissue and/or temporal specificity. The promoter may be any suitable known promoter, for example, the human cytomegalovirus (CMV) promoter, the CMV immediate early promoter, the HSV thymidine kinase, the early and late SV40 promoters or the promoters of retroviral LTRs, such as those of the Rous Sarcoma virus (RSV) and metallothionine promoters such as the mouse metallothionine-I promoter. The promoter may comprise the minimum comprised for promoter activity (such as a TATA element, optionally without enhancer element) for example, the minimum sequence of the CMV promoter. Preferably, the promoter is contiguous to the nucleic acid sequence.

As stated herein, the nucleic acid construct may be in the form of a vector. Vectors frequently include one or more expression markers which enable selection of cells transfected (or transformed) with them, and preferably, to enable a selection of cells containing vectors incorporating heterologous DNA. A suitable start and stop signal will generally be present.

The vector may be any suitable expression vector, such as pET. The vector may include such additional control sequences as desired, for example selectable markers (e.g. antibiotic resistance, fluorescence, etc.), transcriptional control sequences and promoters, including initiation and termination sequences.

The promoter may be any suitable promoter for causing expression of the protein encoded by a nucleic acid sequence of the invention, e.g. a CMV promoter, human phosphoglycerate kinase (hPGK) promoter.

Such vectors may be present in a host cell. Representative examples of appropriate host cells for expression of the nucleic acid construct of the invention include virus packaging cells which allow encapsulation of the nucleic acid into a viral vector; bacterial cells, such as Streptococci, Staphylococci, *E. coli, Streptomyces* and *Bacillus subtilis*; single cells, such as yeast cells, for example, *Saccharomyces cerevisiae*, and *Aspergillus* cells; insect cells such as *Drosophila* S2 and *Spodoptera* Sf9 cells, animal cells such as CHO, COS, C127, 3T3, PHK.293, and Bowes Melanoma cells and other suitable human cells; and plant cells e.g. *Arabidopsis thaliana*. Suitably, the host cell is a eukaryotic cell, such as a CHO cell or a HEK293 cell.

Introduction of an expression vector into the host cell can be achieved by calcium phosphate transfection, DEAE-dextran mediated transfection, microinjection, cationic-lipid-mediated transfection, electroporation, transduction, scrape loading, ballistic introduction, infection or other methods. Such methods are described in many standard laboratory manuals, such as Sambrook et al, Molecular Cloning, a Laboratory Manual, Second Edition, Cold Spring Harbor Laboratory Press, Cold Spring Harbor, N.Y. (1989).

Mature proteins can be expressed in host cells, including mammalian cells such as CHO cells, yeast, bacteria, or other cells under the control of appropriate promoters. Cell-free translation systems can be employed to produce such proteins using RNAs derived from the nucleic acid construct of the third aspect of the present invention. Appropriate cloning and expression vectors for use with prokaryotic and eukaryotic hosts are described by Sambrook et al, Molecular Cloning, a Laboratory Manual, Second Edition, Cold Spring Harbor Laboratory Press, Cold Spring Harbor, N.Y. (1989).

The invention also provides a host cell comprising any of the polynucleotides and/or vectors of the invention described herein. According to the invention, there is provided a process for the production of an antigen specific antigen binding molecule or multi-domain specific binding molecule of the invention, comprising the step of expressing a nucleic acid sequence encoding said molecule in a suitable host cell as defined herein.

Proteins can be recovered and purified from recombinant cell cultures by standard methods including ammonium sulphate or ethanol precipitation, acid extraction, anion or cation exchange chromatography, phosphocellulose chromatography, hydrophobic interaction chromatography, affinity chromatography, hydroxyapatite chromatography, lectin and/or heparin chromatography. For therapy, the nucleic acid construct, e.g. in the form of a recombinant vector, may be purified by techniques known in the art, such as by means of column chromatography as described in Sambrook et al, Molecular Cloning, a Laboratory Manual, Second Edition, Cold Spring Harbor Laboratory Press, Cold Spring Harbor, N.Y. (1989).

This aspect of the invention therefore extends to processes for preparing a fusion protein of the invention comprising production of the fusion protein recombinantly by expression in a host cell, purification of the expressed fusion protein by means of peptide bond linkage, hydrogen or salt bond or chemical cross linking. In some embodiments of this aspect of the invention, the fusion protein could be prepared using hydrogen or salt bonds where the peptide is capable or multimerisation, for example dimerisation or trimerisation.

The antigen specific antigen binding molecule or multi-domain specific binding molecule may comprise additional N-terminal or C-terminal sequences which are cleaved off prior to use which may assist in purification and/or isolation during processes for the production of the molecule as described herein. For example, $(Ala)_3(His)_6$ at the C-terminal end of the molecule.

Also included within the invention are variants, analogues, derivatives and fragments having the amino acid sequence of the protein in which several e.g. 5 to 10, or 1 to 5, or 1 to 3, 2, 1 or no amino acid residues are substituted, deleted or added in any combination. Especially preferred among these are silent substitutions, additions and deletions, which do not alter the properties and activities of the protein of the present invention. Also especially preferred in this regard are conservative substitutions where the properties of a protein of the present invention are preserved in the variant form compared to the original form. Variants also include fusion proteins comprising an antigen specific antigen binding molecule according to the invention.

As discussed above, an example of a variant of the present invention includes a protein in which there is a substitution of one or more amino acids with one or more other amino acids. The skilled person is aware that various amino acids have similar properties. One or more such amino acids of a substance can often be substituted by one or more other such amino acids without interfering with or eliminating a desired activity of that substance. Such substitutions may be referred to as "non-conservative" amino acid substitutions.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

Amino acid deletions or insertions may also be made relative to the amino acid sequence for the fusion protein referred to above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence of the fusion protein above can also be made. This may be done to alter the properties of a substance of the present invention (e.g. to assist in identification, purification or expression, as explained above in relation to fusion proteins).

Amino acid changes relative to the sequence for the fusion protein of the invention can be made using any suitable technique e.g. by using site-directed mutagenesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

A protein according to the invention may have additional N-terminal and/or C-terminal amino acid sequences. Such sequences can be provided for various reasons, for example, glycosylation.

A fusion protein may comprise an antigen specific antigen binding molecule of the present invention fused to a heterologous peptide or protein sequence providing a structural element to the fusion protein. In other embodiments, the fusion protein may comprise an antigen specific antigen binding molecule of the present invention fused with a molecule having biological activity. The molecule may be a peptide or protein sequence, or another biologically active molecule.

For example, the antigen specific antigen binding molecule may be fused to a heterologous peptide sequence which may be a poly-amino acid sequence, for example a plurality of histidine residues or a plurality of lysine residues (suitably 2, 3, 4, 5, or 6 residues), or an immunoglobulin domain (for example an Fc domain).

References to heterologous peptides sequences include sequences from other mammalian species, such as murine and human and any heterologous peptides sequences originated from other VNAR domains.

Where the fusion protein comprises an antigen specific antigen binding molecule of the present invention fused with a molecule having biological activity, a biologically active moiety may be a peptide or protein having biological activity such as an enzyme, immunoglobulin, cytokine or a fragment thereof. Alternatively, the biologically active molecule may be an antibiotic, an anti-cancer drug, an NSAID, a steroid, an analgesic, a toxin or other pharmaceutically active agent. Anti-cancer drugs may include cytotoxic or cytostatic drugs.

In some embodiments, the fusion protein may comprise an antigen specific antigen binding molecule of the invention fused to another immunoglobulin variable or constant region, or another antigen specific antigen binding molecule of the invention. In other words, fusions of antigen specific antigen binding molecules of the invention of variable length, e.g. dimers, trimers, tetramers, or higher multimer (i.e. pentamers, hexamers, heptamers octamers, nonamers, or decamers, or greater). In specific embodiments this can be represented as a multimer of monomer VNAR subunits.

In fusion proteins of the present invention, the antigen specific antigen binding molecule may be directly fused or linked via a linker moiety to the other elements of the fusion protein. The linker may be a peptide, peptide nucleic acid, or polyamide linkage. Suitable peptide linkers may include a plurality of amino acid residues, for example, 4, 5, 6, 7, 8, 9, 10, 15, 20 or 25 amino acids., such as $(Gly)_4$, $(Gly)_5$, $(Gly)_4Ser$, $(Gly)_4(Ser)(Gly)_4$, or combinations thereof or a multimer thereof (for example a dimer, a trimer, or a tetramer, or greater). For example, a suitable linker may be $(GGGGS)_3$. Alternative linkers include $(Ala)_3(His)_6$ or multimers thereof. Also included is a sequence which has at least 50%, 60%, 70%, 80%, 90%, 95% or 99% identity, using the default parameters of the BLAST computer program provided by HGMP, thereto.

Vectors constructed as described in accordance with the invention are introduced into a host cell for amplification and/or expression. Vectors can be introduced into host cells using standard transformation methods including electroporation, calcium phosphate precipitation and the like. If the vector is an infectious particle such as a virus, the vector itself provides for entry into the host cell. Transfection of host cells containing a replicable expression vector which encodes the gene fusion and production of phage particles according to standard procedures provides phage particles in which the fusion protein is displayed on the surface of the phage particle.

Replicable expression vectors are introduced into host cells using a variety of methods. In one embodiment, vectors can be introduced into cells using: Cells are grown in culture in standard culture broth, optionally for about 6-48 hours (or to OD600=0.6-0.8) at about 37° C., and then the broth is centrifuged and the supernatant removed (e.g. decanted). Initial purification is preferably by resuspending the cell pellet in a buffer solution (e.g. 1.0 mM HEPES pH 7.4) followed by recentrifugation and removal of supernatant. The resulting cell pellet is resuspended in dilute glycerol (e.g. 5-20% v/v) and again recentrifuged to form a cell pellet and the supernatant removed. The final cell concentration is obtained by resuspending the cell pellet in water or dilute glycerol to the desired concentration.

The use of higher DNA concentrations during electroporation (about 10×) increases the transformation efficiency and increases the amount of DNA transformed into the host cells. The use of high cell concentrations also increases the efficiency (about 10×). The larger amount of transferred DNA produces larger libraries having greater diversity and representing a greater number of unique members of a combinatorial library. Transformed cells are generally selected by growth on antibiotic containing medium.

Pharmaceutical Compositions and Uses

According to the invention, there is provided a pharmaceutical composition of antigen specific antigen binding molecule or multi-domain specific binding molecule of the invention. Such compositions include fusion proteins comprising said antigen specific antigen binding molecules.

The pharmaceutical composition may also comprise an antigen specific antigen binding molecule of the present invention fused to a therapeutic protein, or a fragment thereof. The therapeutic protein may be a hormone, a growth factor (e.g. TGFβ, epidermal growth factor (EGF), platelet derived growth factor (PDGF), nerve growth factor (NGF), colony stimulating factor (CSF), hepatocyte growth factor, insulin-like growth factor, placenta growth factor); a differentiation factor; a blood clotting factor (for example, Factor VIIa, Factor VIII, Factor IX, VonWillebrand Factor or Protein C) or another protein from the blood coagulation cascade (for example, antithrombin); a cytokine e.g. an interleukin, (e.g. IL1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 or IL-33 or an interferon (e.g. IFN-α, IFN-β and IFN-γ), tumour necrosis factor (TNF), IFN-γ inducing factor (IGIF), a bone morphogenetic protein (BMP, e.g. BMP-1, BMP-2, BMP-3, BMP-4, BMP-4, BMP-5, BMP-6, BMP-7, BMP-8, BMP-9, BMP10, BMP-11, BMP-12, BMP-13); an interleukin receptor antagonist (e.g. IL-1ra, IL-1RII); a chemokine (e.g. MIPs (Macrophage Inflammatory Proteins) e.g. MIP1α and MIP1β; MCPs (Monocyte Chemotactic Proteins) e.g. MCP1, 2 or 3; RANTES (regulated upon activation normal T-cell expressed and secreted)); a trophic factor; a cytokine inhibitor; a cytokine receptor; an enzyme, for example a free-radical scavenging enzyme e.g. superoxide dismutase or catalase or a pro-drug converting enzyme (e.g. angiotensin converting enzyme, deaminases, dehydrogenases, reductases, kinases and phosphatases); a peptide mimetic; a protease inhibitor; a tissue inhibitor of metalloproteinases (TIMPs e.g. TIMP1, TIMP2, TIMP3 or TIMP4) or a serpin (inhibitors of serine proteases).

In other embodiments of the invention, the therapeutic protein in the fusion protein may be an antibody, or a engineered fragment thereof, including Fab, Fc, $F(ab')_2$ (including chemically linked $F(ab')_2$ chains), Fab', scFv (including multimer forms thereof, i.e. di-scFv, or tri-scFv), sdAb, or BiTE (bi-specific T-cell engager). Antibody fragments also include variable domains and fragments thereof, as well as other VNAR type fragments (IgNAR molecules).

The pharmaceutical composition may be composed of a number of antigen specific antigen binding molecules of the invention, for example dimers, trimers, or higher order multimers, i.e. 2, 3, 4, 5, 6, 7, or 8-mers, fused to the therapeutic protein.

The fusion of the antigen specific antigen binding molecules of the invention to the therapeutic protein may at any convenient site on the protein and may be N-, C- and/or N-/C-terminal fusion(s). In one embodiment of the invention, the fusion of the antigen specific antigen binding molecules of the invention is to both the N- and C-terminals of a therapeutic protein.

Pharmaceutical compositions of the invention may comprise any suitable and pharmaceutically acceptable carrier, diluent, adjuvant or buffer solution. The composition may comprise a further pharmaceutically active agent. Such carriers may include, but are not limited to, saline, buffered saline, dextrose, liposomes, water, glycerol, ethanol and combinations thereof.

Such compositions may comprise a further pharmaceutically active agent as indicated. The additional agents may be therapeutic compounds, e.g. anti-inflammatory drugs, cytotoxic agents, cytostatic agents or antibiotics. Such additional agents may be present in a form suitable for administration to patient in need thereof and such administration may be simultaneous, separate or sequential. The components may be prepared in the form of a kit which may comprise instructions as appropriate.

The pharmaceutical compositions may be administered in any effective, convenient manner effective for treating a patient's disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg, 2 mg/kg or up to 4 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

According to the invention, there is provided an antigen specific antigen binding molecule or multi-domain specific binding molecule of the invention for use in medicine. This aspect of the invention therefore extends to the use of such of an antigen specific antigen binding molecule or multi-domain specific binding molecule of the invention in the manufacture of a medicament for the treatment of a disease in a patient in need thereof. An antigen specific antigen binding molecule of the invention can also be used to prepare a fusion protein comprising such a specific binding molecule as defined above in relation to pharmaceutical compositions of the invention.

Such uses also embrace methods of treatment of diseases in patients in need of treatment comprising administration to the patient of a therapeutically effective dosage of a pharmaceutical composition as defined herein comprising an antigen specific antigen binding molecule or multi-domain specific binding molecule of the invention.

As used herein, the term "treatment" includes any regime that can benefit a human or a non-human animal. The treatment of "non-human animals" in veterinary medicine extends to the treatment of domestic animals, including horses and companion animals (e.g. cats and dogs) and farm/agricultural animals including members of the ovine, caprine, porcine, bovine and equine families. The treatment may be a therapeutic treatment in respect of any existing condition or disorder, or may be prophylactic (preventive treatment). The treatment may be of an inherited or an acquired disease. The treatment may be of an acute or chronic condition. The treatment may be of a condition/disorder associated with inflammation and/or cancer. The antigen specific antigen binding molecules or multi-domain specific binding molecules of the invention may be used in the treatment of a disorder, including, but not limited to osteoarthritis, scleroderma, renal disease, rheumatoid arthritis, inflammatory bowel disease, multiple sclerosis, atherosclerosis, or any inflammatory disease.

The antigen specific antigen binding molecules or multi-domain specific binding molecules of the present invention may also be used to investigate the nature of a disease condition in a patient. The antigen specific antigen binding molecules or multi-domain specific binding molecules may be used to prepare images of sites of disease in the body of a subject using imaging techniques such as X-ray, gamma-ray, or PET scanning, or similar. The invention may therefore extend to a method of imaging a site of disease in a subject, comprising administration of a suitably detectably labeled antigen specific antigen binding molecule or multi-domain specific binding molecules to a subject and scanning the subject's body subsequently. Alternatively, administration of said molecules to a subject may provide for a test result by analysing a sample from the subject following administration of the molecule. Such embodiments may include a method of diagnosis of a disease or medical condition in a subject comprising administration of an antigen specific antigen binding molecule or multi-domain specific binding molecule of the invention. The multi-domain specific binding molecules of the invention may be especially useful with regard to diagnostic sensitivity, in particular when multiple VNARs that target different epitopes on the same antigen are used.

Measurement of Binding

Detection and measurement of binding of a VNAR to a target can be measured in a number of ways well known in the art including ELISA and surface plasmon resonance.

Functional Activity

VNARs of the invention may function in a number of ways including binding to and neutralizing the biological effects of a molecule such as a cytokine, binding to a receptor preventing ligand binding or causing a biological effect post-binding.

Methods of measuring the functional activity of a binding domain are known in the art.

The present invention is illustrated in further details by the following non-limiting examples.

Example 1: Isolation of Specific Antigen Binding VNARs

A. TNF Binding VNARs

Immunization and Selection

Nurse sharks [*Ginglymostoma cirratum*] were placed in containers containing artificial sea water containing 0.1% (w/v) tricaine methanesulfonate [MS-222]. Following attainment of desired level of narcosis, they were removed for immunisation or bleeding. hTNFα [250 μg] emulsified in complete Freund's adjuvant [CFA] was injected using a 20 gauge needle into the lateral fin of the shark. Boosts were given at 4 week intervals intravenously into the caudal vein as soluble antigen in Phosphate buffered saline (PBS) [sample 0.45 μM sterile filtered]. Blood samples were collected from the caudal vein into a 30 ml syringe containing 200 μl porcine heparin [1000 U/ml in PBS]. Blood samples were spun at 2000 rpm for 10 min to separate blood cells from plasma. The plasma supernatant fraction was carefully removed into a sterile tube with RNA stabilisation buffer, stored at −80° C.

Detection of hTNFα Specific IgNAR in Shark Serum

An ELISA plate was coated with 1 μg/ml rhTNFα, incubated at 37° C. for 1 h followed by blocking in 4% (w/v) MPBS for 1 h at 37° C. Shark sera [pre-bleed, bleed 4 and 5] were added to designated wells in a 1:2 dilution series and incubated for 1 h at 37° C. The plate was incubated with 100 μl/well of purified anti-Nurse shark IgNAR monoclonal antibody [GA8] at a dilution of 1:200 in PBS. Binding signal was generated by the addition of anti-mouse IgG-HRP at a dilution of 1:2000 in 0.1% (v/v) Tween-20 PBS (PBST), incubated at room temperature for 1 h. The plate was washed 3× with PBST after every step, and a further 3×PBS after incubation with anti-mouse IgG-horseradish peroxidase (HRP) conjugated antibody [Sigma]. The plate developed by adding SureBlue TMB Microwell Peroxidase Substrate [Thermo Scientific], the reaction stopped with 1 M $H_2SO_4$ and absorbance measured at 450 nm wavelength using a microplate reader.

rhTNFα specific IgNAR response following each immunisation boost was measured by binding ELISA using sera obtained after each boost. GA8, a mouse monoclonal anti-Nurse shark IgNAR antibody, diluted as hybridoma tissue culture supernatant in PBS was used as the detection antibody (Haines et al., 2005; Müller, et al. 2012). Result showed a convincing trend of IgNAR increase over time following immunisation as shown in bleeds 4 and 5, also a background response seen in the pre-bleed sample suggest no significant rhTNFα-specific IgNAR response prior to immunisation [FIG. 1].

Total RNA Isolation from PBLs and PCR Amplification

Peripheral blood lymphocytes [PBLs] were harvested from the plasma of the bleed with the best IgNAR response [Bleed 5] and total RNA prepared. Total RNA from the harvested PBLs was used at approximately 2 μg/μl as template for cDNA synthesis using Superscript III First strand synthesis supermix [Invitrogen]. cDNA was generated with the framework specific primers NARF4For1 [5'-ATA ATC AAG CTT GCG GCC GCA TTC ACA GTC ACG ACA GTG CCA CCT C-3'] (SEQ ID NO. 74) and NARF4For2 [5'-ATA ATC AAG CTT GCG GCC GCA TTC ACA GTC ACG GCA GTG CCA TCT C-3'] (SEQ ID NO. 75) (see Dooley, H., et al, *Mol. Immunol,* 2003. 40(1): p. 25-33). Following cDNA synthesis, the common framework one specific primer NARF1Rev [5'-ATA ATA AGG AAT TCC ATG GCT CGA GTG GAC CAA ACA CCG-3'] (SEQ ID NO. 76) was introduced and IgNAR V region DNA amplified using a 3-step polymerase chain reaction (PCR) amplification protocol. The resultant PCR product of approximately 400 base pairs was ran on 1.5% agarose gel, and NAR V region cut out and purified [QIAquick purification kit, QIAGEN]. Purified DNA was digested at the primer-encoded restriction sites [underlined] with the restriction enzymes NcoI and NotI [New England Biolabs], and re-purified.

Library Construction

The Phagemid vector pHEN2 was digested with the restriction enzymes NcoI and NotI, PCR purified [QIAquick PCR purification] and ligated to similarly prepared PCR product. Ligated material was transformed into Electroporation-competent *E. coli* TG1 cells [Lucigen]. Transformed cells were plated on TYE agar plates containing 2% glucose [w/v], 100 μg/ml ampicillin and grown overnight at 37° C. Library size was calculated and colonies scraped from plates and aliquots of the library stock stored at −80° C.

Phage Display Selection

A single aliquot of library stock equivalent to OD600 of 0.1 was added to 2×TY growth media containing 2% glucose [w/v], 100 μg/ml ampicillin, and grown at 37° C. to mid-log phase [OD600 of 0.4 to 0.6] prior to infection with M13K07 helper phage [New England Biolabs]. Library expression was conducted overnight in 2×TY media, 0.2% glucose, 100 μg/ml ampicillin and 50 μg/ml kanamycin at 30° C. Phage were precipitated from the culture supernatant with polyethylene glycol (PEG) and used for bio-panning. The library was panned against biotinylated rhTNFα captured on Dynabeads® M-280 streptavidin beads [Dynabeads, Invitrogen]. Library phage and Dynabeads® M-280 streptavidin were separately pre-blocked with block solution [3% (w/v) milk, 1% (w/v) BSA in PBS] for 1 h, rotating at room temperature. Biotinylated-rhTNFα [400 nM] was added to blocked beads and incubated for 1 h, rotating at room temperature. In a different tube, library phage was incubated with previously blocked streptavidin beads for 1 h rotating at room temperature. Unbound phage was recovered using the Dynabeads magnetic rack and recovered phage is here-in referred to as deselected phage. Phage were deselected by incubating with blocked beads, 1 h rotating at room temperature. Biotin-rhTNFα decorated beads were incubated with deselected phage for 1 h, rotating at room temperature. Beads were washed 5×PBST and 5×PBS prior to a strict 8 min elution with 400 μl of 100 mM Triethylamine (TEA), and neutralised by adding 200 μl of 1 M Tris-HCl PH 7.5. Mid-log phase *E. coli* TG1 cells [10 ml] were infected with 400 μl eluted phage for 30 min, at 37° C. Then grown overnight at 37° C. on TYE agar plates containing 2% glucose (w/v), 100 μg/ml ampicillin. Three further rounds of selection were conducted and stringency was increased in round 3 and 4 by reducing the concentration of biotin-rhTNFα to 200 nM.

Screening and Selection of Clones

Enrichment of antigen binding monoclonal phage was evaluated using ELISA plates coated with 1 μg/ml rhTNFα, blocked with 4% [w/v] Milk-PBS. Binding was detected with anti-M13-HRP conjugated monoclonal antibody [GE Healthcare]. Also monoclonal phage was analysed for selectivity and specificity against Streptavidin and HSA coated ELISA plates respectively.

The library was subjected to four iterative rounds of panning against rhTNFα. The biopanning antigen concentration was kept constant for rounds 1 and 2 but was reduced by half for subsequent rounds of panning in a bid to favour high-affinity binders. Enrichment of positive monoclonal phage binders were evaluated at the end of each round of biopanning for rhTNFα binding by ELISA. A steady increase in antigen binding was observed from pre-selected clones through round 2, with a drop in the number of monoclonal phage binders after rounds 3 and 4. rhTNFα monoclonal binders increased from about 6% [11/184] in round 0 [pre-selected library] to 99.46% [183/184] following round 2.

A number of unique sequences were identified from the library panning. These include VNARs named D1, C4 and B4.

| | FW1 | CDR1 |
|---|---|---|
| D1 | ARVDQTPQTITKETGESL TINCVLRDS | HCATSS |
| C4 | ARVDQTPQTITKETGESL TINCVLRDS | NCGLSS |
| B4 | ARVDQTPQTITKETGESL TINCVLRDS | NCALSS |
| | FW2 | HV2 |
| D1 | TYWYRKKSGS | TNEESISKG |
| C4 | TYWYRKKSGS | TNEESISKG |
| B4 | MYWYRKKSGS | TNEESISKG |
| | FW3a | HV4 |
| D1 | GRYVETVN | SGSKS |
| C4 | GRYVETIN | EGSKS |
| B4 | GRYVETVN | SGSKS |
| | FW3b | CDR3 |
| D1 | FSLRINDLTVEDSGTY RCAS | ECQYGLAEY_____________DV |
| C4 | FSLRINDLTVEDSGTY RCKL | SWWTQNWRCSNS__________DV |
| B4 | FSLRINDLTVEDSGTY RCKV | YIPCIDELVYMISGGTSGPIH_DV |
| | FW4 | |
| D1 | YGGGTVVTVN SEQ ID NO 2 | |
| C4 | YGGGTVVTVN SEQ ID NO 7 | |
| B4 | YGGGTVVTVN SEQ ID NO 12 | |

-continued

The Cysteine (C) residues in CDR1 and CDR3 (double underlined) are typical of Type II VNARs and are observed to form a second disulphide bridge in addition to the canonical Immunoglobulin superfamily bridge between the Cysteines in FW1 and FW3b (single underlined).

Expression of VNARs that Bind to TNFα

Preparation of Soluble VNAR Protein in Cytoplasm of SHuffle Cells

The IgNAR V region inserts of interest identified from the monoclonal phage screening were cloned into the expression vector pET28b (+) (Novagen) via the XbaI and EcoRI restriction enzyme sites. VNAR DNA was prepared from *E. coli* TG1 culture (using QIAprep miniprep kit, QIAGEN) and PCR amplified using in-house designed primer pair XbaI_NARFW1_#127 (SEQ ID 26) and EcoRI_stop_myc_#129 (SEQ ID 29) introducing cloning sites XbaI and EcoRI respectively, while primer SEQ ID 29 incorporated c-myc, 6× Histidine tags and a stop codon into the VNAR gene sequence. Purified VNAR DNA PCR product and pET28b (+) plasmid DNA were digested at 37° C., 2 h with 50 U XbaI and 10 U EcoRI-HF. Digested samples were purified, ligated and transformed into electrocompetent *E. coli* SHuffle® T7 Express cells [New England Biolabs], and selected on TYE agar plates containing 50 μg/ml kanamycin. The VNAR anti-hTNFα-D1, C4 and B4 fusion proteins were expressed in the cytoplasm of SHuffle® cells upon induction with IPTG at 30° C. Cells were harvested by centrifugation, and the cell pellet treated with Bugbuster™ protein extraction reagent [Novagen] to lyse cells and release soluble protein. The VNAR soluble protein was purified by immobilised metal affinity chromatography [IMAC] via the hexa-histidine tail, and eluted from IMAC resin with 500 mM Imidazole, pH 8. Protein samples were dialysed against PBS, pH 7.4 before use. Protein concentration was determined using Ultraspec 6300 pro UV/Visible spectrophotometer [Amersham, Biosciences].

Total purified protein was visualised on Coomassie blue stained SDS-PAGE. The purified VNAR monomeric protein migrated as a single band of approximately 14 kDa [including hexa-histidine and c-myc tags] with no evidence of protein aggregation. Purity was estimated to be about 90% based on an SDS-PAGE gel

Determination of Protein Integrity and Purity

Denaturing sodium dodecyl sulphate-polyacrylamide gel electrophoresis [SDS-PAGE] was used to assess purified protein purity and size. Protein samples were prepared in NuPAGE® LDS sample buffer [Life Technologies] containing 5% β-mercaptoethanol and heated to 95° C. for 5 min. Denatured protein samples were loaded onto NuPAGER 4-12% Bis-Tris Gel [Life Technologies] immersed in a MES SDS running buffer, and electrophoresis carried out at 160 volts, for 55 min. A Full Range recombinant protein molecular weight marker [GE Healthcare] was used as molecular weight ladder standard. The gel was washed in distilled water, and stained with Coomassie blue for 1 h followed by an overnight de-staining process in distilled water.

Determination of Selectivity and Specificity

Specificity and selectivity of binding was determined on ELISA plates coated with either 1 µg/ml Biotin-TNF and rhTNFα, or 10 µg/ml HSA, BSA, streptavidin, single stranded DNA, thyroglobulin or lysozyme. ELISA plates were suitably blocked in 4% [w/v] Milk-PBS, and protein samples loaded at a top concentration of 1 µg/ml and serial dilution performed. Binding was detected with an anti-c-myc-HRP conjugated monoclonal antibody [Roche].

To obtain more accurate binding data certain molecules were also measured using surface plasmon resonance with BIACore T200 or Octet RED96 instruments.

BIACore™ T200 (GE Healthcare)

Amine coupling is a very common approach for immobilising the ligand to the chip surface. The chip surface has a dextran matrix derivatised with carboxyl groups, which after activation with N-hydroxysuccinimide (NHS) and 1-ethyl-3-(3-dimethylaminopropyl)carbodiimide (EDC), form reactive succinimide esters which allows the covalent capturing of the ligand via any available primary amine groups (e.g. Lysine) on the ligand.

TNFα was diluted 1/10 in 10 mM Sodium acetate buffer pH 5.5 and injected unto the activated chip. An "aim for" software immobilisation wizard or a specific time period may be used to aim-for 200 RU of immobilised TNFα. In addition the run buffer was changed to PBS in absence of 0.05% Tween20 as it was thought perhaps the detergent may affect ligand activity. A final ligand immobilised level of 202 RU was obtained.

Start-up cycles were composed of a 60s buffer injection at a flow rate of 30 µl/min followed by a 30s dissociation period. The anti-TNFα sample cycles included a 120s injection of sample at 30 µl/min followed by a regeneration step of a 60 s injection of 10 mM glycine pH2 at 30 µl/min. Finally, a 120s stabilisation period was included at the end of each cycle to allow for baseline equilibration prior to beginning the next cycle.

The concentration series screened and the dissociation periods were variable and were as follows: All samples were assayed at a top start concentration of 100 nM and a 1200s dissociation time, with the exception of all monomeric domains D1, C4, B4, TNF43 and TNF30 where the dissociation time was 600 s. B4 and TNF43 VNAR were assayed at top start concentrations of 500 nM and 5 µM respectively. 5 blank sample cycles were included to be used to generate double referenced datasets.

Binding responses for domain were analysed using the BIACore™ T200 evaluation software and double referenced data was fitted to a 1: 1 Langmuir model to obtain kinetic and affinity characterisation.

OCTET® RED96 [ForteBio™]

Biolayer interferometry (BLI) was used to determine the equilibrium dissociation constant ($K_D$). Dip and read streptavidin biosensors were rehydrated for at least 30 min in PBS, pH 7.4. Sensors were loaded with 20 µg/ml biotinylated hTNF-α and anti-TNF-α VNAR proteins were serially diluted with top concentration of 100 nM while TNF43 and VNAR negative controls were assayed at top concentration of 1 µM. Binding association was monitored for 10 min followed by a 5 min dissociation time. For all anti-TNF-α VNAR measurements, kinetic data sets were fitted using a two-site model since the curve fit data showed complex multiphasic curves, however for the control anti-TNF-α nanobody, TNF30 a 1:1 Langmuir binding with Mass Transport model was used.

The data obtained is shown in TABLE 1. TABLE 1 indicates that the monomer VNARs tested have at least a 500 fold lower binding affinity for TNFα compared with the TNF 43 VNAR.

TABLE 1

TNF VNAR SPR binding data

| Binding molecule | $K_a$ ($M^{-1} S^{-1}$) | $K_d$ ($S^{-1}$) | KD [BIAcore T200] | KD [Octet ForteBio] |
|---|---|---|---|---|
| D1 | 1.2E+03 | 2.06E−02 | 50 nM | 1.9 nM |
| C4 | 2.8E+05 | 3.3E−02 | 70 nM | 6.4 nM |
| TNF30 VHH | 5E+04 | 1.6E−07 | 16 nM | N/A |
| TNF43 VNAR | Very Weak affinity- No binding data obtained. Highest conc tested 500 nM | | | >1000 nM |
| BB10 | Negative control- No binding data obtained | | | >1000 nM |
| D1-D1 | 5E+05 | 3.16E−04 | n/a | 0.6 nM |
| D1-C4 | 1.8E+05 | 1.07E−04 | 5 nM | 0.17 nM |
| D1-B4 | 2.7E+05 | 5E−04 | n/a | 15.9 nM |
| TNF30-TNF30 | 3E+04 | 3E−05 | n/a | 0.4 nM |
| D1-BA11-D1 | 1.9E+06 | 2E−04 | 4 nM | 0.1 nM |
| D1-BA11-C4 | 2E+05 | 1.6E−04 | 0.6 nM | 0.13 nM |
| D1-BA11-B4 | 1.7E+06 | 6E−03 | n/a | 0.33 nM |
| TNF30-BA11-TNF30 | 9E+04 | 1.5E−05 | 0.4 nM | 0.38 nM |

In Vitro Neutralisation Assay

To determine the neutralisation capacity and $ND_{50}$ for the VNAR domains, mouse fibrosarcoma cell line L929 [ATCC, CCL-1] was grown in Dulbecco modified eagle medium [GIBCO] supplemented with 10% heat inactivated fetal bovine serum [GIBCO] and 1 µg/ml actinomycin D [R & D systems]. For each VNAR clone 5,000 cells per well were incubated in a 96 well plate in duplicate for 24 h at 37° C.

with 5% $CO_2$ and humidity. $LD_{50}$ [1× at 0.25 ng/ml] and 10×$LD_{50}$ [2.5 ng/ml] of rhTNFα was added to wells containing either VNAR proteins serially diluted or cells alone. Plates were then incubated for 24 h at 37° C. with 5% $CO_2$ and humidity. Cytotoxicity or cell survival was measured by adding 50 μl of 1:20 dilution WST-1 cell proliferation reagent [Roche], and incubated for 4-8 h at 37° C. with 5% $CO_2$ and humidity. Absorbance was read at 450-560 nm.

TNFα in the presence of 1 μg/ml actinomycin D causes cytotoxicity in L929 fibrosarcoma cells, with an $LD_{50}$ between 0.25-0.3 ng/ml. We demonstrated that our VNAR protein domains at nanomolar concentrations were capable of neutralising up to ten times the $LD_{50}$ of rhTNFα [FIG. 3]. In this experiment the VNARs were joined at their C terminal end by peptide linkers to the IgG Fc domains so as to form bivalent molecules for comparison to the control anti-TNFα antibody MAB210.

When measured as single domains in the neutralization assay the D1 and C4 VNARs did not appear as efficacious as the TNF30 VHH nanobody (FIG. 2). This appears to correlate with single site binding affinity. However when combined as a mixture (FIG. 3) or in bivalent or bispecific formats (Figures xxxx) they unexpectedly demonstrated improved properties over dimeric TNF30 VHH nanobody.

Paracellular Flux Assay

Human epithelial colorectal adenocarcinoma cells (Caco-2) were cultured in DMEM supplemented with 10 (% v/v) heat inactivated FBS and 1% (v/v) Penicillin-Streptomycin (10,000 units/ml and 10,000 μg/ml respectively). Cells were grown to 90% confluence in T75 flasks before seeding on 24 wells, 0.4 μm semipermeable tissue culture transwell inserts (Corning Inc.). Viable cells number was determined by suspending 10 μl cell suspension in 90 μl of 0.4% trypan blue exclusion dye (Beckman Coulter), and carefully transferring the mixture onto a haemocytometer with a cover slip attached.

Following viable cell number determination, $1\times10^5$ cells were seeded per transwell inserts in a final DMEM volume of 100 μl, while 600 μl DMEM without cells was transferred into the outer containing wells. Transwell plates were incubated at 37° C. with 5% (v/v) CO2, and spent DMEM+10% (v/V) FBS replaced every 48 h. Cell proliferation was monitored under a phase contrast microscope (40× magnification objective) until cells attain 100% confluence, usually between 5-7 days post-seeding. Caco-2 cells were grown for a further 21 days allowing differentiation, with spent medium changed every 48 h until differentiation.

Designated insert wells containing polarised cells (apical side) in 100 μl DMEM with 10% (v/v) HI-FBS were treated with 10 ng/ml hTNFα, IFNγ, LPS with or without anti-TNFα VNAR proteins. Treated cells were incubated for 18 h at 37° C. with 5% (v/v) CO2. Following incubation for 18 h with cytokines±anti-TNFα VNARs, phase contrast images of treated cells were captured followed by the addition of 5 μl of 10 mg/ml Fluorescein isothiocyanate-labelled dextran, molecular weight (3-5 kDa) to apical side (insert wells) of Caco-2 monolayer. Medium from the basolateral side of the transwell chamber was collected 24 h after addition of FITC-dextran.

Fluorescence intensity was measured using a Synergy HT (BioTek®) microplate reader at 485 nm excitation and 520 nm emission wavelengths.

Epithelial Resistance Dysfunction Assay

Human epithelial colorectal adenocarcinoma cells (Caco-2) were cultured in DMEM supplemented with 10 (% v/v) heat inactivated FBS and 1% (v/v) Penicillin-Streptomycin (10,000 units/ml and 10,000 μg/ml respectively). Cells were grown to 90% confluence in T75 flasks before seeding on 12 or 24 wells, 0.4 μm semipermeable tissue culture transwell inserts (Corning Inc.). The protocol described previously was followed until cells achieved full differentiation.

Designated insert wells containing polarised cells (apical side) in 200 μl DMEM with 10% (v/V) HI-FBS were treated with 10 ng/ml hTNFα, and IFNγ with or without anti-TNFα VNAR proteins. Treated cells were incubated for 24 h at 37° ° C. with 5% (v/v) CO2, and humidity. Following incubation for 24 h with cytokines±anti-TNFα VNARs, transepithelial electrical resistance (TEER) was measured in the apical chamber using Millicell® ERS-2 Epithelial (Volt/Ohm) meter and MERSSTX01 probe (Merck Millipore). Measured resistance values were normalised to the surface area under treatment.

It is important to note that 12 well tissue culture transwell inserts were seeded with $5\times10^6$ cells/well containing 500 μl DMEM with outer well (basolateral side) containing 1.5 ml DMEM. Also during TEER measurement, DMEM volume in the insert and outer wells were increased to 500 μl and 1.5 ml respectively to allow volt-ohm meter electrodes to fully submerge in the medium without touching the base of the wells.

B. ICOSL Binding VNARS

The isolation and characterization of ICOSL binding VNARS 2D4 and CC3 are disclosed in WO2014/173975 and WO2014/173959.

2. Formation of Multivalent and Multispecific VNARs.

A TNF Binding Domains

FIG. 3 indicated that the combination of the D1-Fc and C4-Fc molecules showed increased neutralisation capability in the bivalent form. Therefore VNARs D1 and C4 and other combinations were prepared as bivalent or bispecific fusions to demonstrate that when combined together as fusions the same improvement in neutralisation capacity is seen.

Construction of Dimers and Trimers

FIG. 4 provides a diagram of the format of bivalent and bispecific constructs Two or three separate PCR reactions were set up to amplify the N-terminal, middle terminal [in the case of a trimer], and C-terminal VNAR domains using the oligonucleotide combinations listed below, and each oligonucleotide habouring a specific/unique cloning site, and/or 6× his-tag and c-myc tag for ease of purification and detection respectively.

Dimer Construction PCR Oligos

N-Terminal Fragment Oligonucleotide Pair

```
XbaI_FW1 TNF_#127:
                                           SEQ ID 15
GCTAGGCTCTAGAAATAATTTTGTTTAACTTTAAGAAGGAGATATACCAT

GGCTCGAGTGGACCAAACACC
```

-continued

GS_BamHI_Rev_#130:

SEQ ID 16

CGCGCCGGATCCGCCACCTCCGCTACCGCCACCTCCGCTACCGCCACCTC

CGCTACCGCCACCTCCATTCACAGTCACGACAGTGCC

C-Terminal Oligonucleotide Pair

GS_BamHI_For_#132:

SEQ ID 17

GGTGGCGGatccGGCGCGCACTCCGCTCGAGTGGACCAAACACCGC

EcoRI_stop_myc_#129:

SEQ ID 18

GTCCGGAATTCTCACAGATCCTCTTCTGAGATGAGTTTTTGTTCTGCG
GCCCC

Trimer construction PCR oligonucleotides: Here we utilized an in-house designed DNA cassette habouring BA11 gene as the middle fragment flanked by Xba1/BamH1 and APA1/EcoR1 cloning sites on its N- and C-terminals respectively. Oligonucleotide pairs listed above can be utilised in the PCR amplification steps, as well as oligonucleotides habouring both Xba1 and BssH11 site in the N-terminal forward oligonucleotide, thus allowing sub-cloning the trimer gene into an in-house eukaryotic expression vector, pEEE2A. Otherwise all clonings are carried out in pET28b (+) expression vector.

Xba1/BssH11-FW1NAR_#197 [Trimer cassette]:

SEQ ID 19

AATTCCCCTCTAGAAGGCGCGCACTCCGCTCGAGTGGACCAAACACCG

A PCR reaction of 2 μl VNAR DNA (50-100 ng), 2 μl forward and reverse oligonucleotide primers (final concentration 1 μM), 5 μl of 10×Taq polymerase buffer, 0.25 μl of Taq polymerase (final concentration 25 U/ml), 0.5 μl dNTPs (final concentration 0.1 mM), and 38.25 μl $H_2O$ with a final reaction volume of 50 μl. A PCR program was started with 5 min at 98° C. This was followed by a 30 cycle of 94° C. for 30 seconds, 56° C. for 30 seconds and 72° C. for 1 min. A final extension at 72° ° C. for 5 min. Amplicons were checked by agarose gel electrophoresis, and purified using QIAquick PCR purification kit. Eluted DNA digested with appropriate restriction endonuclease.

Expression of Dimers and Trimers in *E. coli* SHuffle® T7 Express Cells

The VNAR regions cloned into the expression vector pET28b (+) via the XbaI and EcoRI restriction enzyme sites, and resulting purified plasmid containing VNAR gene was transformed into electrocompetent *E. coli* SHuffle® T7 Express cells [NEB], and selected on TYE agar plates containing 50 μg/ml kanamycin. The anti-hTNFα VNAR-D1, C4 and B4 fusion proteins were expressed in the cytoplasm of SHuffle cells upon induction with IPTG at 30° C.

Single colony of transformed *E. coli* SHuffle® T7 Express cells was grown in 5 ml 2×TY-Kanamycin medium until $OD_{600}$ 0.4-0.6 usually achieved between 4-6 h incubation at 37° C., 250 rpm. This log phase culture was used to inoculate 50 ml TB medium containing kanamycin and $PO_4$ salts, incubated overnight at 30° C., 250 rpm until they attain $OD_{600}$ 6.0-10.0. Cells were centrifuged at 4000 rpm, 30° C. for 15 min, then resuspended in fresh TB-kanamycin-$PO_4$ salt medium and allowed to recover for 1-2 h at 30° C., 250 rpm. Cytoplasmic protein expression was induced using a final IPTG concentration of 1 mM, cells incubated at 30° C., 200 rpm for 12-16 h post-induction. Cells were harvested by centrifugation at 6000 rpm, 25° C. for 10 min, and cell pellet wet weight determined. Cell pellet was resuspended in 5 ml/gram of wet cell paste BugBuster™ protein extraction reagent plus Benzonase® (Novagen, UK), and cell suspension was placed on a shaking platform at 10-15 rpm, room temperature for 20 min. Cell suspension was centrifuged at 6000 rpm, 4° C. for 20 min, and soluble protein collected in the supernatant was ready for affinity purification via polyhistidine tag using immobilised metal affinity chromatography (IMAC) resin (nickel-nitrilotriacetic acid, Ni-NTA or Ni-Sepharose). VNAR fusion protein was eluted with 300-500 mM imidazole, pH 8.0 and eluate dialysed against PBS (1 L PBS/1 ml eluted protein), pH 7.4 overnight and then PBS replaced for a further 3-4 h dialysis. Protein quality was assessed via SDS-PAGE and quantified using the Ultraspec 6300 pro uv/visible spectrophotometer (Amersham Biosciences, GE Healthcare).

For eukaryotic cell expression, domains cloned into the BA11 trimer cassette were digested using BssHII and EcoR1 enzymes, and subcloned into pEEE2A eukaryotic expression vector utilising a CMV promoter, and transformed into an *E. coli* strain for plasmid propagation. Isolated and purified plasmid vector containing the VNAR trimer gene was co-incubated with linear polyethylenimine [PEI] for 20 minutes at room temperature. The mixture of plasmid DNA: PEI was transferred unto a cell culture flask containing HEK293 cells with cell growth density of 90% confluence. Transfected HEK293 cells were incubated at 37° C., 5% v/v $CO_2$ for 5-7 days. Cell culture supernatant was harvested, and expressed protein purified using IMAC resin, and dialysed against PBS.

Binding and TNF Neutralization Data

FIG. 5 shows ELISA binding of dimeric and bispecific constructs to TNFα.

The initial ELISA data indicated that the bispecific D1-C4 construct had increased avidity (combined binding affinity) compared to the TNF30 nanobody dimeric construct.

A number of these were later measured for binding to immobilized TNF in surface plasmon resonance.

TABLE 1 indicates that of the dimeric molecules measured, the D1-C4 bispecific molecule showed superior binding affinity (avidity) compared to the TNF30 bivalent nanobody construct.

FIG. 6 shows TNF neutralization data for a number of bivalent or bispecific VNAR fusions, compared to the bivalent TNF nanobody. When the binding molecules were tested for TNF neutralisation in the L929 assay, the D1-C4 dimer was equivalent to or superior to the TNF30 nanobody dimeric construct. In this experiment the D1-D1 dimer was inferior to the D1-B4 dimer.

TABLE 1 Shows SPR binding data for the trimeric constructs tested. This indicates that the introduction of the additional domain, acting as a spacer between the TNFα binding domains, appears significantly to improve the relative affinity (avidity) of the molecules for TNFα.

When measured in the TNFα neutralisation assay, the D1-BA11-C4 trimeric construct was equivalent to adalimumab and superior to the TNF30 nanobody construct. In this assay the bivalent molecule comprising the D1 domains was equivalent in efficacy to the TNF30 nanobody construct.

FIG. 7 shows the results of an experiment to measure the ability of the various VNAR formats to neutralize TNFα function.

TABLE 2 summarizes the neutralisation data. When the spacer domain is included both the D1-BA11-D1 and D1-BA11-C4 show a ten-fold or better improvement in neutralisation ability, with the D1-BA11-C4 showing approximately equivalent efficacy to adalimumab and MAB210. The TNF30-BA11-TNF30 also shows an improvement over the TNF30-TNF30 dimeric form but not as markedly. The GlySer linker length of D1-C4 construct (SEQ ID NO 27 & 28) was extended from a (Gly4Ser)2 to a (Gly4Ser)3 with a consequent improvement in hTNF-alpha neutralizing potency.

The data from these experiments are shown in table 2. Further comparative data is given in table 3.

TABLE 2

TNF Neutralisation data using 0.3 ng/ml (LD80) of hTNF-alpha (unless otherwise stated)

| Binding Molecule | $ND_{50}$ (nM) [≥n = 3 ± SEM; except otherwise stated] |
|---|---|
| TNF43 [Horn Shark VNAR] | 7100 nM (Publication: Camacho-Villegas, Tanya, et al. MAbs 5(1): 2013; U.S. Pat. No. 8,496,933. 30 Jul. 2013) |
| TNF43 [Horn Shark VNAR] | No neutralisation seen in vitro at concentrations up to 500 nM (also see FIG. 15 at 100 nM) |
| D1 | 30 ± 3.5 |
| C4 | 100 ± 0.1 |
| TNF30 [VHH] | 9.2 ± 2.1 |
| D1-Fc | 0.9 ± 0.14 |
| C4-Fc | 0.52 ± 0.2 |
| TNF30-Fc | 0.7 ± 0.07 |
| D1-D1 | 7.0 ± 2.4 |
| D1-C4 | 0.76 ± 0.06 |
| D1-C4 $(Gly_4Ser)_3$ | 0.08 ± 0.02*** (n = 2 with 3 replicates each) |
| D1-B4 | 8.0 ± 25 |
| TNF30-TNF30 | 0.8 ± 0.27 |
| Adalimumab | 0.03 ± 0.009 |
| D1-BA11-D1 | 0.38 ± 0.03 |
| D1-BA11-C4 | 0.02 ± 0.09 |
| TNF30-BA11-TNF30 | 0.3 ± 0.14 |
| D1-Fc-C4 (Quad-X ™) | 0.002 ± 0.0011 |
| D1-C4-Fc (Quad-Y ™) | 0.005 ± 0.0005 (n = 2 ± SD) |
| C4-D1-Fc (Quad-Y ™) | 0.012 ± 0.0016 (n = 2 ± SD) |

A. Binding (B) and Neutralisation (N) Data Obtained by the Inventors

| | Human (Bind/Neutralise) B/N | Dog (B/N) | Cynomolgus (B/N) | Rat (B/N) | Mouse (B/N) | Rabbit (B/N) | Pig (B/N) | Human TNF-β (B/N) |
|---|---|---|---|---|---|---|---|---|
| Lead anti-hTNF-α VNARs (D1 and C4) | +++/+++ | +++/+++ | +++/+++ | −/− | −/− | −/− | −/− | −/− |
| Nanobody Lead (VHH) TNF 30 | +++/+++ | +++/+++ | +++/+++ | −/− | −/− | −/− | +/+ | ++/− |
| Adalimumab (Humira) | +++/+++ | +++/+++ | +++/+++ | −/− | ++/++ | −/− | −/− | −/− |

Note:
+++denotes strong binding/neutralisation activity, ++ moderate; + very weak activity and − denotes no binding/neutralisation activity observed.

B. Cross-Reactivity Data of Clinically Available Anti-hTNF-Alpha Biologics as Reported in the Literature

[Assessment Report for Cimzia, European Medicines Agency (2009). Doc. Ref.: EMEA/664021/2009;
Assessment Report for Simponi. European Medicines Agency (2009). Doc Ref.: EMEA/446762/2009;
Assessment Report for Enbrel. European Medicines Agency (2008). Procedure No. EMEA/H/C/262/11/94;
Scientific Discussion on Remicade, European Medicines Agency (2005)
(http://www.ema.europa.eu/docs/en_GB/document_library/EPAR_-_Scientific_Discussion/human/000240/WC500050885.pdf) Last assessed on 21 Sep. 2017;
Scientific Discussion on Humira, European Medicines Agency (2004).
(http://www.ema.europa.eu/docs/en_GB/document_library/EPAR_-_Scientific_Discussion/human/000481/WC500050867.pdf). Last assessed on 21 Sep. 2017]

TABLE 3

Cross-reactivity profile of anti-hTNF-alpha VNAR lead construct compared to commercially available anti-hTNF-alpha mAbs and pre-clinical VHH TNF30

| | Human (Bind/Neutralise) B/N | Dog (B/N) | Cynomolgus (B/N) | Rat (B/N) | Mouse (B/N) | Rabbit (B/N) | Pig (B/N) | Human TNF-β (B/N) |
|---|---|---|---|---|---|---|---|---|
| Adalimumab (Humira) | +/+ | +/+ | +/+ | −/− | +/+ | −/− | −/− | −/− |
| Infliximab (Remicade) | +/+ | −/− | −/− | −/− | −/− | −/− | −/− | −/− |
| Etanercept (Enbrel) | +/+ | −/− | +/+ | | +/+ | | | +/+ |
| Certolizumab (Cimzia) | +/+ | −/− | +/+ | | | | | |
| Golimumab (Simponi) | +/+ | +/+ | +/+ | −/− | −/− | +/+ | | −/− |

Note:
+/− denotes yes or no binding/neutralisation respectively.

Functional Activity

Background

Human epithelial colorectal adenocarcinoma cells (Caco-2) develop morphological characteristics of normal enterocytes when grown on suitable platform (e.g., plastic dishes, nitrocellulose filters). More so collagen coated polycarbonate or polyester membrane have been demonstrated to be suitable for Caco-2 monolayers as an intestinal epithelial transport model systems (Wang, F., et al. *Am. J. Path.* 166.2 (2005): 409-419.; Hidalgo, I. J., et al *Gastroenterology* 1989. 96: 736-49.).

A principle function of epithelial membrane is the maintenance of a barrier to hydrophilic solutes such as Inulin and Dextran. This barrier is compromised in certain diseases involving the intestinal epithelium, which include but not limited to infectious, immune-mediated and idiopathic diseases (Clayburgh, D. R., et al *Lab Invest.* 2004. 84(3): 282-291; Wang, F., et al. *Am. J. Path.* 2005. 166(2): 409-419). Intestinal barrier dysfunctions, measured as increases in paracellular permeability and reduction of intestinal epithelial resistance are closely associated with inflammatory bowel diseases (IBD), such as Crohn's disease (Irvine E. J. and Marshall J. K., *Gastroenterology* 2000. 119.6: 1740-1744.; Wyatt et al., *The Lancet* 1993. 341(8858): 1437-1439.). Also there are evidence supporting the reduction of epithelial tight junction proteins in IBD, consequently contributing to the loss of solutes resulting in leak flux diarrhea (Schulzke J. D. et al., *Ann N Y Acad Sci.* 2009 1165:294-300; Schmitz H. et al., *J. Cell Sci* 1999. 112(1): 137-146). Finally Interferon-γ (IFN-γ), TNFα and Lipopolysaccharide (LPS) have been shown to synergistically induce intestinal epithelial barrier dysfunction in human epithelial cell lines (Wang et al., *J. Cell Science* 1999. 112(1): 137-146; Schuerer-Maly C. C et al., *Immunology* 1994. 81(1): 85).

Anti-TNFα treatment have been shown to repair the intestinal barrier dysfunction in Crohn's disease (Suenaert P. et al., *Am J Gastroenterol* 2002. 97(8): 2000-2004) thus we examined our anti-TNF VNAR domains to demonstrate these would repair these dysfunctions induced in-vitro. We hypothesized that bi-specific/multivalent VNAR domains would be more effective in the prevention of these dysfunctions when compared to VNAR monomers.

FITC-Dextran Paracellular Flux Across Polarised Monolayer of Caco-2 Cells

Human epithelial colorectal adenocarcinoma cells (Caco-2) were cultured in DMEM supplemented with 10 (% v/v) heat inactivated FBS and 1% (v/v) Penicillin-Streptomycin (10,000 units/ml and 10,000 μg/ml respectively). Cells were grown to 90% confluence in T75 flasks before seeding on 24 wells, 0.4 μm semipermeable tissue culture transwell inserts (Corning Inc.). Viable cells number was determined by suspending 10 μl cell suspension in 90 μl of 0.4% trypan blue exclusion dye (Beckman Coulter), and carefully transferring the mixture onto a haemocytometer with a cover slip attached.

Following viable cell number determination, $1\times10^5$ cells were seeded per transwell inserts in a final DMEM volume of 100 μl, while 600 μl DMEM without cells was transferred into the outer containing wells. Transwell plates were incubated at 37° C. with 5% (v/v) $CO_2$, and humidity, and spent DMEM+10% (v/V) FBS replaced every 48 h. Cell proliferation was monitored under a phase contrast microscope (40× magnification objective) until cells attain 100% confluence, usually between 5-7 days post-seeding. Caco-2 cells are grown for a further 21 days allowing differentiation, with spent medium changed every 48 h until differentiation.

Designated insert wells containing polarised cells (apical side) in 100 μl DMEM with 10% (v/v) HI-FBS were treated with 10 ng/ml hTNFα, IFN-γ and LPS with or without anti-TNFα VNAR proteins. Treated cells were incubated for 18 h at 37° C. with 5% (v/v) $CO_2$, and humidity. Following incubation for 18 h with cytokines±anti-TNFα VNARs, phase contrast images of treated cells were captured followed by the addition of 5 μl of 10 mg/ml Fluorescein isothiocyanate-labelled dextran, molecular weight (3-5 kDa) to apical side (insert wells) of Caco-2 monolayer. Medium from the basolateral side of the transwell chamber was collected 24 h after addition of FITC-dextran.

Fluorescence intensity was measured using a Synergy HT (BioTek®) microplate reader at 485 nm excitation and 520 nm emission wavelengths.

FIG. 8 shows the permeability data from an experiment measuring paracellular flux across polarised monolayer of Caco-2 cells comparing several of the TNF VNAR multi-domain binding molecules. This experiment shows that the various bivalent and bispecific forms show improved function over the monomer forms as a lower concentration of dimer or trimer delivered an increased level of protection of challenged cells.

Epithelial Resistance Dysfunction Assay in Polarised Caco-2 Cell Monolayer

Human epithelial colorectal adenocarcinoma cells (Caco-2) were cultured in DMEM supplemented with 10 (% v/v)

heat inactivated FBS and 1% (v/v) Penicillin-Streptomycin (10,000 units/ml and 10,000 μg/ml respectively). Cells were grown to 90% confluence in T75 flasks before seeding on 12 or 24 wells, 0.4 μm semipermeable tissue culture transwell inserts (Corning Inc.). The protocol described previously in section 0 was followed until cells achieved full differentiation.

Designated insert wells containing polarised cells (apical side) in 200 μl DMEM with 10% (v/v) HI-FBS were treated with 10 ng/ml hTNFα, and IFN-γ with or without anti-TNFα VNAR proteins. Treated cells were incubated for 24 h at 37° C. with 5% (v/v) $CO_2$, and humidity. Following incubation for 24 h with cytokines±anti-TNFα VNARs, transepithelial electrical resistance (TEER) was measured in the apical chamber using Millicell® ERS-2 Epithelial (Volt/Ohm) meter and MERSSTX01 probes (Merck Millipore). Measured resistance values were normalised to the surface area under treatment.

It is important to note that 12 well tissue culture transwell inserts were seeded with $5\times10^6$ cells/well containing 500 μl DMEM with outer well (basolateral side) containing 1.5 ml DMEM. Also during TEER measurement, DMEM volume in the insert and outer wells were increased to 500 μl and 1.5 ml respectively to allow volt-ohm meter electrodes to fully submerge in the medium without touching the base of the wells.

FIG. 9 shows an assay measuring epithelial resistance in polarized Caco-2 cells. This experiment shows that the various bivalent and bispecific forms show improved function over the monomer forms.

B ICOSL Binding Domains

Construction of Multivalent Forms and Enhanced Efficacy Data

2D4 and CC3 Fc Fusions

FIG. 10 shows formats for multivalent and multispecific VNARs of the invention incorporating ICOSL VNARs (and human IgG Fc, which provides additional improved functional characteristics.

Method

Selected VNAR monomeric domains were PCR amplified and subcloned into a eukaryotic expression vector. This cloning was onto the 5' terminal end of a Human IgG1 Fc encoding DNA fragment (this Human IgG1 Fc fragment also encoded a full length Human IgG1 hinge sequence with the 5 prime most Cys residue which normally disulphide bridges to the light chain mutated to a Serine).

Whilst subject to PCR amplification oligonucleotides were used to introduce amino acid residues inserting a linker sequence between the carboxyl terminal end of the VNAR domain and the N terminal residue of the Human IgG1 hinge region as well as restriction endonuclease sites compatible with mammalian vector expression system. The linker sequences introduced by this process were either GGGGSGGGGRT whereby the nucleic acid sequence encoding the underlined RT amino acid residues introduces a BsiW1 restriction endonuclease site or GGGGSGGGADQ in which codon usage of the underlined GADQ amino acid residues introduces a Bcl1 site. Both of these sites are compatible with cloning sites in different versions of the Fc eukaryotic expression vector. At the 5' end of all amplicons a unique BssHII site is introduced which is compatible with eukaryotic vector construction.

DNA sequences to introduce linker VNAR domain fusions to the carboxyl terminal end of the Fc were designed and synthesis of these intermediate fragments was carried out by GeneArt (Invitrogen). The N-terminus of these fragments utilized a naturally-occurring BsrGI site within the human IgG1-derived CH3 region, and an EcoR1 site in the vector. These constructs introduced a linker with amino acid sequence TAAAATAAAATAAAATAAAA between the carboxyl terminal end of the Fc domain and the amino terminal end of the VNAR domain. Codon usage at the underlined triple alanine region of the linker allows for the introduction of a NotI restriction site which can be utilised in subsequent cloning work to assemble further bispecific VNAR constructs.

Post PEI-mediated transfection and transient expression in suspension HEK 293 cells using serum free media, expression levels of NAR Fc fusion proteins were determined by ELISA. Protein A affinity chromatography to purify the VNAR Fc proteins was performed after an initial 0.2 μm filtration clarification step to remove cell debris. A second chromatographic step to polish affinity purified protein was performed using ion exchange or size exclusion chromatography with buffer exchange as appropriate between steps. Proteins were concentrated using Amicon ultra filtration units and final protein concentrations determined by UV spectroscopy. Analytical SEC and SDS PAGE was used to determine integrity of final purified proteins.

ICOSL Neutralization Assay

Ligand-receptor neutralisation assays were conducted as follows: CHO cells expressing human ICOS receptor were grown to confluency in DMEM/F12+5% FBS media in 96-well cell culture plates (Greiner, Bio-One). A total of 20 μl at 1 μg/ml of rmB7-H2/Fc (158-B7, R&D Systems) was preincubated for 1 h with 40 μl of serially diluted anti-ICOSL-VNAR-Fc in DMEM/F12+2% FBS and then added to the cells. Following 1 h incubation at 16° C., cells were gently washed three times with DMEM/F12+2% FBS and incubated for 40 min at 16° C. with goat anti-human Fc-HRP (SIGMA) diluted 1:10,000 in the same media. Cells were washed and developed with TMB substrate.

Figure 1:
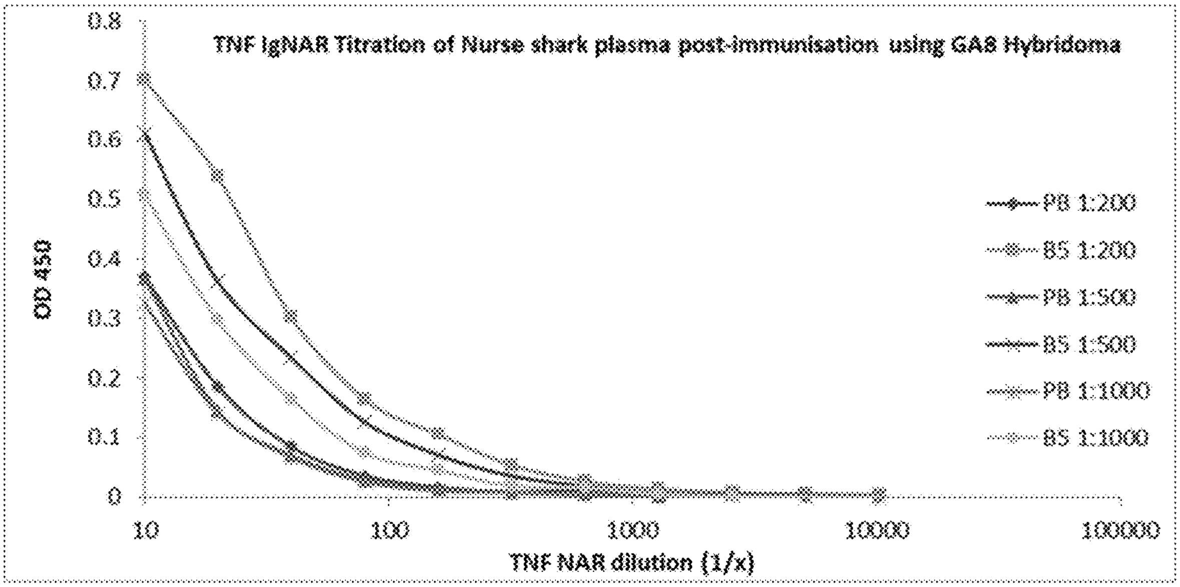
Figure 2:
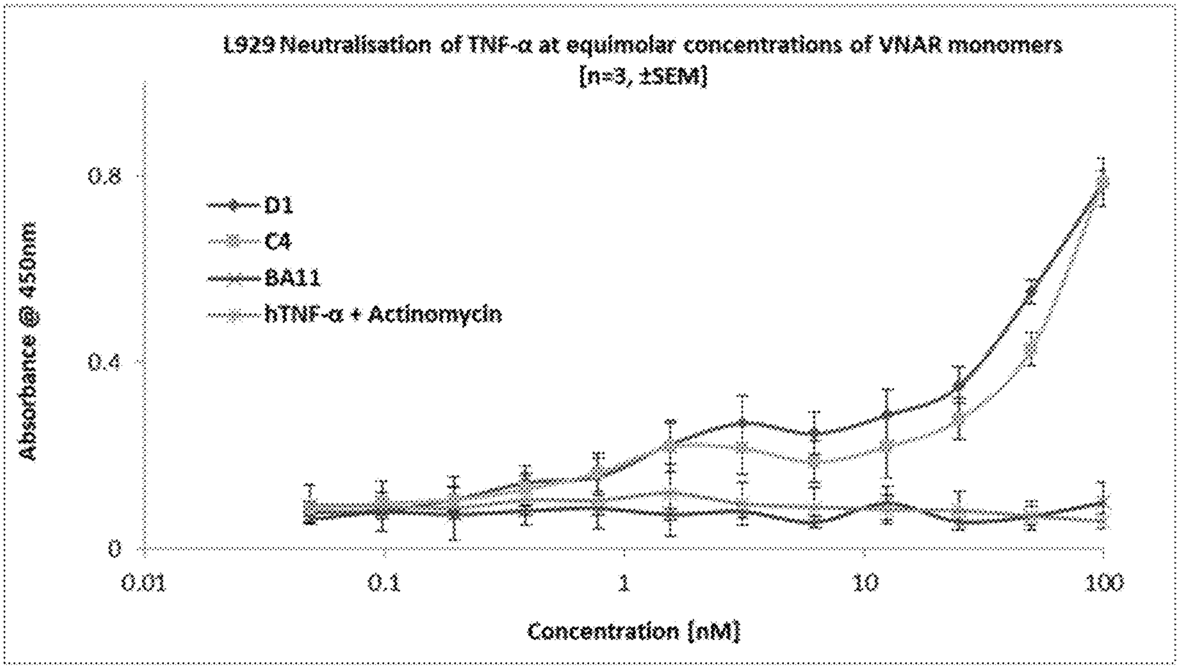
Figure 3:
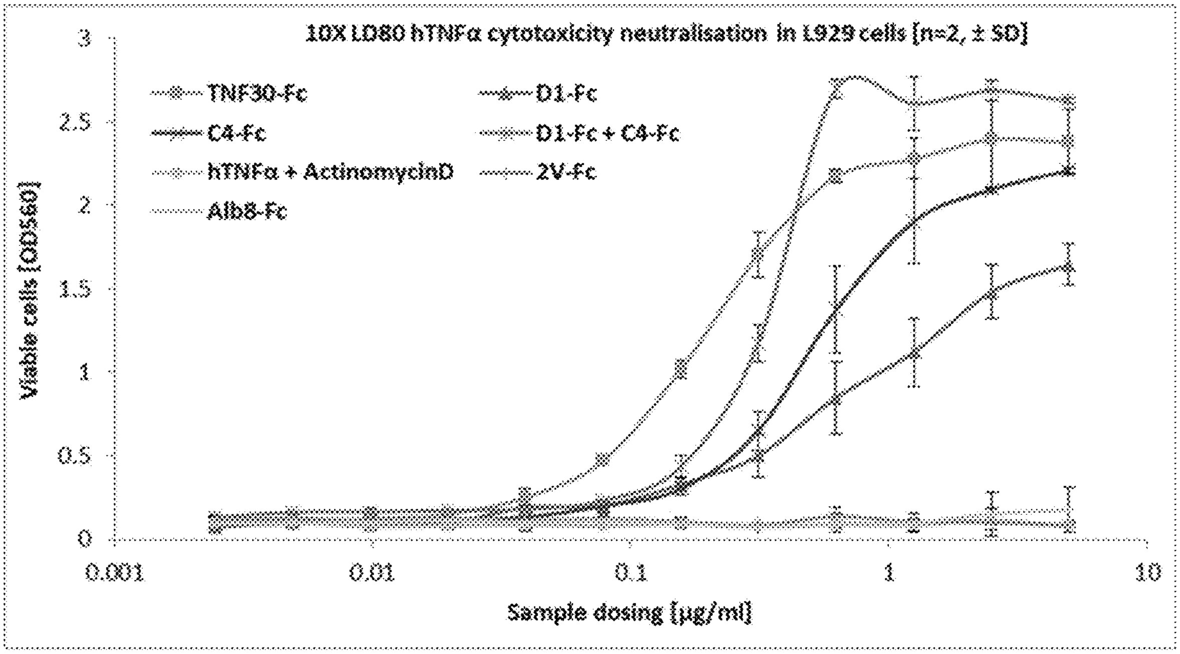
Figure 4:
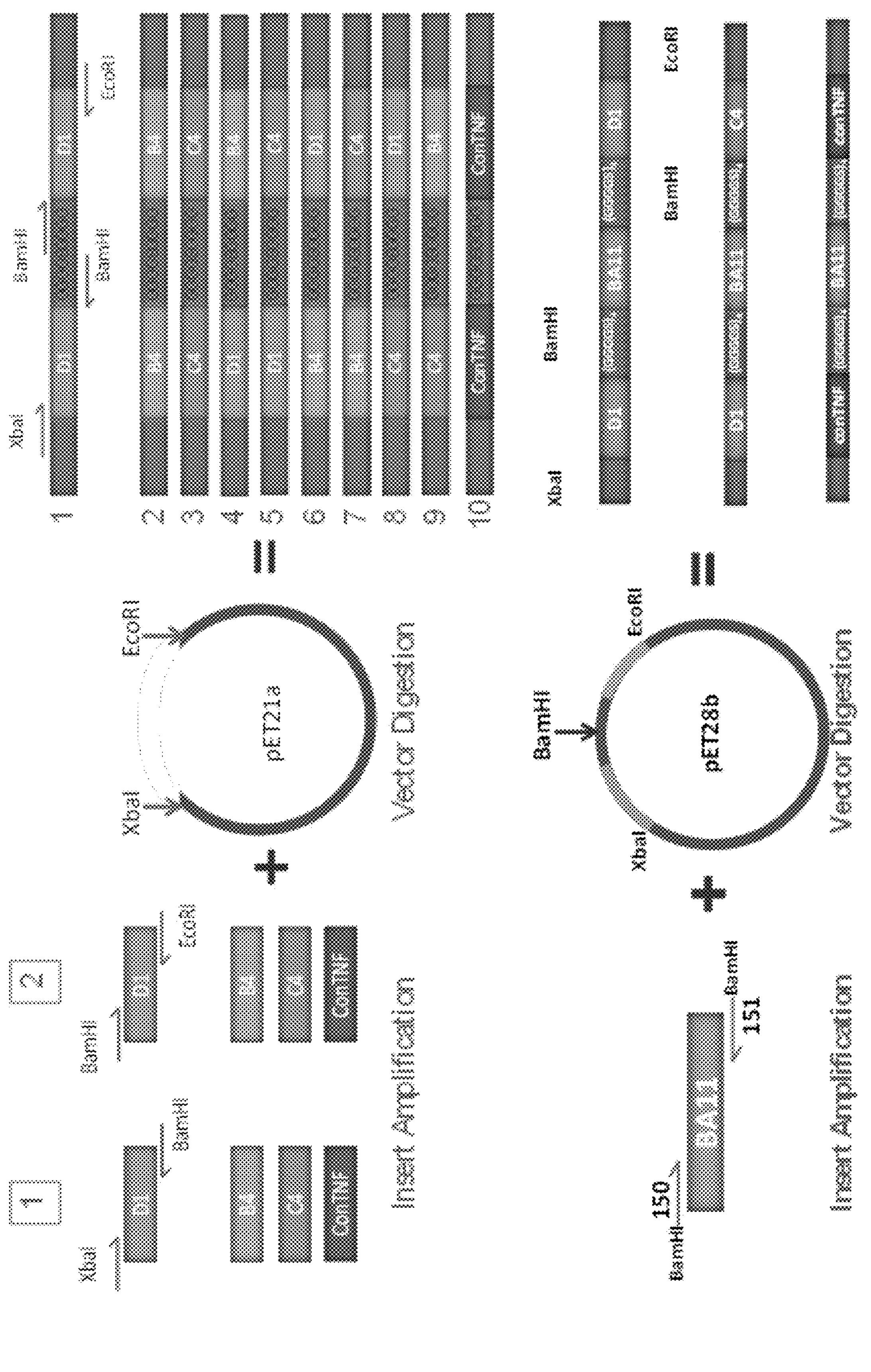
Figure 5:
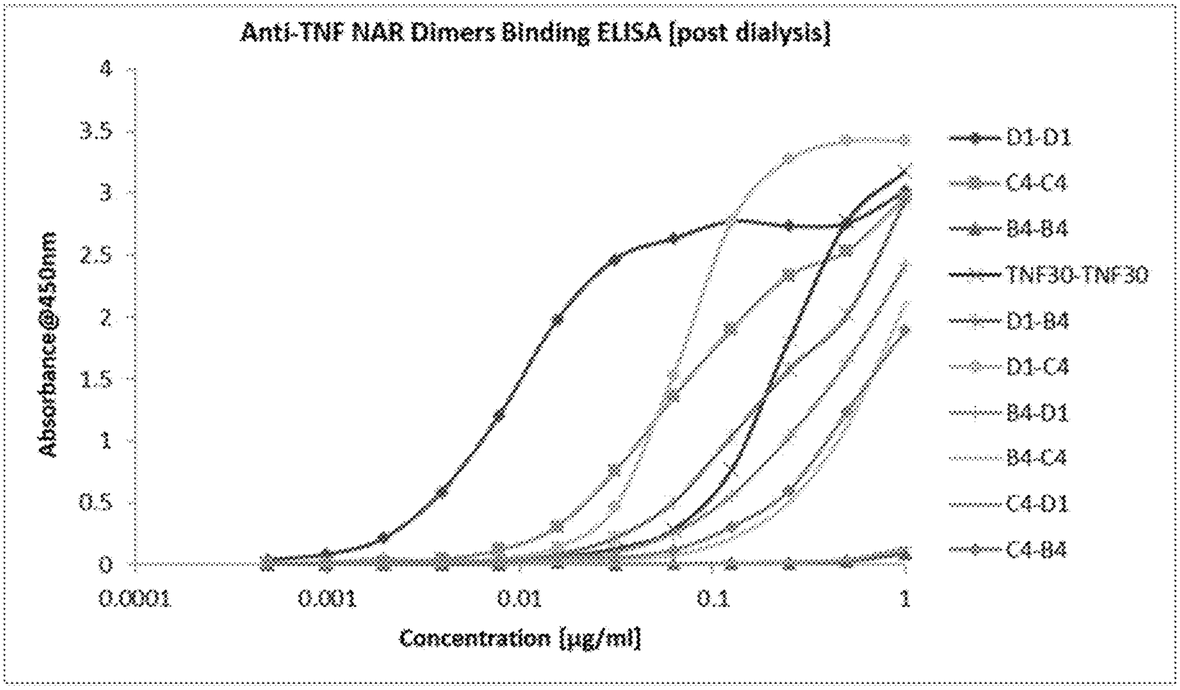
Figure 6:
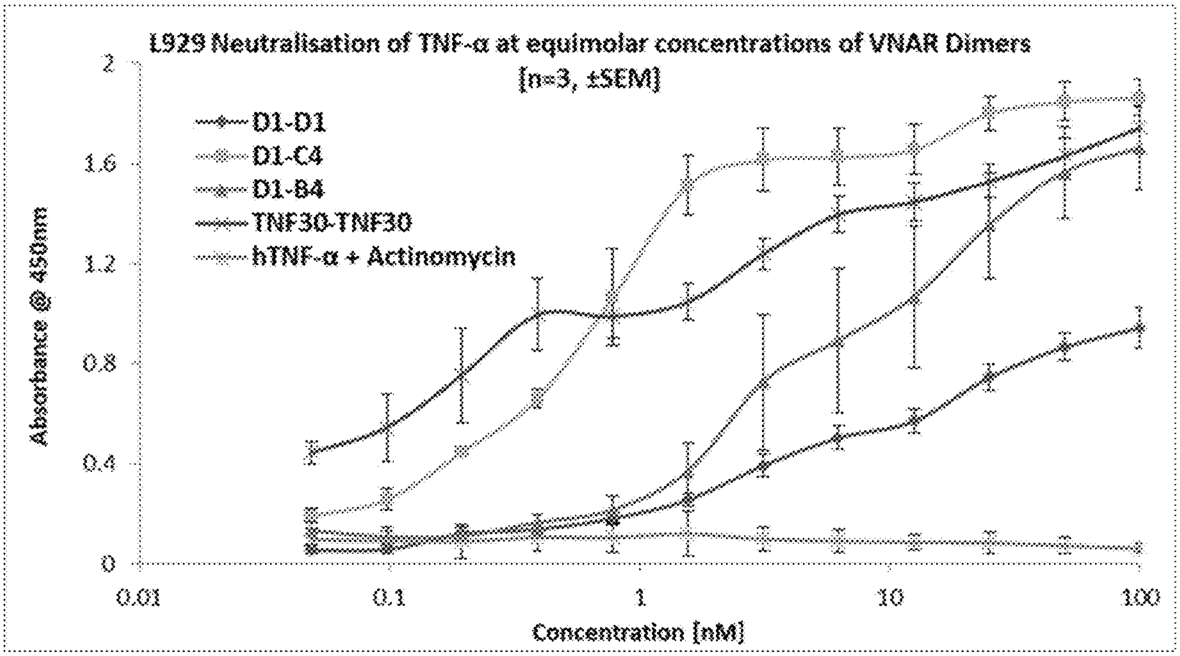
Figure 7:
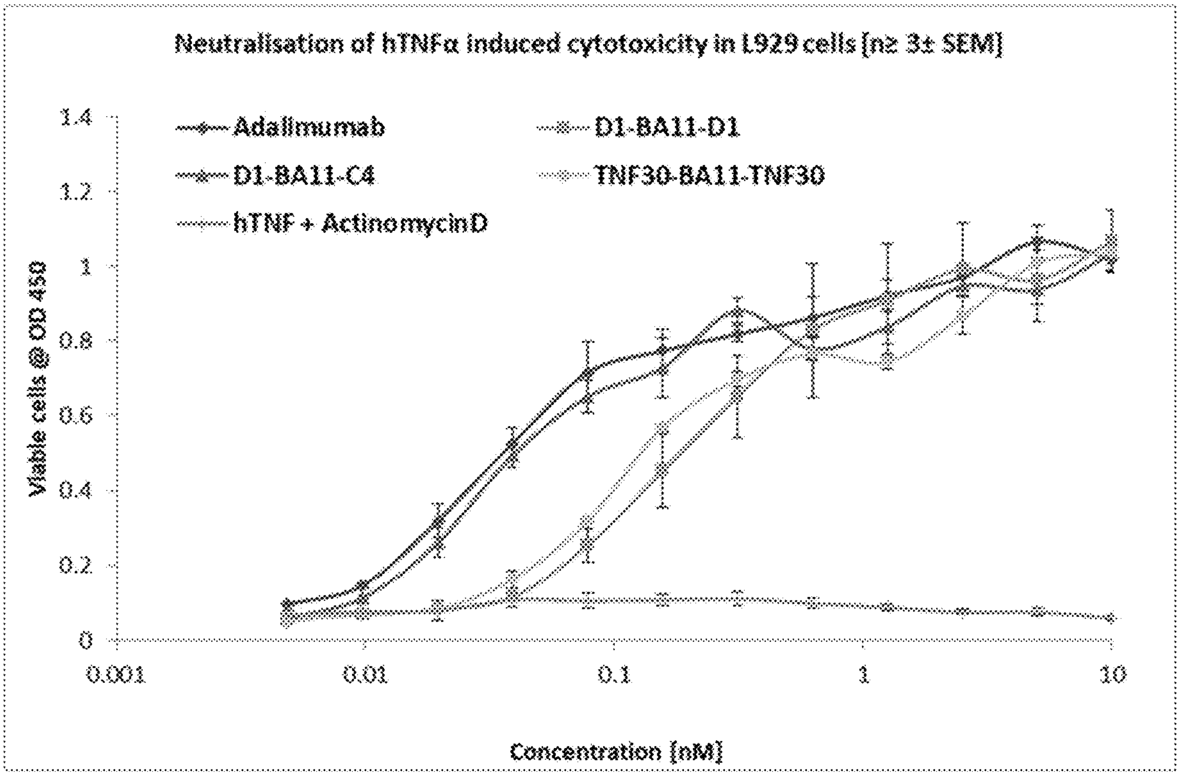
Figure 8:
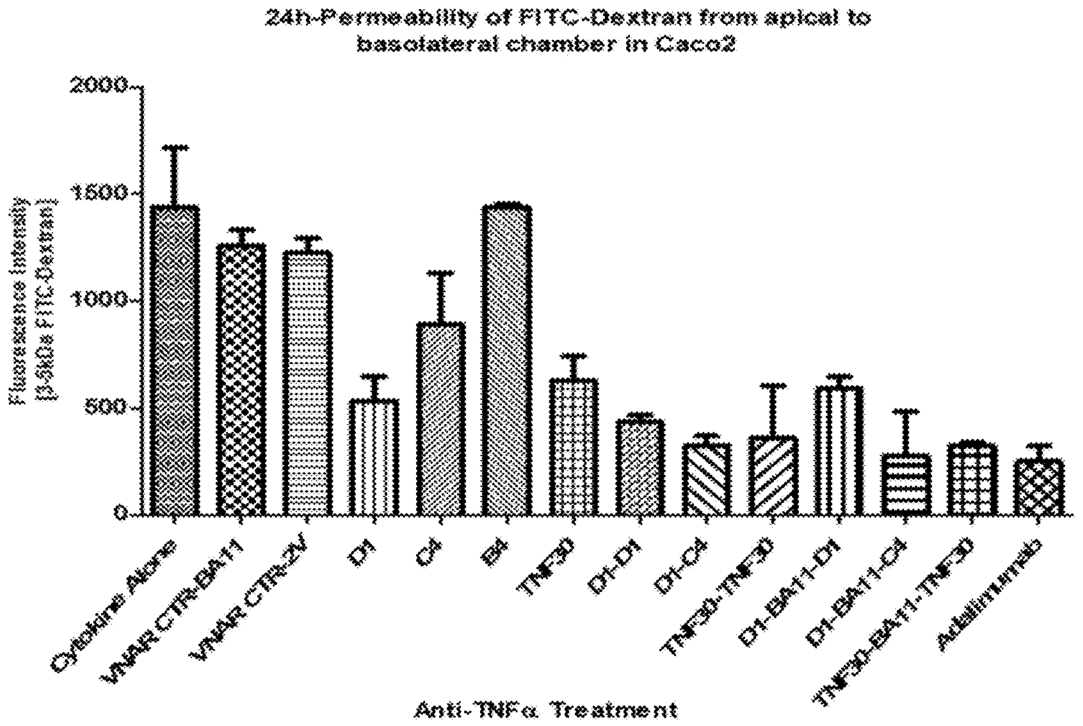
Figure 9:
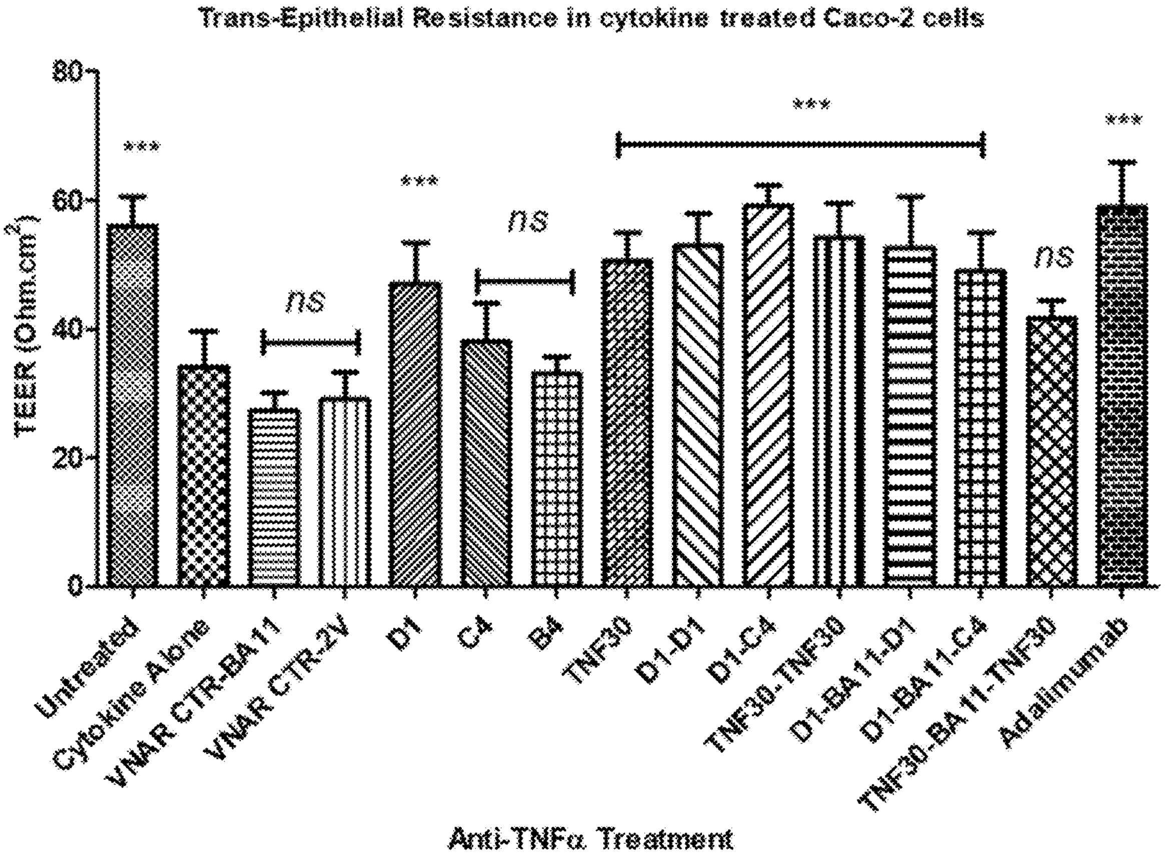
Figure 10:
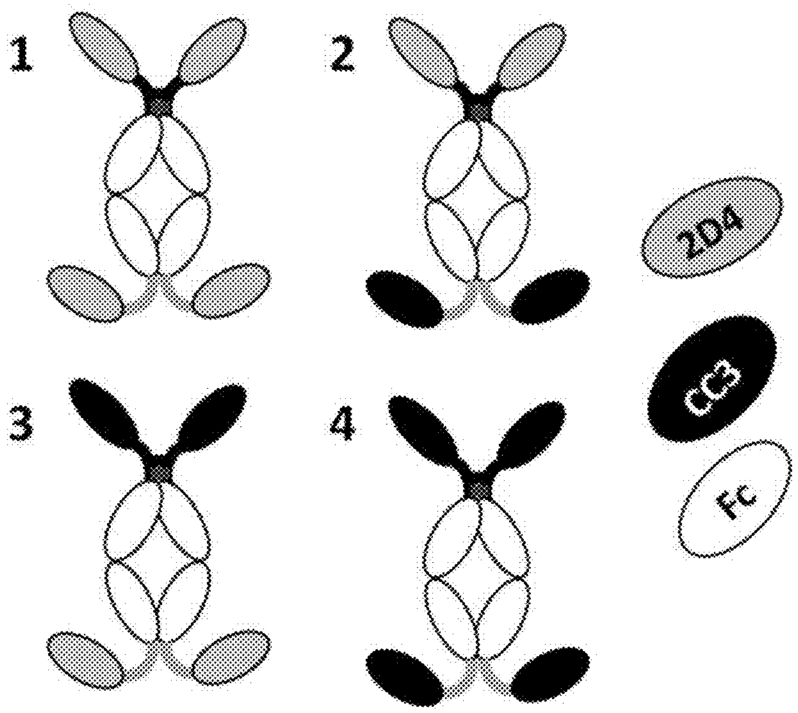
Figure 11:
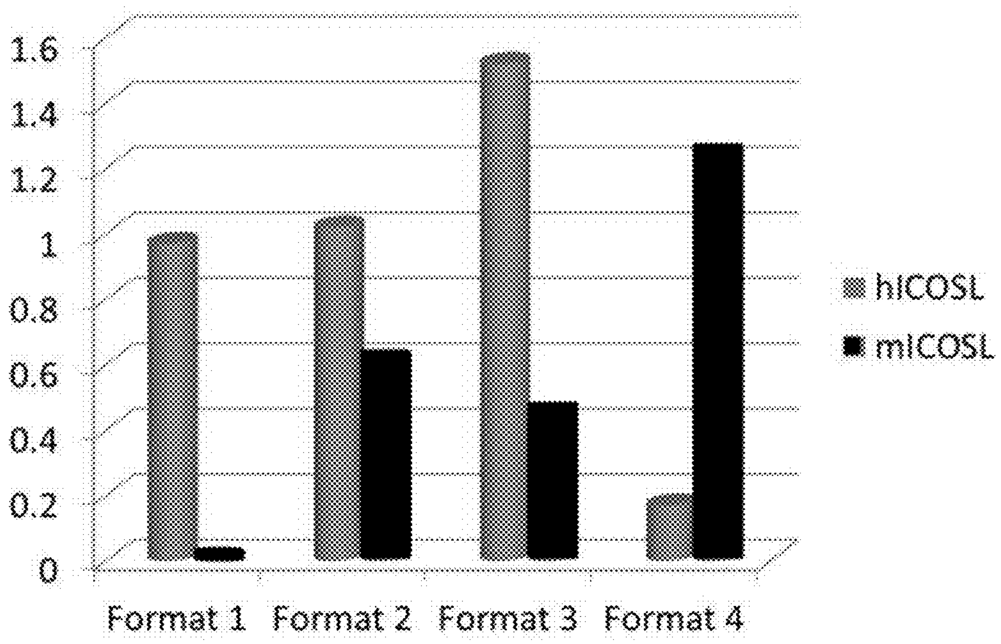
FIG. 11 shows ELISA binding data, indicating that the ICOSL VNARS bind to their cognate antigens in these formats
Figure 12:
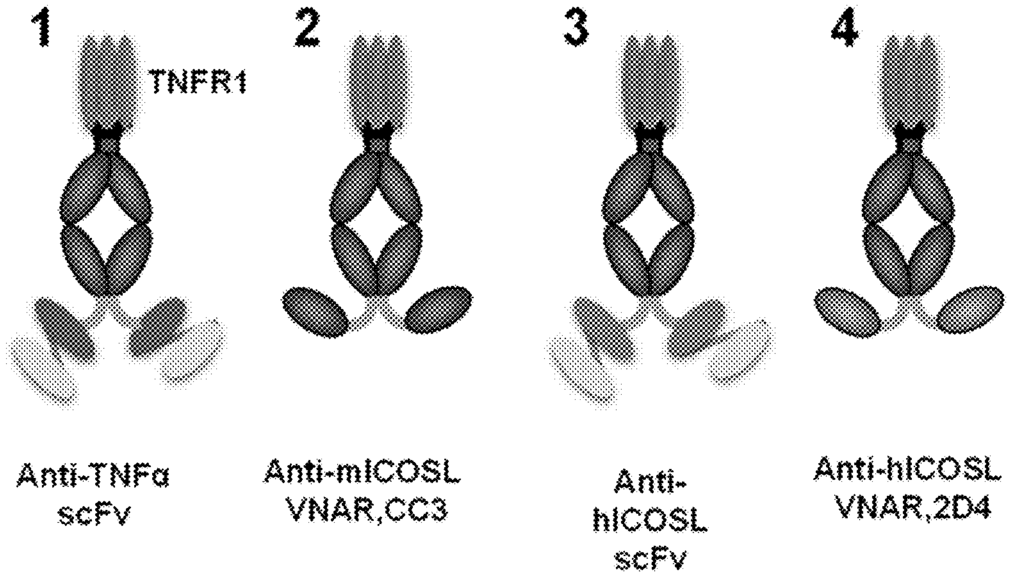
FIG. 12 shows formats for multivalent and multispecific VNARs of the invention incorporating the TNF R1 domain, ICOSL VNARs and human IgG Fc, which provides additional improved functional characteristics.
Figure 13:
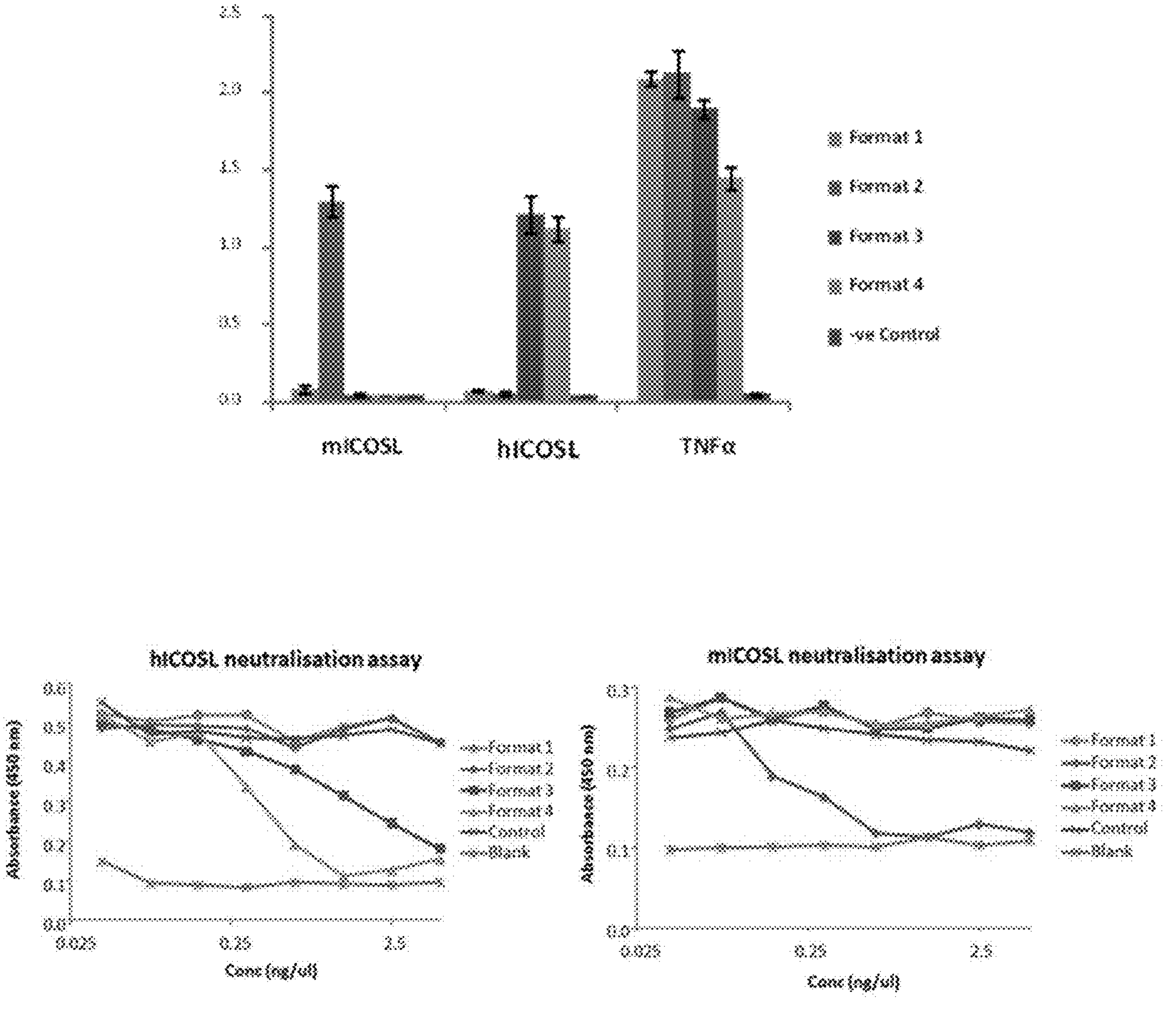
FIG. 13 shows efficacy data for multivalent and multispecific VNARs of the invention incorporating the TNF R1 domain, ICOSL VNARs and human IgG Fc, which provides additional improved functional characteristics.
Figure 14:
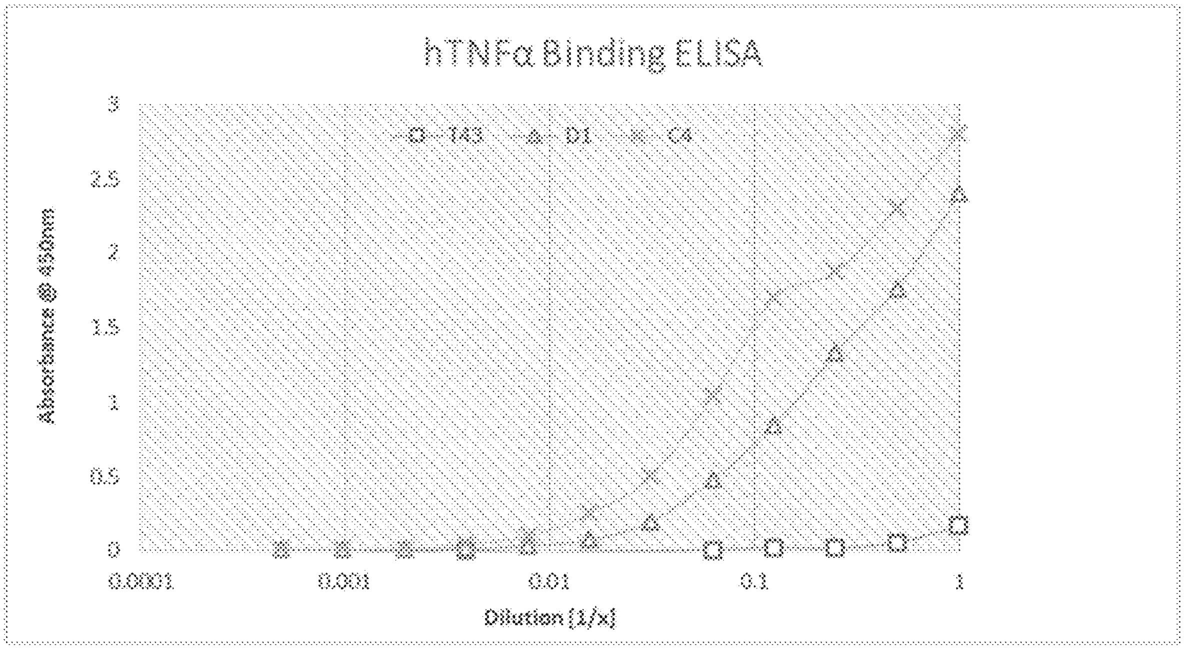
Figure 15:
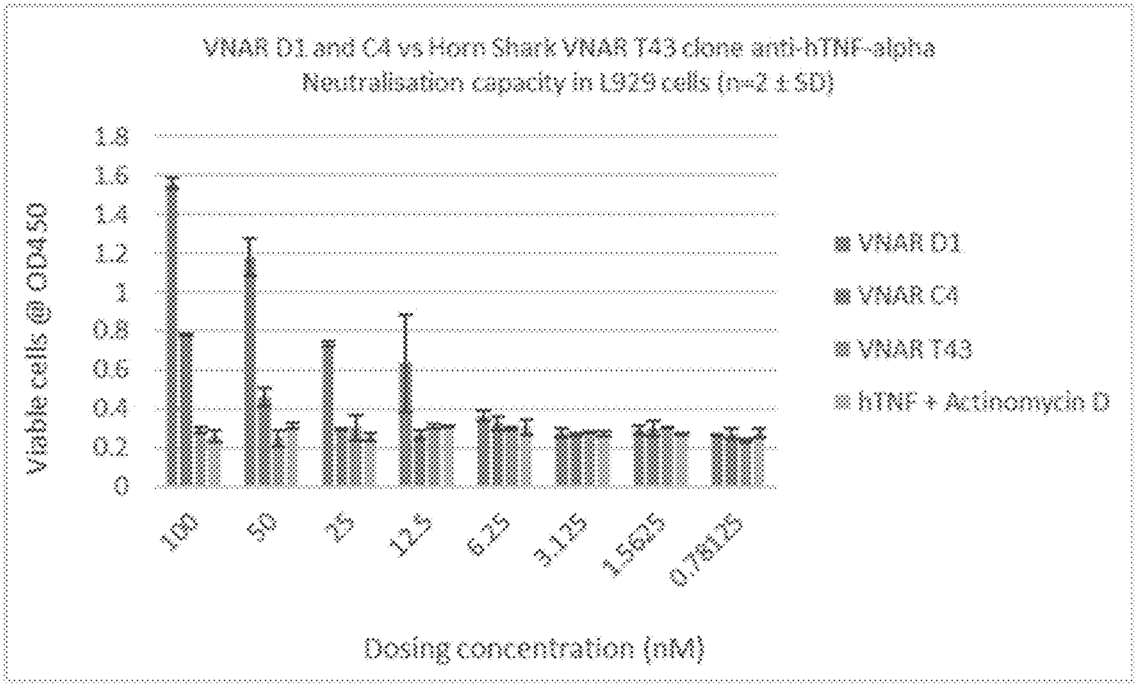
Figure 16:
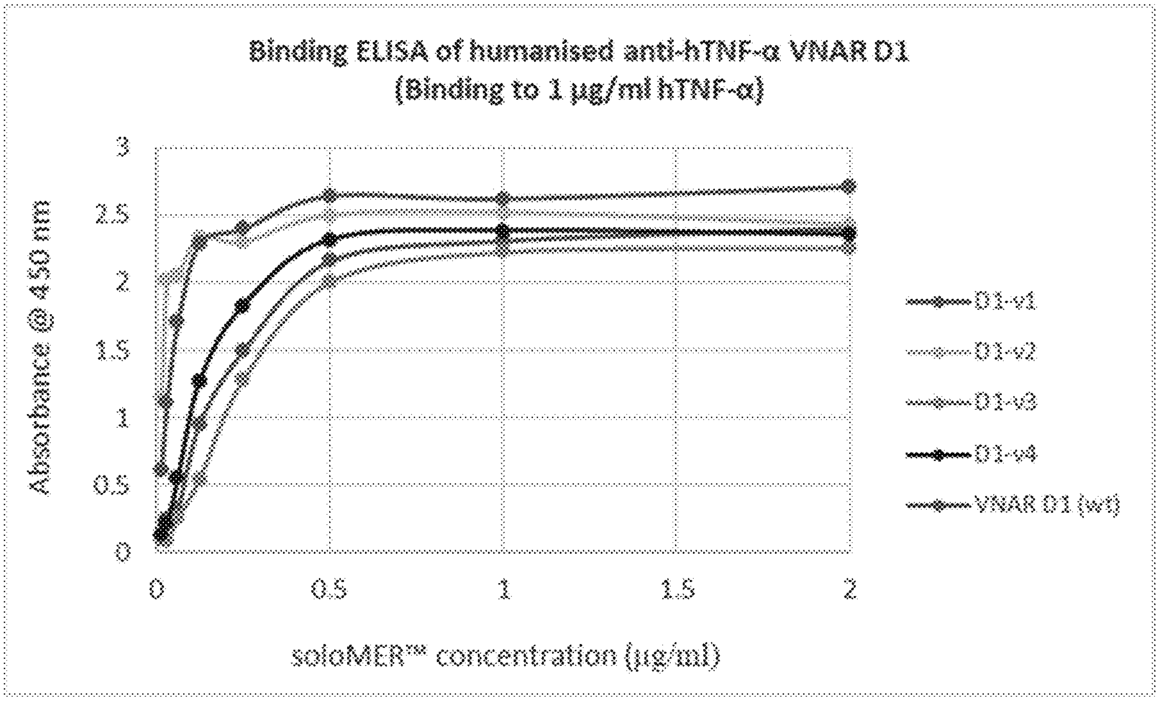
Figure 17:
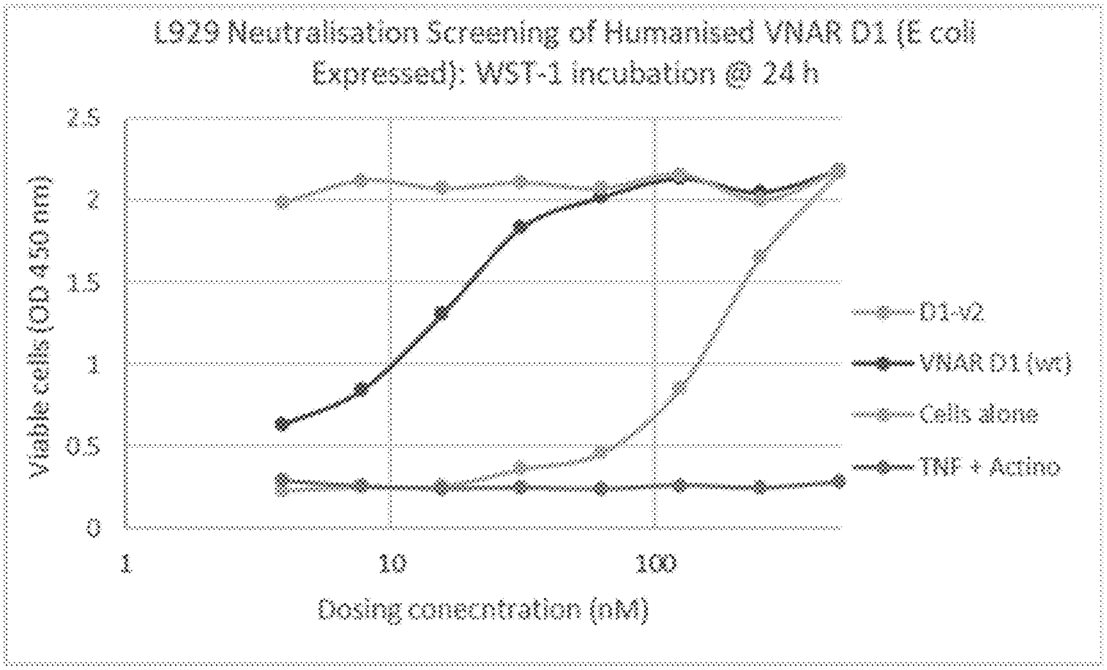
Figure 18:
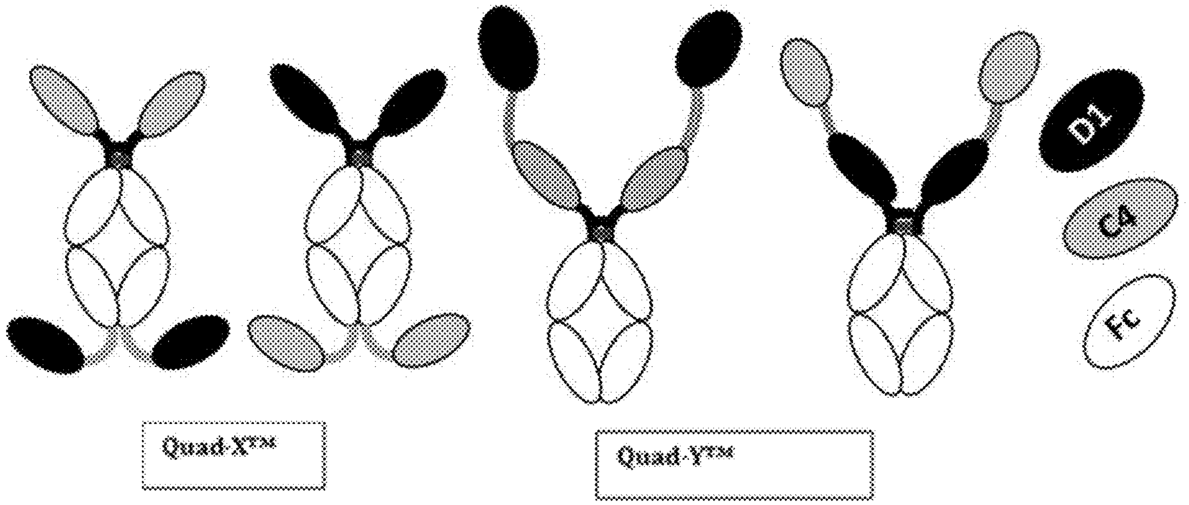
Figure 19:
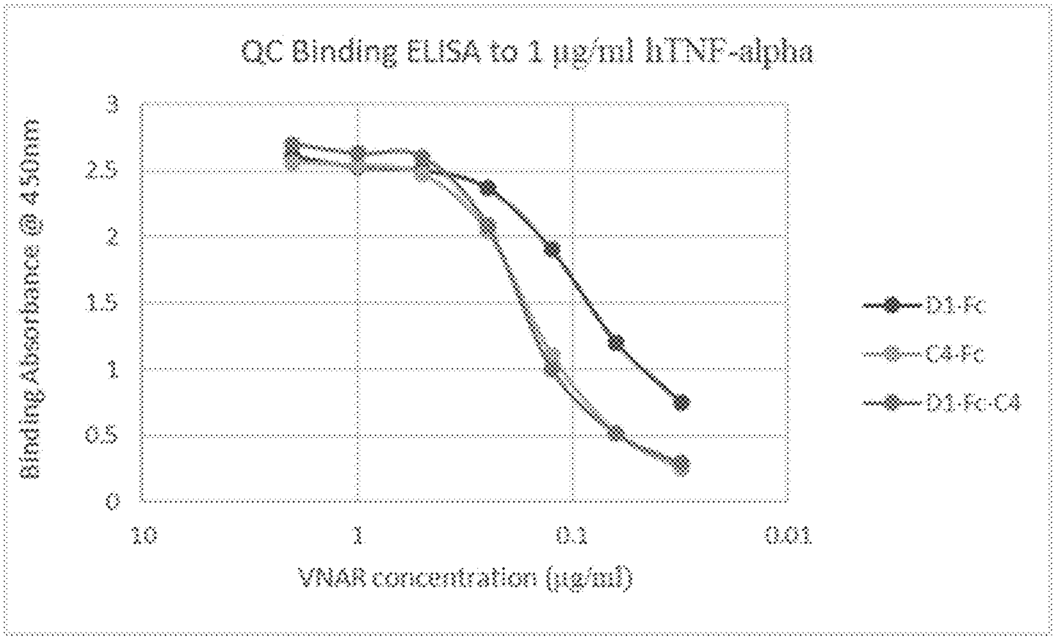
Figure 20:
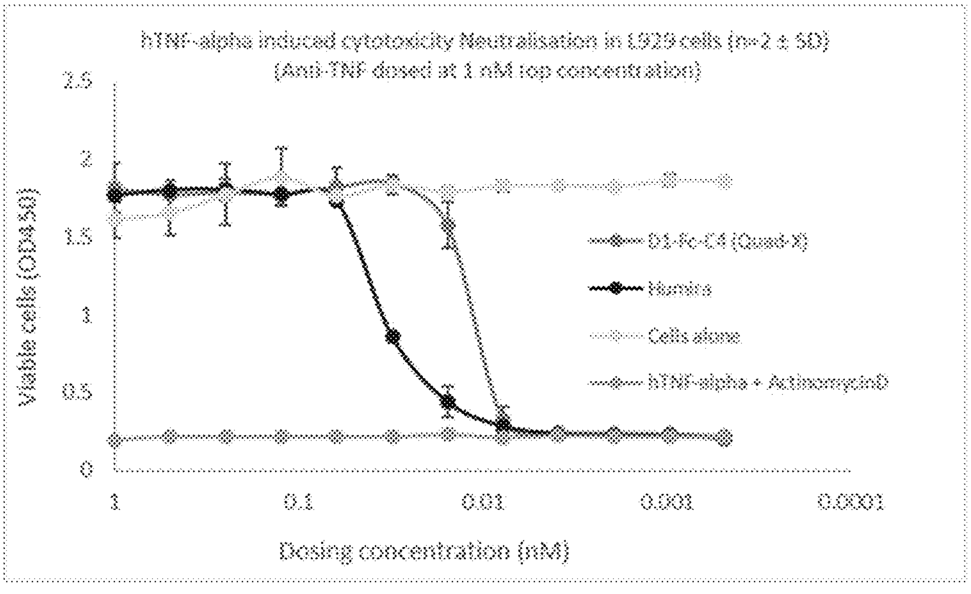
Figure 21:
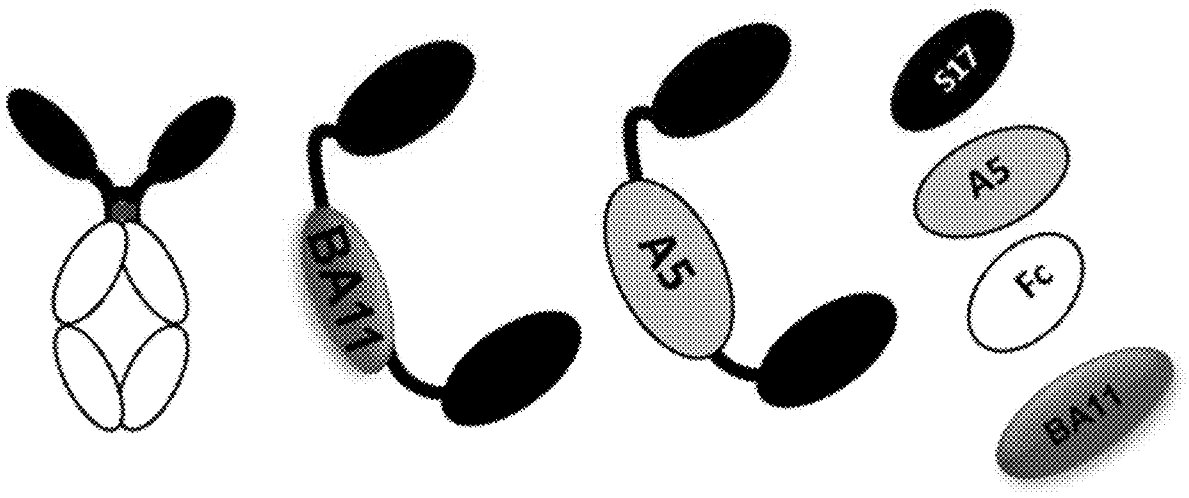
Figure 22A:
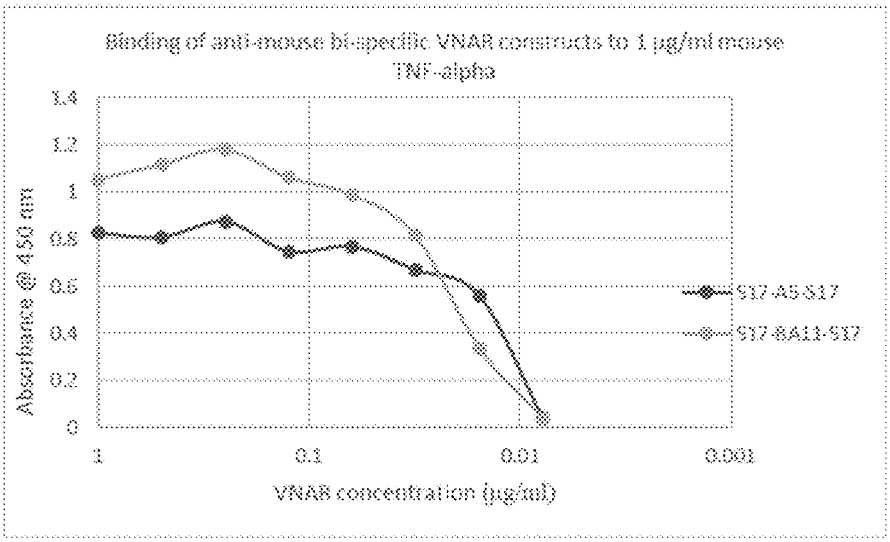
Figure 22B:
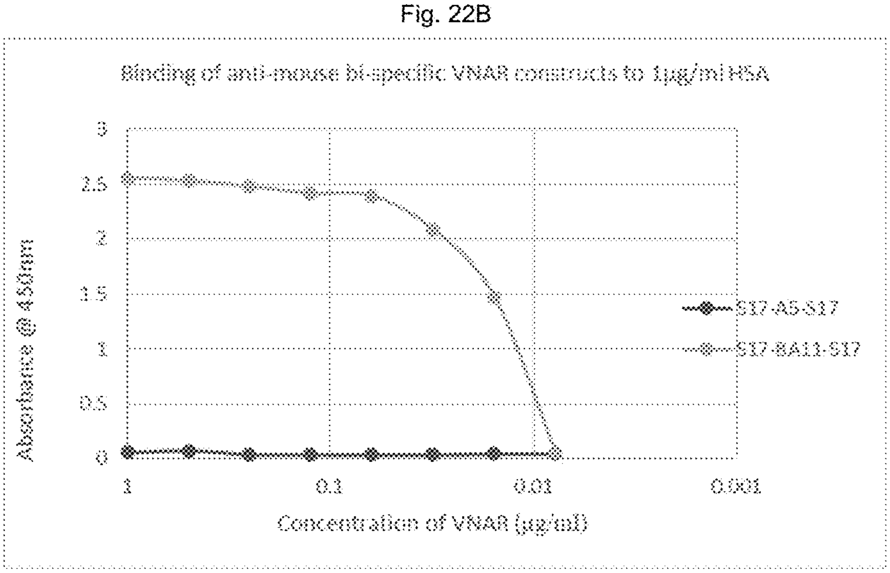
Figure 22C:
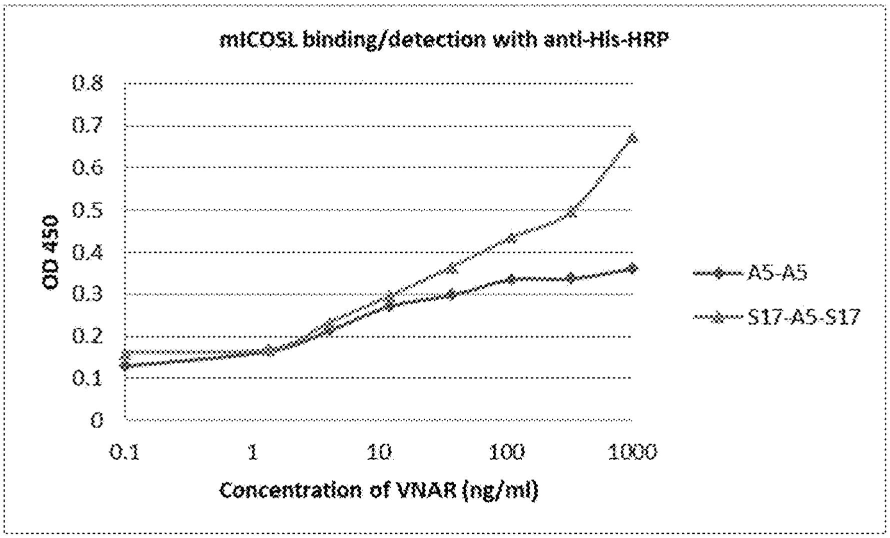
Figure 23A:
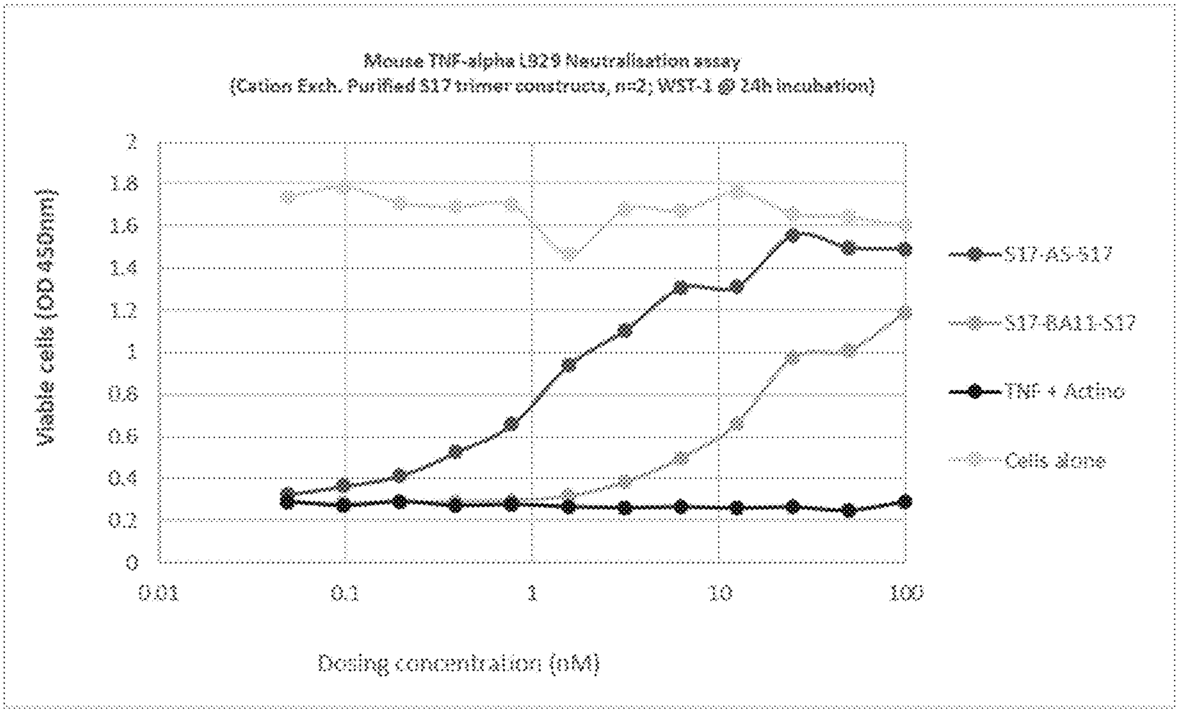
Figure 23B:
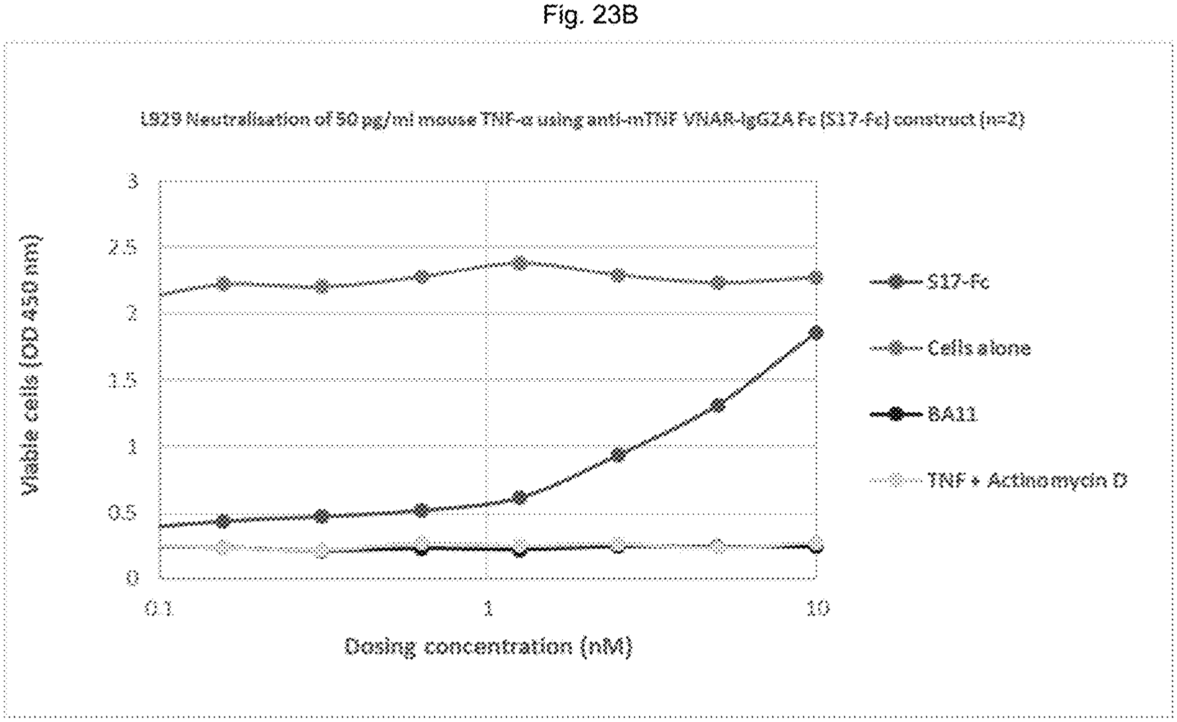
Figure 24:
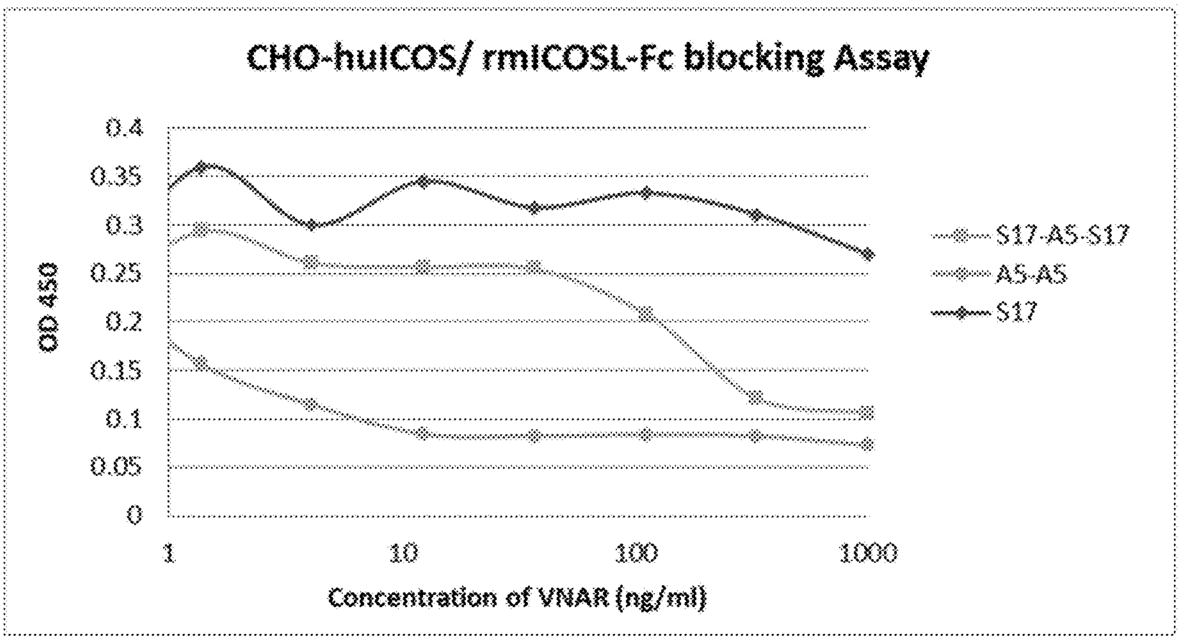
Figure 25:
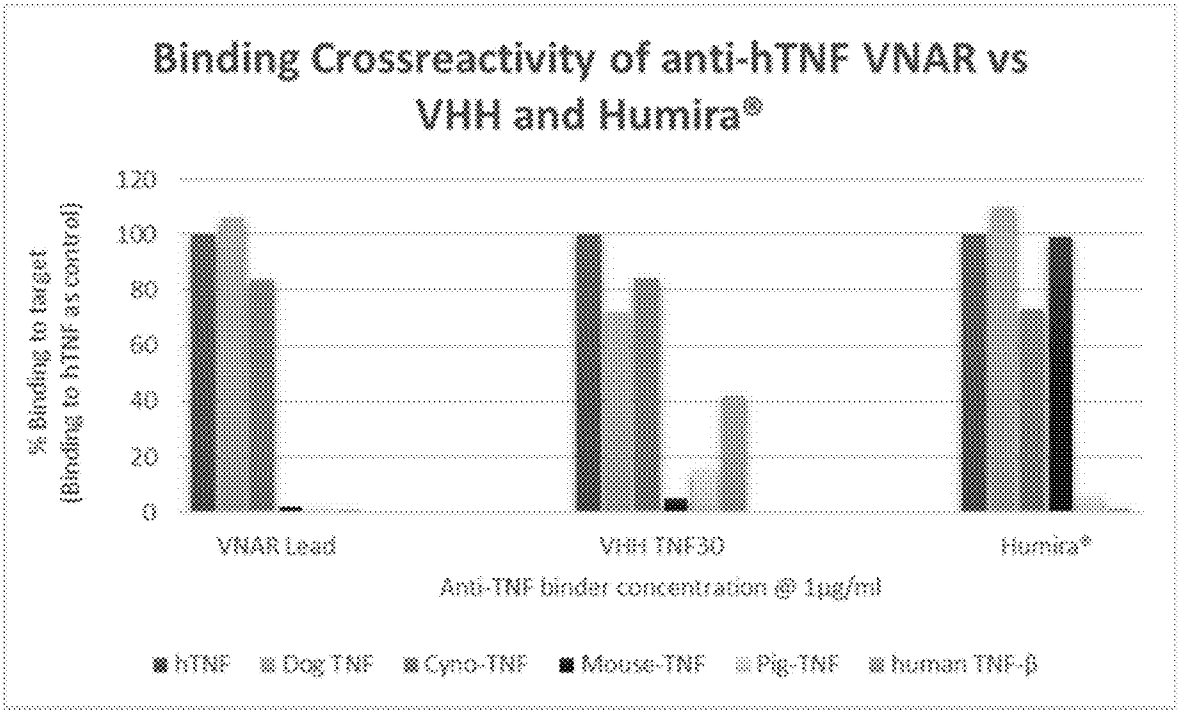
Figure 26:
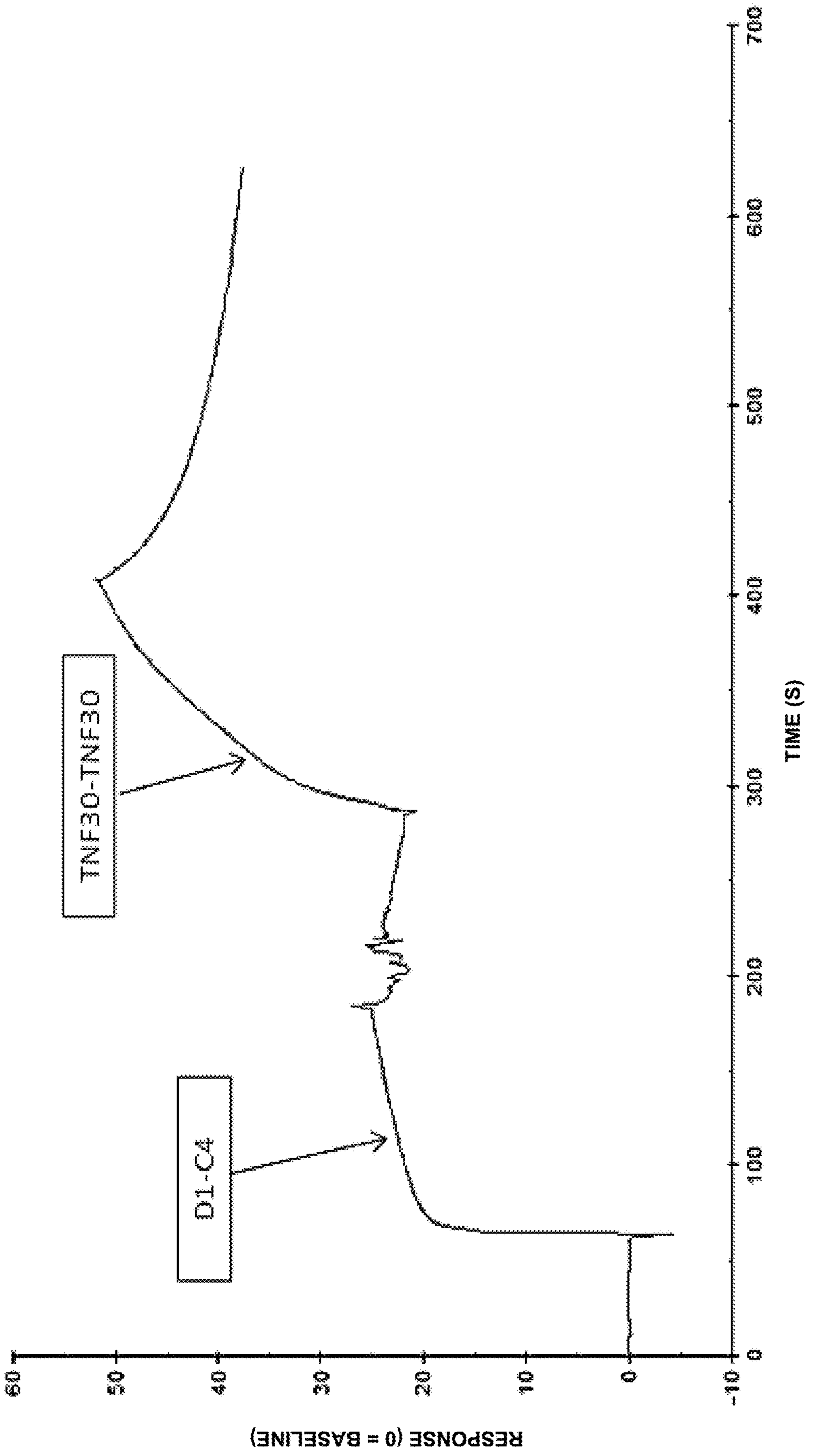
Figure 27:
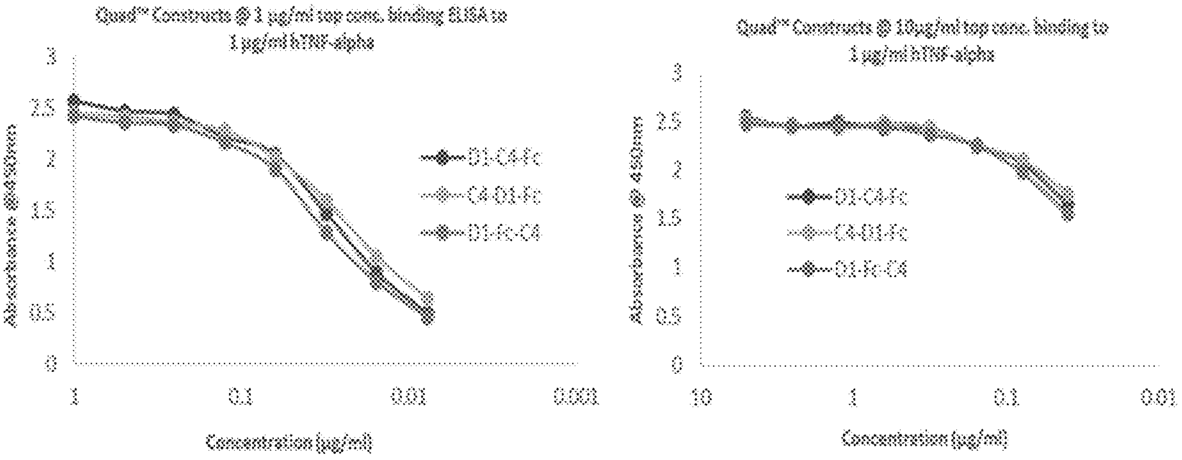
Figure 28:
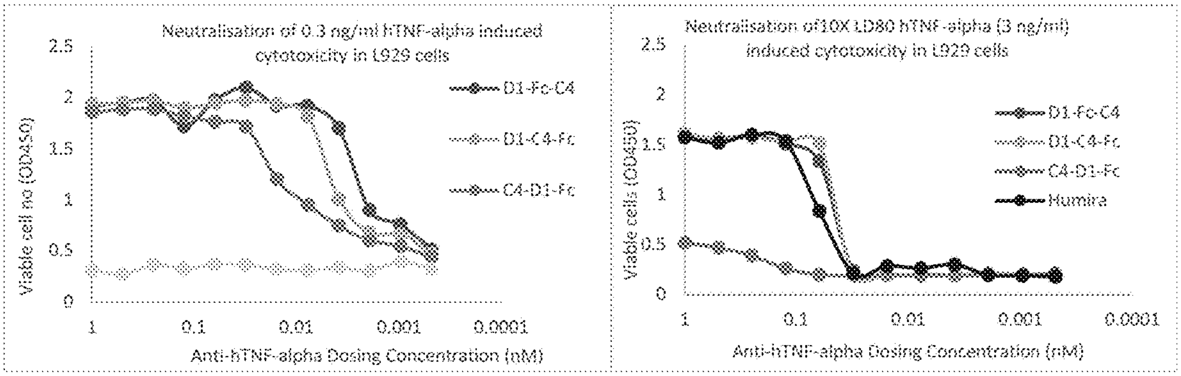
Figure 29:
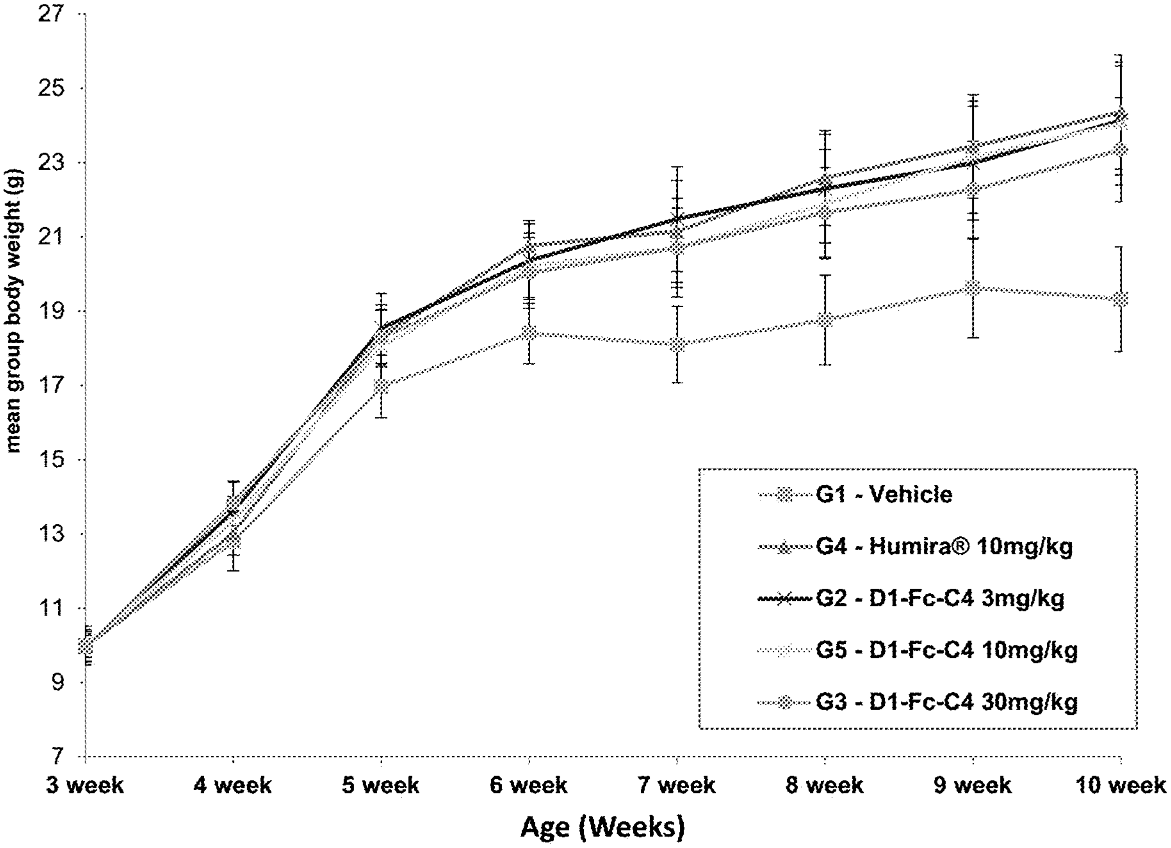

The data shows that the fusions are able to bind to TNF via TNFR1, and to mICOSL and hICOSL via the VNAR domains. The constructs are able to inhibit binding of m or hICOSL to their cognate CHO-expressed receptors These data demonstrate that VNARs combined into multivalent formats are capable of binding to their targets and the molecules are able to show improved properties over the monomer VNARs In Vivo Pre-Clinical Studies Background of the Study The Tg197 murine model of rheumatoid arthritis is a transgenic mouse line carrying and expressing wild type and 3'-modified human tumour necrosis factor (hTNF-α) transgenes. These transgenic mice develop chronic polyarthritis with 100% incidence at 4-7 weeks of age, dependent on the over expression of bioactive human TNF-α (Keffer et al. 1991, EMBO J., Vol. 10, pp. 4025-4031). The exemplification of the therapeutic efficacy of the first anti-TNF-α therapeutic antibody, Remicade® and other anti-TNF-alpha biologics were established using the Tg197 mouse model (Shealy et al., 2002, Arthritis Research & Therapy, 4(5), p.R7; Shealy et al., 2010, MAbs (Vol. 2, No. 4, pp. 428-439). Taylor & Francis).

The aim of the study was to evaluate the therapeutic efficacy of anti-TNF-α D1-Fc-C4 (Quad-X™) in comparison to Humira® in preventing arthritic symptoms in the Tg197 transgenic mouse model of arthritis.

Methods

A total of 40 mice were allocated to each of the 5 test groups, G1-G5 (Table 4). For the purpose of this study, transgenic mice were allocated to groups consisting of 8 mice each that received the test compounds or vehicle buffer (Phosphate buffered saline, PBS, pH 7.4), twice weekly subcutaneously starting at the third week of age, prior to the establishment of arthritis, and continuing over 7 weeks, until the 10th week of age. One additional group of transgenic mice (2 male and 2 female) untreated animals were used as 3-week old control mice for histopathological status, and were sacrificed prior to the first dose administration.

Mice were allocated into groups prior to performing the first arthritis scoring. Age and gender balanced study consisted of 8 ((4♂ and 4♀) heterozygous Tg197 for groups G1-G5 mice that were pooled from different litters of synchronized mating upon weaning. The assignment of the mice to the different experimental groups was performed in a fashion that ensured equal distribution of body weight among the different groups at the start of the study. In vivo arthritis scores was evaluated as described in Table 5. At the 10th week of age, all animals were sacrificed and the blood (serum isolated and stored at −80° C.) and the two ankle joints of each animal were collected. Ankle joints of all experimental animals were dissected, calcified and further processed to perform histopathological evaluation of arthritis. Ankle histopathology was assessed by microscopic examination according to the histopathology scoring systems described in Table 6, and only representative images were included in the results section.

TABLE 4

Experimental groups

| Group No.[1] | Test article | Dose (mg/kg) | Dose frequency (weeks)[2] | Duration of administration (weeks) | Dose volume (ml/kg) | Route of administration | Animal number | Age at sacrifice (weeks)[3] |
|---|---|---|---|---|---|---|---|---|
| G1 | Vehicle | 0 | 2/wk | 7 | 10 | s.c. | 8(4♂/4♀) | 10 |
| G4 | Humira ® | 10 | 2/wk | 7 | 10 | s.c. | 8(4♂/4♀) | 10 |
| G2 | Test article (D1-Fc-C4) | 3 | 2/wk | 7 | 10 | s.c. | 8(4♂/4♀) | 10 |
| G5 | Test article (D1-Fc-C4) | 10 | 2/wk | 7 | 10 | s.c. | 8(4♂/4♀) | 10 |
| G3 | Test article (D1-Fc-C4) | 30 | 2/wk | 7 | 10 | s.c. | 8(4♂/4♀) | 10 |
| 3-wk old control mice | — | — | — | — | — | — | 4(2♂/2♀) | 3 |

[1]The study was performed in a blinded fashion resulting in the random order of groups described in the table above.

[2]Administration was initiated at the age of 3 weeks.

[3]All mice of groups 1-5 were sacrificed 48 hours after the last dose administration. 3-week old control animals were sacrificed at the study initiation just before the first dose administration.

TABLE 5

Evaluation of in vivo arthritis score

| ARTHRITIS SCORE[1] | CHARACTERISTICS |
|---|---|
| 0/no disease | no arthritis (normal appearance, mouse can support its weight clinging to an inverted or tilted surface such as a wire grid or a cage lid for a period of time, whole body flexibility/evasiveness normal, grip strength maximum) |
| 0.5/mild disease | onset of arthritis (mild joint swelling, all other parameters as above) |
| 1/mild to moderate disease | mild to moderate (joint distortion by swelling, inflamed paw, all other parameters as above) |
| 1.5/moderate disease | moderate arthritis (joint-paw swelling, distortion + last finger inward deformation, brief support clinging to an inverted or tilted surface such as a wire grid or a cage lid, whole body flexibility reduced, reduced grip strength) |
| 2/moderate to severe disease | moderate to severe arthritis (severe joint, paw and finger swelling, joint-leg deformation, no support clinging to an inverted or tilted surface such as a wire grid or a cage lid, no whole-body flexibility, no grip strength, climbing/feeding affected, starts shaking when trying to move, but manages to move forward) |
| 2.5/severe disease | severe arthritis (as above 2+ finger deformation in front paws, mouse movement impaired, shaking not willing to move) |
| 3/very severe disease | very severe arthritis (ankylosis detected on flexion and severely impaired movement, mouse moribund, not shaking anymore, cannot turn/flip around readily when tilted to the side). |

[1]The addition of an extra 0.25 on the scoring of some assessments signifies a tendency towards the next more severe phenotype, i.e. when one, but not all the criteria from the next scale of severity are present. For example, "1.75" means "1.5" with severe swelling but no joint deformation and some strength on flexion.

In vivo arthritis scores with group average scores are depicted as graph in the results section.

TABLE 6

Cumulative histopathological criteria for scoring arthritic phenotype in the ankle joints

| SCORE[1] | DISEASE | CRITERIA |
|---|---|---|
| 0 | Normal | no detectable pathology |
| 1 | Mild | hyperplasia of the synovial membrane and presence of polymorphonuclear infiltrates. Mild tendonitis may be present. |
| 2 | Moderate | pannus and fibrous tissue formation and focal subchondrial bone erosion |
| 3 | Moderate-Severe | cartilage destruction and bone erosion |
| 4 | Severe | extensive cartilage destruction and bone erosion. Bone outline structure is lost |

(Adapted from: Pettit, A. R., et al., 2001, The American journal of pathology, 159(5), pp. 1689-1699; Mould, A. W., et al., 2003, Arthritis & Rheumatology, 48(9), pp. 2660-2669)
[1]Half marks are given when some but not all of the features from the next higher score are present. Hence, a score of "2.5" means pannus and fibrous tissue formation and focal subchondrial bone erosion (score 2), with more bone erosion spread outside and around subchondrial foci, but not as broad and with cartilage destruction, as to justify a score "3".

Histopathological scores with group average scores are depicted as bar graph in the results section and tables in the appendix. Illustrative histopathology images at 25× magnification are also presented in the appendix.

Results

The evaluation of the efficacy of the anti-hTNF-α D1-Fc-C4 (Quad-X™) and Humira® on the Tg197 arthritis model was performed following a prophylactic administration scheme, i.e. starting treatment at the 3rd week of age of the mice when they exhibited mild evidence of in vivo arthritis pathology and early histopathological lesions. By the 10th week of age, the in vivo arthritic score in the vehicle treated control group G1 increased dramatically compared to the 3-week old untreated animals, while at the same age the histopathological lesions observed in the animals of G1 were statistically more severe than that seen in the 3-week control mice group.

Efficacy Evaluation of the Therapeutic Effect of the Test Article D1-Fc-C4 Anti-hTNFα in the In Vivo and Histopathological as Well as Body Weight Arthritis Symptoms The 3, 10 and 30 mg/kg dose regimens of D1-Fc-C4 test article afforded statistical significant robust inhibition of the Tg197 in vivo and histopathological arthritic pathology compared to the vehicle treated mice in G1. More specifically, after 14 doses administered twice weekly for a period of 7 weeks, the dose regimens resulted in:

- 88 inhibition of the in vivo and ~86% inhibition of arthritis histopathology score following the 3 mg/kg D1-Fc-D4 test article treatment of animals in G2
- 88% significant inhibition of the in vivo and ~83% inhibition of arthritis histopathology score following the 10 mg/kg D1-Fc-C4 test article treatment of animals in G5
- 88% significant inhibition of the in vivo and ~86% inhibition of arthritis histopathology score following the 30 mg/kg D1-Fc-C4 test article treatment of animals in G3

Similar findings were observed in mean body weight curves of the D1-Fc-C4 test article treated mice which appeared to gain more body weight in all dose levels compared to the vehicle treated mice in G1 although statistical significance was achieved only in the 3 mg/kg and in the 10 mg/kg dose regimens.

D1-Fc-C4 Test Article Dose Response Efficacy Evaluation

Treatment with the 3, 10 and 30 mg/Kg doses of D1-Fc-D4 test article did not exhibit a dose-dependent response efficact as shown by the in vivo arthritic evaluations and body weight scores as well as from the histopathological evaluations in which all doses acted similarly and their therapeutic effects were statistically undifferentiated.

Efficacy Evaluation of the Therapeutic Effect of Humira® in the In Vivo and Histopathological as Well as Body Weight Arthritis Symptoms The 10 mg/kg dose regimen of Humira® afforded robust statistical significant inhibition of the Tg197 in vivo and histological arthritic pathology compared to the vehicle treated mice in G1. More specifically, after 14 doses administered twice weekly for a period of 7 weeks, we observed:

- 82% inhibition of the in vivo and ~86% inhibition of the arthritis histopathology score following the 10 mg/kg Humira® treatment of animals in G4

Similar findings were observed in mean body weight curve of the Humira® treated mice which appeared to gain more body weight compared to the vehicle treated mice in G1.

Dose Response Comparison Between D1-Fc-C4 Test Article and Humira®

The comparative examination of the inhibitory effects between D1-Fc-C4 test article and Humira® across the 10 mg/kg dose revealed that they were statistically undifferentiated in all parameters evaluated, including body weights, in vivo arthritic scores and histopathological evaluations.

Histopathological Comparison of the Effect of D1-Fc-C4 Test Article and Humira® to the 3-Week old control animals The inhibitory effects of the 3, 10 and 30 mg/Kg of the D1-Fc-C4 test article as well as the 10 mg/Kg Humira resulted in lower histopathology lesions at week 10 and statistically differentiated from the 3-week old control untreated animals.

TABLE 7

| Mean group body weights | | | | | | | | |
|---|---|---|---|---|---|---|---|---|
| Mean group body weight[1] (g) | Week 3 | Week 4 | Week 5 | Week 6 | Week 7 | Week 8 | Week 9 | Week 10 |
| 3-week old control mice | 9.8 ± 0.2 | — | — | — | — | — | — | — |
| G1-Vehicle | 10.0 ± 0.5 | 12.8 ± 0.8 | 17.0 ± 0.8 | 18.4 ± 0.8 | 18.1 ± 1.0 | 18.8 ± 1.2 | 19.6 ± 1.3 | 19.3 ± 1.4 |
| G4-Humira ® 10 mg/kg | 10.0 ± 0.3 | 13.0 ± 0.6 | 18.3 ± 0.8 | 20.8 ± 0.7 | 21.2 ± 1.4 | 22.6 ± 1.3 | 23.4 ± 1.4 | 24.4 ± 1.5 |
| G2-D1-Fc-C4 3 mg/kg | 10.0 ± 0.4 | 13.6 ± 0.8 | 18.5 ± 0.9 | 20.4 ± 1.0 | 21.5 ± 1.4 | 22.3 ± 1.5 | 23.0 ± 1.5 | 24.1 ± 1.5 |
| G5-D1-Fc-C4 10 mg/kg | 10.0 ± 0.3 | 13.4 ± 0.7 | 18.1 ± 1.0 | 20.2 ± 0.9 | 20.7 ± 1.3 | 21.9 ± 1.5 | 23.2 ± 1.5 | 24.1 ± 1.7 |
| G3-D1-Fc-C4 30 mg/kg | 10.0 ± 0.4 | 13.8 ± 0.6 | 18.3 ± 0.7 | 20.0 ± 1.0 | 20.7 ± 1.1 | 21.7 ± 1.2 | 22.3 ± 1.3 | 23.4 ± 1.4 |

[1]Data are presented as mean ± SEM

TABLE 8

| Mean group in vivo arthritis scores | | | | | | | | |
|---|---|---|---|---|---|---|---|---|
| Mean group in vivo arthritic scores[1] | Week 3 | Week 4 | Week 5 | Week 6 | Week 7 | Week 8 | Week 9 | Week 10 |
| 3-week old control mice | 0.13 ± 0.05 | — | — | — | — | — | — | — |
| G1-Vehicle | 0.14 ± 0.03 | 0.34 ± 0.03 | 0.58 ± 0.04 | 0.84 ± 0.05 | 0.94 ± 0.04 | 0.98 ± 0.04 | 1.20 ± 0.06 | 1.36 ± 0.07 |
| G4-Humira ® 10 mg/kg | 0.17 ± 0.04 | 0.28 ± 0.04 | 0.23 ± 0.05 | 0.19 ± 0.04 | 0.33 ± 0.04 | 0.25 ± 0.05 | 0.28 ± 0.04 | 0.25 ± 0.05 |
| G2-D1-Fc-C4 3 mg/kg | 0.13 ± 0.04 | 0.20 ± 0.03 | 0.17 ± 0.04 | 0.17 ± 0.04 | 0.19 ± 0.04 | 0.17 ± 0.03 | 0.16 ± 0.03 | 0.17 ± 0.04 |
| G5-D1-Fc-C4 10 mg/kg | 0.19 ± 0.04 | 0.20 ± 0.04 | 0.17 ± 0.03 | 0.28 ± 0.03 | 0.25 ± 0.03 | 0.27 ± 0.03 | 0.25 ± 0.02 | 0.17 ± 0.04 |
| G3-D1-Fc-C4 30 mg/kg | 0.09 ± 0.03 | 0.17 ± 0.04 | 0.17 ± 0.04 | 0.19 ± 0.05 | 0.22 ± 0.04 | 0.22 ± 0.04 | 0.20 ± 0.03 | 0.17 ± 0.04 |

[1]Data are presented as mean ± SEM

TABLE 9

| Mean group arthritis histopathology scores | | |
|---|---|---|
| Mean group histopathology scores[1] | Week 3 | Week 10 |
| 3-week old control mice | 1.22 ± 0.10 | — |
| G1-Vehicle | — | 2.94 ± 0.12 |
| G4-Humira ® 10 mg/kg | — | 0.42 ± 0.07 |
| G2-D1-Fc-C4 3 mg/kg | — | 0.41 ± 0.03 |
| G5-D1-Fc-C4 10 mg/kg | — | 0.50 ± 0.05 |
| G3-D1-Fc-C4 30 mg/kg | — | 0.42 ± 0.07 |

[1]Data are presented as mean ± SEM

In addition, a second exemplification of the in vitro potency enhancement using the VNAR S17 Quad-X™ construct targeting mouse TNF-alpha was conducted.

Figure 30:
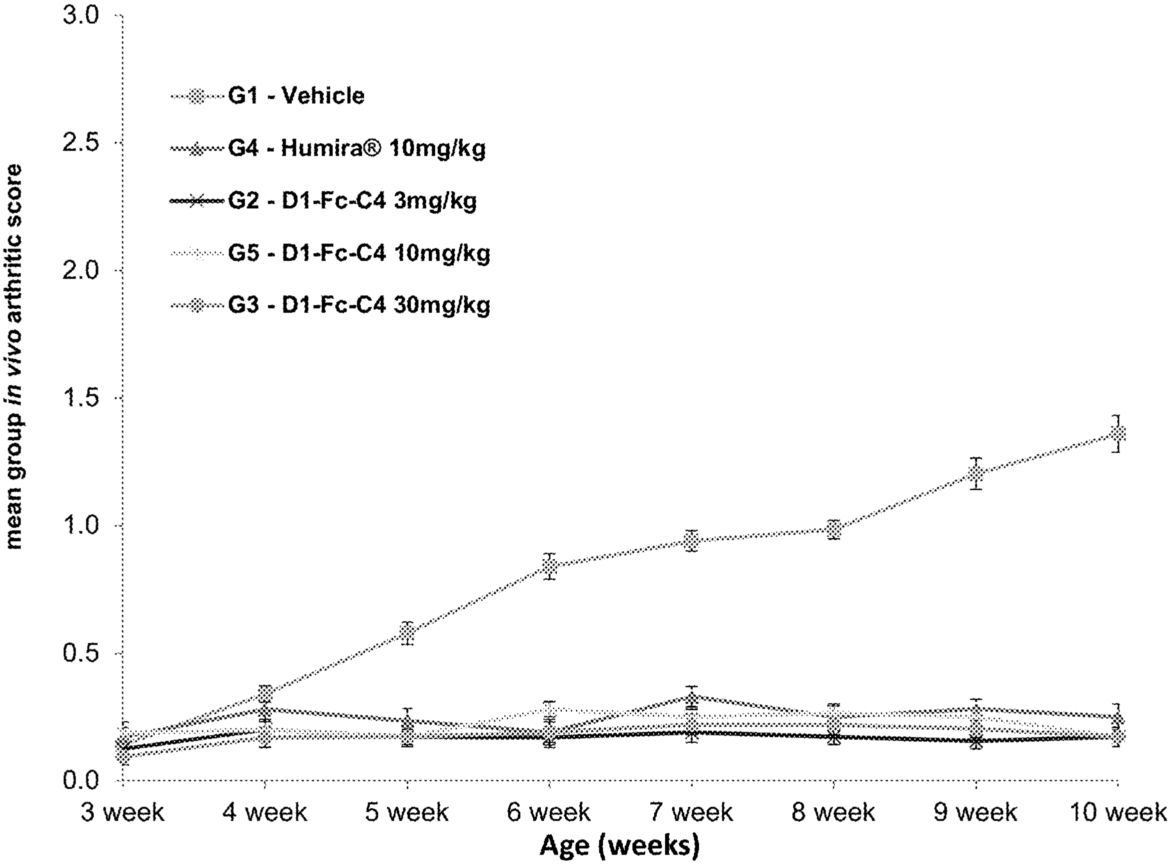

VNAR S17 is a specific anti-mouse TNF-alpha with no binding or neutralizing activity against human TNF-alpha. VNAR S17-Fc is a potent neutralizer of mouse TNF-alpha with in vitro potency (ND50) of approximately 8 nM. When designed as a Quad-X™ construct (S17-Fc-S17), in vitro neutralizing potency improved by ≈40-fold to 0.2 nM (FIG. 30).

Figure 31:
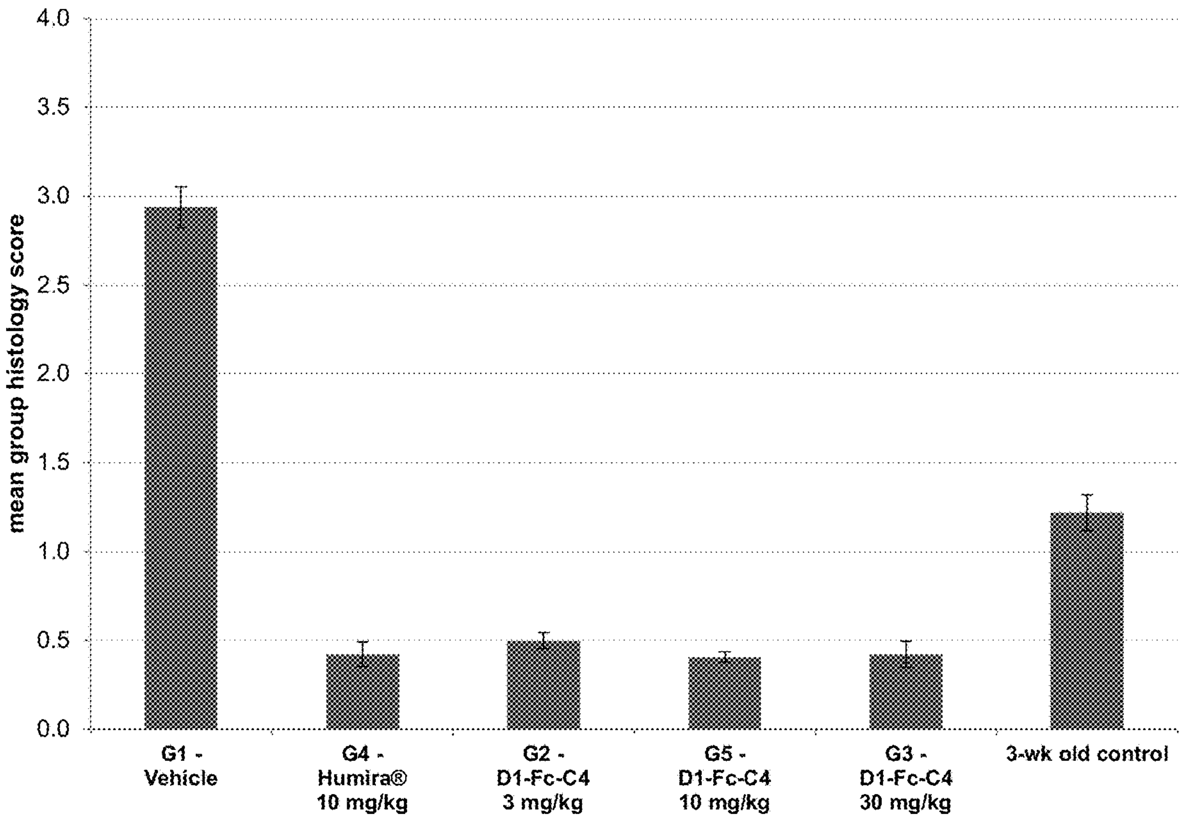
Figure 32:
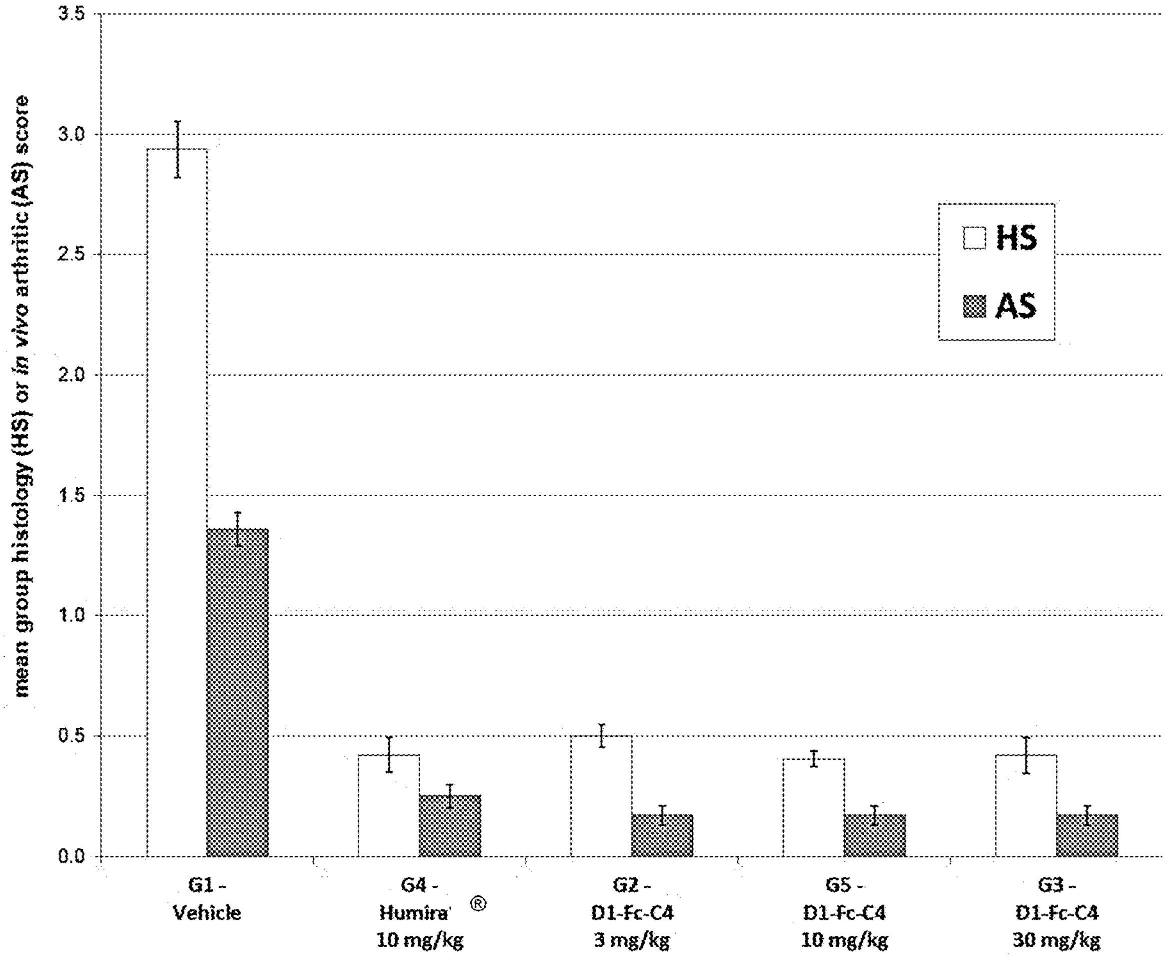

Furthermore, it has been demonstrated that the S17 Quad-X™ and D1-C4 Quad-X™ constructs recognize distinct species of TNF-alpha (FIG. 31).

DISCUSSION AND CONCLUSION

The results of this study show that the reference Humira® and D1-Fc-C4 (Quad-X™) and D1-BA11-C4 anti-hTNF-α articles inhibited the arthritic phenotype observed in Tg197 animals thus resulting in increased body weight and reduced in vivo and histopathological arthritic pathology as compared to the vehicle treated animals.

Figure 33:
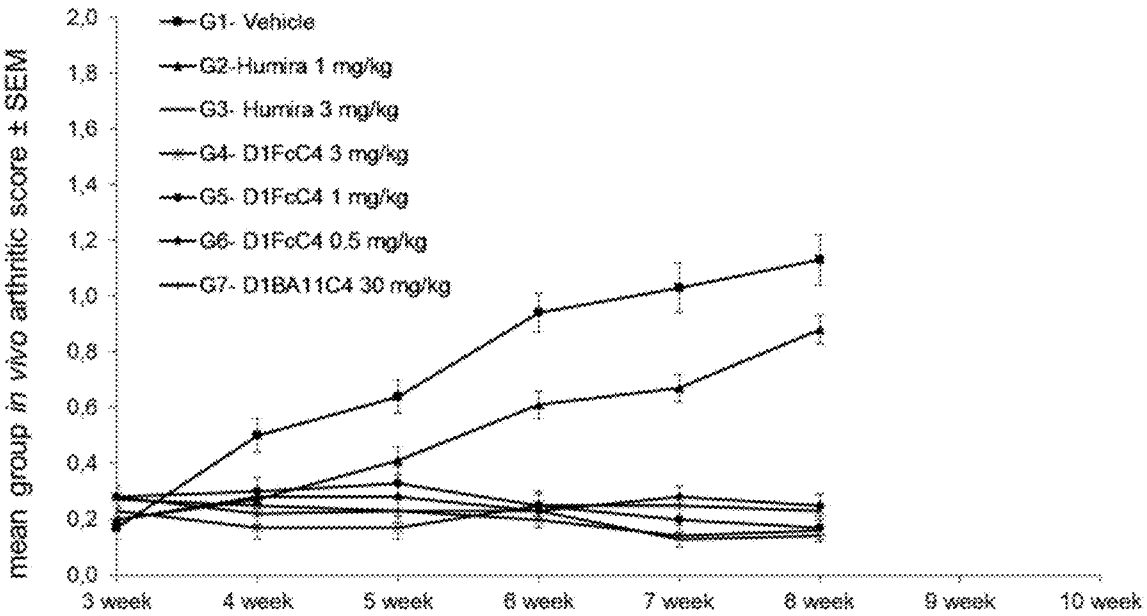
Figure 35:
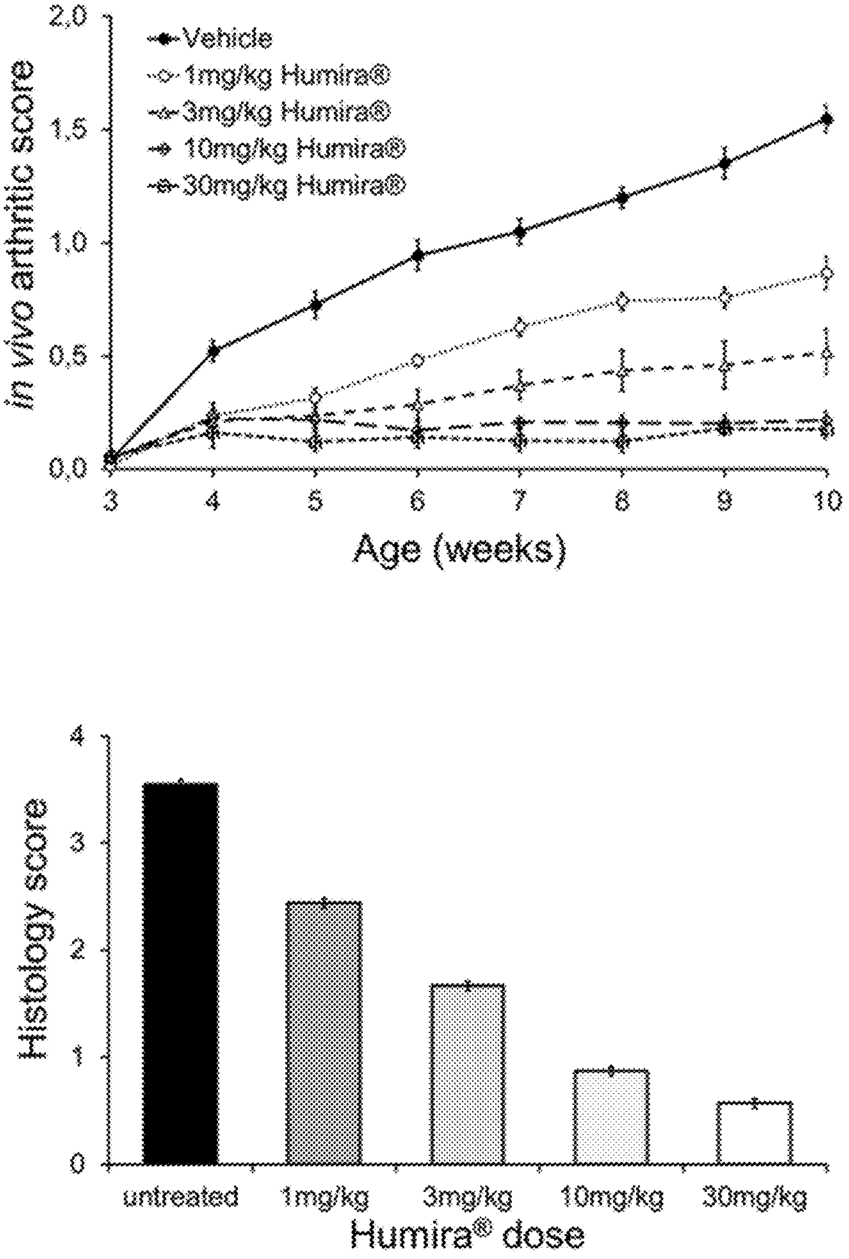

The therapeutic effect of the reference Humira® was evaluated at 10 mg/kg dose (FIG. 29-32) and resulted in statistically significant inhibition of the in vivo arthritic and ankle histopathological evaluations when compared to the vehicle treated mice. In FIG. 33, 1 mg/kg Humira® show significant disease breakthrough at 8 weeks. In a previous Tg197 mice model study using a dosing regimen of 1 mg/kg, 3 mg/kg, 10 mg/kg and 30 mg/kg Humira®, it was shown that there was significant disease breakthrough in the group of mice treated with either 1 mg/kg (FIG. 33) or 3 mg/kg Humira® (FIG. 35). These groups of mice had time-dependent disease progression similar to the untreated group, and in vivo arthritic (AS) and histopathology scores (HS) significantly higher than the groups treated with either 10 mg/kg or 30 mg/kg Humira® (FIG. 33).

The D1-Fc-C4 (Quad-X™) test articles did not exhibit a dose-dependent response as all evaluated doses, i.e. 0.5, 1, 3 mg/kg, 10 mg/kg and 30 mg/kg demonstrated similar and statistically undifferentiated therapeutic effects with complete control of the disease. Furthermore, in vivo arthritic and histopathological evaluations revealed that the therapeutic effect of the 3 mg/kg dose of D1-Fc-C4 test article was statistically comparable to that of 10 mg/kg Humira®.

We also did not observe any sign of disease breakthrough in the 3 mg/kg D1-Fc-C4 treated mice at 10 weeks of age, neither did we observe any with 0.5 and 1 mg/kg D1-Fc-C4 at 8 weeks of age.

Figure 34:
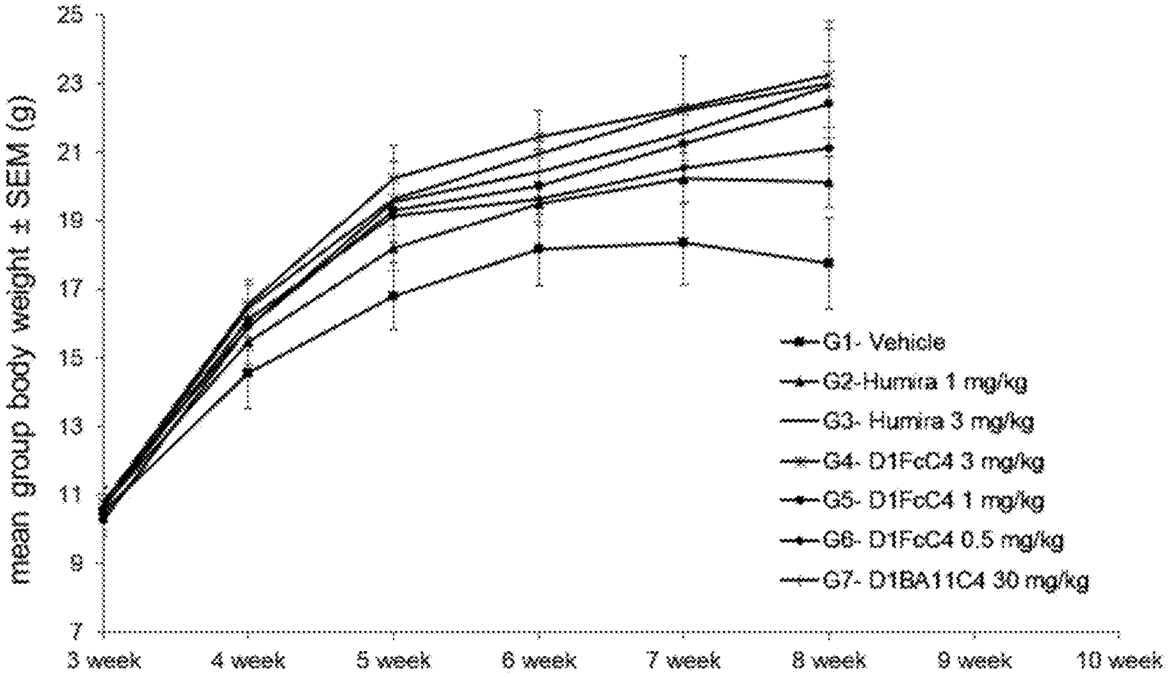

We have therefore further exemplified that the D1-Fc-C4 anti-hTNF-α domain is more potent than the standard therapy, Humira® in neutralising the effects of TNF-alpha both in vitro (L929 and Caco2 data—FIGS. 2, 3, 6 to 8, 20, 23 and 28) and in vivo (FIGS. 29-35). We have also demonstrated the in vivo efficacy of a non-Fc based tandem multivalent VNAR, D1-BA11-C4 (FIGS. 33 and 34).

Figure 36:
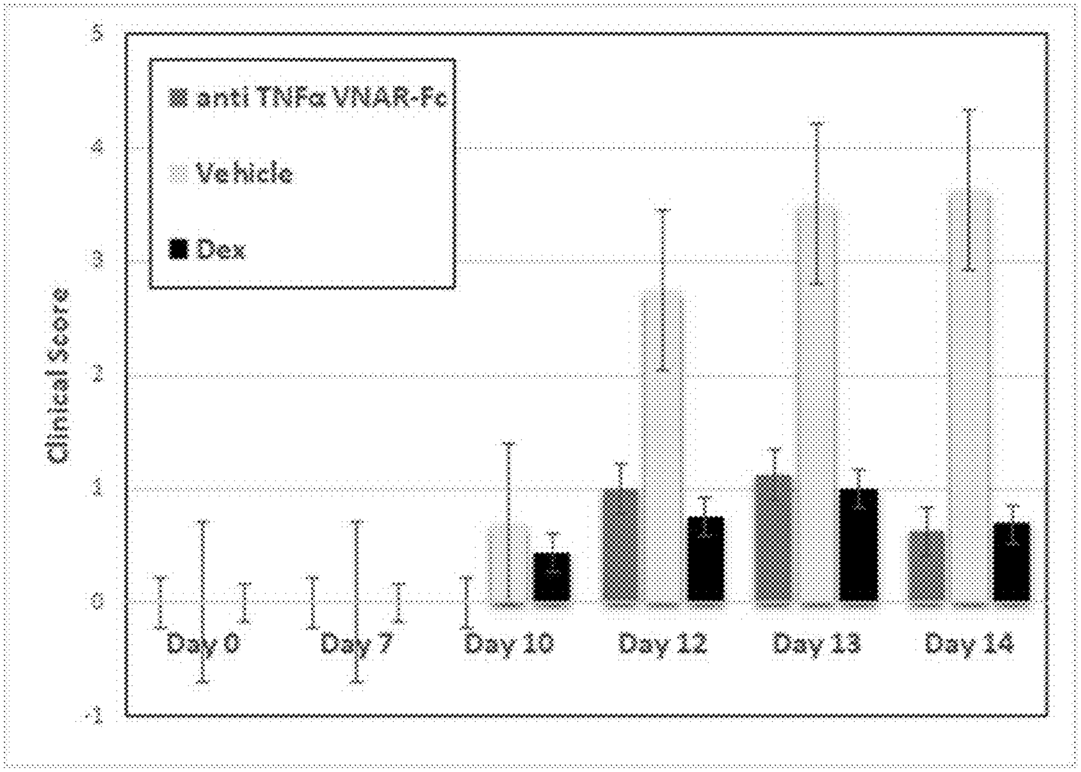
Figure 37A:
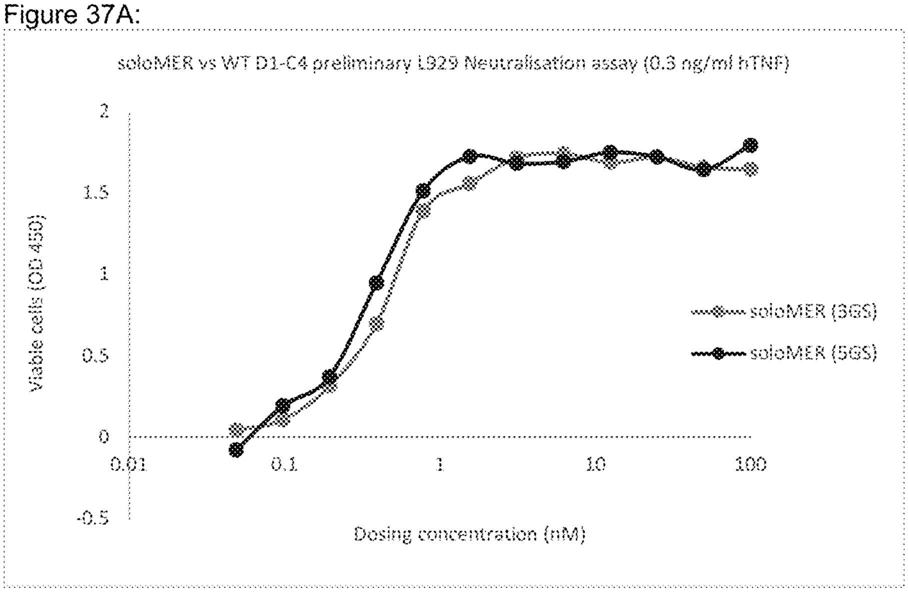
Figure 37B:
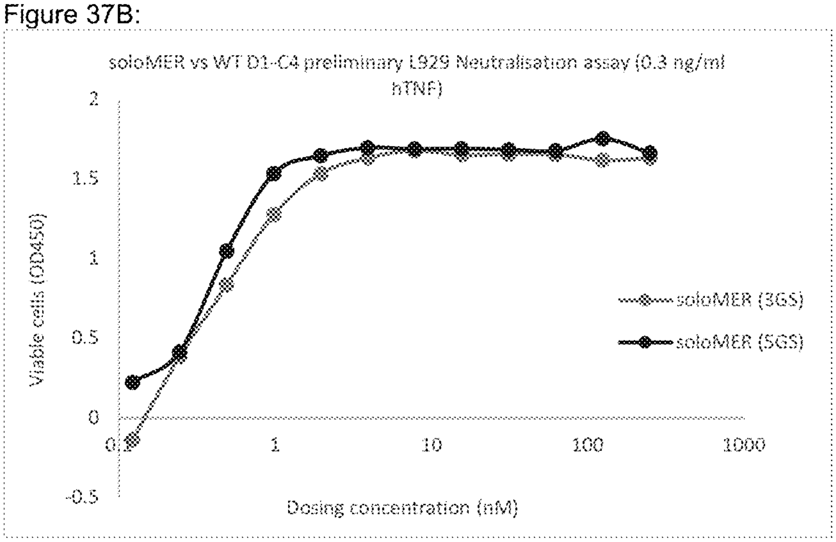
Figure 38:
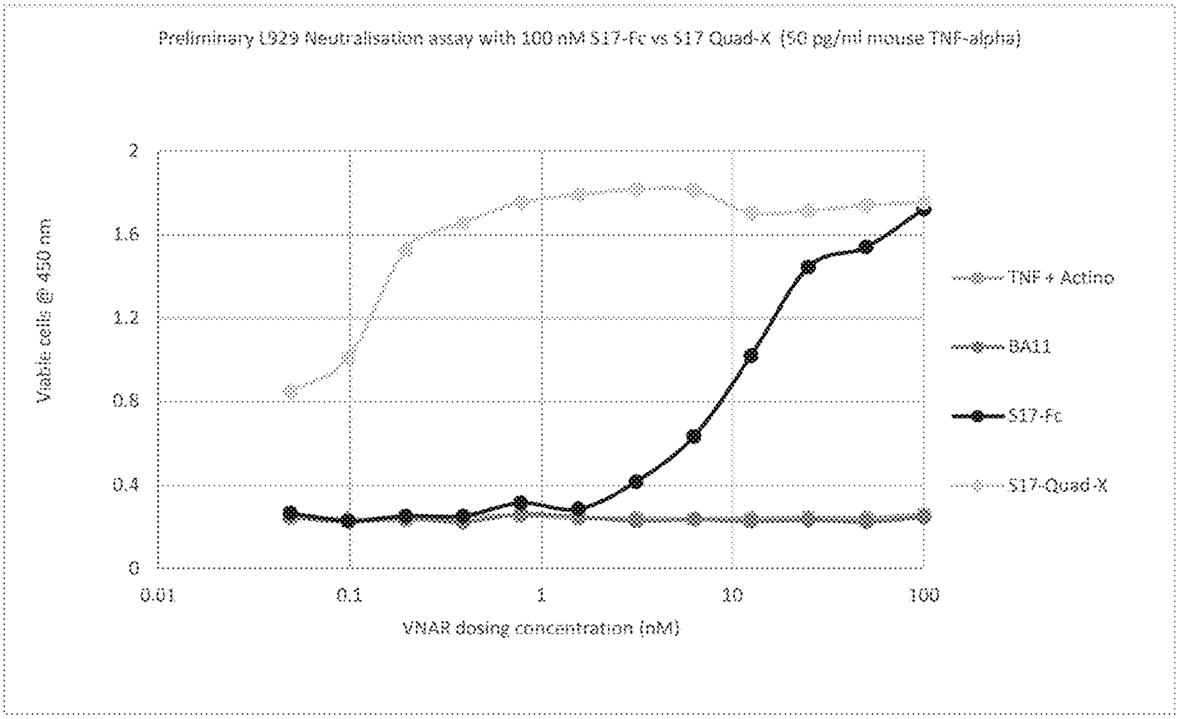
Figure 39A:
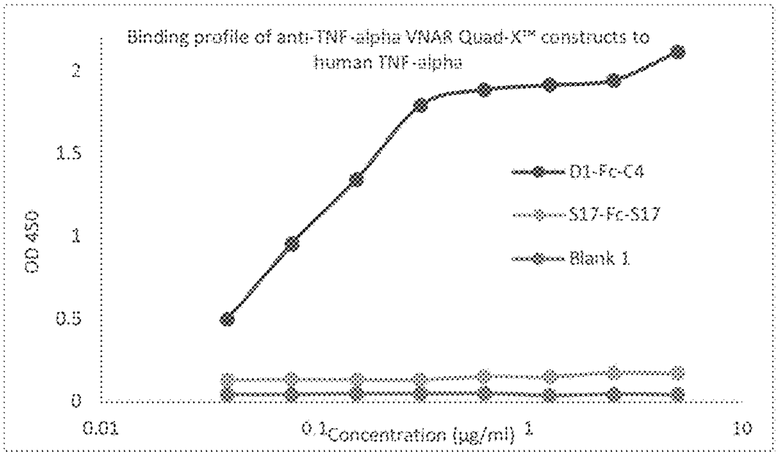
Figure 39B:
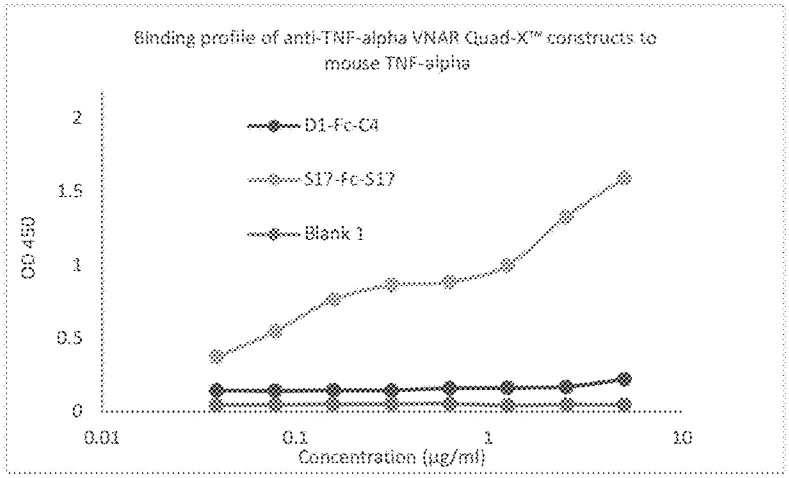
Figure 39C:
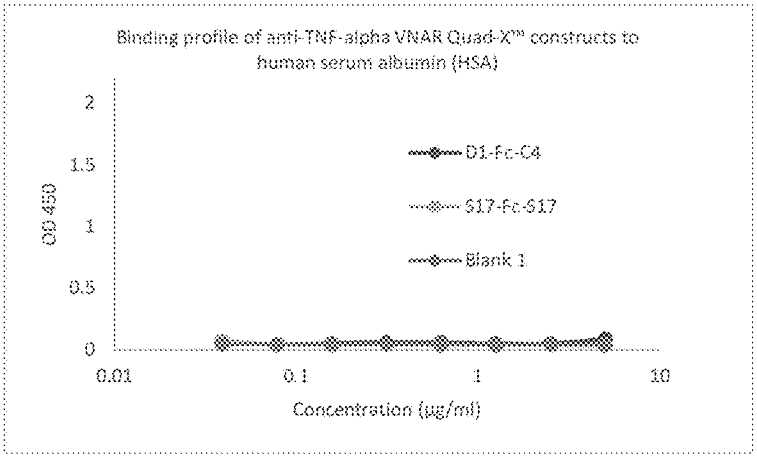

Finally we were able to show that an anti-TNF VNAR (D1-Fc) was also able to control and treat Uveitis (with a similar potency to Dexamethasone) in a rat model of inflammatory eye disease if administered systemically in an Fc alone format (FIG. 36).

We claim:

1. A TNF-alpha specific VNAR binding domain comprising the following CDRs and hyper-variable regions (HV):

a) CDR1 having the consensus amino acid sequence H/N-C-A/G-T/L-S-S (SEQ ID NO: 68-70);

b) HV2: (SEQ ID NO: 71)
TNEESISKG;

c) HV4 having the consensus amino acid sequence S/E-G-S-K-S (SEQ ID NO: 72-73); and d) CDR3: (SEQ ID NO. 1)
ECQYGLAEYDV
or
(SEQ ID NO. 6)
SWWTQNWRCSNSDV
or
(SEQ ID NO. 11)
YIPCIDELVYMISGGTSGPIHDV.

2. The TNF-alpha specific VNAR binding domain of claim 1, wherein the VNAR binding domain comprises a combination of CDRs and hyper-variable regions (HV) selected from:

a) CDR1 of (SEQ ID NO. 68)
HCATSS,
HV2 of (SEQ ID NO: 71)
TNEESISKG,
HV4 of (SEQ ID NO: 72)
SGSKS
and
CDR3 of (SEQ ID NO: 1)
ECQYGLAEYDV;

b) CDR1 of (SEQ ID NO: 69)
NCGLSS,
HV2 of (SEQ ID NO: 71)
TNEESISKG,
HV4 of (SEQ ID NO: 73)
EGSKS
and
CDR3 of (SEQ ID NO: 6)
SWWTQNWRCSNSDV;

-continued or c) CDR1 of (SEQ ID NO: 70)
NCALSS,
HV2 of (SEQ ID NO: 71)
TNEESISKG,
HV4 of (SEQ ID NO: 72)
SGSKS
and
CDR3 of (SEQ ID NO: 11)
YIPCIDELVYMISGGTSGPIHDV.

3. The TNF-alpha specific VNAR binding domain of claim 1, wherein the VNAR binding domain comprises the amino acid sequence of SEQ ID NO: 2, 7, or 12.

4. The TNF-alpha specific VNAR binding domain of claim 1, wherein the VNAR domain is humanized or de-immunized.

5. The TNF-alpha specific VNAR binding domain of claim 4, wherein the humanized or de-immunized VNAR binding domain comprises the amino acid sequence of:

(amino acids 1-106 of SEQ ID NO: 51)
a) ARVDQSPSSLSASVGDRVTITCVLRDSHCATSSTYWYRKKSGSTNEES
ISKGGRYVETVNSGSKSFSLRINDLTVEDSGTYRCASECQYGLAEYDVYG
GGTKVEIK;

(amino acids 1-106 of SEQ ID NO: 53)
b) ARVDQSPSSLSASVGDRVTITCVLRDSHCATSSTYWYRKKSGSTNEES
ISKGGRYVETVNSGSKSFTLTISSLQPEDFATYYCASECQYGLAEYDVYG
GGTKVEIK;

(amino acids 1-106 of SEQ ID NO: 55)
c) ARVDQSPSSLSASVGDRVTITCVLRDSHCATSSTYWYQQKPGKTNEES
ISKGGRYVETVNSGSKSFTLTISSLQPEDFATYYCASECQYGLAEYDVYG
GGTKVEIK;
or (amino acids 1-106 of SEQ ID NO: 57)
d) ARVDQSPSSLSASVGDRVTITCVLRDSHCATSSTYWYRKKPGSTNEES
ISKGGRFSGSGSSGSKSFTLTISSLQPEDFATYYCASECQYGLAEYDVFG
QGTKVEIK.

6. An isolated nucleic acid comprising a polynucleotide sequence that encodes a binding molecule according to claim 1.

7. A method for preparing a binding molecule, comprising cultivating or maintaining a host cell comprising the polynucleotide of claim 6 under conditions such that said host cell produces the binding molecule, optionally further comprising isolating the binding molecule.

8. A pharmaceutical composition comprising the TNF-alpha specific VNAR binding domain according to claim 1, and optionally at least one pharmaceutically acceptable carrier.

9. The TNF-alpha specific VNAR binding domain according to claim 1, for use in therapy.

10. A method of treating a condition mediated by TNFα, the method comprising administering a therapeutically effective amount of a composition of claim 8.

11. A multi-domain specific binding molecule comprising two or more VNAR domains which bind to the same or different epitopes of one or more specific antigens, further comprising a spacer sequence between the VNAR domains, wherein the spacer sequence is derived from an immunoglobulin Fc region, wherein at least one of the VNAR domains is a TNF-alpha specific VNAR binding domain comprising the following CDRs and hyper-variable regions (HV):

a) CDR1 having the consensus amino acid sequence H/N-C-A/G-T/L-S-S (SEQ ID NO: 68-70);

```
b) HV2:
                                    (SEQ ID NO: 71)
TNEESISKG;

c) HV4 having the consensus sequence
                                 (SEQ ID NO: 72-73)
S/E-G-S-K-S;
and

d) CDR3:
                                     (SEQ ID NO. 1)
ECQYGLAEYDV
or

                                     (SEQ ID NO. 6)
SWWTQNWRCSNSDV
or

                                    (SEQ ID NO. 11)
YIPCIDELVYMISGGTSGPIHDV.
```

12. The multi-domain specific binding molecule of claim 11, wherein at least one of the two or more VNAR domains is humanized or de-immunized.

13. The multi-domain specific binding molecule of claim 11, wherein at least one VNAR binding domain comprises the amino acid sequence of:

```
                      (amino acids 1-106 of SEQ ID NO: 51)
a) ARVDQSPSSLSASVGDRVTITCVLRDSHCATSSTYWYRKKSGSTNEES

ISKGGRYVETVNSGSKSFSLRINDLTVEDSGTYRCASECQYGLAEYDVYG

GGTKVEIK;
```

-continued

```
                      (amino acids 1-106 of SEQ ID NO: 53)
b) ARVDQSPSSLSASVGDRVTITCVLRDSHCATSSTYWYRKKSGSTNEES

ISKGGRYVETVNSGSKSFTLTISSLQPEDFATYYCASECQYGLAEYDVYG

GGTKVEIK;

                      (amino acids 1-106 of SEQ ID NO: 55)
c) ARVDQSPSSLSASVGDRVTITCVLRDSHCATSSTYWYQQKPGKTNEES

ISKGGRYVETVNSGSKSFTLTISSLQPEDFATYYCASECQYGLAEYDVYG

GGTKVEIK;
or

                      (amino acids 1-106 of SEQ ID NO: 57)
d) ARVDQSPSSLSASVGDRVTITCVLRDSHCATSSTYWYRKKPGSTNEES

ISKGGRFSGSGSSGSKSFTLTISSLQPEDFATYYCASECQYGLAEYDVFG

QGTKVEIK.
```

14. The multi-domain specific binding molecule of claim 11, wherein one or more of the VNAR domains in the multi-domain specific binding molecule exhibit higher binding affinity for their target compared to the monomeric VNAR.

15. The multi-domain specific binding molecule of claim 11, wherein the two or more VNAR domains bind to the same or different epitopes of one specific antigen.

16. The multi-domain specific binding molecule of claim 11, wherein the two or more VNAR domains bind to different epitopes of one specific antigen.

17. The multi-domain specific binding molecule of claim 11, wherein the two or more VNAR domains each bind to a different specific antigen.

18. The multi-domain specific binding molecule of claim 11, wherein the spacer sequence is derived from a human immunoglobulin Fc region.

19. The multi-domain specific binding molecule of claim 11, wherein two or more of the VNAR domains have an amino acid sequence selected from the group comprising SEQ ID NO: 2, 7, or 12.

20. An isolated nucleic acid comprising a polynucleotide sequence that encodes a multi-domain specific binding molecule according to claim 11.

21. A method for preparing a binding molecule, comprising cultivating or maintaining a host cell comprising the polynucleotide of claim 20 under conditions such that said host cell produces the binding molecule and isolating the binding molecule.

22. A pharmaceutical composition comprising the multi-domain specific binding molecule of claim 11 and at least one pharmaceutically acceptable carrier.

23. A method of treating a condition mediated by TNFα, the method comprising administering a therapeutically effective amount of a composition of claim 22 to a patient.

* * * * *

```
                       SEQUENCE LISTING

Sequence total quantity: 96
SEQ ID NO: 1            moltype = AA  length = 11
FEATURE                 Location/Qualifiers
REGION                  1..11
                        note = TNF VNAR D1 CDR3
source                  1..11
                        mol_type = protein
                        organism = synthetic construct
SEQUENCE: 1
ECQYGLAEYD V                                                        11

SEQ ID NO: 2            moltype = AA  length = 106
FEATURE                 Location/Qualifiers
REGION                  1..106
                        note = TNF VNAR D1 CDR3
source                  1..106
                        mol_type = protein
                        organism = synthetic construct
SEQUENCE: 2
ARVDQTPQTI TKETGESLTI NCVLRDSHCA TSSTYWYRKK SGSTNEESIS KGGRYVETVN  60
SGSKSFSLRI NDLTVEDSGT YRCASECQYG LAEYDVYGGG TVVTVN                 106

SEQ ID NO: 3            moltype = AA  length = 128
FEATURE                 Location/Qualifiers
REGION                  1..128
                        note = TNF VNAR D1
source                  1..128
                        mol_type = protein
                        organism = synthetic construct
SEQUENCE: 3
ARVDQTPQTI TKETGESLTI NCVLRDSHCA TSSTYWYRKK SGSTNEESIS KGGRYVETVN  60
SGSKSFSLRI NDLTVEDSGT YRCASECQYG LAEYDVYGGG TVVTVNAAAH HHHHHGAAES  120
KLISEEDL                                                           128

SEQ ID NO: 4            moltype = DNA  length = 318
FEATURE                 Location/Qualifiers
misc_feature            1..318
                        note = TNF VNAR D1
source                  1..318
                        mol_type = other DNA
                        organism = synthetic construct
SEQUENCE: 4
gctcgagtgg accaaacacc gcaaacaata acaaaggaga cgggcgaatc actgaccatc  60
aactgtgtcc tacgagatag ccactgtgca acctccagca cgtactggta tcgcaaaaaa  120
tcgggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgcg cttccgagtg ccaatatgga ctggcagaat atgatgtata cggaggtggc  300
actgtcgtga ctgtgaat                                                318

SEQ ID NO: 5            moltype = DNA  length = 384
FEATURE                 Location/Qualifiers
misc_feature            1..384
                        note = TNF VNAR D1 WITH HIS AND MYC TAGS
source                  1..384
                        mol_type = other DNA
                        organism = synthetic construct
SEQUENCE: 5
```

-continued

```
gctcgagtgg accaaacacc gcaaacaata acaaaggaga cgggcgaatc actgaccatc  60
aactgtgtcc tacgagatag ccactgtgca acctccagca cgtactggta tcgcaaaaaa  120
tcgggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgcg cttccgagtg ccaatatgga ctggcagaat atgatgtata cggaggtggc  300
actgtcgtga ctgtgaatgc ggccgcacat catcatcacc atcacggcgc cgcagaatca  360
aaactcatct cagaagagga tctg                                          384

SEQ ID NO: 6            moltype = AA  length = 14
FEATURE                 Location/Qualifiers
REGION                  1..14
                        note = TNF VNAR C4 CDR3
source                  1..14
                        mol_type = protein
                        organism = synthetic construct
SEQUENCE: 6
SWWTQNWRCS NSDV                                                     14

SEQ ID NO: 7            moltype = AA  length = 108
FEATURE                 Location/Qualifiers
REGION                  1..108
                        note = TNF VNAR C4
source                  1..108
                        mol_type = protein
                        organism = synthetic construct
SEQUENCE: 7
RVDQTPQTIT KETGESLTIN CVLRDSNCGL SSTYWYRKKS GSTNEESISK GGRYVETINE  60
GSKSFSLRIN DLTVEDSGTY RCKLSWWTQN WRCSNSDVYG GGTVVTVN                108

SEQ ID NO: 8            moltype = AA  length = 131
FEATURE                 Location/Qualifiers
REGION                  1..131
                        note = TNF VNAR C4 AMINO ACID SEQUENCE WITH HIS AND MYC TAGS
source                  1..131
                        mol_type = protein
                        organism = synthetic construct
SEQUENCE: 8
ARVDQTPQTI TKETGESLTI NCVLRDSNCG LSSTYWYRKK SGSTNEESIS KGGRYVETIN  60
EGSKSFSLRI NDLTVEDSGT YRCKLSWWTQ NWRCSNSDVY GGGTVVTVNA AAHHHHHHGA  120
AESKLISEED L                                                        131

SEQ ID NO: 9            moltype = DNA  length = 327
FEATURE                 Location/Qualifiers
misc_feature            1..327
                        note = TNF VNAR C4
source                  1..327
                        mol_type = other DNA
                        organism = synthetic construct
SEQUENCE: 9
gctcgagtgg accaaacacc gcaaacaata acaaaggaga cgggcgaatc actgaccatc  60
aactgtgtcc tacgagatag caactgtggg ttgtccagca cgtactggta tcgcaaaaaa  120
tcgggctcaa caaacgagga gagcatatcg aaaggtggac gatatgttga aacaattaac  180
gaaggatcaa agtccttttc tttgagaatt aatgatctaa cagttgaaga cagtggcacg  240
tatcgatgca agttaagctg gtggacccag aactggagat gctcaaattc cgatgtatac  300
ggaggtggca ctgtcgtgac tgtgaat                                       327

SEQ ID NO: 10           moltype = DNA  length = 393
FEATURE                 Location/Qualifiers
misc_feature            1..393
                        note = TNF VNAR D1 WITH HIS AND MYC TAGS
source                  1..393
                        mol_type = other DNA
                        organism = synthetic construct
SEQUENCE: 10
gctcgagtgg accaaacacc gcaaacaata acaaaggaga cgggcgaatc actgaccatc  60
aactgtgtcc tacgagatag caactgtggg ttgtccagca cgtactggta tcgcaaaaaa  120
tcgggctcaa caaacgagga gagcatatcg aaaggtggac gatatgttga aacaattaac  180
gaaggatcaa agtccttttc tttgagaatt aatgatctaa cagttgaaga cagtggcacg  240
tatcgatgca agttaagctg gtggacccag aactggagat gctcaaattc cgatgtatac  300
ggaggtggca ctgtcgtgac tgtgaatgcg gccgcacatc atcatcacca tcacggcgcc  360
gcagaatcaa aactcatctc agaagaggat ctg                                393

SEQ ID NO: 11           moltype = AA  length = 23
FEATURE                 Location/Qualifiers
REGION                  1..23
                        note = TNF VNAR B4 CDR3
source                  1..23
                        mol_type = protein
                        organism = synthetic construct
```

-continued

```
SEQUENCE: 11
YIPCIDELVY MISGGTSGPI HDV                                          23

SEQ ID NO: 12          moltype = AA  length = 118
FEATURE                Location/Qualifiers
REGION                 1..118
                       note = TNF VNAR B4
source                 1..118
                       mol_type = protein
                       organism = synthetic construct
SEQUENCE: 12
ARVDQTPQTI TKETGESLTI NCVLRDSNCA LSSMYWYRKK SGSTNEESIS KGGRYVETVN  60
SGSKSFSLRI NDLTVEDSGT YRCKVYIPCI DELVYMISGG TSGPIHDVYG GGTVVTVN    118

SEQ ID NO: 13          moltype = AA  length = 140
FEATURE                Location/Qualifiers
REGION                 1..140
                       note = TNF VNAR B4 AMINO ACID SEQUENCE WITH HIS AND MYC TAGS
source                 1..140
                       mol_type = protein
                       organism = synthetic construct
SEQUENCE: 13
ARVDQTPQTI TKETGESLTI NCVLRDSNCA LSSMYWYRKK SGSTNEESIS KGGRYVETVN  60
SGSKSFSLRI NDLTVEDSGT YRCKVYIPCI DELVYMISGG TSGPIHDVYG GGTVVTVNAA  120
AHHHHHHGAA ESKLISEEDL                                              140

SEQ ID NO: 14          moltype = DNA  length = 354
FEATURE                Location/Qualifiers
misc_feature           1..354
                       note = TNF VNAR B4
source                 1..354
                       mol_type = other DNA
                       organism = synthetic construct
SEQUENCE: 14
gctcgagtgg accaaacacc gcaaacaata acaaaggaga cgggcgaatc actgaccatc  60
aactgtgtcc tacgagatag taactgtgca ttgtccagca tgtactggta tcgcaaaaaa  120
tctggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgca aggtatatat accttgcatc gatgaactgg tatatatgat cagtgggggt  300
acctctggcc cgattcatga tgtatacgga ggtggcactg tcgtgactgt gaat        354

SEQ ID NO: 15          moltype = DNA  length = 71
FEATURE                Location/Qualifiers
misc_feature           1..71
                       note = 15
source                 1..71
                       mol_type = other DNA
                       organism = synthetic construct
SEQUENCE: 15
gctaggctct agaaataatt ttgtttaact ttaagaagga gatataccat ggctcgagtg  60
gaccaaacac c                                                       71

SEQ ID NO: 16          moltype = DNA  length = 87
FEATURE                Location/Qualifiers
misc_feature           1..87
                       note = 16
source                 1..87
                       mol_type = other DNA
                       organism = synthetic construct
SEQUENCE: 16
cgcgccggat ccgccacctc cgctaccgcc acctccgcta ccgccacctc cgctaccgcc  60
acctccattc acagtcacga cagtgcc                                      87

SEQ ID NO: 17          moltype = DNA  length = 46
FEATURE                Location/Qualifiers
misc_feature           1..46
                       note = 17
source                 1..46
                       mol_type = other DNA
                       organism = synthetic construct
SEQUENCE: 17
ggtggcggat ccggcgcgca ctccgctcga gtggaccaaa caccgc                 46

SEQ ID NO: 18          moltype = DNA  length = 53
FEATURE                Location/Qualifiers
misc_feature           1..53
                       note = 18
source                 1..53
                       mol_type = other DNA
```

-continued

```
                      organism = synthetic construct
SEQUENCE: 18
gtccggaatt ctcacagatc ctcttctgag atgagttttt gttctgcggc ccc        53

SEQ ID NO: 19         moltype = DNA  length = 48
FEATURE               Location/Qualifiers
misc_feature          1..48
                      note = 19
source                1..48
                      mol_type = other DNA
                      organism = synthetic construct
SEQUENCE: 19
aattcccctc tagaaggcgc gcactccgct cgagtggacc aaacaccg              48

SEQ ID NO: 20         moltype = DNA  length = 420
FEATURE               Location/Qualifiers
misc_feature          1..420
                      note = TNF VNAR B4 WITH HIS AND MYC TAGS
source                1..420
                      mol_type = other DNA
                      organism = synthetic construct
SEQUENCE: 20
gctcgagtgg accaaacacc gcaaacaata acaaaggaga cgggcgaatc actgaccatc  60
aactgtgtcc tacgagatag taactgtgca ttgtccagca tgtactggta tcgcaaaaaa  120
tctggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgca aggtatatat accttgcatc gatgaactgg tatatatgat cagtgggggt  300
acctctggcc cgattcatga tgtatacgga ggtggcactg tcgtgactgt gaatgcggcc  360
gcacatcatc atcaccatca cggcgccgca gaatcaaaac tcatctcaga agaggatctg  420

SEQ ID NO: 21         moltype = AA  length = 249
FEATURE               Location/Qualifiers
REGION                1..249
                      note = TNF VNAR DIMER D1-D1 AMINO ACID SEQUENCE WITH HIS
                       AND MYC TAGS
source                1..249
                      mol_type = protein
                      organism = synthetic construct
SEQUENCE: 21
ARVDQTPQTI TKETGESLTI NCVLRDSHCA TSSTYWYRKK SGSTNEESIS KGGRYVETVN  60
SGSKSFSLRI NDLTVEDSGT YRCASECQYG LAEYDVYGGG TVVTVNGGGG SGGGGGSGAH  120
SARVDQTPQT ITKETGESLT INCVLRDSHC ATSSTYWYRK KSGSTNEESI SKGGRYVETV  180
NSGSKSFSLR INDLTVEDSG TYRCASECQY GLAEYDVYGG GTVVTVNAAA HHHHHHGAAE  240
SKLISEEDL                                                          249

SEQ ID NO: 22         moltype = DNA  length = 747
FEATURE               Location/Qualifiers
misc_feature          1..747
                      note = TNF VNAR DIMER D1-D1 WITH HIS AND MYC TAGS
source                1..747
                      mol_type = other DNA
                      organism = synthetic construct
SEQUENCE: 22
gctcgagtgg accaaacacc gcaaacaata acaaaggaga cgggcgaatc actgaccatc  60
aactgtgtcc tacgagatag ccactgtgca acctccagca cgtactggta tcgcaaaaaa  120
tcgggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgcg cttccgagtg ccaatatgga ctggcagaat atgatgtata cggaggtggc  300
actgtcgtga ctgtgaatgg aggtggcggt agcggaggtg gtggcggatc cggcgcgcac  360
tccgctcgag tggaccaaac accgcaaaca ataacaaagg agacgggcga atcactgacc  420
atcaactgtg tcctacgaga tagccactgt gcaacctcca gcacgtactg gtatcgcaaa  480
aaatcgggct caacaaacga ggagagcata tcgaaaggtg gacgatatgt tgaaacagtt  540
aacagcggat caaagtcctt ttctttgaga attaatgatc taacagttga agacagtggc  600
acgtatcgat gcgcttccga gtgccaatat ggactggcag aatatgatgt atacggaggt  660
ggcactgtcg tgactgtgaa tgcggccgca catcatcatc accatcacgg ggccgcagaa  720
caaaaactca tctcagaaga ggatctg                                      747

SEQ ID NO: 23         moltype = AA  length = 255
FEATURE               Location/Qualifiers
REGION                1..255
                      note = TNF VNAR DIMER C4-C4 AMINO ACID SEQUENCE WITH HIS
                       AND MYC TAGS
source                1..255
                      mol_type = protein
                      organism = synthetic construct
SEQUENCE: 23
ARVDQTPQTI TKETGESLTI NCVLRDSNCG LSSTYWYRKK SGSTNEESIS KGGRYVETIN  60
EGSKSFSLRI NDLTVEDSGT YRCKLSWWTQ NWRCSNSDVY GGGTVVTVNG GGGSGGGGGS  120
GAHSARVDQT PQTITKETGE SLTINCVLRD SNCGLSSTYW YRKKSGSTNE ESISKGGRYV  180
```

-continued

```
ETINEGSKSF SLRINDLTVE DSGTYRCKLS WWTQNWRCSN SDVYGGGTVV TVNAAAHHHH  240
HHGAAEQKLI SEEDL                                                   255

SEQ ID NO: 24          moltype = DNA  length = 765
FEATURE                Location/Qualifiers
misc_feature           1..765
                       note = TNF VNAR DIMER C4-C4 WITH HIS AND MYC TAGS
source                 1..765
                       mol_type = other DNA
                       organism = synthetic construct
SEQUENCE: 24
gctcgagtgg accaaacacc gcaaacaata acaaaggaga cgggcgaatc actgaccatc  60
aactgtgtcc tacgagatag caactgtggg ttgtccagca cgtactggta tcgcaaaaaa  120
tcgggctcaa caaacgagga gagcatatcg aaaggtggac gatatgttga aacaattaac  180
gaaggatcaa agtccttttc tttgagaatt aatgatctaa cagttgaaga cagtggcacg  240
tatcgatgca agttaagctg gtggacccag aactggagat gctcaaattc cgatgtatac  300
ggaggtggca ctgtcgtgac tgtgaacgga ggtggcggta gcggaggtgg tggcggatcc  360
ggcgcgcact ccgctcgagt ggaccaaaca ccgcaaacaa taacaaagga gacgggcgaa  420
tcactgacca tcaactgtgt cctacgagat agcaactgtg ggttgtccag cacgtactgg  480
tatcgcaaaa aatcgggctc aacaaacgag gagagcatat cgaaaggtgg acgatatgtt  540
gaaacaatta acgaaggatc aaagtccttt tctttgagaa ttaatgatct aacagttgaa  600
gacagtggca cgtatcgatg caagttaagc tggtggaccc agaactggag atgctcaaat  660
tccgatgtat acggaggtgg cactgtcgtg actgtgaacg cggccgcaca tcatcatcac  720
catcacgggg ccgcagaaca aaaactcatc tcagaagagg atctg                  765

SEQ ID NO: 25          moltype = AA  length = 273
FEATURE                Location/Qualifiers
REGION                 1..273
                       note = TNF VNAR DIMER B4-B4 AMINO ACID SEQUENCE WITH HIS
                        AND MYC TAGS
source                 1..273
                       mol_type = protein
                       organism = synthetic construct
SEQUENCE: 25
ARVDQTPQTI TKETGESLTI NCVLRDSNCA LSSMYWYRKK SGSTNEESIS KGGRYVETVN  60
SGSKSFSLRI NDLTVEDSGT YRCKVYIPCI DELVYMISGG TSGPIHDVYG GGTVVTVNGG  120
GGSGGGGGSG AHSARVDQTP QTITKETGES LTINCVLRDS NCALSSMYWY RKKSGSTNEE  180
SISKGGRYVE TVNSGSKSFS LRINDLTVED SGTYRCKVYI PCIDELVYMI SGGTSGPIHD  240
VYGGGTVVTV NAAAHHHHHH GAAEQKLISE EDL                               273

SEQ ID NO: 26          moltype = DNA  length = 819
FEATURE                Location/Qualifiers
misc_feature           1..819
                       note = TNF VNAR DIMER B4-B4 WITH HIS AND MYC TAGS
source                 1..819
                       mol_type = other DNA
                       organism = synthetic construct
SEQUENCE: 26
gctcgagtgg accaaacacc gcaaacaata acaaaggaga cgggcgaatc actgaccatc  60
aactgtgtcc tacgagatag taactgtgca ttgtccagca tgtactggta tcgcaaaaaa  120
tctggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgca aggtatatat accttgcatc gatgaactgg tatatatgat cagtgggggt  300
acctctggcc cgattcatga tgtatacgga ggtggcactg tcgtgactgt gaatggaggt  360
ggcggtagcg gaggtggtgg cggatccggc gcgcactccg ctcgagtgga ccaaacaccg  420
caaacaataa caaaggagac gggcgaatca ctgaccatca actgtgtcct acgagatagt  480
aactgtgcat tgtccagcat gtactggtat cgcaaaaaat ctggctcaac aaacgaggag  540
agcatatcga aaggtggacg atatgttgaa acagttaaca gcggatcaaa gtccttttct  600
ttgagaatta atgatctaac agttgaagac agtggcacgt atcgatgcaa ggtatatata  660
ccttgcatcg atgaactggt atatatgatc agtgggggta cctctggccc gattcatgat  720
gtatacggag gtggcactgt cgtgactgtg aatgcggccg cacatcatca tcaccatcac  780
ggggccgcag aacaaaaact catctcagaa gaggatctg                         819

SEQ ID NO: 27          moltype = AA  length = 252
FEATURE                Location/Qualifiers
REGION                 1..252
                       note = TNF VNAR DIMER D1-C4 AMINO ACID SEQUENCE WITH HIS
                        AND MYC TAGS
source                 1..252
                       mol_type = protein
                       organism = synthetic construct
SEQUENCE: 27
ARVDQTPQTI TKETGESLTI NCVLRDSHCA TSSTYWYRKK SGSTNEESIS KGGRYVETVN  60
SGSKSFSLRI NDLTVEDSGT YRCASECQYG LAEYDVYGGG TVVTVNGGGG SGGGGGSGAH  120
SARVDQTPQT ITKETGESLT INCVLRDSNC GLSSTYWYRK KSGSTNEESI SKGGRYVETI  180
NEGSKSFSLR INDLTVEDSG TYRCKLSWWT QNWRCSNSDV YGGGTVVTVN AAAHHHHHHG  240
AAEQKLISEE DL                                                      252

SEQ ID NO: 28          moltype = DNA  length = 756
```

-continued

```
FEATURE                Location/Qualifiers
misc_feature           1..756
                       note = TNF VNAR DIMER D1-C4 WITH HIS AND MYC TAGS
source                 1..756
                       mol_type = other DNA
                       organism = synthetic construct
SEQUENCE: 28
gctcgagtgg accaaacacc gcaaacaata acaaaggaga cgggcgaatc actgaccatc  60
aactgtgtcc tacgagatag ccactgtgca acctccagca cgtactggta tcgcaaaaaa  120
tcgggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgcg cttccgagtg ccaatatgga ctggcagaat atgatgtata cggaggtggc  300
actgtcgtga ctgtgaatgg aggtggcggt agcggaggtg gtggcggatc cggcgcgcac  360
tccgctcgag tggaccaaac accgcaaaca ataacaaagg agacgggcga atcactgacc  420
atcaactgtg tcctacgaga tagcaactgt gggttgtcca gcacgtactg gtatcgcaaa  480
aaatcgggct caacaaacga ggagagcata tcgaaaggtg gacgatatgt tgaaacaatt  540
aacgaaggat caaagtcctt ttctttgaga attaatgatc taacagttga agacagtggc  600
acgtatcgat gcaagttaag ctggtggacc cagaactgga gatgctcaaa ttccgatgta  660
tacggaggtg gcactgtcgt gactgtgaac gcggccgcac atcatcatca ccatcacggg  720
gccgcagaac aaaaactcat ctcagaagag gatctg                            756

SEQ ID NO: 29          moltype = AA  length = 261
FEATURE                Location/Qualifiers
REGION                 1..261
                       note = TNF VNAR DIMER D1-B4 AMINO ACID SEQUENCE WITH HIS
                        AND MYC TAGS
source                 1..261
                       mol_type = protein
                       organism = synthetic construct
SEQUENCE: 29
ARVDQTPQTI TKETGESLPI NCVLRDSHCA TSSTYWYRKK SGSTNEESIS KGGRYVETVN  60
SGSKSFSLRI NDLTVEDSGT YRCASECQYG LAEYDVYGGG TVVTVNGGGG SGGGGGSGAH  120
SARVDQTPQT ITKETGESLT INCVLRDSNC ALSSMYWYRK KSGSTNEESI SKGGRYVETV  180
NSGSKSFSLR INDLTVEDSG TYRCKVYIPC IDELVYMISG GTSGPIHDVY GGGTVVTVNA  240
AAHHHHHHGA AEQKLISEED L                                            261

SEQ ID NO: 30          moltype = DNA  length = 783
FEATURE                Location/Qualifiers
misc_feature           1..783
                       note = NUCLEOTIDE SEQUENCE CODIGN FOR THE TNF VNAR DIMER
                        D1-B4 NUCLEOTIDE SEQUENCE WITH HIS AND MYC TAGS
source                 1..783
                       mol_type = other DNA
                       organism = synthetic construct
SEQUENCE: 30
gctcgagtgg accaaacacc gcaaacaata acaaaggaga cgggcgaatc actgaccatc  60
aactgtgtcc tacgagatag ccactgtgca acctccagca cgtactggta tcgcaaaaaa  120
tcgggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgcg cttccgagtg ccaatatgga ctggcagaat atgatgtata cggaggtggc  300
actgtcgtga ctgtgaatgg aggtggcggt agcggaggtg gtggcggatc cggcgcgcac  360
tccgctcgag tggaccaaac accgcaaaca ataacaaagg agacgggcga atcactgacc  420
atcaactgtg tcctacgaga tagtaactgt gcattgtcca gcatgtactg gtatcgcaaa  480
aaatctggct caacaaacga ggagagcata tcgaaaggtg gacgatatgt tgaaacagtt  540
aacagcggat caaagtcctt ttctttgaga attaatgatc taacagttga agacagtggc  600
acgtatcgat gcaaggtata tataccttgc atcgatgaac tggtatatat gatcagtggg  660
ggtacctctg gcccgattca tgatgtatac ggaggtggca ctgtcgtgac tgtgaatgcg  720
gccgcacatc atcatcacca tcacggggcc gcagaacaaa aactcatctc agaagaggat  780
ctg                                                                783

SEQ ID NO: 31          moltype = AA  length = 261
FEATURE                Location/Qualifiers
REGION                 1..261
                       note = TNF VNAR DIMER B4-D1 AMINO ACID SEQUENCE
source                 1..261
                       mol_type = protein
                       organism = synthetic construct
SEQUENCE: 31
ARVDQTPQTI TKETGESLTI NCVLRDSNCA LSSMYWYRKK SGSTNEESIS KGGRYVETVN  60
SGSKSFSLRI NDLTVEDSGT YRCKVYIPCI DELVYMISGG TSGPIHDVYG GGTVVTVNGG  120
GGSGGGGGSG AHSARVDQTP QTITKETGES LPINCVLRDS HCATSSTYWY RKKSGSTNEE  180
SISKGGRYVE TVNSGSKSFS LRINDLTVED SGTYRCASEC QYGLAEYDVY GGGTVVTVNA  240
AAHHHHHHGA AEQKLISEED L                                            261

SEQ ID NO: 32          moltype = DNA  length = 783
FEATURE                Location/Qualifiers
misc_feature           1..783
                       note = TNF VNAR DIMER B4-D1 NUCLEOTIDE SEQUENCE
source                 1..783
```

-continued

```
                        mol_type = other DNA
                        organism = synthetic construct
SEQUENCE: 32
gctcgagtgg accaaacacc gcaaacaata acaaaggaga cgggcgaatc actgaccatc  60
aactgtgtcc tacgagatag taactgtgca ttgtccagca tgtactggta tcgcaaaaaa  120
tctggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgca aggtatatat accttgcatc gatgaactgg tatatatgat cagtgggggt  300
acctctggcc cgattcatga tgtatacgga ggtggcactg tcgtgactgt gaatggaggt  360
ggcggtagcg gaggtggtgg cggatccggc gcgcactccg ctcgagtgga ccaaacaccg  420
caaacaataa caaaggagac gggcgaatca ctgaccatca actgtgtcct acgagatagc  480
cactgtgcaa cctccagcac gtactggtat cgcaaaaaat cgggctcaac aaacgaggag  540
agcatatcga aaggtggacg atatgttgaa acagttaaca gcggatcaaa gtccttttct  600
ttgagaatta atgatctaac agttgaagac agtggcacgt atcgatgcgc ttccgagtgc  660
caatatggac tggcagaata tgatgtatac ggaggtggca ctgtcgtgac tgtgaatgcg  720
gccgcacatc atcatcacca tcacggggcc gcagaacaaa aactcatctc agaagaggat  780
ctg                                                                783

SEQ ID NO: 33           moltype = AA  length = 263
FEATURE                 Location/Qualifiers
REGION                  1..263
                        note = TNF VNAR DIMER C4-B4 AMINO ACID SEQUENCE
source                  1..263
                        mol_type = protein
                        organism = synthetic construct
SEQUENCE: 33
ARVDQTPQTI TKETGESLTI NCVLRDSNCG LSSTYWYRKK SGSTNEESIS KGGRYVETIN  60
EGSKSFSLRI NDLTVEDSGT YRCKLSWWTQ NWRCSNSDVY GGGTVVTVNG GGGSGGGGGS  120
GAHSARVDQT PQTITKETGE SLTINCVLRD SNCALSSMYW YRKKSGSTNE ESISKGGRYV  180
ETVNSGSKSF SLRINDLTVE DSGTYRCKVY IPCIDELVYM ISGGTSGPIH DVYGGGTVVT  240
VNAAAHHHHH HGAAEQKLIS EED                                          263

SEQ ID NO: 34           moltype = DNA  length = 792
FEATURE                 Location/Qualifiers
misc_feature            1..792
                        note = TNF VNAR DIMER C4-B4 NUCLEOTIDE SEQUENCE
source                  1..792
                        mol_type = other DNA
                        organism = synthetic construct
SEQUENCE: 34
gctcgagtgg accaaacacc gcaaacaata acaaaggaga cgggcgaatc actgaccatc  60
aactgtgtcc tacgagatag caactgtggg ttgtccagca cgtactggta tcgcaaaaaa  120
tcgggctcaa caaacgagga gagcatatcg aaaggtggac gatatgttga aacaattaac  180
gaaggatcaa agtccttttc tttgagaatt aatgatctaa cagttgaaga cagtggcacg  240
tatcgatgca agttaagctg gtggacccag aactggagat gctcaaattc cgatgtatac  300
ggaggtggca ctgtcgtgac tgtgaacgga ggtggcggta gcggaggtgg tggcggatcc  360
ggcgcgcact ccgctcgagt ggaccaaaca ccgcaaacaa taacaaagga gacgggcgaa  420
tcactgacca tcaactgtgt cctacgagat agtaactgtg cattgtccag catgtactgg  480
tatcgcaaaa aatctggctc aacaaacgag gagagcatat cgaaaggtgg acgatatgtt  540
gaaacagtta acagcggatc aaagtccttt tctttgagaa ttaatgatct aacagttgaa  600
gacagtggca cgtatcgatg caaggtatat ataccttgca tcgatgaact ggtatatatg  660
atcagtgggg gtacctctgg cccgattcat gatgtatacg gaggtggcac tgtcgtgact  720
gtgaatgcgg ccgcacatca tcatcaccat cacggggccg cagaacaaaa actcatctca  780
gaagaggatc tg                                                      792

SEQ ID NO: 35           moltype = AA  length = 263
FEATURE                 Location/Qualifiers
REGION                  1..263
                        note = TNF VNAR DIMER B4-C4 AMINO ACID SEQUENCE
source                  1..263
                        mol_type = protein
                        organism = synthetic construct
SEQUENCE: 35
ARVDQTPQTI TKETGESLTI NCVLRDSNCA LSSMYWYRKK SGSTNEESIS KGGRYVETVN  60
SGSKSFSLRI NDLTVEDSGT YRCKVYIPCI DELVYMISGG TSGPIHDVYG GGTVVTVNGG  120
GGSGGGGGSG AHSARVDQTP QTITKETGES LTINCVLRDS NCGLSSTYWY RKKSGSTNEE  180
SISKGGRYVE TINEGSKSFS LRINDLTVED SGTYRCKLSW WTQNWRCSNS DVYGGGTVVT  240
VNAAAHHHHH HGAAEQKLIS EED                                          263

SEQ ID NO: 36           moltype = DNA  length = 792
FEATURE                 Location/Qualifiers
misc_feature            1..792
                        note = TNF VNAR DIMER B4-C4 NUCLEOTIDE SEQUENCE
source                  1..792
                        mol_type = other DNA
                        organism = synthetic construct
SEQUENCE: 36
gctcgagtgg accaaacacc gcaaacaata acaaaggaga cgggcgaatc actgaccatc  60
aactgtgtcc tacgagatag taactgtgca ttgtccagca tgtactggta tcgcaaaaaa  120
```

-continued

```
tctggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgca aggtatatat accttgcatc gatgaactgg tatatatgat cagtgggggt  300
acctctggcc cgattcatga tgtatacgga ggtggcactg tcgtgactgt gaatggaggt  360
ggcggtagcg gaggtggtgg cggatccggc gcgcactccg ctcgagtgga ccaaacaccg  420
caaacaataa caaaggagac gggcgaatca ctgaccatca actgtgtcct acgagatagc  480
aactgtgggt tgtccagcac gtactggtat cgcaaaaaat cgggctcaac aaacgaggag  540
agcatatcga aaggtggacg atatgttgaa acaattaacg aaggatcaaa gtccttttct  600
ttgagaatta atgatctaac agttgaagac agtggcacgt atcgatgcaa gttaagctgg  660
tggacccaga actggagatg ctcaaattcc gatgtatacg gaggtggcac tgtcgtgact  720
gtgaacgcgg ccgcacatca tcatcaccat cacggggccg cagaacaaaa actcatctca  780
gaagaggatc tg                                                       792

SEQ ID NO: 37          moltype = AA  length = 383
FEATURE                Location/Qualifiers
REGION                 1..383
                       note = TNF VNAR D1-BA11-C4 AMINO ACID SEQUENCE WITH HIS AND
                        MYC TAGS
source                 1..383
                       mol_type = protein
                       organism = synthetic construct
SEQUENCE: 37
ARVDQTPQTI TKETGESLTI NCVLRDSHCA TSSTYWYRKK SGSTNEESIS KGGRYVETVN  60
SGSKSFSLRI NDLTVEDSGT YRCASECQYG LAEYDVYGGG TVVTVNGGGG SGGGGSGGGG  120
SGGGGSGAHS TRVDQSPSSL SASVGDRVTI TCVLTDTSYP LYSTYWYRKN PGSSNKEQIS  180
ISGRYSESVN KGTKSFTLTI SSLQPEDSAT YYCRAMSTNI WTGDGAGTKV EIKGGGGSGG  240
GGSGGGGSGG GGSGAHSARV DQTPQTITKE TGESLTINCV LRDSNCGLSS TYWYRKKSGS  300
TNEESISKGG RYVETINEGS KSFSLRINDL TVEDSGTYRC KLSWWTQNWR CSNSDVYGGG  360
TVVTVNHHHH HHHEQKLISE EDL                                           383

SEQ ID NO: 38          moltype = DNA  length = 1149
FEATURE                Location/Qualifiers
misc_feature           1..1149
                       note = NUCLEOTIDE SEQUENCE CODING FOR THE TNF VNAR
                        D1-BA11-C4 WITH HIS AND MYC TAGS
source                 1..1149
                       mol_type = other DNA
                       organism = synthetic construct
SEQUENCE: 38
gctcgagtgg accaaacacc gcaaacaata acaaaggaga cgggcgaatc actgaccatc  60
aactgtgtcc tacgagatag ccactgtgca acctccagca cgtactggta tcgcaaaaaa  120
tcgggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgcg cttccgagtg ccaatatgga ctggcagaat atgatgtata cggaggtggc  300
actgtcgtga ctgtgaatgg aggtggcgga tccgggggtg gcggtagcgg aggtggcggt  360
agcggaggtg gcggtagtgg agctcattca acaagagtgg accaaagtcc aagctctctg  420
tccgccagtg tgggcgaccg cgtgaccatc acctgcgtcc tgactgatac cagctatcct  480
ctgtacagca catactggta tcggaagaat cccggttcca gcaacaagga gcagatttcc  540
atctccggcc gctatagtga atcagtcaac aagggcacta agtcctttac cctgacaatc  600
agttccctgc agcccgagga ctccgccacc tattactgca gagctatgag tacaaatatc  660
tggaccgggg acggagctgg taccaaggtg gagatcaagg gaggtggcgg ttccggaggt  720
ggcggtagcg gaggtggcgg tagcggaggt ggcggtagcg gggcccattc tgctcgagtg  780
gaccaaacac cgcaaacaat aacaaaggag acgggcgaat cactgaccat caactgtgtc  840
ctacgagata gcaactgtgg gttgtccagc acgtactggt atcgcaaaaa atcgggctca  900
acaaacgagg agagcatatc gaaaggtgga cgatatgttg aaacaattaa cgaaggatca  960
aagtcctttt ctttgagaat taatgatcta acagttgaag acagtggcac gtatcgatgc  1020
aagttaagct ggtggaccca gaactggaga tgctcaaatt ccgatgtata cggaggtggc  1080
actgtcgtga ctgtgaatca tcaccatcac catcaccatg aacaaaaact catctcagaa  1140
gaggatctg                                                           1149

SEQ ID NO: 39          moltype = AA  length = 380
FEATURE                Location/Qualifiers
REGION                 1..380
                       note = TNF VNAR D1-BA11-D1 AMINO ACID SEQUENCE WITH HIS AND
                        MYC TAGS
source                 1..380
                       mol_type = protein
                       organism = synthetic construct
SEQUENCE: 39
ARVDQTPQTI TKETGESLTI NCVLRDSHCA TSSTYWYRKK SGSTNEESIS KGGRYVETVN  60
SGSKSFSLRI NDLTVEDSGT YRCASECQYG LAEYDVYGGG TVVTVNGGGG SGGGGSGGGG  120
SGGGGSGAHS TRVDQSPSSL SASVGDRVTI TCVLTDTSYP LYSTYWYRKN PGSSNKEQIS  180
ISGRYSESVN KGTKSFTLTI SSLQPEDSAT YYCRAMSTNI WTGDGAGTKV EIKGGGGSGG  240
GGSGGGGSGG GGSGAHSARV DQTPQTITKE TGESLTINCV LRDSHCATSS TYWYRKKSGS  300
TNEESISKGG RYVETVNSGS KSFSLRINDL TVEDSGTYRC ASECQYGLAE YDVYGGGTVV  360
TVNHHHHHHH EQKLISEEDL                                               380

SEQ ID NO: 40          moltype = DNA  length = 1140
FEATURE                Location/Qualifiers
```

```
misc_feature          1..1140
                      note = NUCLEOTIDE SEQUENCE CODING FOR THE TNF VNAR
                       D1-BA11-D1 WITH HIS AND MYC TAGS
source                1..1140
                      mol_type = other DNA
                      organism = synthetic construct
SEQUENCE: 40
gctcgagtgg accaaacacc gcaaacaata acaaaggaga cgggcgaatc actgaccatc  60
aactgtgtcc tacgagatag ccactgtgca acctccagca cgtactggta tcgcaaaaaa  120
tcgggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgcg cttccgagtg ccaatatgga ctggcagaat atgatgtata cggaggtggc  300
actgtcgtga ctgtgaatgg aggtggcgga tccgggggtg gcggtagcgg aggtggcggt  360
agcggaggtg gcggtagtgg agctcattca acaagagtgg accaaagtcc aagctctctg  420
tccgccagtg tgggcgaccg cgtgaccatc acctgcgtcc tgactgatac cagctatcct  480
ctgtacagca catactggta tcggaagaat cccggttcca gcaacaagga gcagatttcc  540
atctccggcc gctatagtga atcagtcaac aagggcacta agtcctttac cctgacaatc  600
agttccctgc agcccgagga ctccgccacc tattactgca gagctatgag tacaaatatc  660
tggaccgggg acggagctgg taccaaggtg gagatcaagg gaggtggcgg ttccggaggt  720
ggcggtagcg gaggtggcgg tagcggaggt ggcggtagcg gggcccattc tgctcgagtg  780
gaccaaacac cgcaaacaat aacaaaggag acgggcgaat cactgaccat caactgtgtc  840
ctacgagata gccactgtgc aacctccagc acgtactggt atcgcaaaaa atcgggctca  900
acaaacgagg agagcatatc gaaaggtgga cgatatgttg aaacagttaa cagcggatca  960
aagtcctttt ctttgagaat taatgatcta acagttgaag acagtggcac gtatcgatgc  1020
gcttccgagt gccaatatgg actggcagaa tatgatgtat acggaggtgg cactgtcgtg  1080
actgtgaatc atcaccatca ccatcaccat gaacaaaaac tcatctcaga agaggatctg  1140

SEQ ID NO: 41         moltype = AA  length = 392
FEATURE               Location/Qualifiers
REGION                1..392
                      note = TNF VNAR D1-BA11-B4 AMINO ACID SEQUENCE WITH HIS AND
                       MYC TAGS
source                1..392
                      mol_type = protein
                      organism = synthetic construct
SEQUENCE: 41
ARVDQTPQTI TKETGESLTI NCVLRDSHCA TSSTYWYRKK SGSTNEESIS KGGRYVETVN  60
SGSKSFSLRI NDLTVEDSGT YRCASECQYG LAEYDVYGGG TVVTVNGGGG SGGGGSGGGG  120
SGGGGSGAHS TRVDQSPSSL SASVGDRVTI TCVLTDTSYP LYSTYWYRKN PGSSNKEQIS  180
ISGRYSESVN KGTKSFTLTI SSLQPEDSAT YYCRAMSTNI WTGDGAGTKV EIKGGGGSGG  240
GGSGGGGSGG GGSGAHSARV DQTPQTITKE TGESLTINCV LRDSNCALSS MYWYRKKSGS  300
TNEESISKGG RYVETVNSGS KSFSLRINDL TVEDSGTYRC KVYIPCIDEL VYMISGGTSG  360
PIHDVYGGGT VVTVNHHHHH HHEQKLISEE DL                                392

SEQ ID NO: 42         moltype = DNA  length = 1176
FEATURE               Location/Qualifiers
misc_feature          1..1176
                      note = NUCLEOTIDE SEQUENCE CODING FOR THE TNF VNAR
                       D1-BA11-B4 WITH HIS AND MYC TAGS
source                1..1176
                      mol_type = other DNA
                      organism = synthetic construct
SEQUENCE: 42
gctcgagtgg accaaacacc gcaaacaata acaaaggaga cgggcgaatc actgaccatc  60
aactgtgtcc tacgagatag ccactgtgca acctccagca cgtactggta tcgcaaaaaa  120
tcgggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgcg cttccgagtg ccaatatgga ctggcagaat atgatgtata cggaggtggc  300
actgtcgtga ctgtgaatgg aggtggcgga tccgggggtg gcggtagcgg aggtggcggt  360
agcggaggtg gcggtagtgg agctcattca acaagagtgg accaaagtcc aagctctctg  420
tccgccagtg tgggcgaccg cgtgaccatc acctgcgtcc tgactgatac cagctatcct  480
ctgtacagca catactggta tcggaagaat cccggttcca gcaacaagga gcagatttcc  540
atctccggcc gctatagtga atcagtcaac aagggcacta agtcctttac cctgacaatc  600
agttccctgc agcccgagga ctccgccacc tattactgca gagctatgag tacaaatatc  660
tggaccgggg acggagctgg taccaaggtg gagatcaagg gaggtggcgg ttccggaggt  720
ggcggtagcg gaggtggcgg tagcggaggt ggcggtagcg gggcccattc tgctcgagtg  780
gaccaaacac cgcaaacaat aacaaaggag acgggcgaat cactgaccat caactgtgtc  840
ctacgagata gtaactgtgc attgtccagc atgtactggt atcgcaaaaa atctggctca  900
acaaacgagg agagcatatc gaaaggtgga cgatatgttg aaacagttaa cagcggatca  960
aagtcctttt ctttgagaat taatgatcta acagttgaag acagtggcac gtatcgatgc  1020
aaggtatata taccttgcat cgatgaactg gtatatatga tcagtggggg tacctctggc  1080
ccgattcatg atgtatacgg aggtggcact gtcgtgactg tgaatcatca ccatcaccat  1140
caccatgaac aaaaactcat ctcagaagag gatctg                            1176

SEQ ID NO: 43         moltype = AA  length = 485
FEATURE               Location/Qualifiers
REGION                1..485
                      note = ICOS VNAR 2D4-Fc-2D4 AMINO ACID SEQUENCE
source                1..485
```

```
                          mol_type = protein
                          organism = synthetic construct
SEQUENCE: 43
TRVDQTPRTA TKETGESLTI NCVLTDTDYG LFSTSWFRKN PGTTDWERMS IGGRYVESVN  60
KGAKSFSLRI KDLTVADSAT YYCKAFTWPW EWPDRWFRPW YDGAGTVLTV NGGGGSGGGA  120
DQEPKSSDKT HTCPPCPAPE LLGGPSVFLF PPKPKDTLMI SRTPEVTCVV VDVSHEDPEV  180
KFNWYVDGVE VHNAKTKPRE EQYNSTYRVV SVLTVLHQDW LNGKEYKCKV SNKALPAPIE  240
KTISKAKGQP REPQVYTLPP SREEMTKNQV SLTCLVKGFY PSDIAVEWES NGQPENNYKT  300
TPPVLDSDGS FFLYSKLTVD KSRWQQGNVF SCSVMHEALH NHYTQKSLSL SPGKTAAAAT  360
AAAATAAAAT AAAATRVDQT PRTATKETGE SLTINCVLTD TDYGLFSTSW FRKNPGTTDW  420
ERMSIGGRYV ESVNKGAKSF SLRIKDLTVA DSATYYCKAF TWPWEWPDRW FRPWYDGAGT  480
VLTVN                                                              485

SEQ ID NO: 44             moltype = DNA  length = 1455
FEATURE                   Location/Qualifiers
misc_feature              1..1455
                          note = ICOS VNAR 2D4-Fc-2D4
source                    1..1455
                          mol_type = other DNA
                          organism = synthetic construct
SEQUENCE: 44
acacgtgttg accagacacc gcgtaccgca accaaagaaa ccggtgaaag cctgaccatt  60
aattgtgttc tgaccgatac cgattatggt ttgttctcca ccagctggtt tcgtaaaaat  120
ccgggtacaa ccgattggga acgtatgagc attggtggtc gttatgttga aagcgtgaat  180
aaaggtgcca aaagctttag cctgcgcatt aaagatctga ccgttgcaga tagcgcaacc  240
tattactgta aagcattcac ttggccgtgg gaatggccgg accgttggtt ccgtccgtgg  300
tatgatggtg caggcaccgt tctgaccgtt aatggcggtg gtggttctgg tggtggtgct  360
gatcaggagc ccaaatcttc tgacaaaact cacacatgtc caccgtgccc agcacctgaa  420
ctcctgggtg gaccgtcagt cttcctcttc cccccaaaac ccaaggacac cctcatgatc  480
tcccggaccc ctgaggtcac atgcgtggtg gtggacgtga gccacgaaga ccctgaggtc  540
aagttcaact ggtacgtgga cggcgtggag gtgcataatg ccaagacaaa gccgcgggag  600
gagcagtaca acagcacgta ccgtgtggtc agcgtcctca ccgtcctgca ccaggactgg  660
ctgaatggca aggagtacaa gtgcaaggtc tccaacaaag ccctcccagc ccccatcgag  720
aaaaccatct ccaaagccaa agggcagccc cgagaaccac aggtgtacac cctgccccca  780
tcccgggagg agatgaccaa gaaccaggtc agcctgacct gcctggtcaa aggcttctat  840
cccagcgaca tcgccgtgga gtgggagagc aatgggcagc cggagaacaa ctacaagacc  900
acgcctcccg tgctggactc cgacggctcc ttcttcctct atagcaagct caccgtggac  960
aagagcaggt ggcagcaggg gaacgtcttc tcatgctccg tgatgcatga ggctctgcac  1020
aaccactaca cgcagaagag cctctccctg tccccgggta aaaccgccgc cgccgccacc  1080
gccgccgccg ccaccgccgc cgccgccacc gccgcggccg ccacacgtgt tgatcagaca  1140
ccgcgtaccg caaccaaaga aaccggtgaa agcctgacca ttaattgtgt tctgaccgat  1200
accgattatg gtttgttctc caccagctgg tttcgtaaaa atccgggtac aaccgattgg  1260
gaacgtatga gcattggtgg tcgttatgtt gaaagcgtga ataaaggtgc caaaagcttt  1320
agcctgcgca ttaaagatct gaccgttgca gatagcgcaa cctattactg taaagcattc  1380
acttggccgt gggaatggcc ggaccgttgg ttccgtccgt ggtatgatgg tgcaggcacc  1440
gttctgaccg ttaat                                                   1455

SEQ ID NO: 45             moltype = AA  length = 481
FEATURE                   Location/Qualifiers
REGION                    1..481
                          note = ICOS VNAR 2D4-Fc-CC3 AMINO ACID SEQUENCE
source                    1..481
                          mol_type = protein
                          organism = synthetic construct
SEQUENCE: 45
TRVDQTPRTA TKETGESLTI NCVLTDTDYG LFSTSWFRKN PGTTDWERMS IGGRYVESVN  60
KGAKSFSLRI KDLTVADSAT YYCKAFTWPW EWPDRWFRPW YDGAGTVLTV NGGGGSGGGA  120
DQEPKSSDKT HTCPPCPAPE LLGGPSVFLF PPKPKDTLMI SRTPEVTCVV VDVSHEDPEV  180
KFNWYVDGVE VHNAKTKPRE EQYNSTYRVV SVLTVLHQDW LNGKEYKCKV SNKALPAPIE  240
KTISKAKGQP REPQVYTLPP SREEMTKNQV SLTCLVKGFY PSDIAVEWES NGQPENNYKT  300
TPPVLDSDGS FFLYSKLTVD KSRWQQGNVF SCSVMHEALH NHYTQKSLSL SPGKTAAAAT  360
AAAATAAAAT AAAATRVDQT PRTATKETGE SLTINCVLTD TEYGLFSTSW FRKNPGTTDW  420
ERMSIGGRYV ESVNKGAKSF SLRIKDLTVA DSATYYCKAL GWWPPAFPHW YDGAGTVLTV  480
N                                                                  481

SEQ ID NO: 46             moltype = DNA  length = 1443
FEATURE                   Location/Qualifiers
misc_feature              1..1443
                          note = ICOS VNAR 2D4-Fc-CC3
source                    1..1443
                          mol_type = other DNA
                          organism = synthetic construct
SEQUENCE: 46
acacgtgttg accagacacc gcgtaccgca accaaagaaa ccggtgaaag cctgaccatt  60
aattgtgttc tgaccgatac cgattatggt ttgttctcca ccagctggtt tcgtaaaaat  120
ccgggtacaa ccgattggga acgtatgagc attggtggtc gttatgttga aagcgtgaat  180
aaaggtgcca aaagctttag cctgcgcatt aaagatctga ccgttgcaga tagcgcaacc  240
tattactgta aagcattcac ttggccgtgg gaatggccgg accgttggtt ccgtccgtgg  300
tatgatggtg caggcaccgt tctgaccgtt aatggcggtg gtggttctgg tggtggtgct  360
```

```
gatcaggagc ccaaatcttc tgacaaaact cacacatgtc caccgtgccc agcacctgaa  420
ctcctgggtg gaccgtcagt cttcctcttc cccccaaaac ccaaggacac cctcatgatc  480
tcccggaccc ctgaggtcac atgcgtggtg gtggacgtga gccacgaaga ccctgaggtc  540
aagttcaact ggtacgtgga cggcgtggag gtgcataatg ccaagacaaa gccgcgggag  600
gagcagtaca acagcacgta ccgtgtggtc agcgtcctca ccgtcctgca ccaggactgg  660
ctgaatggca aggagtacaa gtgcaaggtc tccaacaaag ccctcccagc ccccatcgag  720
aaaaccatct ccaaagccaa agggcagccc cgagaaccac aggtgtacac cctgccccca  780
tcccgggagg agatgaccaa gaaccaggtc agcctgacct gcctggtcaa aggcttctat  840
cccagcgaca tcgccgtgga gtgggagagc aatgggcagc cggagaacaa ctacaagacc  900
acgcctcccg tgctggactc cgacggctcc ttcttcctct atagcaagct caccgtggac  960
aagagcaggt ggcagcaggg gaacgtcttc tcatgctccg tgatgcatga ggctctgcac  1020
aaccactaca cgcagaagag cctctccctg tccccgggta aaaccgccgc cgccgccacc  1080
gccgccgccg ccaccgccgc cgccgccacc gccgcggccg ccacacgtgt tgatcagaca  1140
ccgcgtaccg caaccaaaga aaccggtgaa agcctgacca ttaattgtgt tctgaccgat  1200
accgagtatg gtttgttctc caccagctgg tttcgtaaaa atccgggtac aaccgattgg  1260
gaacgtatga gcattggtgg tcgttatgtt gaaagcgtga ataaaggtgc caaaagcttt  1320
agcctgcgca ttaaagatct gaccgttgca gatagcgcaa cctattactg taaagcactg  1380
ggttggtggc cgccggcttt cccgcattgg tatgatggtg caggcaccgt tctgaccgtt  1440
aat                                                                1443
```

```
SEQ ID NO: 47          moltype = AA  length = 481
FEATURE                Location/Qualifiers
REGION                 1..481
                       note = ICOS VNAR CC3-Fc-2D4 AMINO ACID SEQUENCE
source                 1..481
                       mol_type = protein
                       organism = synthetic construct
SEQUENCE: 47
TRVDQTPRTA TKETGESLTI NCVLTDTEYG LFSTSWFRKN PGTTDWERMS IGGRYVESVN  60
KGAKSFSLRI KDLTVADSAT YYCKALGWWP PAFPHWYDGA GTVLTVNGGG GSGGGGRTEP  120
KSSDKTHTCP PCPAPEAAGA PSVFLFPPKP KDTLMISRTP EVTCVVVDVS HEDPEVKFNW  180
YVDGVEVHNA KTKPREEQYN STYRVVSVLT VLHQDWLNGK EYKCKVSNKA LPAPIEKTIS  240
KAKGQPREPQ VYTLPPSREE MTKNQVSLTC LVKGFYPSDI AVEWESNGQP ENNYKTTPPV  300
LDSDGSFFLY SKLTVDKSRW QQGNVFSCSV MHEALHNHYT QKSLSLSPGK TAAAATAAAA  360
TAAAATAAAA TRVDQTPRTA TKETGESLTI NCVLTDTDYG LFSTSWFRKN PGTTDWERMS  420
IGGRYVESVN KGAKSFSLRI KDLTVADSAT YYCKAFTWPW EWPDRWFRPW YDGAGTVLTV  480
N                                                                 481
```

```
SEQ ID NO: 48          moltype = DNA  length = 1443
FEATURE                Location/Qualifiers
misc_feature           1..1443
                       note = ICOS VNAR CC3-Fc-2D4
source                 1..1443
                       mol_type = other DNA
                       organism = synthetic construct
SEQUENCE: 48
acacgtgttg atcagacacc gcgtaccgca accaaagaaa ccggtgaaag cctgaccatt  60
aattgtgttc tgaccgatac cgagtatggt ttgttctcca ccagctggtt tcgtaaaaat  120
ccgggtacaa ccgattggga acgtatgagc attggtggtc gttatgttga aagcgtgaat  180
aaaggtgcca aaagctttag cctgcgcatt aaagatctga ccgttgcaga tagcgcaacc  240
tattactgta aagcactggg ttggtggccg ccggctttcc cgcattggta tgatggtgca  300
ggcaccgttc tgaccgttaa tggcggtggt ggttctggtg gtggtggtcg tacggagccc  360
aaatcttctg acaaaactca cacatgccca ccgtgcccag cacctgaagc cgctggggca  420
ccgtcagtct tcctcttccc cccaaaaccc aaggacaccc tcatgatctc ccggacccct  480
gaggtcacat gcgtggtggt ggacgtgagc cacgaagacc ctgaggtcaa gttcaactgg  540
tacgtggacg gcgtggaggt gcataatgcc aagacaaagc cgcgggagga gcagtacaac  600
agcacgtacc gtgtggtcag cgtcctcacc gtcctgcacc aggactggct gaatggcaag  660
gagtacaagt gcaaggtctc caacaaagcc ctcccagccc ccatcgagaa aaccatctcc  720
aaagccaaag ggcagccccg agaaccacag gtgtacaccc tgcccccatc ccgggaggag  780
atgaccaaga accaggtcag cctgacctgc ctggtcaaag gcttctatcc cagcgacatc  840
gccgtggagt gggagagcaa tgggcagccg gagaacaact acaagaccac gcctcccgtg  900
ctggactccg acggctcctt cttcctctat agcaagctca ccgtggacaa gagcaggtgg  960
cagcagggga acgtcttctc atgctccgtg atgcatgagg ctctgcacaa ccactacacg  1020
cagaagagcc tctccctgtc cccgggtaaa accgccgccg ccgccaccgc cgccgccgcc  1080
accgccgccg ccgccaccgc cgcggccgcc acacgtgttg atcagacacc gcgtaccgca  1140
accaaagaaa ccggtgaaag cctgaccatt aattgtgttc tgaccgatac cgattatggt  1200
ttgttctcca ccagctggtt tcgtaaaaat ccgggtacaa ccgattggga acgtatgagc  1260
attggtggtc gttatgttga aagcgtgaat aaaggtgcca aaagctttag cctgcgcatt  1320
aaagatctga ccgttgcaga tagcgcaacc tattactgta aagcattcac ttggccgtgg  1380
gaatggccgg accgttggtt ccgtccgtgg tatgatggtg caggcaccgt tctgaccgtt  1440
aat                                                                1443
```

```
SEQ ID NO: 49          moltype = AA  length = 477
FEATURE                Location/Qualifiers
REGION                 1..477
                       note = ICOS VNAR CC3-Fc-CC3 AMINO ACID SEQUENCE
source                 1..477
                       mol_type = protein
                       organism = synthetic construct
```

-continued

```
SEQUENCE: 49
TRVDQTPRTA TKETGESLTI NCVLTDTEYG LFSTSWFRKN PGTTDWERMS IGGRYVESVN  60
KGAKSFSLRI KDLTVADSAT YYCKALGWWP PAFPHWYDGA GTVLTVNGGG GSGGGGRTEP  120
KSSDKTHTCP PCPAPEAAGA PSVFLFPPKP KDTLMISRTP EVTCVVVDVS HEDPEVKFNW  180
YVDGVEVHNA KTKPREEQYN STYRVVSVLT VLHQDWLNGK EYKCKVSNKA LPAPIEKTIS  240
KAKGQPREPQ VYTLPPSREE MTKNQVSLTC LVKGFYPSDI AVEWESNGQP ENNYKTTPPV  300
LDSDGSFFLY SKLTVDKSRW QQGNVFSCSV MHEALHNHYT QKSLSLSPGK TAAAATAAAA  360
TAAAATAAAA TRVDQTPRTA TKETGESLTI NCVLTDTEYG LFSTSWFRKN PGTTDWERMS  420
IGGRYVESVN KGAKSFSLRI KDLTVADSAT YYCKALGWWP PAFPHWYDGA GTVLTVN     477

SEQ ID NO: 50          moltype = DNA  length = 1431
FEATURE                Location/Qualifiers
misc_feature           1..1431
                       note = ICOS VNAR CC3-Fc-CC3
source                 1..1431
                       mol_type = other DNA
                       organism = synthetic construct
SEQUENCE: 50
acacgtgttg atcagacacc gcgtaccgca accaaagaaa ccggtgaaag cctgaccatt  60
aattgtgttc tgaccgatac cgagtatggt ttgttctcca ccagctggtt tcgtaaaaat  120
ccgggtacaa ccgattggga acgtatgagc attggtggtc gttatgttga aagcgtgaat  180
aaaggtgcca aaagctttag cctgcgcatt aaagatctga ccgttgcaga tagcgcaacc  240
tattactgta aagcactggg ttggtggccg ccggctttcc cgcattggta tgatggtgca  300
ggcaccgttc tgaccgttaa tggcggtggt ggttctggtg gtggtggtcg tacggagccc  360
aaatcttctg acaaaactca cacatgccca ccgtgcccag cacctgaagc cgctggggca  420
ccgtcagtct tcctcttccc cccaaaaccc aaggacaccc tcatgatctc ccggacccct  480
gaggtcacat gcgtggtggt ggacgtgagc cacgaagacc ctgaggtcaa gttcaactgg  540
tacgtggacg gcgtggaggt gcataatgcc aagacaaagc cgcgggagga gcagtacaac  600
agcacgtacc gtgtggtcag cgtcctcacc gtcctgcacc aggactggct gaatggcaag  660
gagtacaagt gcaaggtctc caacaaagcc ctcccagccc ccatcgagaa aaccatctcc  720
aaagccaaag ggcagccccg agaaccacag gtgtacaccc tgcccccatc ccgggaggag  780
atgaccaaga accaggtcag cctgacctgc ctggtcaaag gcttctatcc cagcgacatc  840
gccgtggagt gggagagcaa tgggcagccg gagaacaact acaagaccac gcctcccgtg  900
ctggactccg acggctcctt cttcctctat agcaagctca ccgtggacaa gagcaggtgg  960
cagcagggga acgtcttctc atgctccgtg atgcatgagg ctctgcacaa ccactacacg  1020
cagaagagcc tctccctgtc cccgggtaaa accgccgccg ccgccaccgc cgccgccgcc  1080
accgccgccg ccgccaccgc cgcggccgcc acacgtgttg atcagacacc gcgtaccgca  1140
accaaagaaa ccggtgaaag cctgaccatt aattgtgttc tgaccgatac cgagtatggt  1200
ttgttctcca ccagctggtt tcgtaaaaat ccgggtacaa ccgattggga acgtatgagc  1260
attggtggtc gttatgttga aagcgtgaat aaaggtgcca aaagctttag cctgcgcatt  1320
aaagatctga ccgttgcaga tagcgcaacc tattactgta aagcactggg ttggtggccg  1380
ccggctttcc cgcattggta tgatggtgca ggcaccgttc tgaccgttaa t           1431

SEQ ID NO: 51          moltype = AA  length = 112
FEATURE                Location/Qualifiers
REGION                 1..112
                       note = SoloMER VNAR D1-v1 AMINO ACID SEQUENCE WITH HIS TAG
source                 1..112
                       mol_type = protein
                       organism = synthetic construct
SEQUENCE: 51
ARVDQSPSSL SASVGDRVTI TCVLRDSHCA TSSTYWYRKK SGSTNEESIS KGGRYVETVN  60
SGSKSFSLRI NDLTVEDSGT YRCASECQYG LAEYDVYGGG TKVEIKHHHH HH          112

SEQ ID NO: 52          moltype = DNA  length = 336
FEATURE                Location/Qualifiers
misc_feature           1..336
                       note = NUCLEOTIDE SEQUENCE CODING FOR THE SoloMER VNAR
                        D1-v1 WITH HIS TAG
source                 1..336
                       mol_type = other DNA
                       organism = synthetic construct
SEQUENCE: 52
gcccgcgtgg accagtcccc ctcctccctg tccgcctccg tgggcgaccg cgtgaccatc  60
acctgcgtgc tgcgcgactc ccactgcgcc acctcctcca cctactggta ccgcaagaag  120
tccggctcca ccaacgagga gtccatctcc aagggggggcc gctacgtgga gaccgtgaac  180
tccggctcca agtccttctc cctgcgcatc aacgacctga ccgtggagga ctccggcacc  240
taccgctgcg cctccgagtg ccagtacggc ctggccgagt acgacgtgta cggcggcggc  300
accaaggtgg agatcaagca ccaccaccac caccac                            336

SEQ ID NO: 53          moltype = AA  length = 112
FEATURE                Location/Qualifiers
REGION                 1..112
                       note = SoloMER VNAR D1-v2 AMINO ACID SEQUENCE WITH HIS TAG
source                 1..112
                       mol_type = protein
                       organism = synthetic construct
SEQUENCE: 53
ARVDQSPSSL SASVGDRVTI TCVLRDSHCA TSSTYWYRKK SGSTNEESIS KGGRYVETVN  60
```

SGSKSFTLTI SSLQPEDFAT YYCASECQYG LAEYDVYGGG TKVEIKHHHH HH        112

SEQ ID NO: 54           moltype = DNA   length = 336
FEATURE                 Location/Qualifiers
misc_feature            1..336
                        note = NUCLEOTIDE SEQUENCE CODING FOR THE SoloMER VNAR
                        D1-v2 WITH HIS TAG
source                  1..336
                        mol_type = other DNA
                        organism = synthetic construct
SEQUENCE: 54
gcccgcgtgg accagtcccc ctcctccctg tccgcctccg tgggcgaccg cgtgaccatc    60
acctgcgtgc tgcgcgactc ccactgcgcc acctcctcca cctactggta ccgcaagaag   120
tccggctcca ccaacgagga gtccatctcc aaggggggcc gctacgtgga gaccgtgaac   180
tccggctcca agtccttcac cctgaccatc tcctccctgc agcccgagga cttcgccacc   240
tactactgcg cctccgagtg ccagtacggc ctggccgagt acgacgtgta cggcggcggc   300
accaaggtgg agatcaagca ccaccaccac caccac                             336

SEQ ID NO: 55           moltype = AA   length = 112
FEATURE                 Location/Qualifiers
REGION                  1..112
                        note = SoloMER VNAR D1-v3 AMINO ACID SEQUENCE WITH HIS TAG
source                  1..112
                        mol_type = protein
                        organism = synthetic construct
SEQUENCE: 55
ARVDQSPSSL SASVGDRVTI TCVLRDSHCA TSSTYWYQQK PGKTNEESIS KGGRYVETVN    60
SGSKSFTLTI SSLQPEDFAT YYCASECQYG LAEYDVYGGG TKVEIKHHHH HH           112

SEQ ID NO: 56           moltype = DNA   length = 336
FEATURE                 Location/Qualifiers
misc_feature            1..336
                        note = NUCLEOTIDE SEQUENCE CODING FOR THE SoloMER VNAR
                        D1-v3 WITH HIS TAG
source                  1..336
                        mol_type = other DNA
                        organism = synthetic construct
SEQUENCE: 56
gcccgcgtgg accagtcccc ctcctccctg tccgcctccg tgggcgaccg cgtgaccatc    60
acctgcgtgc tgcgcgactc ccactgcgcc acctcctcca cctactggta ccagcagaag   120
cccggcaaga ccaacgagga gtccatctcc aaggggggcc gctacgtgga gaccgtgaac   180
tccggctcca agtccttcac cctgaccatc tcctccctgc agcccgagga cttcgccacc   240
tactactgcg cctccgagtg ccagtacggc ctggccgagt acgacgtgta cggcggcggc   300
accaaggtgg agatcaagca ccaccaccac caccac                             336

SEQ ID NO: 57           moltype = AA   length = 112
FEATURE                 Location/Qualifiers
REGION                  1..112
                        note = SoloMER VNAR D1-v4 AMINO ACID SEQUENCE WITH HIS TAG
source                  1..112
                        mol_type = protein
                        organism = synthetic construct
SEQUENCE: 57
ARVDQSPSSL SASVGDRVTI TCVLRDSHCA TSSTYWYRKK PGSTNEESIS KGGRFSGSGS    60
SGSKSFTLTI SSLQPEDFAT YYCASECQYG LAEYDVFGQG TKVEIKHHHH HH           112

SEQ ID NO: 58           moltype = DNA   length = 336
FEATURE                 Location/Qualifiers
misc_feature            1..336
                        note = NUCLEOTIDE SEQUENCE CODING FOR THE SoloMER VNAR
                        D1-v4 WITH HIS TAG
source                  1..336
                        mol_type = other DNA
                        organism = synthetic construct
SEQUENCE: 58
gcccgcgtgg accagtcccc ctcctccctg tccgcctccg tgggcgaccg cgtgaccatc    60
acctgcgtgc tgcgcgactc ccactgcgcc acctcctcca cctactggta ccgcaagaag   120
cccggctcca ccaacgagga gtccatctcc aaggggggcc gcttctccgg ctccggctcc   180
tccggctcca agtccttcac cctgaccatc tcctccctgc agcccgagga cttcgccacc   240
tactactgcg cctccgagtg ccagtacggc ctggccgagt acgacgtgtt cggccagggc   300
accaaggtgg agatcaagca ccaccaccac caccac                             336

SEQ ID NO: 59           moltype = AA   length = 483
FEATURE                 Location/Qualifiers
REGION                  1..483
                        note = Quad-X D1-Fc-C4 AMINO ACID SEQUENCE
source                  1..483
                        mol_type = protein
                        organism = synthetic construct -continued

```
SEQUENCE: 59
ARVDQTPQTI TKETGESLTI NCVLRDSHCA TSSTYWYRKK SGSTNEESIS KGGRYVETVN  60
SGSKSFSLRI NDLTVEDSGT YRCASECQYG LAEYDVYGGG TVVTVNGSGG GSGGGGSGEP  120
KSSDKTHTCP PCPAPELLGG PSVFLFPPKP KDTLMISRTP EVTCVVVDVS HEDPEVKFNW  180
YVDGVEVHNA KTKPREEQYN STYRVVSVLT VLHQDWLNGK EYKCKVSNKA LPAPIEKTIS  240
KAKGQPREPQ VYTLPPSRDE LTKNQVSLTC LVKGFYPSDI AVEWESNGQP ENNYKTTPPV  300
LDSDGSFFLY SKLTVDKSRW QQGNVFSCSV MHEALHNHYT QKSLSLSPGK GGGGSGGGGS  360
GGGGSGGGGS GAHSARVDQT PQTITKETGE SLTINCVLRD SNCGLSSTYW YRKKSGSTNE  420
ESISKGGRYV ETINEGSKSF SLRINDLTVE DSGTYRCKLS WWTQNWRCSN SDVYGGGTVV  480
TVN                                                                483

SEQ ID NO: 60           moltype = DNA  length = 1449
FEATURE                 Location/Qualifiers
misc_feature            1..1449
                        note = NUCLEOTIDE SEQUENCE CODING FOR THE Quad-X D1-Fc-C4
source                  1..1449
                        mol_type = other DNA
                        organism = synthetic construct
SEQUENCE: 60
gctcgagtgg accaaacacc gcaaacaata acaaaggaga cgggcgaatc actgaccatc  60
aactgtgtcc tacgagatag ccactgtgca acctccagca cgtactggta tcgcaaaaaa  120
tcgggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgcg cttccgagtg ccaatatgga ctggcagaat atgatgtata cggaggtggc  300
actgtcgtga ctgtgaatgg atccggtggt gggtccggag gaggtggctc aggagagccc  360
aaatctagcg acaaaactca cacatgccca ccgtgcccag cacctgaact cctgggggga  420
ccgtcagtct tcctcttccc cccaaaaccc aaggacaccc tcatgatctc ccggacccct  480
gaggtcacat gcgtggtggt ggacgtgagc cacgaagacc ctgaggtcaa gttcaactgg  540
tacgtggacg gcgtggaggt gcataatgcc aagacaaagc cgcgggagga gcagtacaac  600
agcacgtacc gggtggtcag cgtcctcacc gtcctgcacc aggactggct gaatggcaag  660
gagtacaagt gcaaggtctc caacaaagcc ctcccagccc ccatcgagaa aaccatctcc  720
aaagccaaag ggcagccccg agaaccacag gtgtacaccc tgcccccatc ccgggatgag  780
ctgaccaaga accaggtcag cctgacctgc ctggtcaaag gcttctatcc cagcgacatc  840
gccgtggagt gggagagcaa tgggcagccg gagaacaact acaagaccac gcctcccgtg  900
ctggactccg acggctcctt cttcctctac agcaagctca ccgtggacaa gagcaggtgg  960
cagcagggga acgtcttctc atgctccgtg atgcatgagg ctctgcacaa ccactacacg  1020
cagaagagcc tctccctgtc tccggggaaa ggaggtggcg gttccggagg tggcggtagc  1080
ggaggtggcg gtagcggagg tggcggtagc ggggcccatt ctgctcgagt ggaccaaaca  1140
ccgcaaacaa taacaaagga gacgggcgaa tcactgacca tcaactgtgt cctacgagat  1200
agcaactgtg ggttgtccag cacgtactgg tatcgcaaaa aatcgggctc aacaaacgag  1260
gagagcatat cgaaaggtgg acgatatgtt gaaacaatta acgaaggatc aaagtccttt  1320
tctttgagaa ttaatgatct aacagttgaa gacagtggca cgtatcgatg caagttaagc  1380
tggtggaccc agaactggag atgctcaaat tccgatgtat acggaggtgg cactgtcgtg  1440
actgtgaat                                                          1449

SEQ ID NO: 61           moltype = AA  length = 472
FEATURE                 Location/Qualifiers
REGION                  1..472
                        note = Quad-Y-D1C4 D1-C4-Fc AMINO ACID SEQUENCE
source                  1..472
                        mol_type = protein
                        organism = synthetic construct
SEQUENCE: 61
ARVDQTPQTI TKETGESLTI NCVLRDSHCA TSSTYWYRKK SGSTNEESIS KGGRYVETVN  60
SGSKSFSLRI NDLTVEDSGT YRCASECQYG LAEYDVYGGG TVVTVNGGGG SGGGGSGAH   120
SARVDQTPQT ITKETGESLT INCVLRDSNC GLSSTYWYRK KSGSTNEESI SKGGRYVETI  180
NEGSKSFSLR INDLTVEDSG TYRCKLSWWT QNWRCSNSDV YGGGTVVTVN GGGSGGGGSG  240
EPKSSDKTHT CPPCPAPELL GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 62           moltype = DNA  length = 1416
FEATURE                 Location/Qualifiers
misc_feature            1..1416
                        note = NUCLEOTIDE SEQUENCE CODING FOR THE Quad-Y-D1C4 AMINO
                         ACID SEQUENCE
source                  1..1416
                        mol_type = other DNA
                        organism = synthetic construct
SEQUENCE: 62
gctcgagtgg accaaacacc gcaaacaata acaaaggaga cgggcgaatc actgaccatc  60
aactgtgtcc tacgagatag ccactgtgca acctccagca cgtactggta tcgcaaaaaa  120
tcgggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgcg cttccgagtg ccaatatgga ctggcagaat atgatgtata cggaggtggc  300
actgtcgtga ctgtgaatgg aggtggcggt agcggaggtg gtggcggatc cggggcgcac  360
tccgctcgag tggaccaaac accgcaaaca ataacaaagg agacgggcga atcactgacc  420
atcaactgtg tcctacgaga tagcaactgt gggttgtcca gcacgtactg gtatcgcaaa  480
```

-continued

```
aaatcgggct caacaaacga ggagagcata tcgaaaggtg gacgatatgt tgaaacaatt  540
aacgaaggat caaagtcctt ttctttgaga attaatgatc taacagttga agacagtggc  600
acgtatcgat gcaagttaag ctggtggacc cagaactgga gatgctcaaa ttccgatgta  660
tacggaggtg gcactgtcgt gactgtgaac ggtggtgggt ccggaggagg tggctcagga  720
gagcccaaat ctagcgacaa aactcacaca tgcccaccgt gcccagcacc tgaactcctg  780
gggggaccgt cagtcttcct cttcccccca aaacccaagg acaccctcat gatctcccgg  840
acccctgagg tcacatgcgt ggtggtggac gtgagccacg aagaccctga ggtcaagttc  900
aactggtacg tggacggcgt ggaggtgcat aatgccaaga caaagccgcg ggaggagcag  960
tacaacagca cgtaccgtgt ggtcagcgtc ctcaccgtcc tgcaccagga ctggctgaat  1020
ggcaaggagt acaagtgcaa ggtctccaac aaagccctcc cagcccccat cgagaaaacc  1080
atctccaaag ccaaagggca gccccgagaa ccacaggtgt acaccctgcc cccatcccgg  1140
gatgagctga ccaagaacca ggtcagcctg acctgcctgg tcaaaggctt ctatcccagc  1200
gacatcgccg tggagtggga gagcaatggg cagccggaga acaactacaa gaccacgcct  1260
cccgtgctgg actccgacgg ctccttcttc ctctacagca agctcaccgt ggacaagagc  1320
aggtggcagc aggggaacgt cttctcatgc tccgtgatgc atgaggctct gcacaaccac  1380
tacacgcaga agagcctctc cctgtctccg ggaaa                            1416

SEQ ID NO: 63          moltype = AA  length = 472
FEATURE                Location/Qualifiers
REGION                 1..472
                       note = Quad-Y-C4D1 C4-D1-Fc AMINO ACID SEQUENCE
source                 1..472
                       mol_type = protein
                       organism = synthetic construct
SEQUENCE: 63
ARVDQTPQTI TKETGESLTI NCVLRDSNCG LSSTYWYRKK SGSTNEESIS KGGRYVETIN  60
EGSKSFSLRI NDLTVEDSGT YRCKLSWWTQ NWRCSNSDVY GGGTVVTVNG GGGSGGGGGS  120
GAHSARVDQT PQTITKETGE SLTINCVLRD SHCATSSTYW YRKKSGSTNE ESISKGGRYV  180
ETVNSGSKSF SLRINDLTVE DSGTYRCASE CQYGLAEYDV YGGGTVVTVN GGGSGGGGSG  240
EPKSSDKTHT CPPCPAPELL GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 64          moltype = AA  length = 1416
FEATURE                Location/Qualifiers
REGION                 1..1416
                       note = NUCLEOTIDE SEQUENCE CODING FOR THE Quad-Y-C4D1 AMINO
                        ACID SEQUENCE
source                 1..1416
                       mol_type = protein
                       organism = synthetic construct
SEQUENCE: 64
GCTCGAGTGG ACCAAACACC GCAAACAATA ACAAAGGAGA CGGGCGAATC ACTGACCATC  60
AACTGTGTCC TACGAGATAG CAACTGTGGG TTGTCCAGCA CGTACTGGTA TCGCAAAAAA  120
TCGGGCTCAA CAAACGAGGA GAGCATATCG AAAGGTGGAC GATATGTTGA AACAATTAAC  180
GAAGGATCAA AGTCCTTTTC TTTGAGAATT AATGATCTAA CAGTTGAAGA CAGTGGCACG  240
TATCGATGCA AGTTAAGCTG GTGGACCCAG AACTGGAGAT GCTCAAATTC CGATGTATAC  300
GGAGGTGGCA CTGTCGTGAC TGTGAACGGA GGTGGCGGTA GCGGAGGTGG TGGCGGATCC  360
GGGGCGCACT CCGCTCGAGT GGACCAAACA CCGCAAACAA TAACAAAGGA GACGGGCGAA  420
TCACTGACCA TCAACTGTGT CCTACGAGAT AGCCACTGTG CAACCTCCAG CACGTACTGG  480
TATCGCAAAA AATCGGGCTC AACAAACGAG GAGAGCATAT CGAAAGGTGG ACGATATGTT  540
GAAACAGTTA ACAGCGGATC AAAGTCCTTT TCTTTGAGAA TTAATGATCT AACAGTTGAA  600
GACAGTGGCA CGTATCGATG CGCTTCCGAG TGCCAATATG GACTGGCAGA ATATGATGTA  660
TACGGAGGTG GCACTGTCGT GACTGTGAAT GGTGGTGGGT CCGGAGGAGG TGGCTCAGGA  720
GAGCCCAAAT CTAGCGACAA AACTCACACA TGCCCACCGT GCCCAGCACC TGAACTCCTG  780
GGGGGACCGT CAGTCTTCCT CTTCCCCCCA AAACCCAAGG ACACCCTCAT GATCTCCCGG  840
ACCCCTGAGG TCACATGCGT GGTGGTGGAC GTGAGCCACG AAGACCCTGA GGTCAAGTTC  900
AACTGGTACG TGGACGGCGT GGAGGTGCAT AATGCCAAGA CAAAGCCGCG GGAGGAGCAG  960
TACAACAGCA CGTACCGTGT GGTCAGCGTC CTCACCGTCC TGCACCAGGA CTGGCTGAAT  1020
GGCAAGGAGT ACAAGTGCAA GGTCTCCAAC AAAGCCCTCC CAGCCCCCAT CGAGAAAACC  1080
ATCTCCAAAG CCAAAGGGCA GCCCCGAGAA CCACAGGTGT ACACCCTGCC CCCATCCCGG  1140
GATGAGCTGA CCAAGAACCA GGTCAGCCTG ACCTGCCTGG TCAAAGGCTT CTATCCCAGC  1200
GACATCGCCG TGGAGTGGGA GAGCAATGGG CAGCCGGAGA ACAACTACAA GACCACGCCT  1260
CCCGTGCTGG ACTCCGACGG CTCCTTCTTC CTCTACAGCA AGCTCACCGT GGACAAGAGC  1320
AGGTGGCAGC AGGGGAACGT CTTCTCATGC TCCGTGATGC ATGAGGCTCT GCACAACCAC  1380
TACACGCAGA AGAGCCTCTC CCTGTCTCCG GGGAAA                           1416

SEQ ID NO: 65          moltype = AA  length = 111
FEATURE                Location/Qualifiers
REGION                 1..111
                       note = 2D4
source                 1..111
                       mol_type = protein
                       organism = synthetic construct
SEQUENCE: 65
TRVDQTPRTA TKETGESLTI NCVLTDTDYG LFSTSWFRKN PGTTDWERMS IGGRYVESVN  60
KGAKSFSLRI KDLTVADSAT YYCKAFTWPW EWPDRWFRPW YDGAGTVLTV N          111
```

```
SEQ ID NO: 66          moltype = AA  length = 107
FEATURE                Location/Qualifiers
REGION                 1..107
                       note = CC3
source                 1..107
                       mol_type = protein
                       organism = synthetic construct
SEQUENCE: 66
TRVDQTPRTA TKETGESLTI NCVLTDTEYG LFSTSWFRKN PGTTDWERMS IGGRYVESVN  60
KGAKSFSLRI KDLTVADSAT YYCKALGWWP PAFPHWYDGA GTVLTVN               107

SEQ ID NO: 67          moltype = AA  length = 103
FEATURE                Location/Qualifiers
REGION                 1..103
                       note = BA11
source                 1..103
                       mol_type = protein
                       organism = synthetic construct
SEQUENCE: 67
TRVDQSPSSL SASVGDRVTI TCVLTDTSYP LYSTYWYRKN PGSSNKEQIS ISGRYSESVN  60
KGTKSFTLTI SSLQPEDSAT YYCRAMSTNI WTGDGAGTKV EIK                   103

SEQ ID NO: 68          moltype = AA  length = 6
FEATURE                Location/Qualifiers
REGION                 1..6
                       note = TNF-alpha specific VNAR binding domain CDR1
source                 1..6
                       mol_type = protein
                       organism = synthetic construct
SEQUENCE: 68
HCATSS                                                            6

SEQ ID NO: 69          moltype = AA  length = 6
FEATURE                Location/Qualifiers
REGION                 1..6
                       note = TNF-alpha spcific VNAR binding domain CDR1
source                 1..6
                       mol_type = protein
                       organism = synthetic construct
SEQUENCE: 69
NCGLSS                                                            6

SEQ ID NO: 70          moltype = AA  length = 6
FEATURE                Location/Qualifiers
REGION                 1..6
                       note = TNF-alpha specific VNAR binding domain CDR1
source                 1..6
                       mol_type = protein
                       organism = synthetic construct
SEQUENCE: 70
NCALSS                                                            6

SEQ ID NO: 71          moltype = AA  length = 9
FEATURE                Location/Qualifiers
REGION                 1..9
                       note = TNF-alpha specific VNAR binding domain
                        hyper-variable region 2
source                 1..9
                       mol_type = protein
                       organism = synthetic construct
SEQUENCE: 71
TNEESISKG                                                         9

SEQ ID NO: 72          moltype = AA  length = 5
FEATURE                Location/Qualifiers
REGION                 1..5
                       note = TNF-alpha specific VNAR binding domain
                        hyper-variable region 4
source                 1..5
                       mol_type = protein
                       organism = synthetic construct
SEQUENCE: 72
SGSKS                                                             5

SEQ ID NO: 73          moltype = AA  length = 5
FEATURE                Location/Qualifiers
REGION                 1..5
                       note = TNF-alpha specific VNAR binding domain
                        hyper-variable region 4
```

-continued

```
source                  1..5
                        mol_type = protein
                        organism = synthetic construct
SEQUENCE: 73
EGSKS                                                                    5

SEQ ID NO: 74           moltype = DNA  length = 46
FEATURE                 Location/Qualifiers
misc_feature            1..46
                        note = NARF4For1 primer
source                  1..46
                        mol_type = other DNA
                        organism = synthetic construct
SEQUENCE: 74
ataatcaagc ttgcggccgc attcacagtc acgacagtgc cacctc                       46

SEQ ID NO: 75           moltype = DNA  length = 46
FEATURE                 Location/Qualifiers
misc_feature            1..46
                        note = NARF4For2 primer
source                  1..46
                        mol_type = other DNA
                        organism = synthetic construct
SEQUENCE: 75
ataatcaagc ttgcggccgc attcacagtc acggcagtgc catctc                       46

SEQ ID NO: 76           moltype = DNA  length = 39
FEATURE                 Location/Qualifiers
misc_feature            1..39
                        note = NARF1Rev primer
source                  1..39
                        mol_type = other DNA
                        organism = synthetic construct
SEQUENCE: 76
ataataagga attccatggc tcgagtggac caaacaccg                               39

SEQ ID NO: 77           moltype = AA  length = 103
FEATURE                 Location/Qualifiers
REGION                  1..103
                        note = E06
source                  1..103
                        mol_type = protein
                        organism = synthetic construct
SEQUENCE: 77
TRVDQTPRTA TRETGESLTI NCVLTDTSYP LYSTYWYRKN PGSSNKEQIS ISGRYVESVN  60
KGTKSFSLRI KDLTVADSAT YICRAMGTNI WTGDGAGTVL TVN                     103

SEQ ID NO: 78           moltype = AA  length = 103
FEATURE                 Location/Qualifiers
REGION                  1..103
                        note = hE06v1.10
source                  1..103
                        mol_type = protein
                        organism = synthetic construct
SEQUENCE: 78
TRVDQSPSSL SASVGDRVTI TCVLTDTSYP LYSTYWYRKN PGSSNKEQIS ISGRYSESVN  60
KGTKSFTLTI SSLQPEDFAT YYCRAMGTNI WTGDGAGTKV EIK                     103

SEQ ID NO: 79           moltype = AA  length = 103
FEATURE                 Location/Qualifiers
REGION                  1..103
                        note = AC9
source                  1..103
                        mol_type = protein
                        organism = synthetic construct
SEQUENCE: 79
TRVDQSPSSL SASVGDRVTI TCVLTDTSYP LYSTYWYRKN PGSSNKEQIS ISGRYSESVN  60
KGTKSSTLTI SSLQPEDFAT YYCRAMGTNI WTGDGAGTKV EIK                     103

SEQ ID NO: 80           moltype = AA  length = 103
FEATURE                 Location/Qualifiers
REGION                  1..103
                        note = AD4
source                  1..103
                        mol_type = protein
                        organism = synthetic construct
SEQUENCE: 80
TRVDQSPSSL SASVGDRVTI TCVLTDTSYP LYSTYWYRKN PGSSNKEQIS MSGRYSESVN  60
KSTKSFTLTI SSLQPEDFAT YYCRAMGTNI WTGDGAGTKV EIK                     103
```

```
SEQ ID NO: 81          moltype = AA  length = 103
FEATURE                Location/Qualifiers
REGION                 1..103
                       note = AG11
source                 1..103
                       mol_type = protein
                       organism = synthetic construct
SEQUENCE: 81
TRVDQSPSSL SASVGDRVTI TCVLTDTSYP LYSTYWYRKN PGSSNKEQIS ISGRYSESVN  60
KGTKSFTLTI SSLQPEDFAT YYCRAMGTNI WTGDGAGTKV ETK                   103

SEQ ID NO: 82          moltype = AA  length = 103
FEATURE                Location/Qualifiers
REGION                 1..103
                       note = AH7
source                 1..103
                       mol_type = protein
                       organism = synthetic construct
SEQUENCE: 82
TRVDQTPSSL SASVGDRVTI TCVLTDTSYP LYSTYWYRKN PGSSNKEQIS ISGRYSESVN  60
KGTKSSTLTI SSLQPEDFAT YYCRAMGTNI WTGDGAGTKV EIK                   103

SEQ ID NO: 83          moltype = AA  length = 103
FEATURE                Location/Qualifiers
REGION                 1..103
                       note = BB10
source                 1..103
                       mol_type = protein
                       organism = synthetic construct
SEQUENCE: 83
TRVDQSPSSL SASVGDRVTI TCVLTDTSYP LYSTYWYRKN PGSSNKEQIS ISGRYSESVN  60
KGTKSFTLTI SSLQPEDFAT YYCRAMGTNF WTGDGAGTKV EIK                   103

SEQ ID NO: 84          moltype = AA  length = 103
FEATURE                Location/Qualifiers
REGION                 1..103
                       note = BB11
source                 1..103
                       mol_type = protein
                       organism = synthetic construct
SEQUENCE: 84
TRVDQSPSSL SASVGDRVTI TCVLTDTSYP LYSTYWYRKN PGSSNKEQIS ISGRYSESVN  60
KGTKSFTLTI SSLQPEDFAT YYCRAMATNI WTGDGAGTKV EIK                   103

SEQ ID NO: 85          moltype = AA  length = 103
FEATURE                Location/Qualifiers
REGION                 1..103
                       note = BC3
source                 1..103
                       mol_type = protein
                       organism = synthetic construct
SEQUENCE: 85
TRVDQSPSSL SASVGDRVTI TCVLTDTSYP LYSTYWYRKN PGSNNKEQIS ISGRYSESVN  60
KGTKSFTLTI SSLQPEDFAT YYCRAMGTNI WTGDGAGTKV EIK                   103

SEQ ID NO: 86          moltype = AA  length = 103
FEATURE                Location/Qualifiers
REGION                 1..103
                       note = BD12
source                 1..103
                       mol_type = protein
                       organism = synthetic construct
SEQUENCE: 86
TRVDQSPSSL SASVGDRVTI TCVLTDTSYP LYSTYWYRKN PGSSNKEQIS ISGRYSESVN  60
KGTNSFTLTI SSLQPEDFAT YYCRAMGTNI WTGDGAGTKV EIK                   103

SEQ ID NO: 87          moltype = AA  length = 103
FEATURE                Location/Qualifiers
REGION                 1..103
                       note = BE4
source                 1..103
                       mol_type = protein
                       organism = synthetic construct
SEQUENCE: 87
TRVDQSPSSL SASVGDRVTI TCVLTDTSYS LYSTYWYRKN PGSSNKEQIS ISGRYSESVN  60
KGTKSFTLTI SSLQPEDFAT YYCRAMGTNI WTGDGAGTKV EIK                   103

SEQ ID NO: 88          moltype = AA  length = 103
```

```
FEATURE               Location/Qualifiers
REGION                1..103
                      note = BH4
source                1..103
                      mol_type = protein
                      organism = synthetic construct
SEQUENCE: 88
TRVDQSPSSL SASVGDRVTI TCVLTDTSYP LYSTYWYRKN PGSSNKEQIS ISGRYSESVN  60
KGTKSFTLTI SSLQPEDFAT YYCRAMGTNL WTGDGAGTKV EIK                    103

SEQ ID NO: 89         moltype = AA  length = 239
FEATURE               Location/Qualifiers
REGION                1..239
                      note = Artificial Sequence
source                1..239
                      mol_type = protein
                      organism = synthetic construct
SEQUENCE: 89
ARVDQTPQTI TKETGESLTI NCVLRDSHCA TSSTYWYRKK SGSTNEESIS KGGRYVETVN  60
SGSKSFSLRI NDLTVEDSGT YRCASECQYG LAEYDVYGGG TVVTVNGGGG SGGGGGSGGG  120
SARVDQTPQT ITKETGESLT INCVLRDSNC GLSSTYWYRK KSGSTNEESI SKGGRYVETI  180
NEGSKSFSLR INDLTVEDSG TYRCKLSWWT QNWRCSNSDV YGGGTVVTVN AAAHHHHHH   239

SEQ ID NO: 90         moltype = DNA  length = 717
FEATURE               Location/Qualifiers
misc_feature          1..717
                      note = Artificial Sequence
source                1..717
                      mol_type = other DNA
                      organism = synthetic construct
SEQUENCE: 90
gctcgagtgg accaaacacc gcaaacaata acaaaggaga cgggcgaatc actgaccatc  60
aactgtgtcc tacgagatag ccactgtgca acctccagca cgtactggta tcgcaaaaaa  120
tcgggctcaa caaacgagga gagcatatcg aaaggtggac gatatgttga aacagttaac  180
agcggatcaa agtccttttc tttgagaatt aatgatctaa cagttgaaga cagtggcacg  240
tatcgatgcg cttccgagtg ccaatatgga ctggcagaat atgatgtata cggaggtggc  300
actgtcgtga ctgtgaatgg aggtggcggt agcggaggtg gtggcggatc cggcggtggt  360
tccgctcgag tggaccaaac accgcaaaca ataacaaagg agacgggcga atcactgacc  420
atcaactgtg tcctacgaga tagcaactgt gggttgtcca gcacgtactg gtatcgcaaa  480
aaatcgggct caacaaacga ggagagcata tcgaaaggtg gacgatatgt tgaaacaatt  540
aacgaaggat caaagtcctt ttctttgaga attaatgatc taacagttga agacagtggc  600
acgtatcgat gcaagttaag ctggtggacc cagaactgga gatgctcaaa ttccgatgta  660
tacggaggtg gcactgtcgt gactgtgaac gcggccgcac atcatcatca ccatcac     717

SEQ ID NO: 91         moltype = AA  length = 239
FEATURE               Location/Qualifiers
REGION                1..239
                      note = Artificial Sequence
source                1..239
                      mol_type = protein
                      organism = synthetic construct
SEQUENCE: 91
ARVDQSPSSL SASVGDRVTI TCVLRDSHCA TSSTYWYRKK SGSTNEESIS KGGRYVETVN  60
SGSKSFTLTI SSLQPEDFAT YYCASECQYG LAEYDVYGGG TKVEIKGGGG SGGGGGSGGG  120
SARVDQSPSS LSASVGDRVT ITCVLRDSNC GLSSTYWYRK KSGSTNEESI SKGGRYVETI  180
NEGSKSFSLR INDLTVEDSG TYRCKLSWWT QNWRCSNSDV YGGGTKVEIK AAAHHHHHH   239

SEQ ID NO: 92         moltype = DNA  length = 717
FEATURE               Location/Qualifiers
misc_feature          1..717
                      note = Artificial Sequence
source                1..717
                      mol_type = other DNA
                      organism = synthetic construct
SEQUENCE: 92
gcccgcgtgg accagtcccc ctcctccctg tccgcctccg tgggcgaccg cgtgaccatc  60
acctgcgtgc tgcgcgactc ccactgcgcc acctcctcca cctactggta ccgcaagaag  120
tccggctcca ccaacgagga gtccatctcc aagggggggcc gctacgtgga gaccgtgaac  180
tccggctcca agtccttcac cctgaccatc tcctccctgc agcccgagga cttcgccacc  240
tactactgcg cctccgagtg ccagtacggc ctggccgagt acgacgtgta cggcggcggc  300
accaaggtgg agatcaaggg aggtggcggt agcggaggtg gtggcggatc cggcggtggt  360
tccgcccgcg tggaccagtc cccctcctcc ctgtccgcct ccgtgggcga ccgcgtgacc  420
atcacctgcg tgctgcgcga ctccaactgc ggcctgtcct ccacctactg gtaccgcaag  480
aagtccggct ccaccaacga ggagtccatc tccaagggcg gccgctacgt ggagaccatc  540
aacgagggct ccaagtcctt ctccctgcgc atcaacgacc tgaccgtgga ggactccggc  600
acctaccgct gcaagctgtc ctggtggacc cagaactggc gctgctccaa ctccgacgtg  660
tacggcggcg gcaccaaggt ggagatcaag gcggccgcac atcatcatca ccatcac     717

SEQ ID NO: 93         moltype = AA  length = 249
```

-continued

```
FEATURE                Location/Qualifiers
REGION                 1..249
                       note = Artificial Sequence
source                 1..249
                       mol_type = protein
                       organism = synthetic construct
SEQUENCE: 93
ARVDQSPSSL SASVGDRVTI TCVLRDSHCA TSSTYWYRKK SGSTNEESIS KGGRYVETVN  60
SGSKSFTLTI SSLQPEDFAT YYCASECQYG LAEYDVYGGG TKVEIKGGGG SGGGGSGGGG  120
SGGGGSGGGG SARVDQSPSS LSASVGDRVT ITCVLRDSNC GLSSTYWYRK KSGSTNEESI  180
SKGGRYVETI NEGSKSFSLR INDLTVEDSG TYRCKLSWWT QNWRCSNSDV YGGGTKVEIK  240
AAAHHHHHH                                                          249

SEQ ID NO: 94          moltype = DNA  length = 747
FEATURE                Location/Qualifiers
misc_feature           1..747
                       note = Artificial Sequence
source                 1..747
                       mol_type = other DNA
                       organism = synthetic construct
SEQUENCE: 94
gcccgcgtgg accagtcccc ctcctccctg tccgcctccg tgggcgaccg cgtgaccatc  60
acctgcgtgc tgcgcgactc ccactgcgcc acctcctcca cctactggta ccgcaagaag  120
tccggctcca ccaacgagga gtccatctcc aagggggggcc gctacgtgga gaccgtgaac  180
tccggctcca agtccttcac cctgaccatc tcctccctgc agcccgagga cttcgccacc  240
tactactgcg cctccgagtg ccagtacggc ctggccgagt acgacgtgta cggcggcggc  300
accaaggtgg agatcaaggg tggtggtggt agcggtggtg gcggttcagg tggcggtggt  360
tctggcggtg gcggtagtgg cggaggtggt agtgcccgcg tggaccagtc cccctcctcc  420
ctgtccgcct ccgtgggcga ccgcgtgacc atcacctgcg tgctgcgcga ctccaactgc  480
ggcctgtcct ccacctactg gtaccgcaag aagtccggct ccaccaacga ggagtccatc  540
tccaagggcg gccgctacgt ggagaccatc aacgagggct ccaagtcctt ctccctgcgc  600
atcaacgacc tgaccgtgga ggactccggc acctaccgct gcaagctgtc ctggtggacc  660
cagaactggc gctgctccaa ctccgacgtg tacggcggcg gcaccaaggt ggagatcaag  720
gcggccgcac atcatcatca ccatcac                                      747

SEQ ID NO: 95          moltype = AA  length = 484
FEATURE                Location/Qualifiers
REGION                 1..484
                       note = Artificial Sequence
source                 1..484
                       mol_type = protein
                       organism = synthetic construct
SEQUENCE: 95
ASVNQTPRTA TKETGESLTI NCVLTDTHAK VFTTSWFRKN PGTTDWERMS IGGRYVESVN  60
KGAKSFSLRI KDLTVADSAT YICRAGGYLS QPRVYWDVYG AGTVLTVNGG GGSGGGGRTE  120
PRGPTIKPCP PCKCPAPNLL GGPSVFIFPP KIKDVLMISL SPIVTCVVVD VSEDDPDVQI  180
SWFVNNVEVH TAQTQTHRED YNSTLRVVSA LPIQHQDWMS GKEFKCKVNN KDLPAPIERT  240
ISKPKGSVRA PQVYVLPPPE EEMTKKQVTL TCMVTDFMPE DIYVEWTNNG KTELNYKNTE  300
PVLDSDGSYF MYSKLRVEKK NWVERNSYSC SVVHEGLHNH HTTKSFSRTP GKGGGGSGGG  360
GSGGGGSGGG GSGAHSASVN QTPRTATKET GESLTINCVL TDTHAKVFTT SWFRKNPGTT  420
DWERMSIGGR YVESVNKGAK SFSLRIKDLT VADSATYICR AGGYLSQPRV YWDVYGAGTV  480
LTVN                                                               484

SEQ ID NO: 96          moltype = DNA  length = 1452
FEATURE                Location/Qualifiers
misc_feature           1..1452
                       note = Artificial Sequence
source                 1..1452
                       mol_type = other DNA
                       organism = synthetic construct
SEQUENCE: 96
gcaagcgtta atcagacacc gcgtaccgca accaaagaaa ccggtgaaag cctgaccatt  60
aattgtgttc tgaccgatac ccatgctaaa gttttcacta ccagctggtt tcgtaaaaat  120
ccgggtacaa ccgattggga acgtatgagc attggtggtc gttatgttga aagcgtgaat  180
aaaggtgcca aaagctttag cctgcgcatt aaagatctga ccgttgcaga tagcgcaacc  240
tatatctgtc gtgccggtgg ttacctgtct cagccgcgtg tttactggga tgtttatggt  300
gcaggcaccg ttctgaccgt taatggcggt ggtggttctg gtggtggtgg tcgtacggag  360
cctcgaggcc ccacaatcaa gccctgtcct ccatgcaaat gcccagcacc taacctcttg  420
ggtggaccat ccgtcttcat cttccctcca aagatcaagg atgtactcat gatctccctg  480
agccccatag tcacatgtgt ggtggtggat gtgagcgagg atgacccaga tgtccagatc  540
agctggtttg tgaacaacgt ggaagtacac acagctcaga cacaaaccca tagagaggat  600
tacaacagta ctctccgggt ggtcagtgcc ctccccatcc agcaccagga ctggatgagt  660
ggcaaggagt tcaaatgcaa ggtcaacaac aaagacctcc cagcgcccat cgagagaacc  720
atctcaaaac ccaaagggtc agtaagagct ccacaggtat atgtcttgcc tccaccagaa  780
gaagagatga ctaagaaaca ggtcactctg acctgcatgg tcacagactt catgcctgaa  840
gacatttacg tggagtggac caacaacggg aaaacagagc taaactacaa gaacactgaa  900
ccagtcctgg actctgatgg ttcttacttc atgtacagca agctgagagt ggaaaagaag  960
aactgggtgg aaagaaatag ctactcctgt tcagtggtcc acgagggtct gcacaatcac  1020
cacacgacta agagcttctc ccggactccg ggtaaaggag gtggcggttc cggaggtggc  1080
```

-continued

```
ggtagcggag gtggcggtag cggaggtggc ggtagcgggg cccattctgc aagcgttaat  1140
cagacaccgc gtaccgcaac caaagaaacc ggtgaaagcc tgaccattaa ttgtgttctg  1200
accgataccc atgctaaagt tttcactacc agctggtttc gtaaaaatcc gggtacaacc  1260
gattgggaac gtatgagcat tggtggtcgt tatgttgaaa gcgtgaataa aggtgccaaa  1320
agctttagcc tgcgcattaa agatctgacc gttgcagata gcgcaaccta tatctgtcgt  1380
gccggtggtt acctgtctca gccgcgtgtt tactgggatg tttatggtgc aggcaccgtt  1440
ctgaccgtta at                                                     1452
```